United States Patent
Cavaco Paulo et al.

(10) Patent No.: US 12,102,706 B2
(45) Date of Patent: *Oct. 1, 2024

(54) PEPTIDE COMPOSITION AND RESPECTIVE USES

(71) Applicant: Universidade do Minho, Braga (PT)

(72) Inventors: Artur Manuel Cavaco Paulo, Braga (PT); Celia Freitas Da Cruz, Guimaraes (PT); Margarida Maria Macedo Francesko Fernandes, Braga (PT)

(73) Assignee: UNIVERSIDADE DO MINHO, Braga (PT)

( * ) Notice: Subject to any disclaimer, the term of this patent is extended or adjusted under 35 U.S.C. 154(b) by 0 days.

This patent is subject to a terminal disclaimer.

(21) Appl. No.: 18/194,372

(22) Filed: Mar. 31, 2023

(65) Prior Publication Data

US 2023/0338263 A1    Oct. 26, 2023

Related U.S. Application Data

(63) Continuation of application No. 16/439,889, filed on Jun. 13, 2019, now Pat. No. 11,642,298, which is a continuation of application No. 15/030,313, filed as application No. PCT/IB2014/065375 on Oct. 16, 2014, now Pat. No. 10,709,655.

(30) Foreign Application Priority Data

Oct. 18, 2013   (PT) .......................................... 107244

(51) Int. Cl.
*A61K 8/64* (2006.01)
*A61Q 5/00* (2006.01)
*A61Q 5/04* (2006.01)
*A61Q 5/06* (2006.01)

(52) U.S. Cl.
CPC ................ *A61K 8/64* (2013.01); *A61K 8/645* (2013.01); *A61Q 5/002* (2013.01); *A61Q 5/04* (2013.01); *A61Q 5/06* (2013.01); *A61Q 5/065* (2013.01); *A61K 2800/30* (2013.01)

(58) Field of Classification Search
CPC ...... A61K 8/64; A61K 8/645; A61K 2800/30; A61K 38/08; A61K 38/10; A61Q 5/002; A61Q 5/04; A61Q 5/06; A61Q 5/065; A61Q 5/00; A61Q 5/10; A61P 17/14
See application file for complete search history.

(56) References Cited

U.S. PATENT DOCUMENTS

| | | |
|---|---|---|
| 5,028,419 A | 7/1991 | Pigiet |
| 5,635,170 A | 6/1997 | Lang et al. |
| 10,709,655 B2 | 7/2020 | Cavaco et al. |
| 2006/0272103 A1 | 12/2006 | Barbarat |
| 2006/0286655 A1 | 12/2006 | Philippe |
| 2010/0272666 A1 | 10/2010 | Breakspear et al. |
| 2013/0224269 A1 | 8/2013 | Khan et al. |
| 2016/0271043 A1 | 9/2016 | Cavaco Paulo et al. |
| 2019/0307666 A1 | 10/2019 | Cavaco Paulo et al. |
| 2020/0069551 A1 | 3/2020 | Sahib et al. |
| 2021/0393500 A1 | 12/2021 | Cavaco Paulo et al. |
| 2023/0248627 A1 | 8/2023 | Cavaco et al. |
| 2023/0248631 A1 | 8/2023 | Cavaco Paulo et al. |
| 2023/0301894 A1 | 9/2023 | Cavaco Paulo et al. |
| 2023/0355499 A1 | 11/2023 | Sahib et al. |
| 2024/0115481 A1 | 4/2024 | Cavaco Paulo et al. |

FOREIGN PATENT DOCUMENTS

| | | |
|---|---|---|
| CN | 103126949 A | 6/2013 |
| CN | 104940071 A | 9/2015 |
| EP | 0488242 A1 | 6/1992 |
| EP | 1238645 A2 | 9/2002 |
| EP | 1705188 A1 | 9/2006 |
| FR | 2706300 A1 | 12/1994 |
| FR | 2876286 A1 | 4/2006 |
| GB | 103484 A | 1/1918 |
| JP | H0656889 A | 3/1994 |
| JP | H1112138 A | 1/1999 |
| JP | 2005151849 A | 6/2005 |

(Continued)

OTHER PUBLICATIONS

Co-pending U.S. Appl. No. 18/252,712, inventors Cavaco; Paulo Artur Manuel et al., filed on May 11, 2023.

(Continued)

*Primary Examiner* — Jeanette M Lieb
*Assistant Examiner* — Erinne R Dabkowski
(74) *Attorney, Agent, or Firm* — WILSON SONSINI GOODRICH & ROSATI

(57) ABSTRACT

The current application discloses a composition that comprises at least one peptide with a sequence length of 6-12 amino acids, where 2-5 of those amino acids are cysteines for the treatment and cosmetics of animal hair, in preference human hair. There are several hair styling methods that involve breakage and reestablishment of disulfide bonds, allowing relaxation and straightening of the hair. However, the most effective methods currently used to modulate hair contain harmful chemicals. Thus there is a constant demand for formulations that efficiently model the hair fiber without damage. Thus, the present invention aims to provide a composition for treatment of the hair, including animal and human hair, without the use of chemicals harmful to the hair fiber and consumer health and uses of said compositions in shampoo, lotion, serum, cream, conditioner, foam, elixir, oil, aerosol or mask.

8 Claims, No Drawings

Specification includes a Sequence Listing.

(56) References Cited

FOREIGN PATENT DOCUMENTS

| | | |
|---|---|---|
| PT | 103484 A | 11/2007 |
| WO | WO-9711672 A1 | 4/1997 |
| WO | WO-0023039 A2 | 4/2000 |
| WO | WO-0051556 A1 | 9/2000 |
| WO | WO-0064405 A2 | 11/2000 |
| WO | WO-2004048399 A2 | 6/2004 |
| WO | WO-2005049834 A1 | 6/2005 |
| WO | WO-2006001536 A1 | 1/2006 |
| WO | WO-2007136286 A1 | 11/2007 |
| WO | WO-2008081348 A2 | 7/2008 |
| WO | WO-2010010145 A1 | 1/2010 |
| WO | WO-2011072991 A1 | 6/2011 |
| WO | WO-2012013593 A1 | 2/2012 |
| WO | WO-2015056216 A2 | 4/2015 |
| WO | WO-2024073683 A2 | 4/2024 |

OTHER PUBLICATIONS

Co-pending U.S. Appl. No. 18/478,320, inventors Staley; Karis et al., filed on Sep. 29, 2023.
Co-pending U.S. Appl. No. 18/497,900, inventors Cavaco Paulo; Arthur Manuel et al., filed on Oct. 30, 2023.
Co-pending U.S. Appl. No. 18/520,428, inventors Cavaco Paulo; Artur Manuel et al., filed on Nov. 27, 2023.
U.S. Appl. No. 18/164,515 Office Action dated Oct. 12, 2023.
U.S. Appl. No. 18/334,287 Office Action dated Oct. 10, 2023.
Co-pending U.S. Appl. No. 18/164,515, inventors Sahib; Suveen [Us] et al., filed on Feb. 3, 2023.
Co-pending U.S. Appl. No. 18/334,287, inventors Cavaco Paulo; Arthur Manuel et al., filed on Jun. 13, 2023.
Co-pending U.S. Appl. No. 18/339,889, inventors Cavaco; Paulo Artur Manuel et al., filed on Jun. 22, 2023.
Co-pending U.S. Appl. No. 18/339,927, inventors Cavaco; Paulo Artur Manuel et al., filed on Jun. 22, 2023.
U.S. Appl. No. 16/122,796 Office Action dated Apr. 28, 2023.
Blast glossary downloaded from www.ncbi.nlm.nih.gov on May 2, 2020.
Blast search for SEQ ID No. 1, downloaded May 2, 2020 (2020).
Blast search for SEQ ID No. 2, downloaded May 2, 2020 (2020).
Dow, Carbowax Sentry Polyethylene Glycols, published online 2011.
Fernanda Reis Gavazzoni Dias. Hair Cosmetics: An Overview. International Journal of Trichology 7:2-15 (2015).
Fernandes et al. Keratin-based peptide: biological evaluation and strengthening properties on relaxed hair. International Journal of Cosmetic Science 34:338-346 (2012).
Koonin et al. Chapter 2 Evolutionary Concept in Genetics and Genomics. MY. Sequence—Evolution—Function: Computational Approaches in Comparative Genomics. Boston: Kluwer Academic. Available from: https:// www.ncbi.nlnn.nih.gov/books/NBK20260/ (pp. 3 ) (2003).
Marabotti et al. The misuse of terms in scientific literature. Bioinformatics 26(19):2498 (2010).
Naturally Curly, http://www.naturallycurly.com/curlreading/kinky-hair-type-4a/ingredients-commonly-used-in-hair-care-productspeg-modified-materials/, published online Jun. 8, 2010.
PCT/IB2014/065375 International Search Report and Written Opinion dated Jun. 7, 2015.
Romanowski. An introduction to cosmetic technology. American Oil Chemists' Society. Available at https://www.aocs.org/stay-informed/inform-magazine/featured-articles/an-introduction-to-cosmetic-technology-april-2015?SSO=True (8 pgs.) (2015).
Shimomura et al. Human Hair Keratin-Associated Proteins. J Investig Dermatol Symp Proc 10:230-233 (2005).
Thesis from Celia Freitas Da Cruz, Unraveling and modulating human hair morphology features (192 pgs) (2012).
Uniprot Protein Database, protein accession A8MUX0 , Keratin-associated protein 16-1, accessed on Dec. 18, 2019.
Uniprot Protein Database, protein accession P26371 , Keratin-associated protein 5-9, accessed on Dec. 18, 2019.
Uniprot Protein Database, protein accession Q9NSB0, Type II hair keratin 6, accessed on Dec. 18, 2019.
Uniprot Protein Database, protein Accession Q9NSB5, accessed on Nov. 8, 2019.
Uniprot protein database, protein Type II hair keratin 1, protein accession Q9NSB5, accessed on Aug. 28, 2017.
U.S. Forest Service entry on soaps at www.fs.fed.us/wildflowers/ethnobotany/soaps.shtra, downloaded Sep. 29, 2020 (2020).
U.S. Appl. No. 15/030,313 Office Action dated Aug. 29, 2018.
U.S. Appl. No. 15/030,313 Office Action dated Aug. 31, 2017.
U.S. Appl. No. 15/030,313 Office Action dated Jan. 11, 2019.
U.S. Appl. No. 15/030,313 Office Action dated Jan. 24, 2018.
U.S. Appl. No. 15/030,313 Office Action dated Jul. 18, 2019.
U.S. Appl. No. 15/030,313 Office Action dated Mar. 2, 2017.
U.S. Appl. No. 16/122,796 Office Action dated Apr. 15, 2021.
U.S. Appl. No. 16/122,796 Office Action dated Jan. 5, 2023.
U.S. Appl. No. 16/122,796 Office Action dated May 4, 2020.
U.S. Appl. No. 16/122,796 Office Action dated Oct. 1, 2020.
U.S. Appl. No. 16/122,796 Office Action dated Sep. 20, 2022.
U.S. Appl. No. 16/439,889 Office Action dated Apr. 1, 2022.
U.S. Appl. No. 16/439,889 Office Action dated Jan. 3, 2020.
U.S. Appl. No. 16/439,889 Office Action dated Sep. 15, 2022.
Yang. Chapter 36: Hair Care Cosmetics. Cosmetic Science and Technology: Theoretical Principles and Applications (pp. 601-615) (2017).
CN104940071A English Translation Published: Sep. 30, 2015.
EP1238645A2 English Translation Published: Sep. 11, 2002.
U.S. Appl. No. 18/164,515 Office Action dated Jun. 5, 2024.
U.S. Appl. No. 18/339,927 Office Action dated May 8, 2024.

SEQUENCE LISTING

```
Sequence total quantity: 1239
SEQ ID NO: 1            moltype = AA  length = 10
FEATURE                 Location/Qualifiers
source                  1..10
                        mol_type = protein
                        organism = Homo sapiens
SEQUENCE: 1
APCAPRPSCG                                                                10

SEQ ID NO: 2            moltype = AA  length = 10
FEATURE                 Location/Qualifiers
```

```
source                     1..10
                           mol_type = protein
                           organism = Homo sapiens
SEQUENCE: 2
EACVPSVPCP                                                                      10

SEQ ID NO: 3               moltype = AA   length = 10
FEATURE                    Location/Qualifiers
source                     1..10
                           mol_type = protein
                           organism = Homo sapiens
SEQUENCE: 3
ESCGTASGCA                                                                      10

SEQ ID NO: 4               moltype = AA   length = 10
FEATURE                    Location/Qualifiers
source                     1..10
                           mol_type = protein
                           organism = Homo sapiens
SEQUENCE: 4
GLCAGTSACL                                                                      10

SEQ ID NO: 5               moltype = AA   length = 10
FEATURE                    Location/Qualifiers
source                     1..10
                           mol_type = protein
                           organism = Homo sapiens
SEQUENCE: 5
GVCGPSPPCI                                                                      10

SEQ ID NO: 6               moltype = AA   length = 10
FEATURE                    Location/Qualifiers
source                     1..10
                           mol_type = protein
                           organism = Homo sapiens
SEQUENCE: 6
HGCTLPGACN                                                                      10

SEQ ID NO: 7               moltype = AA   length = 10
FEATURE                    Location/Qualifiers
source                     1..10
                           mol_type = protein
                           organism = Homo sapiens
SEQUENCE: 7
HSCTLPGACN                                                                      10

SEQ ID NO: 8               moltype = AA   length = 10
FEATURE                    Location/Qualifiers
source                     1..10
                           mol_type = protein
                           organism = Homo sapiens
SEQUENCE: 8
KDCLQNSLCE                                                                      10

SEQ ID NO: 9               moltype = AA   length = 10
FEATURE                    Location/Qualifiers
source                     1..10
                           mol_type = protein
                           organism = Homo sapiens
SEQUENCE: 9
LPCLPAASCG                                                                      10

SEQ ID NO: 10              moltype = AA   length = 10
FEATURE                    Location/Qualifiers
source                     1..10
                           mol_type = protein
                           organism = Homo sapiens
SEQUENCE: 10
LPCYFTGSCN                                                                      10

SEQ ID NO: 11              moltype = AA   length = 10
FEATURE                    Location/Qualifiers
source                     1..10
                           mol_type = protein
                           organism = Homo sapiens
SEQUENCE: 11
NFCLPSLSCR                                                                      10

SEQ ID NO: 12              moltype = AA   length = 10
```

```
                        -continued

FEATURE                 Location/Qualifiers
source                  1..10
                        mol_type = protein
                        organism = Homo sapiens
SEQUENCE: 12
NPCATTNACD                                                              10

SEQ ID NO: 13           moltype = AA  length = 10
FEATURE                 Location/Qualifiers
source                  1..10
                        mol_type = protein
                        organism = Homo sapiens
SEQUENCE: 13
NPCATTNACE                                                              10

SEQ ID NO: 14           moltype = AA  length = 10
FEATURE                 Location/Qualifiers
source                  1..10
                        mol_type = protein
                        organism = Homo sapiens
SEQUENCE: 14
NPCATTNACS                                                              10

SEQ ID NO: 15           moltype = AA  length = 10
FEATURE                 Location/Qualifiers
source                  1..10
                        mol_type = protein
                        organism = Homo sapiens
SEQUENCE: 15
NPCGLRARCG                                                              10

SEQ ID NO: 16           moltype = AA  length = 10
FEATURE                 Location/Qualifiers
source                  1..10
                        mol_type = protein
                        organism = Homo sapiens
SEQUENCE: 16
NPCGPRSRCG                                                              10

SEQ ID NO: 17           moltype = AA  length = 10
FEATURE                 Location/Qualifiers
source                  1..10
                        mol_type = protein
                        organism = Homo sapiens
SEQUENCE: 17
NPCSTPASCT                                                              10

SEQ ID NO: 18           moltype = AA  length = 10
FEATURE                 Location/Qualifiers
source                  1..10
                        mol_type = protein
                        organism = Homo sapiens
SEQUENCE: 18
NPCSTSPSCV                                                              10

SEQ ID NO: 19           moltype = AA  length = 10
FEATURE                 Location/Qualifiers
source                  1..10
                        mol_type = protein
                        organism = Homo sapiens
SEQUENCE: 19
PACTSSSPCS                                                              10

SEQ ID NO: 20           moltype = AA  length = 10
FEATURE                 Location/Qualifiers
source                  1..10
                        mol_type = protein
                        organism = Homo sapiens
SEQUENCE: 20
SKCHESTVCP                                                              10

SEQ ID NO: 21           moltype = AA  length = 10
FEATURE                 Location/Qualifiers
source                  1..10
                        mol_type = protein
                        organism = Homo sapiens
SEQUENCE: 21
SPCVPRTVCV                                                              10
```

```
SEQ ID NO: 22            moltype = AA   length = 10
FEATURE                  Location/Qualifiers
source                   1..10
                         mol_type = protein
                         organism = Homo sapiens
SEQUENCE: 22
SSCSVETACL                                                                10

SEQ ID NO: 23            moltype = AA   length = 10
FEATURE                  Location/Qualifiers
source                   1..10
                         mol_type = protein
                         organism = Homo sapiens
SEQUENCE: 23
SVCSSGVNCR                                                                10

SEQ ID NO: 24            moltype = AA   length = 10
FEATURE                  Location/Qualifiers
source                   1..10
                         mol_type = protein
                         organism = Homo sapiens
SEQUENCE: 24
TACPLPGTCH                                                                10

SEQ ID NO: 25            moltype = AA   length = 10
FEATURE                  Location/Qualifiers
source                   1..10
                         mol_type = protein
                         organism = Homo sapiens
SEQUENCE: 25
TNCSPRPICV                                                                10

SEQ ID NO: 26            moltype = AA   length = 10
FEATURE                  Location/Qualifiers
source                   1..10
                         mol_type = protein
                         organism = Homo sapiens
SEQUENCE: 26
TSCVPPAPCT                                                                10

SEQ ID NO: 27            moltype = AA   length = 10
FEATURE                  Location/Qualifiers
source                   1..10
                         mol_type = protein
                         organism = Homo sapiens
SEQUENCE: 27
TTCTSSNTCE                                                                10

SEQ ID NO: 28            moltype = AA   length = 10
FEATURE                  Location/Qualifiers
source                   1..10
                         mol_type = protein
                         organism = Homo sapiens
SEQUENCE: 28
VPCVPSVPCT                                                                10

SEQ ID NO: 29            moltype = AA   length = 10
FEATURE                  Location/Qualifiers
source                   1..10
                         mol_type = protein
                         organism = Homo sapiens
SEQUENCE: 29
ATCGPSACIT                                                                10

SEQ ID NO: 30            moltype = AA   length = 10
FEATURE                  Location/Qualifiers
source                   1..10
                         mol_type = protein
                         organism = Homo sapiens
SEQUENCE: 30
GPCISNPCGL                                                                10

SEQ ID NO: 31            moltype = AA   length = 10
FEATURE                  Location/Qualifiers
source                   1..10
                         mol_type = protein
                         organism = Homo sapiens
SEQUENCE: 31
GPCLSNPCTS                                                                10
```

```
SEQ ID NO: 32            moltype = AA   length = 10
FEATURE                  Location/Qualifiers
source                   1..10
                         mol_type = protein
                         organism = Homo sapiens
SEQUENCE: 32
GSCVTNPCGP                                                              10

SEQ ID NO: 33            moltype = AA   length = 10
FEATURE                  Location/Qualifiers
source                   1..10
                         mol_type = protein
                         organism = Homo sapiens
SEQUENCE: 33
LTCFSITCSS                                                              10

SEQ ID NO: 34            moltype = AA   length = 10
FEATURE                  Location/Qualifiers
source                   1..10
                         mol_type = protein
                         organism = Homo sapiens
SEQUENCE: 34
NPCSTPSCTT                                                              10

SEQ ID NO: 35            moltype = AA   length = 10
FEATURE                  Location/Qualifiers
source                   1..10
                         mol_type = protein
                         organism = Homo sapiens
SEQUENCE: 35
PSCVTAPCAP                                                              10

SEQ ID NO: 36            moltype = AA   length = 10
FEATURE                  Location/Qualifiers
source                   1..10
                         mol_type = protein
                         organism = Homo sapiens
SEQUENCE: 36
SDCSSTHCSP                                                              10

SEQ ID NO: 37            moltype = AA   length = 10
FEATURE                  Location/Qualifiers
source                   1..10
                         mol_type = protein
                         organism = Homo sapiens
SEQUENCE: 37
SLCLPPTCHT                                                              10

SEQ ID NO: 38            moltype = AA   length = 10
FEATURE                  Location/Qualifiers
source                   1..10
                         mol_type = protein
                         organism = Homo sapiens
SEQUENCE: 38
SLCNLGSCGP                                                              10

SEQ ID NO: 39            moltype = AA   length = 10
FEATURE                  Location/Qualifiers
source                   1..10
                         mol_type = protein
                         organism = Homo sapiens
SEQUENCE: 39
SPCLVGNCAW                                                              10

SEQ ID NO: 40            moltype = AA   length = 10
FEATURE                  Location/Qualifiers
source                   1..10
                         mol_type = protein
                         organism = Homo sapiens
SEQUENCE: 40
TACLPGTCAT                                                              10

SEQ ID NO: 41            moltype = AA   length = 10
FEATURE                  Location/Qualifiers
source                   1..10
                         mol_type = protein
                         organism = Homo sapiens
SEQUENCE: 41
```

TSCLPALCLP                                                                                              10

SEQ ID NO: 42              moltype = AA  length = 10
FEATURE                    Location/Qualifiers
source                     1..10
                           mol_type = protein
                           organism = Homo sapiens SEQUENCE: 42
TSCSSRPCVP                                                                                              10

SEQ ID NO: 43              moltype = AA  length = 10
FEATURE                    Location/Qualifiers
source                     1..10
                           mol_type = protein
                           organism = Homo sapiens SEQUENCE: 43
TTCGGGSCGV                                                                                              10

SEQ ID NO: 44              moltype = AA  length = 10
FEATURE                    Location/Qualifiers
source                     1..10
                           mol_type = protein
                           organism = Homo sapiens SEQUENCE: 44
VNCRPELCLG                                                                                              10

SEQ ID NO: 45              moltype = AA  length = 10
FEATURE                    Location/Qualifiers
source                     1..10
                           mol_type = protein
                           organism = Homo sapiens SEQUENCE: 45
YVCQPMACLP                                                                                              10

SEQ ID NO: 46              moltype = AA  length = 10
FEATURE                    Location/Qualifiers
source                     1..10
                           mol_type = protein
                           organism = Homo sapiens SEQUENCE: 46
AFSCISACGP                                                                                              10

SEQ ID NO: 47              moltype = AA  length = 10
FEATURE                    Location/Qualifiers
source                     1..10
                           mol_type = protein
                           organism = Homo sapiens SEQUENCE: 47
GSVCSAPCNG                                                                                              10

SEQ ID NO: 48              moltype = AA  length = 10
FEATURE                    Location/Qualifiers
source                     1..10
                           mol_type = protein
                           organism = Homo sapiens SEQUENCE: 48
GVVCGDLCAS                                                                                              10

SEQ ID NO: 49              moltype = AA  length = 10
FEATURE                    Location/Qualifiers
source                     1..10
                           mol_type = protein
                           organism = Homo sapiens SEQUENCE: 49
GVVCGDLCVS                                                                                              10

SEQ ID NO: 50              moltype = AA  length = 10
FEATURE                    Location/Qualifiers
source                     1..10
                           mol_type = protein
                           organism = Homo sapiens SEQUENCE: 50
LTGCLLPCYF                                                                                              10

SEQ ID NO: 51              moltype = AA  length = 10
FEATURE                    Location/Qualifiers
source                     1..10
                           mol_type = protein
                           organism = Homo sapiens

```
SEQUENCE: 51
NEDCKLPCNP                                                                              10

SEQ ID NO: 52            moltype = AA  length = 10
FEATURE                  Location/Qualifiers
source                   1..10
                         mol_type = protein
                         organism = Homo sapiens
SEQUENCE: 52
NFSCVSACGP                                                                              10

SEQ ID NO: 53            moltype = AA  length = 10
FEATURE                  Location/Qualifiers
source                   1..10
                         mol_type = protein
                         organism = Homo sapiens
SEQUENCE: 53
PPTCHTACPL                                                                              10

SEQ ID NO: 54            moltype = AA  length = 10
FEATURE                  Location/Qualifiers
source                   1..10
                         mol_type = protein
                         organism = Homo sapiens
SEQUENCE: 54
PQPCATACKP                                                                              10

SEQ ID NO: 55            moltype = AA  length = 10
FEATURE                  Location/Qualifiers
source                   1..10
                         mol_type = protein
                         organism = Homo sapiens
SEQUENCE: 55
SEDCKLPCNP                                                                              10

SEQ ID NO: 56            moltype = AA  length = 10
FEATURE                  Location/Qualifiers
source                   1..10
                         mol_type = protein
                         organism = Homo sapiens
SEQUENCE: 56
SLGCRTSCSS                                                                              10

SEQ ID NO: 57            moltype = AA  length = 10
FEATURE                  Location/Qualifiers
source                   1..10
                         mol_type = protein
                         organism = Homo sapiens
SEQUENCE: 57
SLSCRTSCSS                                                                              10

SEQ ID NO: 58            moltype = AA  length = 10
FEATURE                  Location/Qualifiers
source                   1..10
                         mol_type = protein
                         organism = Homo sapiens
SEQUENCE: 58
SSSCPLGCTM                                                                              10

SEQ ID NO: 59            moltype = AA  length = 10
FEATURE                  Location/Qualifiers
source                   1..10
                         mol_type = protein
                         organism = Homo sapiens
SEQUENCE: 59
TGSCNSPCLV                                                                              10

SEQ ID NO: 60            moltype = AA  length = 10
FEATURE                  Location/Qualifiers
source                   1..10
                         mol_type = protein
                         organism = Homo sapiens
SEQUENCE: 60
TSSCPLGCTM                                                                              10

SEQ ID NO: 61            moltype = AA  length = 10
FEATURE                  Location/Qualifiers
source                   1..10
                         mol_type = protein
```

```
                            organism = Homo sapiens
SEQUENCE: 61
VGSCGSSCRK                                                                       10

SEQ ID NO: 62           moltype = AA  length = 10
FEATURE                 Location/Qualifiers
source                  1..10
                        mol_type = protein
                        organism = Homo sapiens
SEQUENCE: 62
VGVCGGSCKR                                                                       10

SEQ ID NO: 63           moltype = AA  length = 10
FEATURE                 Location/Qualifiers
source                  1..10
                        mol_type = protein
                        organism = Homo sapiens
SEQUENCE: 63
VSNCNWFCEG                                                                       10

SEQ ID NO: 64           moltype = AA  length = 10
FEATURE                 Location/Qualifiers
source                  1..10
                        mol_type = protein
                        organism = Homo sapiens
SEQUENCE: 64
ACGPRPGRCC                                                                       10

SEQ ID NO: 65           moltype = AA  length = 10
FEATURE                 Location/Qualifiers
source                  1..10
                        mol_type = protein
                        organism = Homo sapiens
SEQUENCE: 65
ACGPRPSRCC                                                                       10

SEQ ID NO: 66           moltype = AA  length = 10
FEATURE                 Location/Qualifiers
source                  1..10
                        mol_type = protein
                        organism = Homo sapiens
SEQUENCE: 66
CAPRPSCGPC                                                                       10

SEQ ID NO: 67           moltype = AA  length = 10
FEATURE                 Location/Qualifiers
source                  1..10
                        mol_type = protein
                        organism = Homo sapiens
SEQUENCE: 67
CEPCSAYVIC                                                                       10

SEQ ID NO: 68           moltype = AA  length = 10
FEATURE                 Location/Qualifiers
source                  1..10
                        mol_type = protein
                        organism = Homo sapiens
SEQUENCE: 68
CGLRARCGPC                                                                       10

SEQ ID NO: 69           moltype = AA  length = 10
FEATURE                 Location/Qualifiers
source                  1..10
                        mol_type = protein
                        organism = Homo sapiens
SEQUENCE: 69
CGPRPGRCCI                                                                       10

SEQ ID NO: 70           moltype = AA  length = 10
FEATURE                 Location/Qualifiers
source                  1..10
                        mol_type = protein
                        organism = Homo sapiens
SEQUENCE: 70
CGPRPSRCCI                                                                       10

SEQ ID NO: 71           moltype = AA  length = 10
FEATURE                 Location/Qualifiers
source                  1..10
```

```
                        mol_type = protein
                        organism = Homo sapiens
SEQUENCE: 71
CGPRSRCGPC                                                              10

SEQ ID NO: 72           moltype = AA   length = 10
FEATURE                 Location/Qualifiers
source                  1..10
                        mol_type = protein
                        organism = Homo sapiens
SEQUENCE: 72
CGTSQKGCCN                                                              10

SEQ ID NO: 73           moltype = AA   length = 10
FEATURE                 Location/Qualifiers
source                  1..10
                        mol_type = protein
                        organism = Homo sapiens
SEQUENCE: 73
CHGCTLPGAC                                                              10

SEQ ID NO: 74           moltype = AA   length = 10
FEATURE                 Location/Qualifiers
source                  1..10
                        mol_type = protein
                        organism = Homo sapiens
SEQUENCE: 74
CHSCTLPGAC                                                              10

SEQ ID NO: 75           moltype = AA   length = 10
FEATURE                 Location/Qualifiers
source                  1..10
                        mol_type = protein
                        organism = Homo sapiens
SEQUENCE: 75
CLPCLPAASC                                                              10

SEQ ID NO: 76           moltype = AA   length = 10
FEATURE                 Location/Qualifiers
source                  1..10
                        mol_type = protein
                        organism = Homo sapiens
SEQUENCE: 76
CLPPTCHTAC                                                              10

SEQ ID NO: 77           moltype = AA   length = 10
FEATURE                 Location/Qualifiers
source                  1..10
                        mol_type = protein
                        organism = Homo sapiens
SEQUENCE: 77
CLSNPCTSCV                                                              10

SEQ ID NO: 78           moltype = AA   length = 10
FEATURE                 Location/Qualifiers
source                  1..10
                        mol_type = protein
                        organism = Homo sapiens
SEQUENCE: 78
CLVGNCAWCE                                                              10

SEQ ID NO: 79           moltype = AA   length = 10
FEATURE                 Location/Qualifiers
source                  1..10
                        mol_type = protein
                        organism = Homo sapiens
SEQUENCE: 79
CNPCSTPASC                                                              10

SEQ ID NO: 80           moltype = AA   length = 10
FEATURE                 Location/Qualifiers
source                  1..10
                        mol_type = protein
                        organism = Homo sapiens
SEQUENCE: 80
CNPCSTPSCT                                                              10

SEQ ID NO: 81           moltype = AA   length = 10
FEATURE                 Location/Qualifiers
```

```
source                    1..10
                          mol_type = protein
                          organism = Homo sapiens
SEQUENCE: 81
CNPCSTSPSC                                                                        10

SEQ ID NO: 82             moltype = AA   length = 10
FEATURE                   Location/Qualifiers
source                    1..10
                          mol_type = protein
                          organism = Homo sapiens
SEQUENCE: 82
CNSPCLVGNC                                                                        10

SEQ ID NO: 83             moltype = AA   length = 10
FEATURE                   Location/Qualifiers
source                    1..10
                          mol_type = protein
                          organism = Homo sapiens
SEQUENCE: 83
CRTSCSSRPC                                                                        10

SEQ ID NO: 84             moltype = AA   length = 10
FEATURE                   Location/Qualifiers
source                    1..10
                          mol_type = protein
                          organism = Homo sapiens
SEQUENCE: 84
CSLKEHCSAC                                                                        10

SEQ ID NO: 85             moltype = AA   length = 10
FEATURE                   Location/Qualifiers
source                    1..10
                          mol_type = protein
                          organism = Homo sapiens
SEQUENCE: 85
CSPRPICVPC                                                                        10

SEQ ID NO: 86             moltype = AA   length = 10
FEATURE                   Location/Qualifiers
source                    1..10
                          mol_type = protein
                          organism = Homo sapiens
SEQUENCE: 86
CSSTMSYSCC                                                                        10

SEQ ID NO: 87             moltype = AA   length = 10
FEATURE                   Location/Qualifiers
source                    1..10
                          mol_type = protein
                          organism = Homo sapiens
SEQUENCE: 87
CSTPASCTSC                                                                        10

SEQ ID NO: 88             moltype = AA   length = 10
FEATURE                   Location/Qualifiers
source                    1..10
                          mol_type = protein
                          organism = Homo sapiens
SEQUENCE: 88
CSTPSCTTCV                                                                        10

SEQ ID NO: 89             moltype = AA   length = 10
FEATURE                   Location/Qualifiers
source                    1..10
                          mol_type = protein
                          organism = Homo sapiens
SEQUENCE: 89
CTSCVPPAPC                                                                        10

SEQ ID NO: 90             moltype = AA   length = 10
FEATURE                   Location/Qualifiers
source                    1..10
                          mol_type = protein
                          organism = Homo sapiens
SEQUENCE: 90
CTSSNTCEPC                                                                        10

SEQ ID NO: 91             moltype = AA   length = 10
```

```
FEATURE                 Location/Qualifiers
source                  1..10
                        mol_type = protein
                        organism = Homo sapiens
SEQUENCE: 91
CVPPAPCTPC                                                                    10

SEQ ID NO: 92           moltype = AA  length = 10
FEATURE                 Location/Qualifiers
source                  1..10
                        mol_type = protein
                        organism = Homo sapiens
SEQUENCE: 92
CVPPSCHGCT                                                                    10

SEQ ID NO: 93           moltype = AA  length = 10
FEATURE                 Location/Qualifiers
source                  1..10
                        mol_type = protein
                        organism = Homo sapiens
SEQUENCE: 93
CVPPSCHSCT                                                                    10

SEQ ID NO: 94           moltype = AA  length = 10
FEATURE                 Location/Qualifiers
source                  1..10
                        mol_type = protein
                        organism = Homo sapiens
SEQUENCE: 94
DCKLPCNPCA                                                                    10

SEQ ID NO: 95           moltype = AA  length = 10
FEATURE                 Location/Qualifiers
source                  1..10
                        mol_type = protein
                        organism = Homo sapiens
SEQUENCE: 95
DCKLPCNPCS                                                                    10

SEQ ID NO: 96           moltype = AA  length = 10
FEATURE                 Location/Qualifiers
source                  1..10
                        mol_type = protein
                        organism = Homo sapiens
SEQUENCE: 96
PCGTSQKGCC                                                                    10

SEQ ID NO: 97           moltype = AA  length = 10
FEATURE                 Location/Qualifiers
source                  1..10
                        mol_type = protein
                        organism = Homo sapiens
SEQUENCE: 97
PCLSNPCTSC                                                                    10

SEQ ID NO: 98           moltype = AA  length = 10
FEATURE                 Location/Qualifiers
source                  1..10
                        mol_type = protein
                        organism = Homo sapiens
SEQUENCE: 98
PCLVGNCAWC                                                                    10

SEQ ID NO: 99           moltype = AA  length = 10
FEATURE                 Location/Qualifiers
source                  1..10
                        mol_type = protein
                        organism = Homo sapiens
SEQUENCE: 99
PCNPCSTPSC                                                                    10

SEQ ID NO: 100          moltype = AA  length = 10
FEATURE                 Location/Qualifiers
source                  1..10
                        mol_type = protein
                        organism = Homo sapiens
SEQUENCE: 100
PCSTPSCTTC                                                                    10
```

```
SEQ ID NO: 101              moltype = AA   length = 10
FEATURE                     Location/Qualifiers
source                      1..10
                            mol_type = protein
                            organism = Homo sapiens
SEQUENCE: 101
PCTTCGPTCG                                                                  10

SEQ ID NO: 102              moltype = AA   length = 10
FEATURE                     Location/Qualifiers
source                      1..10
                            mol_type = protein
                            organism = Homo sapiens
SEQUENCE: 102
PCVPPSCHGC                                                                  10

SEQ ID NO: 103              moltype = AA   length = 10
FEATURE                     Location/Qualifiers
source                      1..10
                            mol_type = protein
                            organism = Homo sapiens
SEQUENCE: 103
PCVPPSCHSC                                                                  10

SEQ ID NO: 104              moltype = AA   length = 10
FEATURE                     Location/Qualifiers
source                      1..10
                            mol_type = protein
                            organism = Homo sapiens
SEQUENCE: 104
SCCLPSLGCR                                                                  10

SEQ ID NO: 105              moltype = AA   length = 10
FEATURE                     Location/Qualifiers
source                      1..10
                            mol_type = protein
                            organism = Homo sapiens
SEQUENCE: 105
SCSEELQCCQ                                                                  10

SEQ ID NO: 106              moltype = AA   length = 10
FEATURE                     Location/Qualifiers
source                      1..10
                            mol_type = protein
                            organism = Homo sapiens
SEQUENCE: 106
SCSPCSTTCT                                                                  10

SEQ ID NO: 107              moltype = AA   length = 10
FEATURE                     Location/Qualifiers
source                      1..10
                            mol_type = protein
                            organism = Homo sapiens
SEQUENCE: 107
ASCSTSGTCG                                                                  10

SEQ ID NO: 108              moltype = AA   length = 10
FEATURE                     Location/Qualifiers
source                      1..10
                            mol_type = protein
                            organism = Homo sapiens
SEQUENCE: 108
ASCYIPVGCQ                                                                  10

SEQ ID NO: 109              moltype = AA   length = 10
FEATURE                     Location/Qualifiers
source                      1..10
                            mol_type = protein
                            organism = Homo sapiens
SEQUENCE: 109
ASCYVPVSCQ                                                                  10

SEQ ID NO: 110              moltype = AA   length = 10
FEATURE                     Location/Qualifiers
source                      1..10
                            mol_type = protein
                            organism = Homo sapiens
SEQUENCE: 110
AVCTLPSSCQ                                                                  10
```

```
SEQ ID NO: 111            moltype = AA   length = 10
FEATURE                   Location/Qualifiers
source                    1..10
                          mol_type = protein
                          organism = Homo sapiens
SEQUENCE: 111
DLCPTSVSCG                                                                10

SEQ ID NO: 112            moltype = AA   length = 10
FEATURE                   Location/Qualifiers
source                    1..10
                          mol_type = protein
                          organism = Homo sapiens
SEQUENCE: 112
EICWEPTSCQ                                                                10

SEQ ID NO: 113            moltype = AA   length = 10
FEATURE                   Location/Qualifiers
source                    1..10
                          mol_type = protein
                          organism = Homo sapiens
SEQUENCE: 113
ETCGEPTSCQ                                                                10

SEQ ID NO: 114            moltype = AA   length = 10
FEATURE                   Location/Qualifiers
source                    1..10
                          mol_type = protein
                          organism = Homo sapiens
SEQUENCE: 114
ETCNETTSCQ                                                                10

SEQ ID NO: 115            moltype = AA   length = 10
FEATURE                   Location/Qualifiers
source                    1..10
                          mol_type = protein
                          organism = Homo sapiens
SEQUENCE: 115
ETCWRPNSCQ                                                                10

SEQ ID NO: 116            moltype = AA   length = 10
FEATURE                   Location/Qualifiers
source                    1..10
                          mol_type = protein
                          organism = Homo sapiens
SEQUENCE: 116
GYCGYRPFCF                                                                10

SEQ ID NO: 117            moltype = AA   length = 10
FEATURE                   Location/Qualifiers
source                    1..10
                          mol_type = protein
                          organism = Homo sapiens
SEQUENCE: 117
KTCWEPASCQ                                                                10

SEQ ID NO: 118            moltype = AA   length = 10
FEATURE                   Location/Qualifiers
source                    1..10
                          mol_type = protein
                          organism = Homo sapiens
SEQUENCE: 118
KTCWEPTSCQ                                                                10

SEQ ID NO: 119            moltype = AA   length = 10
FEATURE                   Location/Qualifiers
source                    1..10
                          mol_type = protein
                          organism = Homo sapiens
SEQUENCE: 119
LDCVDTTPCK                                                                10

SEQ ID NO: 120            moltype = AA   length = 10
FEATURE                   Location/Qualifiers
source                    1..10
                          mol_type = protein
                          organism = Homo sapiens
SEQUENCE: 120
```

```
LGCGYGSFCG                                                                              10

SEQ ID NO: 121           moltype = AA   length = 10
FEATURE                  Location/Qualifiers
source                   1..10
                         mol_type = protein
                         organism = Homo sapiens SEQUENCE: 121
NSCGYGSGCG                                                                              10

SEQ ID NO: 122           moltype = AA   length = 10
FEATURE                  Location/Qualifiers
source                   1..10
                         mol_type = protein
                         organism = Homo sapiens SEQUENCE: 122
NYCPSNTMCE                                                                              10

SEQ ID NO: 123           moltype = AA   length = 10
FEATURE                  Location/Qualifiers
source                   1..10
                         mol_type = protein
                         organism = Homo sapiens SEQUENCE: 123
PACVTSYSCR                                                                              10

SEQ ID NO: 124           moltype = AA   length = 10
FEATURE                  Location/Qualifiers
source                   1..10
                         mol_type = protein
                         organism = Homo sapiens SEQUENCE: 124
PDCHVEGTCL                                                                              10

SEQ ID NO: 125           moltype = AA   length = 10
FEATURE                  Location/Qualifiers
source                   1..10
                         mol_type = protein
                         organism = Homo sapiens SEQUENCE: 125
PDCRVEGTCL                                                                              10

SEQ ID NO: 126           moltype = AA   length = 10
FEATURE                  Location/Qualifiers
source                   1..10
                         mol_type = protein
                         organism = Homo sapiens SEQUENCE: 126
PICSEPSPCS                                                                              10

SEQ ID NO: 127           moltype = AA   length = 10
FEATURE                  Location/Qualifiers
source                   1..10
                         mol_type = protein
                         organism = Homo sapiens SEQUENCE: 127
PICYIFKPCQ                                                                              10

SEQ ID NO: 128           moltype = AA   length = 10
FEATURE                  Location/Qualifiers
source                   1..10
                         mol_type = protein
                         organism = Homo sapiens SEQUENCE: 128
PLCYISNSCQ                                                                              10

SEQ ID NO: 129           moltype = AA   length = 10
FEATURE                  Location/Qualifiers
source                   1..10
                         mol_type = protein
                         organism = Homo sapiens SEQUENCE: 129
PPCGQPTPCS                                                                              10

SEQ ID NO: 130           moltype = AA   length = 10
FEATURE                  Location/Qualifiers
source                   1..10
                         mol_type = protein
                         organism = Homo sapiens
```

```
SEQUENCE: 130
PPCHIPQPCV                                                                    10

SEQ ID NO: 131          moltype = AA  length = 10
FEATURE                 Location/Qualifiers
source                  1..10
                        mol_type = protein
                        organism = Homo sapiens
SEQUENCE: 131
PSCGRLASCG                                                                    10

SEQ ID NO: 132          moltype = AA  length = 10
FEATURE                 Location/Qualifiers
source                  1..10
                        mol_type = protein
                        organism = Homo sapiens
SEQUENCE: 132
PSCSESSICQ                                                                    10

SEQ ID NO: 133          moltype = AA  length = 10
FEATURE                 Location/Qualifiers
source                  1..10
                        mol_type = protein
                        organism = Homo sapiens
SEQUENCE: 133
PSCSEVTSCP                                                                    10

SEQ ID NO: 134          moltype = AA  length = 10
FEATURE                 Location/Qualifiers
source                  1..10
                        mol_type = protein
                        organism = Homo sapiens
SEQUENCE: 134
PSCSTSGTCG                                                                    10

SEQ ID NO: 135          moltype = AA  length = 10
FEATURE                 Location/Qualifiers
source                  1..10
                        mol_type = protein
                        organism = Homo sapiens
SEQUENCE: 135
PSCSVSSGCQ                                                                    10

SEQ ID NO: 136          moltype = AA  length = 10
FEATURE                 Location/Qualifiers
source                  1..10
                        mol_type = protein
                        organism = Homo sapiens
SEQUENCE: 136
PSCTESDSCK                                                                    10

SEQ ID NO: 137          moltype = AA  length = 10
FEATURE                 Location/Qualifiers
source                  1..10
                        mol_type = protein
                        organism = Homo sapiens
SEQUENCE: 137
PSCYQTSSCG                                                                    10

SEQ ID NO: 138          moltype = AA  length = 10
FEATURE                 Location/Qualifiers
source                  1..10
                        mol_type = protein
                        organism = Homo sapiens
SEQUENCE: 138
PTCFLLNSCQ                                                                    10

SEQ ID NO: 139          moltype = AA  length = 10
FEATURE                 Location/Qualifiers
source                  1..10
                        mol_type = protein
                        organism = Homo sapiens
SEQUENCE: 139
PTCSVTSSCQ                                                                    10

SEQ ID NO: 140          moltype = AA  length = 10
FEATURE                 Location/Qualifiers
source                  1..10
                        mol_type = protein
```

```
                              organism = Homo sapiens
SEQUENCE: 140
PTCWLLNNCH                                                                          10

SEQ ID NO: 141              moltype = AA   length = 10
FEATURE                     Location/Qualifiers
source                      1..10
                            mol_type = protein
                            organism = Homo sapiens
SEQUENCE: 141
PTCYQRTSCV                                                                          10

SEQ ID NO: 142              moltype = AA   length = 10
FEATURE                     Location/Qualifiers
source                      1..10
                            mol_type = protein
                            organism = Homo sapiens
SEQUENCE: 142
PTCYRRTSCV                                                                          10

SEQ ID NO: 143              moltype = AA   length = 10
FEATURE                     Location/Qualifiers
source                      1..10
                            mol_type = protein
                            organism = Homo sapiens
SEQUENCE: 143
PTCYVVKRCP                                                                          10

SEQ ID NO: 144              moltype = AA   length = 10
FEATURE                     Location/Qualifiers
source                      1..10
                            mol_type = protein
                            organism = Homo sapiens
SEQUENCE: 144
PVCFEATICE                                                                          10

SEQ ID NO: 145              moltype = AA   length = 10
FEATURE                     Location/Qualifiers
source                      1..10
                            mol_type = protein
                            organism = Homo sapiens
SEQUENCE: 145
PVCFEATVCE                                                                          10

SEQ ID NO: 146              moltype = AA   length = 10
FEATURE                     Location/Qualifiers
source                      1..10
                            mol_type = protein
                            organism = Homo sapiens
SEQUENCE: 146
PVCSRPASCS                                                                          10

SEQ ID NO: 147              moltype = AA   length = 10
FEATURE                     Location/Qualifiers
source                      1..10
                            mol_type = protein
                            organism = Homo sapiens
SEQUENCE: 147
PVCSWVPACS                                                                          10

SEQ ID NO: 148              moltype = AA   length = 10
FEATURE                     Location/Qualifiers
source                      1..10
                            mol_type = protein
                            organism = Homo sapiens
SEQUENCE: 148
QTCNESSYCL                                                                          10

SEQ ID NO: 149              moltype = AA   length = 10
FEATURE                     Location/Qualifiers
source                      1..10
                            mol_type = protein
                            organism = Homo sapiens
SEQUENCE: 149
QTCWEPTSCQ                                                                          10

SEQ ID NO: 150              moltype = AA   length = 10
FEATURE                     Location/Qualifiers
source                      1..10
```

```
                            mol_type = protein
                            organism = Homo sapiens
SEQUENCE: 150
SFCRLGYGCG                                                                  10

SEQ ID NO: 151              moltype = AA  length = 10
FEATURE                     Location/Qualifiers
source                      1..10
                            mol_type = protein
                            organism = Homo sapiens
SEQUENCE: 151
SFCRRGSGCG                                                                  10

SEQ ID NO: 152              moltype = AA  length = 10
FEATURE                     Location/Qualifiers
source                      1..10
                            mol_type = protein
                            organism = Homo sapiens
SEQUENCE: 152
SLCGYGYGCG                                                                  10

SEQ ID NO: 153              moltype = AA  length = 10
FEATURE                     Location/Qualifiers
source                      1..10
                            mol_type = protein
                            organism = Homo sapiens
SEQUENCE: 153
SLCSTEVSCG                                                                  10

SEQ ID NO: 154              moltype = AA  length = 10
FEATURE                     Location/Qualifiers
source                      1..10
                            mol_type = protein
                            organism = Homo sapiens
SEQUENCE: 154
SNCFGQLNCL                                                                  10

SEQ ID NO: 155              moltype = AA  length = 10
FEATURE                     Location/Qualifiers
source                      1..10
                            mol_type = protein
                            organism = Homo sapiens
SEQUENCE: 155
SPCGQPTPCS                                                                  10

SEQ ID NO: 156              moltype = AA  length = 10
FEATURE                     Location/Qualifiers
source                      1..10
                            mol_type = protein
                            organism = Homo sapiens
SEQUENCE: 156
SSCDQSSSCA                                                                  10

SEQ ID NO: 157              moltype = AA  length = 10
FEATURE                     Location/Qualifiers
source                      1..10
                            mol_type = protein
                            organism = Homo sapiens
SEQUENCE: 157
SSCGQSSSCA                                                                  10

SEQ ID NO: 158              moltype = AA  length = 10
FEATURE                     Location/Qualifiers
source                      1..10
                            mol_type = protein
                            organism = Homo sapiens
SEQUENCE: 158
SVCPEPVSCP                                                                  10

SEQ ID NO: 159              moltype = AA  length = 10
FEATURE                     Location/Qualifiers
source                      1..10
                            mol_type = protein
                            organism = Homo sapiens
SEQUENCE: 159
TFCSFDKSCR                                                                  10

SEQ ID NO: 160              moltype = AA  length = 10
FEATURE                     Location/Qualifiers
```

```
source                          1..10
                                mol_type = protein
                                organism = Homo sapiens
SEQUENCE: 160
TICSSDKSCR                                                                      10

SEQ ID NO: 161                  moltype = AA  length = 10
FEATURE                         Location/Qualifiers
source                          1..10
                                mol_type = protein
                                organism = Homo sapiens
SEQUENCE: 161
TLCVESSPCH                                                                      10

SEQ ID NO: 162                  moltype = AA  length = 10
FEATURE                         Location/Qualifiers
source                          1..10
                                mol_type = protein
                                organism = Homo sapiens
SEQUENCE: 162
TPCYQQSSCQ                                                                      10

SEQ ID NO: 163                  moltype = AA  length = 10
FEATURE                         Location/Qualifiers
source                          1..10
                                mol_type = protein
                                organism = Homo sapiens
SEQUENCE: 163
VTCSRQTTCI                                                                      10

SEQ ID NO: 164                  moltype = AA  length = 10
FEATURE                         Location/Qualifiers
source                          1..10
                                mol_type = protein
                                organism = Homo sapiens
SEQUENCE: 164
YGCGYGSGCG                                                                      10

SEQ ID NO: 165                  moltype = AA  length = 10
FEATURE                         Location/Qualifiers
source                          1..10
                                mol_type = protein
                                organism = Homo sapiens
SEQUENCE: 165
YGCGYGSGCR                                                                      10

SEQ ID NO: 166                  moltype = AA  length = 10
FEATURE                         Location/Qualifiers
source                          1..10
                                mol_type = protein
                                organism = Homo sapiens
SEQUENCE: 166
YGCIHSTHCG                                                                      10

SEQ ID NO: 167                  moltype = AA  length = 10
FEATURE                         Location/Qualifiers
source                          1..10
                                mol_type = protein
                                organism = Homo sapiens
SEQUENCE: 167
AACEPSACQS                                                                      10

SEQ ID NO: 168                  moltype = AA  length = 10
FEATURE                         Location/Qualifiers
source                          1..10
                                mol_type = protein
                                organism = Homo sapiens
SEQUENCE: 168
AACEPSPCQS                                                                      10

SEQ ID NO: 169                  moltype = AA  length = 10
FEATURE                         Location/Qualifiers
source                          1..10
                                mol_type = protein
                                organism = Homo sapiens
SEQUENCE: 169
AACTMSVCSS                                                                      10

SEQ ID NO: 170                  moltype = AA  length = 10
```

-continued

```
FEATURE            Location/Qualifiers
source             1..10
                   mol_type = protein
                   organism = Homo sapiens
SEQUENCE: 170
ADCLGGICLP                                                                      10

SEQ ID NO: 171     moltype = AA  length = 10
FEATURE            Location/Qualifiers
source             1..10
                   mol_type = protein
                   organism = Homo sapiens
SEQUENCE: 171
ALCLPSSCHS                                                                      10

SEQ ID NO: 172     moltype = AA  length = 10
FEATURE            Location/Qualifiers
source             1..10
                   mol_type = protein
                   organism = Homo sapiens
SEQUENCE: 172
ALCSPSTCQL                                                                      10

SEQ ID NO: 173     moltype = AA  length = 10
FEATURE            Location/Qualifiers
source             1..10
                   mol_type = protein
                   organism = Homo sapiens
SEQUENCE: 173
APCLALVCAP                                                                      10

SEQ ID NO: 174     moltype = AA  length = 10
FEATURE            Location/Qualifiers
source             1..10
                   mol_type = protein
                   organism = Homo sapiens
SEQUENCE: 174
APCLSLVCTP                                                                      10

SEQ ID NO: 175     moltype = AA  length = 10
FEATURE            Location/Qualifiers
source             1..10
                   mol_type = protein
                   organism = Homo sapiens
SEQUENCE: 175
APCLTLVCTP                                                                      10

SEQ ID NO: 176     moltype = AA  length = 10
FEATURE            Location/Qualifiers
source             1..10
                   mol_type = protein
                   organism = Homo sapiens
SEQUENCE: 176
APCVALLCRP                                                                      10

SEQ ID NO: 177     moltype = AA  length = 10
FEATURE            Location/Qualifiers
source             1..10
                   mol_type = protein
                   organism = Homo sapiens
SEQUENCE: 177
ASCGSLLCRP                                                                      10

SEQ ID NO: 178     moltype = AA  length = 10
FEATURE            Location/Qualifiers
source             1..10
                   mol_type = protein
                   organism = Homo sapiens
SEQUENCE: 178
ASCLSFLCRP                                                                      10

SEQ ID NO: 179     moltype = AA  length = 10
FEATURE            Location/Qualifiers
source             1..10
                   mol_type = protein
                   organism = Homo sapiens
SEQUENCE: 179
ASCVSLLCRP                                                                      10
```

```
SEQ ID NO: 180            moltype = AA   length = 10
FEATURE                   Location/Qualifiers
source                    1..10
                          mol_type = protein
                          organism = Homo sapiens
SEQUENCE: 180
AVCEPSPCQS                                                                10

SEQ ID NO: 181            moltype = AA   length = 10
FEATURE                   Location/Qualifiers
source                    1..10
                          mol_type = protein
                          organism = Homo sapiens
SEQUENCE: 181
AVCLPVSCQS                                                                10

SEQ ID NO: 182            moltype = AA   length = 10
FEATURE                   Location/Qualifiers
source                    1..10
                          mol_type = protein
                          organism = Homo sapiens
SEQUENCE: 182
AVCVPVRCQS                                                                10

SEQ ID NO: 183            moltype = AA   length = 10
FEATURE                   Location/Qualifiers
source                    1..10
                          mol_type = protein
                          organism = Homo sapiens
SEQUENCE: 183
AVCVPVSCQS                                                                10

SEQ ID NO: 184            moltype = AA   length = 10
FEATURE                   Location/Qualifiers
source                    1..10
                          mol_type = protein
                          organism = Homo sapiens
SEQUENCE: 184
DLCSPSTCQL                                                                10

SEQ ID NO: 185            moltype = AA   length = 10
FEATURE                   Location/Qualifiers
source                    1..10
                          mol_type = protein
                          organism = Homo sapiens
SEQUENCE: 185
DSCGSSSCGP                                                                10

SEQ ID NO: 186            moltype = AA   length = 10
FEATURE                   Location/Qualifiers
source                    1..10
                          mol_type = protein
                          organism = Homo sapiens
SEQUENCE: 186
DSCVQSNCFP                                                                10

SEQ ID NO: 187            moltype = AA   length = 10
FEATURE                   Location/Qualifiers
source                    1..10
                          mol_type = protein
                          organism = Homo sapiens
SEQUENCE: 187
FNCSTRNCSS                                                                10

SEQ ID NO: 188            moltype = AA   length = 10
FEATURE                   Location/Qualifiers
source                    1..10
                          mol_type = protein
                          organism = Homo sapiens
SEQUENCE: 188
GGCGSYGCSQ                                                                10

SEQ ID NO: 189            moltype = AA   length = 10
FEATURE                   Location/Qualifiers
source                    1..10
                          mol_type = protein
                          organism = Homo sapiens
SEQUENCE: 189
GSCGFGSCYG                                                                10
```

| | | |
|---|---|---|
| SEQ ID NO: 190<br>FEATURE<br>source | moltype = AA  length = 10<br>Location/Qualifiers<br>1..10<br>mol_type = protein<br>organism = Homo sapiens | |
| SEQUENCE: 190<br>GSCSSRKCFS | | 10 |
| SEQ ID NO: 191<br>FEATURE<br>source | moltype = AA  length = 10<br>Location/Qualifiers<br>1..10<br>mol_type = protein<br>organism = Homo sapiens | |
| SEQUENCE: 191<br>GVCLPSTCPH | | 10 |
| SEQ ID NO: 192<br>FEATURE<br>source | moltype = AA  length = 10<br>Location/Qualifiers<br>1..10<br>mol_type = protein<br>organism = Homo sapiens | |
| SEQUENCE: 192<br>HSCEGYLCYS | | 10 |
| SEQ ID NO: 193<br>FEATURE<br>source | moltype = AA  length = 10<br>Location/Qualifiers<br>1..10<br>mol_type = protein<br>organism = Homo sapiens | |
| SEQUENCE: 193<br>IVCAAPSCQS | | 10 |
| SEQ ID NO: 194<br>FEATURE<br>source | moltype = AA  length = 10<br>Location/Qualifiers<br>1..10<br>mol_type = protein<br>organism = Homo sapiens | |
| SEQUENCE: 194<br>KTCSTTGCDP | | 10 |
| SEQ ID NO: 195<br>FEATURE<br>source | moltype = AA  length = 10<br>Location/Qualifiers<br>1..10<br>mol_type = protein<br>organism = Homo sapiens | |
| SEQUENCE: 195<br>LACVSQPCQS | | 10 |
| SEQ ID NO: 196<br>FEATURE<br>source | moltype = AA  length = 10<br>Location/Qualifiers<br>1..10<br>mol_type = protein<br>organism = Homo sapiens | |
| SEQUENCE: 196<br>LGCGYGGCGY | | 10 |
| SEQ ID NO: 197<br>FEATURE<br>source | moltype = AA  length = 10<br>Location/Qualifiers<br>1..10<br>mol_type = protein<br>organism = Homo sapiens | |
| SEQUENCE: 197<br>LSCGSRSCSS | | 10 |
| SEQ ID NO: 198<br>FEATURE<br>source | moltype = AA  length = 10<br>Location/Qualifiers<br>1..10<br>mol_type = protein<br>organism = Homo sapiens | |
| SEQUENCE: 198<br>LVCTPVSCVS | | 10 |
| SEQ ID NO: 199<br>FEATURE<br>source | moltype = AA  length = 10<br>Location/Qualifiers<br>1..10<br>mol_type = protein<br>organism = Homo sapiens | |
| SEQUENCE: 199 | | |

-continued

NGCQETYCEP                                                                              10

SEQ ID NO: 200          moltype = AA  length = 10
FEATURE                 Location/Qualifiers
source                  1..10
                        mol_type = protein
                        organism = Homo sapiens
SEQUENCE: 200
NSCRSLSCGS                                                                              10

SEQ ID NO: 201          moltype = AA  length = 10
FEATURE                 Location/Qualifiers
source                  1..10
                        mol_type = protein
                        organism = Homo sapiens
SEQUENCE: 201
PACVISTCPR                                                                              10

SEQ ID NO: 202          moltype = AA  length = 10
FEATURE                 Location/Qualifiers
source                  1..10
                        mol_type = protein
                        organism = Homo sapiens
SEQUENCE: 202
PGCLNQSCGS                                                                              10

SEQ ID NO: 203          moltype = AA  length = 10
FEATURE                 Location/Qualifiers
source                  1..10
                        mol_type = protein
                        organism = Homo sapiens
SEQUENCE: 203
PPCGTAPCLT                                                                              10

SEQ ID NO: 204          moltype = AA  length = 10
FEATURE                 Location/Qualifiers
source                  1..10
                        mol_type = protein
                        organism = Homo sapiens
SEQUENCE: 204
PPCTTALCRP                                                                              10

SEQ ID NO: 205          moltype = AA  length = 10
FEATURE                 Location/Qualifiers
source                  1..10
                        mol_type = protein
                        organism = Homo sapiens
SEQUENCE: 205
PPCYLVSCTP                                                                              10

SEQ ID NO: 206          moltype = AA  length = 10
FEATURE                 Location/Qualifiers
source                  1..10
                        mol_type = protein
                        organism = Homo sapiens
SEQUENCE: 206
PRCTRPICEP                                                                              10

SEQ ID NO: 207          moltype = AA  length = 10
FEATURE                 Location/Qualifiers
source                  1..10
                        mol_type = protein
                        organism = Homo sapiens
SEQUENCE: 207
PSCPVSSCAQ                                                                              10

SEQ ID NO: 208          moltype = AA  length = 10
FEATURE                 Location/Qualifiers
source                  1..10
                        mol_type = protein
                        organism = Homo sapiens
SEQUENCE: 208
PSCQPSVCVP                                                                              10

SEQ ID NO: 209          moltype = AA  length = 10
FEATURE                 Location/Qualifiers
source                  1..10
                        mol_type = protein
                        organism = Homo sapiens

| | | |
|---|---|---|
| SEQUENCE: 209<br>PSCSVSNCYQ | | 10 |
| SEQ ID NO: 210<br>FEATURE<br>source | moltype = AA length = 10<br>Location/Qualifiers<br>1..10<br>mol_type = protein<br>organism = Homo sapiens | |
| SEQUENCE: 210<br>PSCSVSSCAQ | | 10 |
| SEQ ID NO: 211<br>FEATURE<br>source | moltype = AA length = 10<br>Location/Qualifiers<br>1..10<br>mol_type = protein<br>organism = Homo sapiens | |
| SEQUENCE: 211<br>PSCTSVLCRP | | 10 |
| SEQ ID NO: 212<br>FEATURE<br>source | moltype = AA length = 10<br>Location/Qualifiers<br>1..10<br>mol_type = protein<br>organism = Homo sapiens | |
| SEQUENCE: 212<br>PTCKSPSCEP | | 10 |
| SEQ ID NO: 213<br>FEATURE<br>source | moltype = AA length = 10<br>Location/Qualifiers<br>1..10<br>mol_type = protein<br>organism = Homo sapiens | |
| SEQUENCE: 213<br>PTCVISSCPR | | 10 |
| SEQ ID NO: 214<br>FEATURE<br>source | moltype = AA length = 10<br>Location/Qualifiers<br>1..10<br>mol_type = protein<br>organism = Homo sapiens | |
| SEQUENCE: 214<br>PTCVISTCPR | | 10 |
| SEQ ID NO: 215<br>FEATURE<br>source | moltype = AA length = 10<br>Location/Qualifiers<br>1..10<br>mol_type = protein<br>organism = Homo sapiens | |
| SEQUENCE: 215<br>PTCYQTICFR | | 10 |
| SEQ ID NO: 216<br>FEATURE<br>source | moltype = AA length = 10<br>Location/Qualifiers<br>1..10<br>mol_type = protein<br>organism = Homo sapiens | |
| SEQUENCE: 216<br>PVCGGVSCHT | | 10 |
| SEQ ID NO: 217<br>FEATURE<br>source | moltype = AA length = 10<br>Location/Qualifiers<br>1..10<br>mol_type = protein<br>organism = Homo sapiens | |
| SEQUENCE: 217<br>PVCGRVSCHT | | 10 |
| SEQ ID NO: 218<br>FEATURE<br>source | moltype = AA length = 10<br>Location/Qualifiers<br>1..10<br>mol_type = protein<br>organism = Homo sapiens | |
| SEQUENCE: 218<br>PVCNKPVCFV | | 10 |
| SEQ ID NO: 219<br>FEATURE<br>source | moltype = AA length = 10<br>Location/Qualifiers<br>1..10<br>mol_type = protein | |

```
                          organism = Homo sapiens
SEQUENCE: 219
PVCPTPTCSV                                                                      10

SEQ ID NO: 220           moltype = AA  length = 10
FEATURE                  Location/Qualifiers
source                   1..10
                         mol_type = protein
                         organism = Homo sapiens
SEQUENCE: 220
PVCRSTYCVP                                                                      10

SEQ ID NO: 221           moltype = AA  length = 10
FEATURE                  Location/Qualifiers
source                   1..10
                         mol_type = protein
                         organism = Homo sapiens
SEQUENCE: 221
PVCSKSVCYV                                                                      10

SEQ ID NO: 222           moltype = AA  length = 10
FEATURE                  Location/Qualifiers
source                   1..10
                         mol_type = protein
                         organism = Homo sapiens
SEQUENCE: 222
PVCSRPACYS                                                                      10

SEQ ID NO: 223           moltype = AA  length = 10
FEATURE                  Location/Qualifiers
source                   1..10
                         mol_type = protein
                         organism = Homo sapiens
SEQUENCE: 223
PVCYVPTCSE                                                                      10

SEQ ID NO: 224           moltype = AA  length = 10
FEATURE                  Location/Qualifiers
source                   1..10
                         mol_type = protein
                         organism = Homo sapiens
SEQUENCE: 224
QFCLSKSCQP                                                                      10

SEQ ID NO: 225           moltype = AA  length = 10
FEATURE                  Location/Qualifiers
source                   1..10
                         mol_type = protein
                         organism = Homo sapiens
SEQUENCE: 225
RPCERTACQS                                                                      10

SEQ ID NO: 226           moltype = AA  length = 10
FEATURE                  Location/Qualifiers
source                   1..10
                         mol_type = protein
                         organism = Homo sapiens
SEQUENCE: 226
RSCQTSFCGF                                                                      10

SEQ ID NO: 227           moltype = AA  length = 10
FEATURE                  Location/Qualifiers
source                   1..10
                         mol_type = protein
                         organism = Homo sapiens
SEQUENCE: 227
RSCSSLGCGS                                                                      10

SEQ ID NO: 228           moltype = AA  length = 10
FEATURE                  Location/Qualifiers
source                   1..10
                         mol_type = protein
                         organism = Homo sapiens
SEQUENCE: 228
RSCYSVGCGS                                                                      10

SEQ ID NO: 229           moltype = AA  length = 10
FEATURE                  Location/Qualifiers
source                   1..10
```

```
                            mol_type = protein
                            organism = Homo sapiens
SEQUENCE: 229
RVCLPGSCDS                                                                      10

SEQ ID NO: 230              moltype = AA  length = 10
FEATURE                     Location/Qualifiers
source                      1..10
                            mol_type = protein
                            organism = Homo sapiens
SEQUENCE: 230
SFCGFPSCST                                                                      10

SEQ ID NO: 231              moltype = AA  length = 10
FEATURE                     Location/Qualifiers
source                      1..10
                            mol_type = protein
                            organism = Homo sapiens
SEQUENCE: 231
SFCGYPSCST                                                                      10

SEQ ID NO: 232              moltype = AA  length = 10
FEATURE                     Location/Qualifiers
source                      1..10
                            mol_type = protein
                            organism = Homo sapiens
SEQUENCE: 232
SGCDPASCQP                                                                      10

SEQ ID NO: 233              moltype = AA  length = 10
FEATURE                     Location/Qualifiers
source                      1..10
                            mol_type = protein
                            organism = Homo sapiens
SEQUENCE: 233
SGCGGSGCGG                                                                      10

SEQ ID NO: 234              moltype = AA  length = 10
FEATURE                     Location/Qualifiers
source                      1..10
                            mol_type = protein
                            organism = Homo sapiens
SEQUENCE: 234
SGCQPSSCLA                                                                      10

SEQ ID NO: 235              moltype = AA  length = 10
FEATURE                     Location/Qualifiers
source                      1..10
                            mol_type = protein
                            organism = Homo sapiens
SEQUENCE: 235
SHCQPPHCQL                                                                      10

SEQ ID NO: 236              moltype = AA  length = 10
FEATURE                     Location/Qualifiers
source                      1..10
                            mol_type = protein
                            organism = Homo sapiens
SEQUENCE: 236
SICQPATCVA                                                                      10

SEQ ID NO: 237              moltype = AA  length = 10
FEATURE                     Location/Qualifiers
source                      1..10
                            mol_type = protein
                            organism = Homo sapiens
SEQUENCE: 237
SLCVPVSCRP                                                                      10

SEQ ID NO: 238              moltype = AA  length = 10
FEATURE                     Location/Qualifiers
source                      1..10
                            mol_type = protein
                            organism = Homo sapiens
SEQUENCE: 238
SNCLPTSCQP                                                                      10

SEQ ID NO: 239              moltype = AA  length = 10
FEATURE                     Location/Qualifiers
```

```
source                      1..10
                            mol_type = protein
                            organism = Homo sapiens
SEQUENCE: 239
SPCLVSSCQP                                                                      10

SEQ ID NO: 240              moltype = AA  length = 10
FEATURE                     Location/Qualifiers
source                      1..10
                            mol_type = protein
                            organism = Homo sapiens
SEQUENCE: 240
SPCQQSSCQE                                                                      10

SEQ ID NO: 241              moltype = AA  length = 10
FEATURE                     Location/Qualifiers
source                      1..10
                            mol_type = protein
                            organism = Homo sapiens
SEQUENCE: 241
SPCQQSYCVP                                                                      10

SEQ ID NO: 242              moltype = AA  length = 10
FEATURE                     Location/Qualifiers
source                      1..10
                            mol_type = protein
                            organism = Homo sapiens
SEQUENCE: 242
SPCSPAVCVS                                                                      10

SEQ ID NO: 243              moltype = AA  length = 10
FEATURE                     Location/Qualifiers
source                      1..10
                            mol_type = protein
                            organism = Homo sapiens
SEQUENCE: 243
SRCQQPSCQP                                                                      10

SEQ ID NO: 244              moltype = AA  length = 10
FEATURE                     Location/Qualifiers
source                      1..10
                            mol_type = protein
                            organism = Homo sapiens
SEQUENCE: 244
SRCYRPHCGQ                                                                      10

SEQ ID NO: 245              moltype = AA  length = 10
FEATURE                     Location/Qualifiers
source                      1..10
                            mol_type = protein
                            organism = Homo sapiens
SEQUENCE: 245
SSCAPIYCRR                                                                      10

SEQ ID NO: 246              moltype = AA  length = 10
FEATURE                     Location/Qualifiers
source                      1..10
                            mol_type = protein
                            organism = Homo sapiens
SEQUENCE: 246
SSCAPVYCRR                                                                      10

SEQ ID NO: 247              moltype = AA  length = 10
FEATURE                     Location/Qualifiers
source                      1..10
                            mol_type = protein
                            organism = Homo sapiens
SEQUENCE: 247
SSCGKGGCGS                                                                      10

SEQ ID NO: 248              moltype = AA  length = 10
FEATURE                     Location/Qualifiers
source                      1..10
                            mol_type = protein
                            organism = Homo sapiens
SEQUENCE: 248
SSCGKRGCGS                                                                      10

SEQ ID NO: 249              moltype = AA  length = 10
```

```
FEATURE            Location/Qualifiers
source             1..10
                   mol_type = protein
                   organism = Homo sapiens
SEQUENCE: 249
SSCLPVSCRP                                                                      10

SEQ ID NO: 250     moltype = AA  length = 10
FEATURE            Location/Qualifiers
source             1..10
                   mol_type = protein
                   organism = Homo sapiens
SEQUENCE: 250
SSCQPAYCTS                                                                      10

SEQ ID NO: 251     moltype = AA  length = 10
FEATURE            Location/Qualifiers
source             1..10
                   mol_type = protein
                   organism = Homo sapiens
SEQUENCE: 251
SSCQPSYCRQ                                                                      10

SEQ ID NO: 252     moltype = AA  length = 10
FEATURE            Location/Qualifiers
source             1..10
                   mol_type = protein
                   organism = Homo sapiens
SEQUENCE: 252
SSCQPVVCEP                                                                      10

SEQ ID NO: 253     moltype = AA  length = 10
FEATURE            Location/Qualifiers
source             1..10
                   mol_type = protein
                   organism = Homo sapiens
SEQUENCE: 253
SSCTAVVCRP                                                                      10

SEQ ID NO: 254     moltype = AA  length = 10
FEATURE            Location/Qualifiers
source             1..10
                   mol_type = protein
                   organism = Homo sapiens
SEQUENCE: 254
SSCYQPFCRS                                                                      10

SEQ ID NO: 255     moltype = AA  length = 10
FEATURE            Location/Qualifiers
source             1..10
                   mol_type = protein
                   organism = Homo sapiens
SEQUENCE: 255
SSCYRPICGS                                                                      10

SEQ ID NO: 256     moltype = AA  length = 10
FEATURE            Location/Qualifiers
source             1..10
                   mol_type = protein
                   organism = Homo sapiens
SEQUENCE: 256
SSCYRPTCGS                                                                      10

SEQ ID NO: 257     moltype = AA  length = 10
FEATURE            Location/Qualifiers
source             1..10
                   mol_type = protein
                   organism = Homo sapiens
SEQUENCE: 257
SVCMSGSCQA                                                                      10

SEQ ID NO: 258     moltype = AA  length = 10
FEATURE            Location/Qualifiers
source             1..10
                   mol_type = protein
                   organism = Homo sapiens
SEQUENCE: 258
SVCSDQGCDQ                                                                      10
```

-continued

| | | |
|---|---|---|
| SEQ ID NO: 259<br>FEATURE<br>source | moltype = AA  length = 10<br>Location/Qualifiers<br>1..10<br>mol_type = protein<br>organism = Homo sapiens | |
| SEQUENCE: 259<br>SVCSDQGCGL | | 10 |
| SEQ ID NO: 260<br>FEATURE<br>source | moltype = AA  length = 10<br>Location/Qualifiers<br>1..10<br>mol_type = protein<br>organism = Homo sapiens | |
| SEQUENCE: 260<br>SVCSDQGCGQ | | 10 |
| SEQ ID NO: 261<br>FEATURE<br>source | moltype = AA  length = 10<br>Location/Qualifiers<br>1..10<br>mol_type = protein<br>organism = Homo sapiens | |
| SEQUENCE: 261<br>SVCSDQGCSQ | | 10 |
| SEQ ID NO: 262<br>FEATURE<br>source | moltype = AA  length = 10<br>Location/Qualifiers<br>1..10<br>mol_type = protein<br>organism = Homo sapiens | |
| SEQUENCE: 262<br>SVCSDQSCGQ | | 10 |
| SEQ ID NO: 263<br>FEATURE<br>source | moltype = AA  length = 10<br>Location/Qualifiers<br>1..10<br>mol_type = protein<br>organism = Homo sapiens | |
| SEQUENCE: 263<br>SVCSHQGCGQ | | 10 |
| SEQ ID NO: 264<br>FEATURE<br>source | moltype = AA  length = 10<br>Location/Qualifiers<br>1..10<br>mol_type = protein<br>organism = Homo sapiens | |
| SEQUENCE: 264<br>SVCSHQGCGR | | 10 |
| SEQ ID NO: 265<br>FEATURE<br>source | moltype = AA  length = 10<br>Location/Qualifiers<br>1..10<br>mol_type = protein<br>organism = Homo sapiens | |
| SEQUENCE: 265<br>SVCVPVSCRP | | 10 |
| SEQ ID NO: 266<br>FEATURE<br>source | moltype = AA  length = 10<br>Location/Qualifiers<br>1..10<br>mol_type = protein<br>organism = Homo sapiens | |
| SEQUENCE: 266<br>SYCRQASCVS | | 10 |
| SEQ ID NO: 267<br>FEATURE<br>source | moltype = AA  length = 10<br>Location/Qualifiers<br>1..10<br>mol_type = protein<br>organism = Homo sapiens | |
| SEQUENCE: 267<br>TACEPSACQS | | 10 |
| SEQ ID NO: 268<br>FEATURE<br>source | moltype = AA  length = 10<br>Location/Qualifiers<br>1..10<br>mol_type = protein<br>organism = Homo sapiens | |
| SEQUENCE: 268<br>TICTASPCQP | | 10 |

| | | |
|---|---|---|
| SEQ ID NO: 269<br>FEATURE<br>source | moltype = AA   length = 10<br>Location/Qualifiers<br>1..10<br>mol_type = protein<br>organism = Homo sapiens | |
| SEQUENCE: 269<br>TSCPETSCLP | | 10 |
| SEQ ID NO: 270<br>FEATURE<br>source | moltype = AA   length = 10<br>Location/Qualifiers<br>1..10<br>mol_type = protein<br>organism = Homo sapiens | |
| SEQUENCE: 270<br>TSCQMTNCEQ | | 10 |
| SEQ ID NO: 271<br>FEATURE<br>source | moltype = AA   length = 10<br>Location/Qualifiers<br>1..10<br>mol_type = protein<br>organism = Homo sapiens | |
| SEQUENCE: 271<br>TSCQPVHCET | | 10 |
| SEQ ID NO: 272<br>FEATURE<br>source | moltype = AA   length = 10<br>Location/Qualifiers<br>1..10<br>mol_type = protein<br>organism = Homo sapiens | |
| SEQUENCE: 272<br>TSCQPVLCKS | | 10 |
| SEQ ID NO: 273<br>FEATURE<br>source | moltype = AA   length = 10<br>Location/Qualifiers<br>1..10<br>mol_type = protein<br>organism = Homo sapiens | |
| SEQUENCE: 273<br>TSCQPVLCVP | | 10 |
| SEQ ID NO: 274<br>FEATURE<br>source | moltype = AA   length = 10<br>Location/Qualifiers<br>1..10<br>mol_type = protein<br>organism = Homo sapiens | |
| SEQUENCE: 274<br>TSCVGFVCQP | | 10 |
| SEQ ID NO: 275<br>FEATURE<br>source | moltype = AA   length = 10<br>Location/Qualifiers<br>1..10<br>mol_type = protein<br>organism = Homo sapiens | |
| SEQUENCE: 275<br>TSCVSNPCQV | | 10 |
| SEQ ID NO: 276<br>FEATURE<br>source | moltype = AA   length = 10<br>Location/Qualifiers<br>1..10<br>mol_type = protein<br>organism = Homo sapiens | |
| SEQUENCE: 276<br>TTCFQPTCVS | | 10 |
| SEQ ID NO: 277<br>FEATURE<br>source | moltype = AA   length = 10<br>Location/Qualifiers<br>1..10<br>mol_type = protein<br>organism = Homo sapiens | |
| SEQUENCE: 277<br>TTCFQPTCVT | | 10 |
| SEQ ID NO: 278<br>FEATURE<br>source | moltype = AA   length = 10<br>Location/Qualifiers<br>1..10<br>mol_type = protein<br>organism = Homo sapiens | |
| SEQUENCE: 278 | | |

| | | |
|---|---|---|
| TTCFQPTCVY | | 10 |
| SEQ ID NO: 279<br>FEATURE<br>source<br><br>SEQUENCE: 279<br>TTCISNPCST | moltype = AA  length = 10<br>Location/Qualifiers<br>1..10<br>mol_type = protein<br>organism = Homo sapiens | <br><br><br><br><br>10 |
| SEQ ID NO: 280<br>FEATURE<br>source<br><br>SEQUENCE: 280<br>TWCQGSSCQP | moltype = AA  length = 10<br>Location/Qualifiers<br>1..10<br>mol_type = protein<br>organism = Homo sapiens | <br><br><br><br><br>10 |
| SEQ ID NO: 281<br>FEATURE<br>source<br><br>SEQUENCE: 281<br>VGCQSSVCVP | moltype = AA  length = 10<br>Location/Qualifiers<br>1..10<br>mol_type = protein<br>organism = Homo sapiens | <br><br><br><br><br>10 |
| SEQ ID NO: 282<br>FEATURE<br>source<br><br>SEQUENCE: 282<br>VPCQPSTCVF | moltype = AA  length = 10<br>Location/Qualifiers<br>1..10<br>mol_type = protein<br>organism = Homo sapiens | <br><br><br><br><br>10 |
| SEQ ID NO: 283<br>FEATURE<br>source<br><br>SEQUENCE: 283<br>VSCEPSPCQS | moltype = AA  length = 10<br>Location/Qualifiers<br>1..10<br>mol_type = protein<br>organism = Homo sapiens | <br><br><br><br><br>10 |
| SEQ ID NO: 284<br>FEATURE<br>source<br><br>SEQUENCE: 284<br>VSCGGPICLP | moltype = AA  length = 10<br>Location/Qualifiers<br>1..10<br>mol_type = protein<br>organism = Homo sapiens | <br><br><br><br><br>10 |
| SEQ ID NO: 285<br>FEATURE<br>source<br><br>SEQUENCE: 285<br>VSCKPVLCVA | moltype = AA  length = 10<br>Location/Qualifiers<br>1..10<br>mol_type = protein<br>organism = Homo sapiens | <br><br><br><br><br>10 |
| SEQ ID NO: 286<br>FEATURE<br>source<br><br>SEQUENCE: 286<br>VSCPSTSCRP | moltype = AA  length = 10<br>Location/Qualifiers<br>1..10<br>mol_type = protein<br>organism = Homo sapiens | <br><br><br><br><br>10 |
| SEQ ID NO: 287<br>FEATURE<br>source<br><br>SEQUENCE: 287<br>VSCQSSVCMP | moltype = AA  length = 10<br>Location/Qualifiers<br>1..10<br>mol_type = protein<br>organism = Homo sapiens | <br><br><br><br><br>10 |
| SEQ ID NO: 288<br>FEATURE<br>source | moltype = AA  length = 10<br>Location/Qualifiers<br>1..10<br>mol_type = protein<br>organism = Homo sapiens | |

```
SEQUENCE: 288
VSCTRIVCVA                                                                         10

SEQ ID NO: 289         moltype = AA  length = 10
FEATURE                Location/Qualifiers
source                 1..10
                       mol_type = protein
                       organism = Homo sapiens
SEQUENCE: 289
VTCEPSPCQS                                                                         10

SEQ ID NO: 290         moltype = AA  length = 10
FEATURE                Location/Qualifiers
source                 1..10
                       mol_type = protein
                       organism = Homo sapiens
SEQUENCE: 290
VTCQTTVCRP                                                                         10

SEQ ID NO: 291         moltype = AA  length = 10
FEATURE                Location/Qualifiers
source                 1..10
                       mol_type = protein
                       organism = Homo sapiens
SEQUENCE: 291
YGCGYEGCRY                                                                         10

SEQ ID NO: 292         moltype = AA  length = 10
FEATURE                Location/Qualifiers
source                 1..10
                       mol_type = protein
                       organism = Homo sapiens
SEQUENCE: 292
AGSCQPSCSE                                                                         10

SEQ ID NO: 293         moltype = AA  length = 10
FEATURE                Location/Qualifiers
source                 1..10
                       mol_type = protein
                       organism = Homo sapiens
SEQUENCE: 293
ALLCRPLCGV                                                                         10

SEQ ID NO: 294         moltype = AA  length = 10
FEATURE                Location/Qualifiers
source                 1..10
                       mol_type = protein
                       organism = Homo sapiens
SEQUENCE: 294
ALVCEPVCLR                                                                         10

SEQ ID NO: 295         moltype = AA  length = 10
FEATURE                Location/Qualifiers
source                 1..10
                       mol_type = protein
                       organism = Homo sapiens
SEQUENCE: 295
ATICEPSCSV                                                                         10

SEQ ID NO: 296         moltype = AA  length = 10
FEATURE                Location/Qualifiers
source                 1..10
                       mol_type = protein
                       organism = Homo sapiens
SEQUENCE: 296
ATTCEPSCSV                                                                         10

SEQ ID NO: 297         moltype = AA  length = 10
FEATURE                Location/Qualifiers
source                 1..10
                       mol_type = protein
                       organism = Homo sapiens
SEQUENCE: 297
ATVCEPSCSV                                                                         10

SEQ ID NO: 298         moltype = AA  length = 10
FEATURE                Location/Qualifiers
source                 1..10
                       mol_type = protein
```

-continued

```
                       organism = Homo sapiens
SEQUENCE: 298
EGTCLPPCYL                                                                    10

SEQ ID NO: 299         moltype = AA  length = 10
FEATURE                Location/Qualifiers
source                 1..10
                       mol_type = protein
                       organism = Homo sapiens
SEQUENCE: 299
FSTCRPSCSG                                                                    10

SEQ ID NO: 300         moltype = AA  length = 10
FEATURE                Location/Qualifiers
source                 1..10
                       mol_type = protein
                       organism = Homo sapiens
SEQUENCE: 300
GFVCQPMCSH                                                                    10

SEQ ID NO: 301         moltype = AA  length = 10
FEATURE                Location/Qualifiers
source                 1..10
                       mol_type = protein
                       organism = Homo sapiens
SEQUENCE: 301
GLDCGYGCGY                                                                    10

SEQ ID NO: 302         moltype = AA  length = 10
FEATURE                Location/Qualifiers
source                 1..10
                       mol_type = protein
                       organism = Homo sapiens
SEQUENCE: 302
GLGCGYGCGY                                                                    10

SEQ ID NO: 303         moltype = AA  length = 10
FEATURE                Location/Qualifiers
source                 1..10
                       mol_type = protein
                       organism = Homo sapiens
SEQUENCE: 303
GLGCSYGCGH                                                                    10

SEQ ID NO: 304         moltype = AA  length = 10
FEATURE                Location/Qualifiers
source                 1..10
                       mol_type = protein
                       organism = Homo sapiens
SEQUENCE: 304
GLGCSYGCGL                                                                    10

SEQ ID NO: 305         moltype = AA  length = 10
FEATURE                Location/Qualifiers
source                 1..10
                       mol_type = protein
                       organism = Homo sapiens
SEQUENCE: 305
GSGCGYGCGY                                                                    10

SEQ ID NO: 306         moltype = AA  length = 10
FEATURE                Location/Qualifiers
source                 1..10
                       mol_type = protein
                       organism = Homo sapiens
SEQUENCE: 306
GTGCGYGCGY                                                                    10

SEQ ID NO: 307         moltype = AA  length = 10
FEATURE                Location/Qualifiers
source                 1..10
                       mol_type = protein
                       organism = Homo sapiens
SEQUENCE: 307
GVSCHTTCYR                                                                    10

SEQ ID NO: 308         moltype = AA  length = 10
FEATURE                Location/Qualifiers
source                 1..10
```

```
                            mol_type = protein
                            organism = Homo sapiens
SEQUENCE: 308
GYACNFPCSY                                                              10

SEQ ID NO: 309              moltype = AA  length = 10
FEATURE                     Location/Qualifiers
source                      1..10
                            mol_type = protein
                            organism = Homo sapiens
SEQUENCE: 309
GYGCGYGCGF                                                              10

SEQ ID NO: 310              moltype = AA  length = 10
FEATURE                     Location/Qualifiers
source                      1..10
                            mol_type = protein
                            organism = Homo sapiens
SEQUENCE: 310
HSPCQASCYV                                                              10

SEQ ID NO: 311              moltype = AA  length = 10
FEATURE                     Location/Qualifiers
source                      1..10
                            mol_type = protein
                            organism = Homo sapiens
SEQUENCE: 311
HTSCSPACQP                                                              10

SEQ ID NO: 312              moltype = AA  length = 10
FEATURE                     Location/Qualifiers
source                      1..10
                            mol_type = protein
                            organism = Homo sapiens
SEQUENCE: 312
HTSCSSGCQP                                                              10

SEQ ID NO: 313              moltype = AA  length = 10
FEATURE                     Location/Qualifiers
source                      1..10
                            mol_type = protein
                            organism = Homo sapiens
SEQUENCE: 313
IRWCHPDCHV                                                              10

SEQ ID NO: 314              moltype = AA  length = 10
FEATURE                     Location/Qualifiers
source                      1..10
                            mol_type = protein
                            organism = Homo sapiens
SEQUENCE: 314
IRWCRPDCRV                                                              10

SEQ ID NO: 315              moltype = AA  length = 10
FEATURE                     Location/Qualifiers
source                      1..10
                            mol_type = protein
                            organism = Homo sapiens
SEQUENCE: 315
ISSCGTGCGI                                                              10

SEQ ID NO: 316              moltype = AA  length = 10
FEATURE                     Location/Qualifiers
source                      1..10
                            mol_type = protein
                            organism = Homo sapiens
SEQUENCE: 316
KGGCGSGCGG                                                              10

SEQ ID NO: 317              moltype = AA  length = 10
FEATURE                     Location/Qualifiers
source                      1..10
                            mol_type = protein
                            organism = Homo sapiens
SEQUENCE: 317
KGGCGSSCSQ                                                              10

SEQ ID NO: 318              moltype = AA  length = 10
FEATURE                     Location/Qualifiers
```

```
                        -continued source                  1..10
                        mol_type = protein
                        organism = Homo sapiens
SEQUENCE: 318
LVTCQDSCGS                                                              10

SEQ ID NO: 319          moltype = AA   length = 10
FEATURE                 Location/Qualifiers
source                  1..10
                        mol_type = protein
                        organism = Homo sapiens
SEQUENCE: 319
LVTCQESCQP                                                              10

SEQ ID NO: 320          moltype = AA   length = 10
FEATURE                 Location/Qualifiers
source                  1..10
                        mol_type = protein
                        organism = Homo sapiens
SEQUENCE: 320
MSICSSACTD                                                              10

SEQ ID NO: 321          moltype = AA   length = 10
FEATURE                 Location/Qualifiers
source                  1..10
                        mol_type = protein
                        organism = Homo sapiens
SEQUENCE: 321
MSICSSACTN                                                              10

SEQ ID NO: 322          moltype = AA   length = 10
FEATURE                 Location/Qualifiers
source                  1..10
                        mol_type = protein
                        organism = Homo sapiens
SEQUENCE: 322
MSVCSSACSD                                                              10

SEQ ID NO: 323          moltype = AA   length = 10
FEATURE                 Location/Qualifiers
source                  1..10
                        mol_type = protein
                        organism = Homo sapiens
SEQUENCE: 323
PAICEPSCSV                                                              10

SEQ ID NO: 324          moltype = AA   length = 10
FEATURE                 Location/Qualifiers
source                  1..10
                        mol_type = protein
                        organism = Homo sapiens
SEQUENCE: 324
PASCQKSCYR                                                              10

SEQ ID NO: 325          moltype = AA   length = 10
FEATURE                 Location/Qualifiers
source                  1..10
                        mol_type = protein
                        organism = Homo sapiens
SEQUENCE: 325
PIYCRRTCYH                                                              10

SEQ ID NO: 326          moltype = AA   length = 10
FEATURE                 Location/Qualifiers
source                  1..10
                        mol_type = protein
                        organism = Homo sapiens
SEQUENCE: 326
PNSCQTLCVE                                                              10

SEQ ID NO: 327          moltype = AA   length = 10
FEATURE                 Location/Qualifiers
source                  1..10
                        mol_type = protein
                        organism = Homo sapiens
SEQUENCE: 327
PQPCVPTCFL                                                              10

SEQ ID NO: 328          moltype = AA   length = 10
```

```
FEATURE                 Location/Qualifiers
source                  1..10
                        mol_type = protein
                        organism = Homo sapiens
SEQUENCE: 328
PSACQSGCTS                                                                      10

SEQ ID NO: 329          moltype = AA  length = 10
FEATURE                 Location/Qualifiers
source                  1..10
                        mol_type = protein
                        organism = Homo sapiens
SEQUENCE: 329
PSPCEPSCSE                                                                      10

SEQ ID NO: 330          moltype = AA  length = 10
FEATURE                 Location/Qualifiers
source                  1..10
                        mol_type = protein
                        organism = Homo sapiens
SEQUENCE: 330
PSPCQASCYI                                                                      10

SEQ ID NO: 331          moltype = AA  length = 10
FEATURE                 Location/Qualifiers
source                  1..10
                        mol_type = protein
                        organism = Homo sapiens
SEQUENCE: 331
PSPCQSGCIS                                                                      10

SEQ ID NO: 332          moltype = AA  length = 10
FEATURE                 Location/Qualifiers
source                  1..10
                        mol_type = protein
                        organism = Homo sapiens
SEQUENCE: 332
PSPCQSGCTD                                                                      10

SEQ ID NO: 333          moltype = AA  length = 10
FEATURE                 Location/Qualifiers
source                  1..10
                        mol_type = protein
                        organism = Homo sapiens
SEQUENCE: 333
PSPCQSGCTS                                                                      10

SEQ ID NO: 334          moltype = AA  length = 10
FEATURE                 Location/Qualifiers
source                  1..10
                        mol_type = protein
                        organism = Homo sapiens
SEQUENCE: 334
PTACQPTCYQ                                                                      10

SEQ ID NO: 335          moltype = AA  length = 10
FEATURE                 Location/Qualifiers
source                  1..10
                        mol_type = protein
                        organism = Homo sapiens
SEQUENCE: 335
PTACQPTCYR                                                                      10

SEQ ID NO: 336          moltype = AA  length = 10
FEATURE                 Location/Qualifiers
source                  1..10
                        mol_type = protein
                        organism = Homo sapiens
SEQUENCE: 336
PTPCSTTCRT                                                                      10

SEQ ID NO: 337          moltype = AA  length = 10
FEATURE                 Location/Qualifiers
source                  1..10
                        mol_type = protein
                        organism = Homo sapiens
SEQUENCE: 337
PTSCQKSCYR                                                                      10
```

```
SEQ ID NO: 338         moltype = AA   length = 10
FEATURE                Location/Qualifiers
source                 1..10
                       mol_type = protein
                       organism = Homo sapiens
SEQUENCE: 338
PTSCQPSCES                                                              10

SEQ ID NO: 339         moltype = AA   length = 10
FEATURE                Location/Qualifiers
source                 1..10
                       mol_type = protein
                       organism = Homo sapiens
SEQUENCE: 339
PTSCQTSCTL                                                              10

SEQ ID NO: 340         moltype = AA   length = 10
FEATURE                Location/Qualifiers
source                 1..10
                       mol_type = protein
                       organism = Homo sapiens
SEQUENCE: 340
PVICEPSCSV                                                              10

SEQ ID NO: 341         moltype = AA   length = 10
FEATURE                Location/Qualifiers
source                 1..10
                       mol_type = protein
                       organism = Homo sapiens
SEQUENCE: 341
PVSCVPVCSG                                                              10

SEQ ID NO: 342         moltype = AA   length = 10
FEATURE                Location/Qualifiers
source                 1..10
                       mol_type = protein
                       organism = Homo sapiens
SEQUENCE: 342
PVTCVPRCTR                                                              10

SEQ ID NO: 343         moltype = AA   length = 10
FEATURE                Location/Qualifiers
source                 1..10
                       mol_type = protein
                       organism = Homo sapiens
SEQUENCE: 343
PVYCRRTCYH                                                              10

SEQ ID NO: 344         moltype = AA   length = 10
FEATURE                Location/Qualifiers
source                 1..10
                       mol_type = protein
                       organism = Homo sapiens
SEQUENCE: 344
PVYCRRTCYY                                                              10

SEQ ID NO: 345         moltype = AA   length = 10
FEATURE                Location/Qualifiers
source                 1..10
                       mol_type = protein
                       organism = Homo sapiens
SEQUENCE: 345
PVYCVPVCSG                                                              10

SEQ ID NO: 346         moltype = AA   length = 10
FEATURE                Location/Qualifiers
source                 1..10
                       mol_type = protein
                       organism = Homo sapiens
SEQUENCE: 346
QPGCESPCEP                                                              10

SEQ ID NO: 347         moltype = AA   length = 10
FEATURE                Location/Qualifiers
source                 1..10
                       mol_type = protein
                       organism = Homo sapiens
SEQUENCE: 347
QQSCVSSCRR                                                              10
```

```
SEQ ID NO: 348           moltype = AA   length = 10
FEATURE                  Location/Qualifiers
source                   1..10
                         mol_type = protein
                         organism = Homo sapiens SEQUENCE: 348
QTSCGSSCGQ                                                                10

SEQ ID NO: 349           moltype = AA   length = 10
FEATURE                  Location/Qualifiers
source                   1..10
                         mol_type = protein
                         organism = Homo sapiens SEQUENCE: 349
QTTCHPSCGM                                                                10

SEQ ID NO: 350           moltype = AA   length = 10
FEATURE                  Location/Qualifiers
source                   1..10
                         mol_type = protein
                         organism = Homo sapiens SEQUENCE: 350
QTTCRPSCGV                                                                10

SEQ ID NO: 351           moltype = AA   length = 10
FEATURE                  Location/Qualifiers
source                   1..10
                         mol_type = protein
                         organism = Homo sapiens SEQUENCE: 351
RGGCGSGCGG                                                                10

SEQ ID NO: 352           moltype = AA   length = 10
FEATURE                  Location/Qualifiers
source                   1..10
                         mol_type = protein
                         organism = Homo sapiens SEQUENCE: 352
RLACYSLCSG                                                                10

SEQ ID NO: 353           moltype = AA   length = 10
FEATURE                  Location/Qualifiers
source                   1..10
                         mol_type = protein
                         organism = Homo sapiens SEQUENCE: 353
RPACYRPCYS                                                                10

SEQ ID NO: 354           moltype = AA   length = 10
FEATURE                  Location/Qualifiers
source                   1..10
                         mol_type = protein
                         organism = Homo sapiens SEQUENCE: 354
RPFCFRRCYS                                                                10

SEQ ID NO: 355           moltype = AA   length = 10
FEATURE                  Location/Qualifiers
source                   1..10
                         mol_type = protein
                         organism = Homo sapiens SEQUENCE: 355
RPICRPICSG                                                                10

SEQ ID NO: 356           moltype = AA   length = 10
FEATURE                  Location/Qualifiers
source                   1..10
                         mol_type = protein
                         organism = Homo sapiens SEQUENCE: 356
RPLCYRRCYS                                                                10

SEQ ID NO: 357           moltype = AA   length = 10
FEATURE                  Location/Qualifiers
source                   1..10
                         mol_type = protein
                         organism = Homo sapiens

SEQUENCE: 357
```

RSPCQASCYV                                                                                      10

SEQ ID NO: 358          moltype = AA  length = 10
FEATURE                 Location/Qualifiers
source                  1..10
                        mol_type = protein
                        organism = Homo sapiens SEQUENCE: 358
RVSCHTTCYR                                                                                      10

SEQ ID NO: 359          moltype = AA  length = 10
FEATURE                 Location/Qualifiers
source                  1..10
                        mol_type = protein
                        organism = Homo sapiens SEQUENCE: 359
SAICRPTCPR                                                                                      10

SEQ ID NO: 360          moltype = AA  length = 10
FEATURE                 Location/Qualifiers
source                  1..10
                        mol_type = protein
                        organism = Homo sapiens SEQUENCE: 360
SDSCKRDCKK                                                                                      10

SEQ ID NO: 361          moltype = AA  length = 10
FEATURE                 Location/Qualifiers
source                  1..10
                        mol_type = protein
                        organism = Homo sapiens SEQUENCE: 361
SEGCGSGCGG                                                                                      10

SEQ ID NO: 362          moltype = AA  length = 10
FEATURE                 Location/Qualifiers
source                  1..10
                        mol_type = protein
                        organism = Homo sapiens SEQUENCE: 362
SFLCRPACSR                                                                                      10

SEQ ID NO: 363          moltype = AA  length = 10
FEATURE                 Location/Qualifiers
source                  1..10
                        mol_type = protein
                        organism = Homo sapiens SEQUENCE: 363
SGGCGSGCGG                                                                                      10

SEQ ID NO: 364          moltype = AA  length = 10
FEATURE                 Location/Qualifiers
source                  1..10
                        mol_type = protein
                        organism = Homo sapiens SEQUENCE: 364
SGGCGSSCGG                                                                                      10

SEQ ID NO: 365          moltype = AA  length = 10
FEATURE                 Location/Qualifiers
source                  1..10
                        mol_type = protein
                        organism = Homo sapiens SEQUENCE: 365
SGSCQAACGQ                                                                                      10

SEQ ID NO: 366          moltype = AA  length = 10
FEATURE                 Location/Qualifiers
source                  1..10
                        mol_type = protein
                        organism = Homo sapiens SEQUENCE: 366
SLLCHPVCKS                                                                                      10

SEQ ID NO: 367          moltype = AA  length = 10
FEATURE                 Location/Qualifiers
source                  1..10
                        mol_type = protein
                        organism = Homo sapiens

```
SEQUENCE: 367
SLLCHPVCRS                                                                    10

SEQ ID NO: 368            moltype = AA  length = 10
FEATURE                   Location/Qualifiers
source                    1..10
                          mol_type = protein
                          organism = Homo sapiens
SEQUENCE: 368
SLLCRPACSP                                                                    10

SEQ ID NO: 369            moltype = AA  length = 10
FEATURE                   Location/Qualifiers
source                    1..10
                          mol_type = protein
                          organism = Homo sapiens
SEQUENCE: 369
SLLCRPACSR                                                                    10

SEQ ID NO: 370            moltype = AA  length = 10
FEATURE                   Location/Qualifiers
source                    1..10
                          mol_type = protein
                          organism = Homo sapiens
SEQUENCE: 370
SLLCRPICRP                                                                    10

SEQ ID NO: 371            moltype = AA  length = 10
FEATURE                   Location/Qualifiers
source                    1..10
                          mol_type = protein
                          organism = Homo sapiens
SEQUENCE: 371
SLLCRPMCSR                                                                    10

SEQ ID NO: 372            moltype = AA  length = 10
FEATURE                   Location/Qualifiers
source                    1..10
                          mol_type = protein
                          organism = Homo sapiens
SEQUENCE: 372
SLLCRPTCSR                                                                    10

SEQ ID NO: 373            moltype = AA  length = 10
FEATURE                   Location/Qualifiers
source                    1..10
                          mol_type = protein
                          organism = Homo sapiens
SEQUENCE: 373
SLLCRPVCQP                                                                    10

SEQ ID NO: 374            moltype = AA  length = 10
FEATURE                   Location/Qualifiers
source                    1..10
                          mol_type = protein
                          organism = Homo sapiens
SEQUENCE: 374
SLLCRPVCRP                                                                    10

SEQ ID NO: 375            moltype = AA  length = 10
FEATURE                   Location/Qualifiers
source                    1..10
                          mol_type = protein
                          organism = Homo sapiens
SEQUENCE: 375
SLLCRPVCRS                                                                    10

SEQ ID NO: 376            moltype = AA  length = 10
FEATURE                   Location/Qualifiers
source                    1..10
                          mol_type = protein
                          organism = Homo sapiens
SEQUENCE: 376
SLLCRPVCSR                                                                    10

SEQ ID NO: 377            moltype = AA  length = 10
FEATURE                   Location/Qualifiers
source                    1..10
                          mol_type = protein
```

```
SEQUENCE: 377
SNPCQVTCSR                                                                      10

SEQ ID NO: 378          moltype = AA   length = 10
FEATURE                 Location/Qualifiers
source                  1..10
                        mol_type = protein
                        organism = Homo sapiens
SEQUENCE: 378
SRGCGSGCGG                                                                      10

SEQ ID NO: 379          moltype = AA   length = 10
FEATURE                 Location/Qualifiers
source                  1..10
                        mol_type = protein
                        organism = Homo sapiens
SEQUENCE: 379
SRSCQSPCYR                                                                      10

SEQ ID NO: 380          moltype = AA   length = 10
FEATURE                 Location/Qualifiers
source                  1..10
                        mol_type = protein
                        organism = Homo sapiens
SEQUENCE: 380
SRSCQSSCYR                                                                      10

SEQ ID NO: 381          moltype = AA   length = 10
FEATURE                 Location/Qualifiers
source                  1..10
                        mol_type = protein
                        organism = Homo sapiens
SEQUENCE: 381
SSGCGYGCGY                                                                      10

SEQ ID NO: 382          moltype = AA   length = 10
FEATURE                 Location/Qualifiers
source                  1..10
                        mol_type = protein
                        organism = Homo sapiens
SEQUENCE: 382
SSGCPMACPG                                                                      10

SEQ ID NO: 383          moltype = AA   length = 10
FEATURE                 Location/Qualifiers
source                  1..10
                        mol_type = protein
                        organism = Homo sapiens
SEQUENCE: 383
SSICQPICSE                                                                      10

SEQ ID NO: 384          moltype = AA   length = 10
FEATURE                 Location/Qualifiers
source                  1..10
                        mol_type = protein
                        organism = Homo sapiens
SEQUENCE: 384
SSPCHTSCYY                                                                      10

SEQ ID NO: 385          moltype = AA   length = 10
FEATURE                 Location/Qualifiers
source                  1..10
                        mol_type = protein
                        organism = Homo sapiens
SEQUENCE: 385
SSPCQPTCYV                                                                      10

SEQ ID NO: 386          moltype = AA   length = 10
FEATURE                 Location/Qualifiers
source                  1..10
                        mol_type = protein
                        organism = Homo sapiens
SEQUENCE: 386
SSPCQQSCYV                                                                      10

SEQ ID NO: 387          moltype = AA   length = 10
FEATURE                 Location/Qualifiers
source                  1..10
```

```
                                    mol_type = protein
                                    organism = Homo sapiens
SEQUENCE: 387
SSPCQTSCYR                                                                      10

SEQ ID NO: 388                      moltype = AA  length = 10
FEATURE                             Location/Qualifiers
source                              1..10
                                    mol_type = protein
                                    organism = Homo sapiens
SEQUENCE: 388
SSSCQQSCRV                                                                      10

SEQ ID NO: 389                      moltype = AA  length = 10
FEATURE                             Location/Qualifiers
source                              1..10
                                    mol_type = protein
                                    organism = Homo sapiens
SEQUENCE: 389
STVCQPACGV                                                                      10

SEQ ID NO: 390                      moltype = AA  length = 10
FEATURE                             Location/Qualifiers
source                              1..10
                                    mol_type = protein
                                    organism = Homo sapiens
SEQUENCE: 390
TDNCQETCGE                                                                      10

SEQ ID NO: 391                      moltype = AA  length = 10
FEATURE                             Location/Qualifiers
source                              1..10
                                    mol_type = protein
                                    organism = Homo sapiens
SEQUENCE: 391
TQPCYEPCLP                                                                      10

SEQ ID NO: 392                      moltype = AA  length = 10
FEATURE                             Location/Qualifiers
source                              1..10
                                    mol_type = protein
                                    organism = Homo sapiens
SEQUENCE: 392
TSSCGTGCGI                                                                      10

SEQ ID NO: 393                      moltype = AA  length = 10
FEATURE                             Location/Qualifiers
source                              1..10
                                    mol_type = protein
                                    organism = Homo sapiens
SEQUENCE: 393
TSSCQPSCGR                                                                      10

SEQ ID NO: 394                      moltype = AA  length = 10
FEATURE                             Location/Qualifiers
source                              1..10
                                    mol_type = protein
                                    organism = Homo sapiens
SEQUENCE: 394
TSSCTTPCYQ                                                                      10

SEQ ID NO: 395                      moltype = AA  length = 10
FEATURE                             Location/Qualifiers
source                              1..10
                                    mol_type = protein
                                    organism = Homo sapiens
SEQUENCE: 395
TSVCLPGCLN                                                                      10

SEQ ID NO: 396                      moltype = AA  length = 10
FEATURE                             Location/Qualifiers
source                              1..10
                                    mol_type = protein
                                    organism = Homo sapiens
SEQUENCE: 396
TTVCLPGCLN                                                                      10

SEQ ID NO: 397                      moltype = AA  length = 10
FEATURE                             Location/Qualifiers
```

```
source                    1..10
                          mol_type = protein
                          organism = Homo sapiens
SEQUENCE: 397
VANCQAPCST                                                                    10

SEQ ID NO: 398            moltype = AA   length = 10
FEATURE                   Location/Qualifiers
source                    1..10
                          mol_type = protein
                          organism = Homo sapiens
SEQUENCE: 398
VDDCPESCWP                                                                    10

SEQ ID NO: 399            moltype = AA   length = 10
FEATURE                   Location/Qualifiers
source                    1..10
                          mol_type = protein
                          organism = Homo sapiens
SEQUENCE: 399
VKRCPSVCPE                                                                    10

SEQ ID NO: 400            moltype = AA   length = 10
FEATURE                   Location/Qualifiers
source                    1..10
                          mol_type = protein
                          organism = Homo sapiens
SEQUENCE: 400
VSSCQPSCSE                                                                    10

SEQ ID NO: 401            moltype = AA   length = 10
FEATURE                   Location/Qualifiers
source                    1..10
                          mol_type = protein
                          organism = Homo sapiens
SEQUENCE: 401
YEGCRYGCGH                                                                    10

SEQ ID NO: 402            moltype = AA   length = 10
FEATURE                   Location/Qualifiers
source                    1..10
                          mol_type = protein
                          organism = Homo sapiens
SEQUENCE: 402
YGRCRHGCHS                                                                    10

SEQ ID NO: 403            moltype = AA   length = 10
FEATURE                   Location/Qualifiers
source                    1..10
                          mol_type = protein
                          organism = Homo sapiens
SEQUENCE: 403
YGYCRPSCYG                                                                    10

SEQ ID NO: 404            moltype = AA   length = 10
FEATURE                   Location/Qualifiers
source                    1..10
                          mol_type = protein
                          organism = Homo sapiens
SEQUENCE: 404
YRDCQKTCWE                                                                    10

SEQ ID NO: 405            moltype = AA   length = 10
FEATURE                   Location/Qualifiers
source                    1..10
                          mol_type = protein
                          organism = Homo sapiens
SEQUENCE: 405
YRGCQEICWE                                                                    10

SEQ ID NO: 406            moltype = AA   length = 10
FEATURE                   Location/Qualifiers
source                    1..10
                          mol_type = protein
                          organism = Homo sapiens
SEQUENCE: 406
YRGCQETCWR                                                                    10

SEQ ID NO: 407            moltype = AA   length = 10
```

```
FEATURE              Location/Qualifiers
source               1..10
                     mol_type = protein
                     organism = Homo sapiens
SEQUENCE: 407
YRGCQQTCWE                                                              10

SEQ ID NO: 408       moltype = AA  length = 10
FEATURE              Location/Qualifiers
source               1..10
                     mol_type = protein
                     organism = Homo sapiens
SEQUENCE: 408
YRSCRPSCYG                                                              10

SEQ ID NO: 409       moltype = AA  length = 10
FEATURE              Location/Qualifiers
source               1..10
                     mol_type = protein
                     organism = Homo sapiens
SEQUENCE: 409
GGVCGPSPPC                                                              10

SEQ ID NO: 410       moltype = AA  length = 10
FEATURE              Location/Qualifiers
source               1..10
                     mol_type = protein
                     organism = Homo sapiens
SEQUENCE: 410
GVCGPSPPCI                                                              10

SEQ ID NO: 411       moltype = AA  length = 10
FEATURE              Location/Qualifiers
source               1..10
                     mol_type = protein
                     organism = Homo sapiens
SEQUENCE: 411
VCGPSPPCIT                                                              10

SEQ ID NO: 412       moltype = AA  length = 10
FEATURE              Location/Qualifiers
source               1..10
                     mol_type = protein
                     organism = Homo sapiens
SEQUENCE: 412
CGPSPPCITT                                                              10

SEQ ID NO: 413       moltype = AA  length = 10
FEATURE              Location/Qualifiers
source               1..10
                     mol_type = protein
                     organism = Homo sapiens
SEQUENCE: 413
CAPIYCRRTC                                                              10

SEQ ID NO: 414       moltype = AA  length = 10
FEATURE              Location/Qualifiers
source               1..10
                     mol_type = protein
                     organism = Homo sapiens
SEQUENCE: 414
CAPSPCQASC                                                              10

SEQ ID NO: 415       moltype = AA  length = 10
FEATURE              Location/Qualifiers
source               1..10
                     mol_type = protein
                     organism = Homo sapiens
SEQUENCE: 415
CAPSPCQPAC                                                              10

SEQ ID NO: 416       moltype = AA  length = 10
FEATURE              Location/Qualifiers
source               1..10
                     mol_type = protein
                     organism = Homo sapiens
SEQUENCE: 416
CAPVYCRRTC                                                              10
```

-continued

| | | |
|---|---|---|
| SEQ ID NO: 417<br>FEATURE<br>source | moltype = AA length = 10<br>Location/Qualifiers<br>1..10<br>mol_type = protein<br>organism = Homo sapiens | |
| SEQUENCE: 417<br>CASSPCQQAC | | 10 |
| SEQ ID NO: 418<br>FEATURE<br>source | moltype = AA length = 10<br>Location/Qualifiers<br>1..10<br>mol_type = protein<br>organism = Homo sapiens | |
| SEQUENCE: 418<br>CASSSCQPAC | | 10 |
| SEQ ID NO: 419<br>FEATURE<br>source | moltype = AA length = 10<br>Location/Qualifiers<br>1..10<br>mol_type = protein<br>organism = Homo sapiens | |
| SEQUENCE: 419<br>CASSSCQQSC | | 10 |
| SEQ ID NO: 420<br>FEATURE<br>source | moltype = AA length = 10<br>Location/Qualifiers<br>1..10<br>mol_type = protein<br>organism = Homo sapiens | |
| SEQUENCE: 420<br>CCGNFSSHSC | | 10 |
| SEQ ID NO: 421<br>FEATURE<br>source | moltype = AA length = 10<br>Location/Qualifiers<br>1..10<br>mol_type = protein<br>organism = Homo sapiens | |
| SEQUENCE: 421<br>CCGYGGLGCG | | 10 |
| SEQ ID NO: 422<br>FEATURE<br>source | moltype = AA length = 10<br>Location/Qualifiers<br>1..10<br>mol_type = protein<br>organism = Homo sapiens | |
| SEQUENCE: 422<br>CCNYYGNSCG | | 10 |
| SEQ ID NO: 423<br>FEATURE<br>source | moltype = AA length = 10<br>Location/Qualifiers<br>1..10<br>mol_type = protein<br>organism = Homo sapiens | |
| SEQUENCE: 423<br>CCNYYRNSCG | | 10 |
| SEQ ID NO: 424<br>FEATURE<br>source | moltype = AA length = 10<br>Location/Qualifiers<br>1..10<br>mol_type = protein<br>organism = Homo sapiens | |
| SEQUENCE: 424<br>CCSRNFSSCS | | 10 |
| SEQ ID NO: 425<br>FEATURE<br>source | moltype = AA length = 10<br>Location/Qualifiers<br>1..10<br>mol_type = protein<br>organism = Homo sapiens | |
| SEQUENCE: 425<br>CDAGSCQPSC | | 10 |
| SEQ ID NO: 426<br>FEATURE<br>source | moltype = AA length = 10<br>Location/Qualifiers<br>1..10<br>mol_type = protein<br>organism = Homo sapiens | |
| SEQUENCE: 426<br>CDPCSLQEGC | | 10 |

| | | |
|---|---|---|
| SEQ ID NO: 427<br>FEATURE<br>source | moltype = AA   length = 10<br>Location/Qualifiers<br>1..10<br>mol_type = protein<br>organism = Homo sapiens | |
| SEQUENCE: 427<br>CDPSPCEPSC | | 10 |
| SEQ ID NO: 428<br>FEATURE<br>source | moltype = AA   length = 10<br>Location/Qualifiers<br>1..10<br>mol_type = protein<br>organism = Homo sapiens | |
| SEQUENCE: 428<br>CDPVICEPSC | | 10 |
| SEQ ID NO: 429<br>FEATURE<br>source | moltype = AA   length = 10<br>Location/Qualifiers<br>1..10<br>mol_type = protein<br>organism = Homo sapiens | |
| SEQUENCE: 429<br>CDQGLCQETC | | 10 |
| SEQ ID NO: 430<br>FEATURE<br>source | moltype = AA   length = 10<br>Location/Qualifiers<br>1..10<br>mol_type = protein<br>organism = Homo sapiens | |
| SEQUENCE: 430<br>CEATTCEPSC | | 10 |
| SEQ ID NO: 431<br>FEATURE<br>source | moltype = AA   length = 10<br>Location/Qualifiers<br>1..10<br>mol_type = protein<br>organism = Homo sapiens | |
| SEQUENCE: 431<br>CELPCGTPSC | | 10 |
| SEQ ID NO: 432<br>FEATURE<br>source | moltype = AA   length = 10<br>Location/Qualifiers<br>1..10<br>mol_type = protein<br>organism = Homo sapiens | |
| SEQUENCE: 432<br>CEPAICEPSC | | 10 |
| SEQ ID NO: 433<br>FEATURE<br>source | moltype = AA   length = 10<br>Location/Qualifiers<br>1..10<br>mol_type = protein<br>organism = Homo sapiens | |
| SEQUENCE: 433<br>CEPPCGTAPC | | 10 |
| SEQ ID NO: 434<br>FEATURE<br>source | moltype = AA   length = 10<br>Location/Qualifiers<br>1..10<br>mol_type = protein<br>organism = Homo sapiens | |
| SEQUENCE: 434<br>CEPPCSAPSC | | 10 |
| SEQ ID NO: 435<br>FEATURE<br>source | moltype = AA   length = 10<br>Location/Qualifiers<br>1..10<br>mol_type = protein<br>organism = Homo sapiens | |
| SEQUENCE: 435<br>CEPRSCASSC | | 10 |
| SEQ ID NO: 436<br>FEATURE<br>source | moltype = AA   length = 10<br>Location/Qualifiers<br>1..10<br>mol_type = protein<br>organism = Homo sapiens | |
| SEQUENCE: 436 | | |

```
CEPSACQSGC                                                                         10

SEQ ID NO: 437           moltype = AA  length = 10
FEATURE                  Location/Qualifiers
source                   1..10
                         mol_type = protein
                         organism = Homo sapiens
SEQUENCE: 437
CEPSCSVSNC                                                                         10

SEQ ID NO: 438           moltype = AA  length = 10
FEATURE                  Location/Qualifiers
source                   1..10
                         mol_type = protein
                         organism = Homo sapiens
SEQUENCE: 438
CEPSCSVSSC                                                                         10

SEQ ID NO: 439           moltype = AA  length = 10
FEATURE                  Location/Qualifiers
source                   1..10
                         mol_type = protein
                         organism = Homo sapiens
SEQUENCE: 439
CEPSPCQSGC                                                                         10

SEQ ID NO: 440           moltype = AA  length = 10
FEATURE                  Location/Qualifiers
source                   1..10
                         mol_type = protein
                         organism = Homo sapiens
SEQUENCE: 440
CEPTACQPTC                                                                         10

SEQ ID NO: 441           moltype = AA  length = 10
FEATURE                  Location/Qualifiers
source                   1..10
                         mol_type = protein
                         organism = Homo sapiens
SEQUENCE: 441
CEPTSCQTSC                                                                         10

SEQ ID NO: 442           moltype = AA  length = 10
FEATURE                  Location/Qualifiers
source                   1..10
                         mol_type = protein
                         organism = Homo sapiens
SEQUENCE: 442
CEPVCLRPVC                                                                         10

SEQ ID NO: 443           moltype = AA  length = 10
FEATURE                  Location/Qualifiers
source                   1..10
                         mol_type = protein
                         organism = Homo sapiens
SEQUENCE: 443
CETSSCQPRC                                                                         10

SEQ ID NO: 444           moltype = AA  length = 10
FEATURE                  Location/Qualifiers
source                   1..10
                         mol_type = protein
                         organism = Homo sapiens
SEQUENCE: 444
CETTCFQPTC                                                                         10

SEQ ID NO: 445           moltype = AA  length = 10
FEATURE                  Location/Qualifiers
source                   1..10
                         mol_type = protein
                         organism = Homo sapiens
SEQUENCE: 445
CFQPTCVSSC                                                                         10

SEQ ID NO: 446           moltype = AA  length = 10
FEATURE                  Location/Qualifiers
source                   1..10
                         mol_type = protein
                         organism = Homo sapiens
```

```
SEQUENCE: 446
CFQPTCVTSC                                                                     10

SEQ ID NO: 447         moltype = AA   length = 10
FEATURE                Location/Qualifiers
source                 1..10
                       mol_type = protein
                       organism = Homo sapiens
SEQUENCE: 447
CFQPTCVYSC                                                                     10

SEQ ID NO: 448         moltype = AA   length = 10
FEATURE                Location/Qualifiers
source                 1..10
                       mol_type = protein
                       organism = Homo sapiens
SEQUENCE: 448
CGCGFRRLGC                                                                     10

SEQ ID NO: 449         moltype = AA   length = 10
FEATURE                Location/Qualifiers
source                 1..10
                       mol_type = protein
                       organism = Homo sapiens
SEQUENCE: 449
CGCGYRGLDC                                                                     10

SEQ ID NO: 450         moltype = AA   length = 10
FEATURE                Location/Qualifiers
source                 1..10
                       mol_type = protein
                       organism = Homo sapiens
SEQUENCE: 450
CGCNGYYGCY                                                                     10

SEQ ID NO: 451         moltype = AA   length = 10
FEATURE                Location/Qualifiers
source                 1..10
                       mol_type = protein
                       organism = Homo sapiens
SEQUENCE: 451
CGFGSCYGCG                                                                     10

SEQ ID NO: 452         moltype = AA   length = 10
FEATURE                Location/Qualifiers
source                 1..10
                       mol_type = protein
                       organism = Homo sapiens
SEQUENCE: 452
CGGSGCGGSC                                                                     10

SEQ ID NO: 453         moltype = AA   length = 10
FEATURE                Location/Qualifiers
source                 1..10
                       mol_type = protein
                       organism = Homo sapiens
SEQUENCE: 453
CGGSGSSCCV                                                                     10

SEQ ID NO: 454         moltype = AA   length = 10
FEATURE                Location/Qualifiers
source                 1..10
                       mol_type = protein
                       organism = Homo sapiens
SEQUENCE: 454
CGGVSCHTTC                                                                     10

SEQ ID NO: 455         moltype = AA   length = 10
FEATURE                Location/Qualifiers
source                 1..10
                       mol_type = protein
                       organism = Homo sapiens
SEQUENCE: 455
CGKGGCGSCG                                                                     10

SEQ ID NO: 456         moltype = AA   length = 10
FEATURE                Location/Qualifiers
source                 1..10
                       mol_type = protein
```

```
                           organism = Homo sapiens
SEQUENCE: 456
CGKRGCGSCG                                                                    10

SEQ ID NO: 457         moltype = AA  length = 10
FEATURE                Location/Qualifiers
source                 1..10
                       mol_type = protein
                       organism = Homo sapiens
SEQUENCE: 457
CGQDLCQETC                                                                    10

SEQ ID NO: 458         moltype = AA  length = 10
FEATURE                Location/Qualifiers
source                 1..10
                       mol_type = protein
                       organism = Homo sapiens
SEQUENCE: 458
CGQTSCGSSC                                                                    10

SEQ ID NO: 459         moltype = AA  length = 10
FEATURE                Location/Qualifiers
source                 1..10
                       mol_type = protein
                       organism = Homo sapiens
SEQUENCE: 459
CGQVLCQETC                                                                    10

SEQ ID NO: 460         moltype = AA  length = 10
FEATURE                Location/Qualifiers
source                 1..10
                       mol_type = protein
                       organism = Homo sapiens
SEQUENCE: 460
CGRDLCQETC                                                                    10

SEQ ID NO: 461         moltype = AA  length = 10
FEATURE                Location/Qualifiers
source                 1..10
                       mol_type = protein
                       organism = Homo sapiens
SEQUENCE: 461
CGRVSCHTTC                                                                    10

SEQ ID NO: 462         moltype = AA  length = 10
FEATURE                Location/Qualifiers
source                 1..10
                       mol_type = protein
                       organism = Homo sapiens
SEQUENCE: 462
CGSCGFGSCY                                                                    10

SEQ ID NO: 463         moltype = AA  length = 10
FEATURE                Location/Qualifiers
source                 1..10
                       mol_type = protein
                       organism = Homo sapiens
SEQUENCE: 463
CGSCGGSKGC                                                                    10

SEQ ID NO: 464         moltype = AA  length = 10
FEATURE                Location/Qualifiers
source                 1..10
                       mol_type = protein
                       organism = Homo sapiens
SEQUENCE: 464
CGSGCGVPVC                                                                    10

SEQ ID NO: 465         moltype = AA  length = 10
FEATURE                Location/Qualifiers
source                 1..10
                       mol_type = protein
                       organism = Homo sapiens
SEQUENCE: 465
CGSLLCRPTC                                                                    10

SEQ ID NO: 466         moltype = AA  length = 10
FEATURE                Location/Qualifiers
source                 1..10
```

|  |  |  |
|---|---|---|
|  | mol_type = protein<br>organism = Homo sapiens |  |
| SEQUENCE: 466<br>CGSRCYVPVC |  | 10 |
| SEQ ID NO: 467<br>FEATURE<br>source | moltype = AA  length = 10<br>Location/Qualifiers<br>1..10<br>mol_type = protein<br>organism = Homo sapiens |  |
| SEQUENCE: 467<br>CGSSSCGPQC |  | 10 |
| SEQ ID NO: 468<br>FEATURE<br>source | moltype = AA  length = 10<br>Location/Qualifiers<br>1..10<br>mol_type = protein<br>organism = Homo sapiens |  |
| SEQUENCE: 468<br>CGSVCSDQGC |  | 10 |
| SEQ ID NO: 469<br>FEATURE<br>source | moltype = AA  length = 10<br>Location/Qualifiers<br>1..10<br>mol_type = protein<br>organism = Homo sapiens |  |
| SEQUENCE: 469<br>CGSVCSDQSC |  | 10 |
| SEQ ID NO: 470<br>FEATURE<br>source | moltype = AA  length = 10<br>Location/Qualifiers<br>1..10<br>mol_type = protein<br>organism = Homo sapiens |  |
| SEQUENCE: 470<br>CGSVCSHQGC |  | 10 |
| SEQ ID NO: 471<br>FEATURE<br>source | moltype = AA  length = 10<br>Location/Qualifiers<br>1..10<br>mol_type = protein<br>organism = Homo sapiens |  |
| SEQUENCE: 471<br>CGSYGCSQCS |  | 10 |
| SEQ ID NO: 472<br>FEATURE<br>source | moltype = AA  length = 10<br>Location/Qualifiers<br>1..10<br>mol_type = protein<br>organism = Homo sapiens |  |
| SEQUENCE: 472<br>CGVCLPSTCP |  | 10 |
| SEQ ID NO: 473<br>FEATURE<br>source | moltype = AA  length = 10<br>Location/Qualifiers<br>1..10<br>mol_type = protein<br>organism = Homo sapiens |  |
| SEQUENCE: 473<br>CGYEGCRYGC |  | 10 |
| SEQ ID NO: 474<br>FEATURE<br>source | moltype = AA  length = 10<br>Location/Qualifiers<br>1..10<br>mol_type = protein<br>organism = Homo sapiens |  |
| SEQUENCE: 474<br>CGYGCGYGCG |  | 10 |
| SEQ ID NO: 475<br>FEATURE<br>source | moltype = AA  length = 10<br>Location/Qualifiers<br>1..10<br>mol_type = protein<br>organism = Homo sapiens |  |
| SEQUENCE: 475<br>CGYGGCGYGC |  | 10 |
| SEQ ID NO: 476<br>FEATURE | moltype = AA  length = 10<br>Location/Qualifiers |  |

```
                         -continued source                   1..10
                         mol_type = protein
                         organism = Homo sapiens
SEQUENCE: 476
CGYGSFCGCG                                                              10

SEQ ID NO: 477           moltype = AA   length = 10
FEATURE                  Location/Qualifiers
source                   1..10
                         mol_type = protein
                         organism = Homo sapiens
SEQUENCE: 477
CGYGSGCGCG                                                              10

SEQ ID NO: 478           moltype = AA   length = 10
FEATURE                  Location/Qualifiers
source                   1..10
                         mol_type = protein
                         organism = Homo sapiens
SEQUENCE: 478
CHPSCGMSSC                                                              10

SEQ ID NO: 479           moltype = AA   length = 10
FEATURE                  Location/Qualifiers
source                   1..10
                         mol_type = protein
                         organism = Homo sapiens
SEQUENCE: 479
CHPSCSISSC                                                              10

SEQ ID NO: 480           moltype = AA   length = 10
FEATURE                  Location/Qualifiers
source                   1..10
                         mol_type = protein
                         organism = Homo sapiens
SEQUENCE: 480
CHPTCYQTIC                                                              10

SEQ ID NO: 481           moltype = AA   length = 10
FEATURE                  Location/Qualifiers
source                   1..10
                         mol_type = protein
                         organism = Homo sapiens
SEQUENCE: 481
CHTSCSPACQ                                                              10

SEQ ID NO: 482           moltype = AA   length = 10
FEATURE                  Location/Qualifiers
source                   1..10
                         mol_type = protein
                         organism = Homo sapiens
SEQUENCE: 482
CHTSCSSGCQ                                                              10

SEQ ID NO: 483           moltype = AA   length = 10
FEATURE                  Location/Qualifiers
source                   1..10
                         mol_type = protein
                         organism = Homo sapiens
SEQUENCE: 483
CHTTCYRPAC                                                              10

SEQ ID NO: 484           moltype = AA   length = 10
FEATURE                  Location/Qualifiers
source                   1..10
                         mol_type = protein
                         organism = Homo sapiens
SEQUENCE: 484
CHTTCYRPTC                                                              10

SEQ ID NO: 485           moltype = AA   length = 10
FEATURE                  Location/Qualifiers
source                   1..10
                         mol_type = protein
                         organism = Homo sapiens
SEQUENCE: 485
CIHSPCQASC                                                              10

SEQ ID NO: 486           moltype = AA   length = 10
```

```
                    FEATURE            Location/Qualifiers
                    source             1..10
                                       mol_type = protein
                                       organism = Homo sapiens
SEQUENCE: 486
CIHSTHCGCN                                                                    10

SEQ ID NO: 487      moltype = AA   length = 10
FEATURE             Location/Qualifiers
source              1..10
                    mol_type = protein
                    organism = Homo sapiens
SEQUENCE: 487
CIRSPCQASC                                                                    10

SEQ ID NO: 488      moltype = AA   length = 10
FEATURE             Location/Qualifiers
source              1..10
                    mol_type = protein
                    organism = Homo sapiens
SEQUENCE: 488
CISSCYRPQC                                                                    10

SEQ ID NO: 489      moltype = AA   length = 10
FEATURE             Location/Qualifiers
source              1..10
                    mol_type = protein
                    organism = Homo sapiens
SEQUENCE: 489
CISSPCQQSC                                                                    10

SEQ ID NO: 490      moltype = AA   length = 10
FEATURE             Location/Qualifiers
source              1..10
                    mol_type = protein
                    organism = Homo sapiens
SEQUENCE: 490
CKPCSSQSSC                                                                    10

SEQ ID NO: 491      moltype = AA   length = 10
FEATURE             Location/Qualifiers
source              1..10
                    mol_type = protein
                    organism = Homo sapiens
SEQUENCE: 491
CKPSCSQSSC                                                                    10

SEQ ID NO: 492      moltype = AA   length = 10
FEATURE             Location/Qualifiers
source              1..10
                    mol_type = protein
                    organism = Homo sapiens
SEQUENCE: 492
CKPVCFKPIC                                                                    10

SEQ ID NO: 493      moltype = AA   length = 10
FEATURE             Location/Qualifiers
source              1..10
                    mol_type = protein
                    organism = Homo sapiens
SEQUENCE: 493
CKPVCYVPTC                                                                    10

SEQ ID NO: 494      moltype = AA   length = 10
FEATURE             Location/Qualifiers
source              1..10
                    mol_type = protein
                    organism = Homo sapiens
SEQUENCE: 494
CKPVSCVPVC                                                                    10

SEQ ID NO: 495      moltype = AA   length = 10
FEATURE             Location/Qualifiers
source              1..10
                    mol_type = protein
                    organism = Homo sapiens
SEQUENCE: 495
CKPVYCVPVC                                                                    10
```

```
SEQ ID NO: 496       moltype = AA  length = 10
FEATURE              Location/Qualifiers
source               1..10
                     mol_type = protein
                     organism = Homo sapiens
SEQUENCE: 496
CKTVYCKPIC                                                              10

SEQ ID NO: 497       moltype = AA  length = 10
FEATURE              Location/Qualifiers
source               1..10
                     mol_type = protein
                     organism = Homo sapiens
SEQUENCE: 497
CLNQSCGSNC                                                              10

SEQ ID NO: 498       moltype = AA  length = 10
FEATURE              Location/Qualifiers
source               1..10
                     mol_type = protein
                     organism = Homo sapiens
SEQUENCE: 498
CLNQSCGSSC                                                              10

SEQ ID NO: 499       moltype = AA  length = 10
FEATURE              Location/Qualifiers
source               1..10
                     mol_type = protein
                     organism = Homo sapiens
SEQUENCE: 499
CLPGCLNQSC                                                              10

SEQ ID NO: 500       moltype = AA  length = 10
FEATURE              Location/Qualifiers
source               1..10
                     mol_type = protein
                     organism = Homo sapiens
SEQUENCE: 500
CLPGSCDSCS                                                              10

SEQ ID NO: 501       moltype = AA  length = 10
FEATURE              Location/Qualifiers
source               1..10
                     mol_type = protein
                     organism = Homo sapiens
SEQUENCE: 501
CLPPCYLVSC                                                              10

SEQ ID NO: 502       moltype = AA  length = 10
FEATURE              Location/Qualifiers
source               1..10
                     mol_type = protein
                     organism = Homo sapiens
SEQUENCE: 502
CLPTSCQPSC                                                              10

SEQ ID NO: 503       moltype = AA  length = 10
FEATURE              Location/Qualifiers
source               1..10
                     mol_type = protein
                     organism = Homo sapiens
SEQUENCE: 503
CLSFLCRPAC                                                              10

SEQ ID NO: 504       moltype = AA  length = 10
FEATURE              Location/Qualifiers
source               1..10
                     mol_type = protein
                     organism = Homo sapiens
SEQUENCE: 504
CLVSSCQPSC                                                              10

SEQ ID NO: 505       moltype = AA  length = 10
FEATURE              Location/Qualifiers
source               1..10
                     mol_type = protein
                     organism = Homo sapiens
SEQUENCE: 505
CMPSPCQPAC                                                              10
```

| | | |
|---|---|---|
| SEQ ID NO: 506<br>FEATURE<br>source | moltype = AA  length = 10<br>Location/Qualifiers<br>1..10<br>mol_type = protein<br>organism = Homo sapiens | |
| SEQUENCE: 506<br>CMSGSCQAAC | | 10 |
| SEQ ID NO: 507<br>FEATURE<br>source | moltype = AA  length = 10<br>Location/Qualifiers<br>1..10<br>mol_type = protein<br>organism = Homo sapiens | |
| SEQUENCE: 507<br>CNESSYCLPC | | 10 |
| SEQ ID NO: 508<br>FEATURE<br>source | moltype = AA  length = 10<br>Location/Qualifiers<br>1..10<br>mol_type = protein<br>organism = Homo sapiens | |
| SEQUENCE: 508<br>CPASCVSLLC | | 10 |
| SEQ ID NO: 509<br>FEATURE<br>source | moltype = AA  length = 10<br>Location/Qualifiers<br>1..10<br>mol_type = protein<br>organism = Homo sapiens | |
| SEQUENCE: 509<br>CPMACPGSPC | | 10 |
| SEQ ID NO: 510<br>FEATURE<br>source | moltype = AA  length = 10<br>Location/Qualifiers<br>1..10<br>mol_type = protein<br>organism = Homo sapiens | |
| SEQUENCE: 510<br>CPSSCTAVVC | | 10 |
| SEQ ID NO: 511<br>FEATURE<br>source | moltype = AA  length = 10<br>Location/Qualifiers<br>1..10<br>mol_type = protein<br>organism = Homo sapiens | |
| SEQUENCE: 511<br>CPVTCEPSPC | | 10 |
| SEQ ID NO: 512<br>FEATURE<br>source | moltype = AA  length = 10<br>Location/Qualifiers<br>1..10<br>mol_type = protein<br>organism = Homo sapiens | |
| SEQUENCE: 512<br>CQAACEPSAC | | 10 |
| SEQ ID NO: 513<br>FEATURE<br>source | moltype = AA  length = 10<br>Location/Qualifiers<br>1..10<br>mol_type = protein<br>organism = Homo sapiens | |
| SEQUENCE: 513<br>CQAACEPSPC | | 10 |
| SEQ ID NO: 514<br>FEATURE<br>source | moltype = AA  length = 10<br>Location/Qualifiers<br>1..10<br>mol_type = protein<br>organism = Homo sapiens | |
| SEQUENCE: 514<br>CQAACGQSVC | | 10 |
| SEQ ID NO: 515<br>FEATURE<br>source | moltype = AA  length = 10<br>Location/Qualifiers<br>1..10<br>mol_type = protein<br>organism = Homo sapiens | |
| SEQUENCE: 515 | | |

```
CQAPCSTKNC                                                                       10

SEQ ID NO: 516          moltype = AA   length = 10
FEATURE                 Location/Qualifiers
source                  1..10
                        mol_type = protein
                        organism = Homo sapiens SEQUENCE: 516
CQAVCEPSPC                                                                       10

SEQ ID NO: 517          moltype = AA   length = 10
FEATURE                 Location/Qualifiers
source                  1..10
                        mol_type = protein
                        organism = Homo sapiens SEQUENCE: 517
CQDSCGSSSC                                                                       10

SEQ ID NO: 518          moltype = AA   length = 10
FEATURE                 Location/Qualifiers
source                  1..10
                        mol_type = protein
                        organism = Homo sapiens SEQUENCE: 518
CQHSSCQPTC                                                                       10

SEQ ID NO: 519          moltype = AA   length = 10
FEATURE                 Location/Qualifiers
source                  1..10
                        mol_type = protein
                        organism = Homo sapiens SEQUENCE: 519
CQISSCGTGC                                                                       10

SEQ ID NO: 520          moltype = AA   length = 10
FEATURE                 Location/Qualifiers
source                  1..10
                        mol_type = protein
                        organism = Homo sapiens SEQUENCE: 520
CQKSSCQPAC                                                                       10

SEQ ID NO: 521          moltype = AA   length = 10
FEATURE                 Location/Qualifiers
source                  1..10
                        mol_type = protein
                        organism = Homo sapiens SEQUENCE: 521
CQPMCSHAAC                                                                       10

SEQ ID NO: 522          moltype = AA   length = 10
FEATURE                 Location/Qualifiers
source                  1..10
                        mol_type = protein
                        organism = Homo sapiens SEQUENCE: 522
CQPPCTTALC                                                                       10

SEQ ID NO: 523          moltype = AA   length = 10
FEATURE                 Location/Qualifiers
source                  1..10
                        mol_type = protein
                        organism = Homo sapiens SEQUENCE: 523
CQPSCESSFC                                                                       10

SEQ ID NO: 524          moltype = AA   length = 10
FEATURE                 Location/Qualifiers
source                  1..10
                        mol_type = protein
                        organism = Homo sapiens SEQUENCE: 524
CQPSCSESTC                                                                       10

SEQ ID NO: 525          moltype = AA   length = 10
FEATURE                 Location/Qualifiers
source                  1..10
                        mol_type = protein
                        organism = Homo sapiens
```

| | | |
|---|---|---|
| SEQUENCE: 525<br>CQPSCTSVLC | | 10 |
| SEQ ID NO: 526<br>FEATURE<br>source | moltype = AA  length = 10<br>Location/Qualifiers<br>1..10<br>mol_type = protein<br>organism = Homo sapiens | |
| SEQUENCE: 526<br>CQPTCGGSSC | | 10 |
| SEQ ID NO: 527<br>FEATURE<br>source | moltype = AA  length = 10<br>Location/Qualifiers<br>1..10<br>mol_type = protein<br>organism = Homo sapiens | |
| SEQUENCE: 527<br>CQPTCSRPSC | | 10 |
| SEQ ID NO: 528<br>FEATURE<br>source | moltype = AA  length = 10<br>Location/Qualifiers<br>1..10<br>mol_type = protein<br>organism = Homo sapiens | |
| SEQUENCE: 528<br>CQPVCPTPTC | | 10 |
| SEQ ID NO: 529<br>FEATURE<br>source | moltype = AA  length = 10<br>Location/Qualifiers<br>1..10<br>mol_type = protein<br>organism = Homo sapiens | |
| SEQUENCE: 529<br>CQPVLCKSSC | | 10 |
| SEQ ID NO: 530<br>FEATURE<br>source | moltype = AA  length = 10<br>Location/Qualifiers<br>1..10<br>mol_type = protein<br>organism = Homo sapiens | |
| SEQUENCE: 530<br>CQPVVCEPSC | | 10 |
| SEQ ID NO: 531<br>FEATURE<br>source | moltype = AA  length = 10<br>Location/Qualifiers<br>1..10<br>mol_type = protein<br>organism = Homo sapiens | |
| SEQUENCE: 531<br>CQQPSCQPAC | | 10 |
| SEQ ID NO: 532<br>FEATURE<br>source | moltype = AA  length = 10<br>Location/Qualifiers<br>1..10<br>mol_type = protein<br>organism = Homo sapiens | |
| SEQUENCE: 532<br>CQQSCRVPVC | | 10 |
| SEQ ID NO: 533<br>FEATURE<br>source | moltype = AA  length = 10<br>Location/Qualifiers<br>1..10<br>mol_type = protein<br>organism = Homo sapiens | |
| SEQUENCE: 533<br>CQQSCYVPVC | | 10 |
| SEQ ID NO: 534<br>FEATURE<br>source | moltype = AA  length = 10<br>Location/Qualifiers<br>1..10<br>mol_type = protein<br>organism = Homo sapiens | |
| SEQUENCE: 534<br>CQQSGCQPAC | | 10 |
| SEQ ID NO: 535<br>FEATURE<br>source | moltype = AA  length = 10<br>Location/Qualifiers<br>1..10<br>mol_type = protein | |

```
                          organism = Homo sapiens
SEQUENCE: 535
CQQSSCHPAC                                                                    10

SEQ ID NO: 536            moltype = AA   length = 10
FEATURE                   Location/Qualifiers
source                    1..10
                          mol_type = protein
                          organism = Homo sapiens
SEQUENCE: 536
CQQSSCKPAC                                                                    10

SEQ ID NO: 537            moltype = AA   length = 10
FEATURE                   Location/Qualifiers
source                    1..10
                          mol_type = protein
                          organism = Homo sapiens
SEQUENCE: 537
CQQSSCQLAC                                                                    10

SEQ ID NO: 538            moltype = AA   length = 10
FEATURE                   Location/Qualifiers
source                    1..10
                          mol_type = protein
                          organism = Homo sapiens
SEQUENCE: 538
CQQSSCQPAC                                                                    10

SEQ ID NO: 539            moltype = AA   length = 10
FEATURE                   Location/Qualifiers
source                    1..10
                          mol_type = protein
                          organism = Homo sapiens
SEQUENCE: 539
CQQSSCQPTC                                                                    10

SEQ ID NO: 540            moltype = AA   length = 10
FEATURE                   Location/Qualifiers
source                    1..10
                          mol_type = protein
                          organism = Homo sapiens
SEQUENCE: 540
CQQSSCQSAC                                                                    10

SEQ ID NO: 541            moltype = AA   length = 10
FEATURE                   Location/Qualifiers
source                    1..10
                          mol_type = protein
                          organism = Homo sapiens
SEQUENCE: 541
CQQSSCVSCV                                                                    10

SEQ ID NO: 542            moltype = AA   length = 10
FEATURE                   Location/Qualifiers
source                    1..10
                          mol_type = protein
                          organism = Homo sapiens
SEQUENCE: 542
CQQSYCVPVC                                                                    10

SEQ ID NO: 543            moltype = AA   length = 10
FEATURE                   Location/Qualifiers
source                    1..10
                          mol_type = protein
                          organism = Homo sapiens
SEQUENCE: 543
CQSGCISSCT                                                                    10

SEQ ID NO: 544            moltype = AA   length = 10
FEATURE                   Location/Qualifiers
source                    1..10
                          mol_type = protein
                          organism = Homo sapiens
SEQUENCE: 544
CQSGCTDSCT                                                                    10

SEQ ID NO: 545            moltype = AA   length = 10
FEATURE                   Location/Qualifiers
source                    1..10
```

| | | |
|---|---|---|
| | mol_type = protein<br>organism = Homo sapiens | |
| SEQUENCE: 545<br>CQSGCTSSCT | | 10 |
| SEQ ID NO: 546<br>FEATURE<br>source | moltype = AA length = 10<br>Location/Qualifiers<br>1..10<br>mol_type = protein<br>organism = Homo sapiens | |
| SEQUENCE: 546<br>CQSSCYRPTC | | 10 |
| SEQ ID NO: 547<br>FEATURE<br>source | moltype = AA length = 10<br>Location/Qualifiers<br>1..10<br>mol_type = protein<br>organism = Homo sapiens | |
| SEQUENCE: 547<br>CQSVCYQPTC | | 10 |
| SEQ ID NO: 548<br>FEATURE<br>source | moltype = AA length = 10<br>Location/Qualifiers<br>1..10<br>mol_type = protein<br>organism = Homo sapiens | |
| SEQUENCE: 548<br>CQSVYCQPTC | | 10 |
| SEQ ID NO: 549<br>FEATURE<br>source | moltype = AA length = 10<br>Location/Qualifiers<br>1..10<br>mol_type = protein<br>organism = Homo sapiens | |
| SEQUENCE: 549<br>CQTACEPSAC | | 10 |
| SEQ ID NO: 550<br>FEATURE<br>source | moltype = AA length = 10<br>Location/Qualifiers<br>1..10<br>mol_type = protein<br>organism = Homo sapiens | |
| SEQUENCE: 550<br>CQTSSCGTGC | | 10 |
| SEQ ID NO: 551<br>FEATURE<br>source | moltype = AA length = 10<br>Location/Qualifiers<br>1..10<br>mol_type = protein<br>organism = Homo sapiens | |
| SEQUENCE: 551<br>CQTTCHPSCG | | 10 |
| SEQ ID NO: 552<br>FEATURE<br>source | moltype = AA length = 10<br>Location/Qualifiers<br>1..10<br>mol_type = protein<br>organism = Homo sapiens | |
| SEQUENCE: 552<br>CQTTCRPSCG | | 10 |
| SEQ ID NO: 553<br>FEATURE<br>source | moltype = AA length = 10<br>Location/Qualifiers<br>1..10<br>mol_type = protein<br>organism = Homo sapiens | |
| SEQUENCE: 553<br>CQTTCYRTTC | | 10 |
| SEQ ID NO: 554<br>FEATURE<br>source | moltype = AA length = 10<br>Location/Qualifiers<br>1..10<br>mol_type = protein<br>organism = Homo sapiens | |
| SEQUENCE: 554<br>CQTTRCRTTC | | 10 |
| SEQ ID NO: 555<br>FEATURE | moltype = AA length = 10<br>Location/Qualifiers | |

| | | |
|---|---|---|
| source | 1..10<br>mol_type = protein<br>organism = Homo sapiens | |
| SEQUENCE: 555<br>CQVTCEPSPC | | 10 |
| SEQ ID NO: 556<br>FEATURE<br>source | moltype = AA length = 10<br>Location/Qualifiers<br>1..10<br>mol_type = protein<br>organism = Homo sapiens | |
| SEQUENCE: 556<br>CRNTSCQPTC | | 10 |
| SEQ ID NO: 557<br>FEATURE<br>source | moltype = AA length = 10<br>Location/Qualifiers<br>1..10<br>mol_type = protein<br>organism = Homo sapiens | |
| SEQUENCE: 557<br>CRPACSPLAC | | 10 |
| SEQ ID NO: 558<br>FEATURE<br>source | moltype = AA length = 10<br>Location/Qualifiers<br>1..10<br>mol_type = protein<br>organism = Homo sapiens | |
| SEQUENCE: 558<br>CRPACSRLAC | | 10 |
| SEQ ID NO: 559<br>FEATURE<br>source | moltype = AA length = 10<br>Location/Qualifiers<br>1..10<br>mol_type = protein<br>organism = Homo sapiens | |
| SEQUENCE: 559<br>CRPACSRPAC | | 10 |
| SEQ ID NO: 560<br>FEATURE<br>source | moltype = AA length = 10<br>Location/Qualifiers<br>1..10<br>mol_type = protein<br>organism = Homo sapiens | |
| SEQUENCE: 560<br>CRPMCSRPAC | | 10 |
| SEQ ID NO: 561<br>FEATURE<br>source | moltype = AA length = 10<br>Location/Qualifiers<br>1..10<br>mol_type = protein<br>organism = Homo sapiens | |
| SEQUENCE: 561<br>CRPSCGQTTC | | 10 |
| SEQ ID NO: 562<br>FEATURE<br>source | moltype = AA length = 10<br>Location/Qualifiers<br>1..10<br>mol_type = protein<br>organism = Homo sapiens | |
| SEQUENCE: 562<br>CRPSCGVSSC | | 10 |
| SEQ ID NO: 563<br>FEATURE<br>source | moltype = AA length = 10<br>Location/Qualifiers<br>1..10<br>mol_type = protein<br>organism = Homo sapiens | |
| SEQUENCE: 563<br>CRPSCSISSC | | 10 |
| SEQ ID NO: 564<br>FEATURE<br>source | moltype = AA length = 10<br>Location/Qualifiers<br>1..10<br>mol_type = protein<br>organism = Homo sapiens | |
| SEQUENCE: 564<br>CRPSCSQTTC | | 10 |
| SEQ ID NO: 565 | moltype = AA length = 10 | |

-continued

```
FEATURE                 Location/Qualifiers
source                  1..10
                        mol_type = protein
                        organism = Homo sapiens
SEQUENCE: 565
CRPSYCGQSC                                                                              10

SEQ ID NO: 566          moltype = AA  length = 10
FEATURE                 Location/Qualifiers
source                  1..10
                        mol_type = protein
                        organism = Homo sapiens
SEQUENCE: 566
CRPSYCISSC                                                                              10

SEQ ID NO: 567          moltype = AA  length = 10
FEATURE                 Location/Qualifiers
source                  1..10
                        mol_type = protein
                        organism = Homo sapiens
SEQUENCE: 567
CRPSYCQTTC                                                                              10

SEQ ID NO: 568          moltype = AA  length = 10
FEATURE                 Location/Qualifiers
source                  1..10
                        mol_type = protein
                        organism = Homo sapiens
SEQUENCE: 568
CRPTCSRLAC                                                                              10

SEQ ID NO: 569          moltype = AA  length = 10
FEATURE                 Location/Qualifiers
source                  1..10
                        mol_type = protein
                        organism = Homo sapiens
SEQUENCE: 569
CRPTCSSGSC                                                                              10

SEQ ID NO: 570          moltype = AA  length = 10
FEATURE                 Location/Qualifiers
source                  1..10
                        mol_type = protein
                        organism = Homo sapiens
SEQUENCE: 570
CRPTSCQNTC                                                                              10

SEQ ID NO: 571          moltype = AA  length = 10
FEATURE                 Location/Qualifiers
source                  1..10
                        mol_type = protein
                        organism = Homo sapiens
SEQUENCE: 571
CRPVCRSTYC                                                                              10

SEQ ID NO: 572          moltype = AA  length = 10
FEATURE                 Location/Qualifiers
source                  1..10
                        mol_type = protein
                        organism = Homo sapiens
SEQUENCE: 572
CRPVCSRPAC                                                                              10

SEQ ID NO: 573          moltype = AA  length = 10
FEATURE                 Location/Qualifiers
source                  1..10
                        mol_type = protein
                        organism = Homo sapiens
SEQUENCE: 573
CRPVTCVPRC                                                                              10

SEQ ID NO: 574          moltype = AA  length = 10
FEATURE                 Location/Qualifiers
source                  1..10
                        mol_type = protein
                        organism = Homo sapiens
SEQUENCE: 574
CRQSSCQPAC                                                                              10
```

```
SEQ ID NO: 575            moltype = AA  length = 10
FEATURE                   Location/Qualifiers
source                    1..10
                          mol_type = protein
                          organism = Homo sapiens
SEQUENCE: 575
CRTTCFHPIC                                                                10

SEQ ID NO: 576            moltype = AA  length = 10
FEATURE                   Location/Qualifiers
source                    1..10
                          mol_type = protein
                          organism = Homo sapiens
SEQUENCE: 576
CRTTCFQPTC                                                                10

SEQ ID NO: 577            moltype = AA  length = 10
FEATURE                   Location/Qualifiers
source                    1..10
                          mol_type = protein
                          organism = Homo sapiens
SEQUENCE: 577
CRTTCYRPSC                                                                10

SEQ ID NO: 578            moltype = AA  length = 10
FEATURE                   Location/Qualifiers
source                    1..10
                          mol_type = protein
                          organism = Homo sapiens
SEQUENCE: 578
CRTTYCRPSC                                                                10

SEQ ID NO: 579            moltype = AA  length = 10
FEATURE                   Location/Qualifiers
source                    1..10
                          mol_type = protein
                          organism = Homo sapiens
SEQUENCE: 579
CRVTCEPSPC                                                                10

SEQ ID NO: 580            moltype = AA  length = 10
FEATURE                   Location/Qualifiers
source                    1..10
                          mol_type = protein
                          organism = Homo sapiens
SEQUENCE: 580
CRYGCGHRGC                                                                10

SEQ ID NO: 581            moltype = AA  length = 10
FEATURE                   Location/Qualifiers
source                    1..10
                          mol_type = protein
                          organism = Homo sapiens
SEQUENCE: 581
CSAPCVALLC                                                                10

SEQ ID NO: 582            moltype = AA  length = 10
FEATURE                   Location/Qualifiers
source                    1..10
                          mol_type = protein
                          organism = Homo sapiens
SEQUENCE: 582
CSDDSGSCCQ                                                                10

SEQ ID NO: 583            moltype = AA  length = 10
FEATURE                   Location/Qualifiers
source                    1..10
                          mol_type = protein
                          organism = Homo sapiens
SEQUENCE: 583
CSEDSSSCCQ                                                                10

SEQ ID NO: 584            moltype = AA  length = 10
FEATURE                   Location/Qualifiers
source                    1..10
                          mol_type = protein
                          organism = Homo sapiens
SEQUENCE: 584
CSEDSYSCCQ                                                                10
```

```
SEQ ID NO: 585           moltype = AA  length = 10
FEATURE                  Location/Qualifiers
source                   1..10
                         mol_type = protein
                         organism = Homo sapiens
SEQUENCE: 585
CSEGCGSGCG                                                                10

SEQ ID NO: 586           moltype = AA  length = 10
FEATURE                  Location/Qualifiers
source                   1..10
                         mol_type = protein
                         organism = Homo sapiens
SEQUENCE: 586
CSESSPSCCQ                                                                10

SEQ ID NO: 587           moltype = AA  length = 10
FEATURE                  Location/Qualifiers
source                   1..10
                         mol_type = protein
                         organism = Homo sapiens
SEQUENCE: 587
CSESSSSCCQ                                                                10

SEQ ID NO: 588           moltype = AA  length = 10
FEATURE                  Location/Qualifiers
source                   1..10
                         mol_type = protein
                         organism = Homo sapiens
SEQUENCE: 588
CSFDKSCRCG                                                                10

SEQ ID NO: 589           moltype = AA  length = 10
FEATURE                  Location/Qualifiers
source                   1..10
                         mol_type = protein
                         organism = Homo sapiens
SEQUENCE: 589
CSGASSLCCQ                                                                10

SEQ ID NO: 590           moltype = AA  length = 10
FEATURE                  Location/Qualifiers
source                   1..10
                         mol_type = protein
                         organism = Homo sapiens
SEQUENCE: 590
CSGASSPCCQ                                                                10

SEQ ID NO: 591           moltype = AA  length = 10
FEATURE                  Location/Qualifiers
source                   1..10
                         mol_type = protein
                         organism = Homo sapiens
SEQUENCE: 591
CSGASSSCCQ                                                                10

SEQ ID NO: 592           moltype = AA  length = 10
FEATURE                  Location/Qualifiers
source                   1..10
                         mol_type = protein
                         organism = Homo sapiens
SEQUENCE: 592
CSGASTSCCQ                                                                10

SEQ ID NO: 593           moltype = AA  length = 10
FEATURE                  Location/Qualifiers
source                   1..10
                         mol_type = protein
                         organism = Homo sapiens
SEQUENCE: 593
CSGGCGSGCG                                                                10

SEQ ID NO: 594           moltype = AA  length = 10
FEATURE                  Location/Qualifiers
source                   1..10
                         mol_type = protein
                         organism = Homo sapiens
SEQUENCE: 594
```

```
                                                    -continued
CSGGCGSSCG                                                            10

SEQ ID NO: 597          moltype = AA  length = 10
FEATURE                 Location/Qualifiers
source                  1..10
                        mol_type = protein
                        organism = Homo sapiens
SEQUENCE: 595
CSGISSSCCQ                                                            10

SEQ ID NO: 596          moltype = AA  length = 10
FEATURE                 Location/Qualifiers
source                  1..10
                        mol_type = protein
                        organism = Homo sapiens
SEQUENCE: 596
CSKDSSSCCQ                                                            10

SEQ ID NO: 597          moltype = AA  length = 10
FEATURE                 Location/Qualifiers
source                  1..10
                        mol_type = protein
                        organism = Homo sapiens
SEQUENCE: 597
CSKGACGSCG                                                            10

SEQ ID NO: 598          moltype = AA  length = 10
FEATURE                 Location/Qualifiers
source                  1..10
                        mol_type = protein
                        organism = Homo sapiens
SEQUENCE: 598
CSLSCGSRSC                                                            10

SEQ ID NO: 599          moltype = AA  length = 10
FEATURE                 Location/Qualifiers
source                  1..10
                        mol_type = protein
                        organism = Homo sapiens
SEQUENCE: 599
CSQDLCQETC                                                            10

SEQ ID NO: 600          moltype = AA  length = 10
FEATURE                 Location/Qualifiers
source                  1..10
                        mol_type = protein
                        organism = Homo sapiens
SEQUENCE: 600
CSRGCGSGCG                                                            10

SEQ ID NO: 601          moltype = AA  length = 10
FEATURE                 Location/Qualifiers
source                  1..10
                        mol_type = protein
                        organism = Homo sapiens
SEQUENCE: 601
CSRLSSACCG                                                            10

SEQ ID NO: 602          moltype = AA  length = 10
FEATURE                 Location/Qualifiers
source                  1..10
                        mol_type = protein
                        organism = Homo sapiens
SEQUENCE: 602
CSSCGKGGCG                                                            10

SEQ ID NO: 603          moltype = AA  length = 10
FEATURE                 Location/Qualifiers
source                  1..10
                        mol_type = protein
                        organism = Homo sapiens
SEQUENCE: 603
CSSCGKRGCG                                                            10

SEQ ID NO: 604          moltype = AA  length = 10
FEATURE                 Location/Qualifiers
source                  1..10
                        mol_type = protein
                        organism = Homo sapiens
```

| | | |
|---|---|---|
| SEQUENCE: 604<br>CSSDKSCRCG | | 10 |
| SEQ ID NO: 605<br>FEATURE<br>source | moltype = AA length = 10<br>Location/Qualifiers<br>1..10<br>mol_type = protein<br>organism = Homo sapiens | |
| SEQUENCE: 605<br>CSSGNFSSCC | | 10 |
| SEQ ID NO: 606<br>FEATURE<br>source | moltype = AA length = 10<br>Location/Qualifiers<br>1..10<br>mol_type = protein<br>organism = Homo sapiens | |
| SEQUENCE: 606<br>CSSSGCGSFC | | 10 |
| SEQ ID NO: 607<br>FEATURE<br>source | moltype = AA length = 10<br>Location/Qualifiers<br>1..10<br>mol_type = protein<br>organism = Homo sapiens | |
| SEQUENCE: 607<br>CSSSGCGSSC | | 10 |
| SEQ ID NO: 608<br>FEATURE<br>source | moltype = AA length = 10<br>Location/Qualifiers<br>1..10<br>mol_type = protein<br>organism = Homo sapiens | |
| SEQUENCE: 608<br>CSTPCYQPIC | | 10 |
| SEQ ID NO: 609<br>FEATURE<br>source | moltype = AA length = 10<br>Location/Qualifiers<br>1..10<br>mol_type = protein<br>organism = Homo sapiens | |
| SEQUENCE: 609<br>CSTTCRTSSC | | 10 |
| SEQ ID NO: 610<br>FEATURE<br>source | moltype = AA length = 10<br>Location/Qualifiers<br>1..10<br>mol_type = protein<br>organism = Homo sapiens | |
| SEQUENCE: 610<br>CSWVPACSCT | | 10 |
| SEQ ID NO: 611<br>FEATURE<br>source | moltype = AA length = 10<br>Location/Qualifiers<br>1..10<br>mol_type = protein<br>organism = Homo sapiens | |
| SEQUENCE: 611<br>CTFSPCQQAC | | 10 |
| SEQ ID NO: 612<br>FEATURE<br>source | moltype = AA length = 10<br>Location/Qualifiers<br>1..10<br>mol_type = protein<br>organism = Homo sapiens | |
| SEQUENCE: 612<br>CTMSVCSSAC | | 10 |
| SEQ ID NO: 613<br>FEATURE<br>source | moltype = AA length = 10<br>Location/Qualifiers<br>1..10<br>mol_type = protein<br>organism = Homo sapiens | |
| SEQUENCE: 613<br>CTRPICEPCR | | 10 |
| SEQ ID NO: 614<br>FEATURE<br>source | moltype = AA length = 10<br>Location/Qualifiers<br>1..10<br>mol_type = protein | |

```
                    organism = Homo sapiens
SEQUENCE: 614
CTSSPCQHAC                                                                      10

SEQ ID NO: 615          moltype = AA  length = 10
FEATURE                 Location/Qualifiers
source                  1..10
                        mol_type = protein
                        organism = Homo sapiens
SEQUENCE: 615
CTSSPCQQAC                                                                      10

SEQ ID NO: 616          moltype = AA  length = 10
FEATURE                 Location/Qualifiers
source                  1..10
                        mol_type = protein
                        organism = Homo sapiens
SEQUENCE: 616
CTSSPCQQSC                                                                      10

SEQ ID NO: 617          moltype = AA  length = 10
FEATURE                 Location/Qualifiers
source                  1..10
                        mol_type = protein
                        organism = Homo sapiens
SEQUENCE: 617
CTSSSCQQAC                                                                      10

SEQ ID NO: 618          moltype = AA  length = 10
FEATURE                 Location/Qualifiers
source                  1..10
                        mol_type = protein
                        organism = Homo sapiens
SEQUENCE: 618
CVALLCRPLC                                                                      10

SEQ ID NO: 619          moltype = AA  length = 10
FEATURE                 Location/Qualifiers
source                  1..10
                        mol_type = protein
                        organism = Homo sapiens
SEQUENCE: 619
CVALVCEPVC                                                                      10

SEQ ID NO: 620          moltype = AA  length = 10
FEATURE                 Location/Qualifiers
source                  1..10
                        mol_type = protein
                        organism = Homo sapiens
SEQUENCE: 620
CVFSSCNTTC                                                                      10

SEQ ID NO: 621          moltype = AA  length = 10
FEATURE                 Location/Qualifiers
source                  1..10
                        mol_type = protein
                        organism = Homo sapiens
SEQUENCE: 621
CVGFVCQPMC                                                                      10

SEQ ID NO: 622          moltype = AA  length = 10
FEATURE                 Location/Qualifiers
source                  1..10
                        mol_type = protein
                        organism = Homo sapiens
SEQUENCE: 622
CVPRCTRPIC                                                                      10

SEQ ID NO: 623          moltype = AA  length = 10
FEATURE                 Location/Qualifiers
source                  1..10
                        mol_type = protein
                        organism = Homo sapiens
SEQUENCE: 623
CVPSPCQVAC                                                                      10

SEQ ID NO: 624          moltype = AA  length = 10
FEATURE                 Location/Qualifiers
source                  1..10
```

```
                            mol_type = protein
                            organism = Homo sapiens
SEQUENCE: 624
CVPSRCQASC                                                          10

SEQ ID NO: 625              moltype = AA  length = 10
FEATURE                     Location/Qualifiers
source                      1..10
                            mol_type = protein
                            organism = Homo sapiens
SEQUENCE: 625
CVPSSCQASC                                                          10

SEQ ID NO: 626              moltype = AA  length = 10
FEATURE                     Location/Qualifiers
source                      1..10
                            mol_type = protein
                            organism = Homo sapiens
SEQUENCE: 626
CVPVCNKPVC                                                          10

SEQ ID NO: 627              moltype = AA  length = 10
FEATURE                     Location/Qualifiers
source                      1..10
                            mol_type = protein
                            organism = Homo sapiens
SEQUENCE: 627
CVPVCSKSVC                                                          10

SEQ ID NO: 628              moltype = AA  length = 10
FEATURE                     Location/Qualifiers
source                      1..10
                            mol_type = protein
                            organism = Homo sapiens
SEQUENCE: 628
CVPVRCKPVC                                                          10

SEQ ID NO: 629              moltype = AA  length = 10
FEATURE                     Location/Qualifiers
source                      1..10
                            mol_type = protein
                            organism = Homo sapiens
SEQUENCE: 629
CVSLLCRPAC                                                          10

SEQ ID NO: 630              moltype = AA  length = 10
FEATURE                     Location/Qualifiers
source                      1..10
                            mol_type = protein
                            organism = Homo sapiens
SEQUENCE: 630
CVSLLCRPMC                                                          10

SEQ ID NO: 631              moltype = AA  length = 10
FEATURE                     Location/Qualifiers
source                      1..10
                            mol_type = protein
                            organism = Homo sapiens
SEQUENCE: 631
CVSLLCRPTC                                                          10

SEQ ID NO: 632              moltype = AA  length = 10
FEATURE                     Location/Qualifiers
source                      1..10
                            mol_type = protein
                            organism = Homo sapiens
SEQUENCE: 632
CVSLLCRPVC                                                          10

SEQ ID NO: 633              moltype = AA  length = 10
FEATURE                     Location/Qualifiers
source                      1..10
                            mol_type = protein
                            organism = Homo sapiens
SEQUENCE: 633
CVSNPCQVTC                                                          10

SEQ ID NO: 634              moltype = AA  length = 10
FEATURE                     Location/Qualifiers
```

```
source                    1..10
                          mol_type = protein
                          organism = Homo sapiens
SEQUENCE: 634
CVSRCYRPHC                                                           10

SEQ ID NO: 635            moltype = AA  length = 10
FEATURE                   Location/Qualifiers
source                    1..10
                          mol_type = protein
                          organism = Homo sapiens
SEQUENCE: 635
CVSSCFRPQC                                                           10

SEQ ID NO: 636            moltype = AA  length = 10
FEATURE                   Location/Qualifiers
source                    1..10
                          mol_type = protein
                          organism = Homo sapiens
SEQUENCE: 636
CVSSICQPIC                                                           10

SEQ ID NO: 637            moltype = AA  length = 10
FEATURE                   Location/Qualifiers
source                    1..10
                          mol_type = protein
                          organism = Homo sapiens
SEQUENCE: 637
CVSSPCQPTC                                                           10

SEQ ID NO: 638            moltype = AA  length = 10
FEATURE                   Location/Qualifiers
source                    1..10
                          mol_type = protein
                          organism = Homo sapiens
SEQUENCE: 638
CVVSCTPPSC                                                           10

SEQ ID NO: 639            moltype = AA  length = 10
FEATURE                   Location/Qualifiers
source                    1..10
                          mol_type = protein
                          organism = Homo sapiens
SEQUENCE: 639
CVVSCTPPTC                                                           10

SEQ ID NO: 640            moltype = AA  length = 10
FEATURE                   Location/Qualifiers
source                    1..10
                          mol_type = protein
                          organism = Homo sapiens
SEQUENCE: 640
CYCPKNSIFC                                                           10

SEQ ID NO: 641            moltype = AA  length = 10
FEATURE                   Location/Qualifiers
source                    1..10
                          mol_type = protein
                          organism = Homo sapiens
SEQUENCE: 641
CYEPCLPRGC                                                           10

SEQ ID NO: 642            moltype = AA  length = 10
FEATURE                   Location/Qualifiers
source                    1..10
                          mol_type = protein
                          organism = Homo sapiens
SEQUENCE: 642
CYRRCYSSCY                                                           10

SEQ ID NO: 643            moltype = AA  length = 10
FEATURE                   Location/Qualifiers
source                    1..10
                          mol_type = protein
                          organism = Homo sapiens
SEQUENCE: 643
GCCGYGGLGC                                                           10

SEQ ID NO: 644            moltype = AA  length = 10
```

-continued

```
FEATURE                 Location/Qualifiers
source                  1..10
                        mol_type = protein
                        organism = Homo sapiens
SEQUENCE: 644
GCGGCGSGCA                                                                    10

SEQ ID NO: 645          moltype = AA  length = 10
FEATURE                 Location/Qualifiers
source                  1..10
                        mol_type = protein
                        organism = Homo sapiens
SEQUENCE: 645
GCGGCGSGCG                                                                    10

SEQ ID NO: 646          moltype = AA  length = 10
FEATURE                 Location/Qualifiers
source                  1..10
                        mol_type = protein
                        organism = Homo sapiens
SEQUENCE: 646
GCGGCGSSCG                                                                    10

SEQ ID NO: 647          moltype = AA  length = 10
FEATURE                 Location/Qualifiers
source                  1..10
                        mol_type = protein
                        organism = Homo sapiens
SEQUENCE: 647
GCGGCSSSCG                                                                    10

SEQ ID NO: 648          moltype = AA  length = 10
FEATURE                 Location/Qualifiers
source                  1..10
                        mol_type = protein
                        organism = Homo sapiens
SEQUENCE: 648
GCGGSGSSCC                                                                    10

SEQ ID NO: 649          moltype = AA  length = 10
FEATURE                 Location/Qualifiers
source                  1..10
                        mol_type = protein
                        organism = Homo sapiens
SEQUENCE: 649
GCGSGCAGCG                                                                    10

SEQ ID NO: 650          moltype = AA  length = 10
FEATURE                 Location/Qualifiers
source                  1..10
                        mol_type = protein
                        organism = Homo sapiens
SEQUENCE: 650
GCGSGCGGCG                                                                    10

SEQ ID NO: 651          moltype = AA  length = 10
FEATURE                 Location/Qualifiers
source                  1..10
                        mol_type = protein
                        organism = Homo sapiens
SEQUENCE: 651
GCGSGCGGCS                                                                    10

SEQ ID NO: 652          moltype = AA  length = 10
FEATURE                 Location/Qualifiers
source                  1..10
                        mol_type = protein
                        organism = Homo sapiens
SEQUENCE: 652
GCGSSCGGCD                                                                    10

SEQ ID NO: 653          moltype = AA  length = 10
FEATURE                 Location/Qualifiers
source                  1..10
                        mol_type = protein
                        organism = Homo sapiens
SEQUENCE: 653
GCGSSCGGCG                                                                    10
```

| | | |
|---|---|---|
| SEQ ID NO: 654<br>FEATURE<br>source | moltype = AA length = 10<br>Location/Qualifiers<br>1..10<br>mol_type = protein<br>organism = Homo sapiens | |
| SEQUENCE: 654<br>GCGSSCSQCS | | 10 |
| SEQ ID NO: 655<br>FEATURE<br>source | moltype = AA length = 10<br>Location/Qualifiers<br>1..10<br>mol_type = protein<br>organism = Homo sapiens | |
| SEQUENCE: 655<br>GCGYSSSCCG | | 10 |
| SEQ ID NO: 656<br>FEATURE<br>source | moltype = AA length = 10<br>Location/Qualifiers<br>1..10<br>mol_type = protein<br>organism = Homo sapiens | |
| SEQUENCE: 656<br>GCKGGCGSCG | | 10 |
| SEQ ID NO: 657<br>FEATURE<br>source | moltype = AA length = 10<br>Location/Qualifiers<br>1..10<br>mol_type = protein<br>organism = Homo sapiens | |
| SEQUENCE: 657<br>GCSGCSGGCG | | 10 |
| SEQ ID NO: 658<br>FEATURE<br>source | moltype = AA length = 10<br>Location/Qualifiers<br>1..10<br>mol_type = protein<br>organism = Homo sapiens | |
| SEQUENCE: 658<br>ICSGASSLCC | | 10 |
| SEQ ID NO: 659<br>FEATURE<br>source | moltype = AA length = 10<br>Location/Qualifiers<br>1..10<br>mol_type = protein<br>organism = Homo sapiens | |
| SEQUENCE: 659<br>ICSGASSPCC | | 10 |
| SEQ ID NO: 660<br>FEATURE<br>source | moltype = AA length = 10<br>Location/Qualifiers<br>1..10<br>mol_type = protein<br>organism = Homo sapiens | |
| SEQUENCE: 660<br>MCCNYYGNSC | | 10 |
| SEQ ID NO: 661<br>FEATURE<br>source | moltype = AA length = 10<br>Location/Qualifiers<br>1..10<br>mol_type = protein<br>organism = Homo sapiens | |
| SEQUENCE: 661<br>MCCNYYRNSC | | 10 |
| SEQ ID NO: 662<br>FEATURE<br>source | moltype = AA length = 10<br>Location/Qualifiers<br>1..10<br>mol_type = protein<br>organism = Homo sapiens | |
| SEQUENCE: 662<br>MCYGYGCGCG | | 10 |
| SEQ ID NO: 663<br>FEATURE<br>source | moltype = AA length = 10<br>Location/Qualifiers<br>1..10<br>mol_type = protein<br>organism = Homo sapiens | |
| SEQUENCE: 663<br>NCCSRNFSSC | | 10 |

```
SEQ ID NO: 664          moltype = AA  length = 10
FEATURE                 Location/Qualifiers
source                  1..10
                        mol_type = protein
                        organism = Homo sapiens
SEQUENCE: 664
PCSLQEGCCR                                                                    10

SEQ ID NO: 665          moltype = AA  length = 10
FEATURE                 Location/Qualifiers
source                  1..10
                        mol_type = protein
                        organism = Homo sapiens
SEQUENCE: 665
PCSSQSSCCV                                                                    10

SEQ ID NO: 666          moltype = AA  length = 10
FEATURE                 Location/Qualifiers
source                  1..10
                        mol_type = protein
                        organism = Homo sapiens
SEQUENCE: 666
SCCAPASSCQ                                                                    10

SEQ ID NO: 667          moltype = AA  length = 10
FEATURE                 Location/Qualifiers
source                  1..10
                        mol_type = protein
                        organism = Homo sapiens
SEQUENCE: 667
SCCAPASTCQ                                                                    10

SEQ ID NO: 668          moltype = AA  length = 10
FEATURE                 Location/Qualifiers
source                  1..10
                        mol_type = protein
                        organism = Homo sapiens
SEQUENCE: 668
SCCAPTSSCQ                                                                    10

SEQ ID NO: 669          moltype = AA  length = 10
FEATURE                 Location/Qualifiers
source                  1..10
                        mol_type = protein
                        organism = Homo sapiens
SEQUENCE: 669
SCCGYRPLCY                                                                    10

SEQ ID NO: 670          moltype = AA  length = 10
FEATURE                 Location/Qualifiers
source                  1..10
                        mol_type = protein
                        organism = Homo sapiens
SEQUENCE: 670
SCCVPASSCQ                                                                    10

SEQ ID NO: 671          moltype = AA  length = 10
FEATURE                 Location/Qualifiers
source                  1..10
                        mol_type = protein
                        organism = Homo sapiens
SEQUENCE: 671
SCCVPTSSCQ                                                                    10

SEQ ID NO: 672          moltype = AA  length = 10
FEATURE                 Location/Qualifiers
source                  1..10
                        mol_type = protein
                        organism = Homo sapiens
SEQUENCE: 672
SCGCSKGACG                                                                    10

SEQ ID NO: 673          moltype = AA  length = 10
FEATURE                 Location/Qualifiers
source                  1..10
                        mol_type = protein
                        organism = Homo sapiens
SEQUENCE: 673
```

```
SCGGCDSSCG                                                                          10

SEQ ID NO: 674          moltype = AA  length = 10
FEATURE                 Location/Qualifiers
source                  1..10
                        mol_type = protein
                        organism = Homo sapiens SEQUENCE: 674
SCGGCGSGCG                                                                          10

SEQ ID NO: 675          moltype = AA  length = 10
FEATURE                 Location/Qualifiers
source                  1..10
                        mol_type = protein
                        organism = Homo sapiens SEQUENCE: 675
SCGGCGSSCG                                                                          10

SEQ ID NO: 676          moltype = AA  length = 10
FEATURE                 Location/Qualifiers
source                  1..10
                        mol_type = protein
                        organism = Homo sapiens SEQUENCE: 676
SCGGCKGGCG                                                                          10

SEQ ID NO: 677          moltype = AA  length = 10
FEATURE                 Location/Qualifiers
source                  1..10
                        mol_type = protein
                        organism = Homo sapiens SEQUENCE: 677
SCGGSKGCCG                                                                          10

SEQ ID NO: 678          moltype = AA  length = 10
FEATURE                 Location/Qualifiers
source                  1..10
                        mol_type = protein
                        organism = Homo sapiens SEQUENCE: 678
SCGSGCRGCG                                                                          10

SEQ ID NO: 679          moltype = AA  length = 10
FEATURE                 Location/Qualifiers
source                  1..10
                        mol_type = protein
                        organism = Homo sapiens SEQUENCE: 679
SCYGCGYGCI                                                                          10

SEQ ID NO: 680          moltype = AA  length = 10
FEATURE                 Location/Qualifiers
source                  1..10
                        mol_type = protein
                        organism = Homo sapiens SEQUENCE: 680
TCCVPVPSCG                                                                          10

SEQ ID NO: 681          moltype = AA  length = 10
FEATURE                 Location/Qualifiers
source                  1..10
                        mol_type = protein
                        organism = Homo sapiens SEQUENCE: 681
TCSDDSGSCC                                                                          10

SEQ ID NO: 682          moltype = AA  length = 10
FEATURE                 Location/Qualifiers
source                  1..10
                        mol_type = protein
                        organism = Homo sapiens SEQUENCE: 682
TCSEDSSSCC                                                                          10

SEQ ID NO: 683          moltype = AA  length = 10
FEATURE                 Location/Qualifiers
source                  1..10
                        mol_type = protein
                        organism = Homo sapiens
```

```
SEQUENCE: 683
TCSEDSYSCC                                                                      10

SEQ ID NO: 684          moltype = AA  length = 10
FEATURE                 Location/Qualifiers
source                  1..10
                        mol_type = protein
                        organism = Homo sapiens
SEQUENCE: 684
TCSESSPSCC                                                                      10

SEQ ID NO: 685          moltype = AA  length = 10
FEATURE                 Location/Qualifiers
source                  1..10
                        mol_type = protein
                        organism = Homo sapiens
SEQUENCE: 685
TCSESSSSCC                                                                      10

SEQ ID NO: 686          moltype = AA  length = 10
FEATURE                 Location/Qualifiers
source                  1..10
                        mol_type = protein
                        organism = Homo sapiens
SEQUENCE: 686
TCSKDSSSCC                                                                      10

SEQ ID NO: 687          moltype = AA  length = 10
FEATURE                 Location/Qualifiers
source                  1..10
                        mol_type = protein
                        organism = Homo sapiens
SEQUENCE: 687
TCSRLSSACC                                                                      10

SEQ ID NO: 688          moltype = AA  length = 10
FEATURE                 Location/Qualifiers
source                  1..10
                        mol_type = protein
                        organism = Homo sapiens
SEQUENCE: 688
VCCQPTPICD                                                                      10

SEQ ID NO: 689          moltype = AA  length = 10
FEATURE                 Location/Qualifiers
source                  1..10
                        mol_type = protein
                        organism = Homo sapiens
SEQUENCE: 689
VCSEDSSSCC                                                                      10

SEQ ID NO: 690          moltype = AA  length = 10
FEATURE                 Location/Qualifiers
source                  1..10
                        mol_type = protein
                        organism = Homo sapiens
SEQUENCE: 690
VCSGASSLCC                                                                      10

SEQ ID NO: 691          moltype = AA  length = 10
FEATURE                 Location/Qualifiers
source                  1..10
                        mol_type = protein
                        organism = Homo sapiens
SEQUENCE: 691
VCSGASSPCC                                                                      10

SEQ ID NO: 692          moltype = AA  length = 10
FEATURE                 Location/Qualifiers
source                  1..10
                        mol_type = protein
                        organism = Homo sapiens
SEQUENCE: 692
VCSGASSSCC                                                                      10

SEQ ID NO: 693          moltype = AA  length = 10
FEATURE                 Location/Qualifiers
source                  1..10
                        mol_type = protein
```

-continued

```
                        organism = Homo sapiens
SEQUENCE: 693
VCSGASTSCC                                                              10

SEQ ID NO: 694          moltype = AA  length = 10
FEATURE                 Location/Qualifiers
source                  1..10
                        mol_type = protein
                        organism = Homo sapiens
SEQUENCE: 694
VCSGDSSCCQ                                                              10

SEQ ID NO: 695          moltype = AA  length = 10
FEATURE                 Location/Qualifiers
source                  1..10
                        mol_type = protein
                        organism = Homo sapiens
SEQUENCE: 695
VCSGISSSCC                                                              10

SEQ ID NO: 696          moltype = AA  length = 10
FEATURE                 Location/Qualifiers
source                  1..10
                        mol_type = protein
                        organism = Homo sapiens
SEQUENCE: 696
YCVPIPSCCA                                                              10

SEQ ID NO: 697          moltype = AA  length = 10
FEATURE                 Location/Qualifiers
source                  1..10
                        mol_type = protein
                        organism = Homo sapiens
SEQUENCE: 697
CASSCCTPSC                                                              10

SEQ ID NO: 698          moltype = AA  length = 10
FEATURE                 Location/Qualifiers
source                  1..10
                        mol_type = protein
                        organism = Homo sapiens
SEQUENCE: 698
CCDNCPPPCH                                                              10

SEQ ID NO: 699          moltype = AA  length = 10
FEATURE                 Location/Qualifiers
source                  1..10
                        mol_type = protein
                        organism = Homo sapiens
SEQUENCE: 699
CCEPCLPRGC                                                              10

SEQ ID NO: 700          moltype = AA  length = 10
FEATURE                 Location/Qualifiers
source                  1..10
                        mol_type = protein
                        organism = Homo sapiens
SEQUENCE: 700
CCGAASSCCR                                                              10

SEQ ID NO: 701          moltype = AA  length = 10
FEATURE                 Location/Qualifiers
source                  1..10
                        mol_type = protein
                        organism = Homo sapiens
SEQUENCE: 701
CCGCGGSGCG                                                              10

SEQ ID NO: 702          moltype = AA  length = 10
FEATURE                 Location/Qualifiers
source                  1..10
                        mol_type = protein
                        organism = Homo sapiens
SEQUENCE: 702
CCGPSSSCCQ                                                              10

SEQ ID NO: 703          moltype = AA  length = 10
FEATURE                 Location/Qualifiers
source                  1..10
```

```
                        mol_type = protein
                        organism = Homo sapiens
SEQUENCE: 703
CCGSGCGGCG                                                              10

SEQ ID NO: 704          moltype = AA  length = 10
FEATURE                 Location/Qualifiers
source                  1..10
                        mol_type = protein
                        organism = Homo sapiens
SEQUENCE: 704
CCKPYCSQCS                                                              10

SEQ ID NO: 705          moltype = AA  length = 10
FEATURE                 Location/Qualifiers
source                  1..10
                        mol_type = protein
                        organism = Homo sapiens
SEQUENCE: 705
CCMPVSSCCA                                                              10

SEQ ID NO: 706          moltype = AA  length = 10
FEATURE                 Location/Qualifiers
source                  1..10
                        mol_type = protein
                        organism = Homo sapiens
SEQUENCE: 706
CCNYYRNCCG                                                              10

SEQ ID NO: 707          moltype = AA  length = 10
FEATURE                 Location/Qualifiers
source                  1..10
                        mol_type = protein
                        organism = Homo sapiens
SEQUENCE: 707
CCPSCVVSSC                                                              10

SEQ ID NO: 708          moltype = AA  length = 10
FEATURE                 Location/Qualifiers
source                  1..10
                        mol_type = protein
                        organism = Homo sapiens
SEQUENCE: 708
CCPSYCVSSC                                                              10

SEQ ID NO: 709          moltype = AA  length = 10
FEATURE                 Location/Qualifiers
source                  1..10
                        mol_type = protein
                        organism = Homo sapiens
SEQUENCE: 709
CCQPICGSSC                                                              10

SEQ ID NO: 710          moltype = AA  length = 10
FEATURE                 Location/Qualifiers
source                  1..10
                        mol_type = protein
                        organism = Homo sapiens
SEQUENCE: 710
CCQPICVTSC                                                              10

SEQ ID NO: 711          moltype = AA  length = 10
FEATURE                 Location/Qualifiers
source                  1..10
                        mol_type = protein
                        organism = Homo sapiens
SEQUENCE: 711
CCQPTCLSSC                                                              10

SEQ ID NO: 712          moltype = AA  length = 10
FEATURE                 Location/Qualifiers
source                  1..10
                        mol_type = protein
                        organism = Homo sapiens
SEQUENCE: 712
CCQPTCLTSC                                                              10

SEQ ID NO: 713          moltype = AA  length = 10
FEATURE                 Location/Qualifiers
```

```
source                      1..10
                            mol_type = protein
                            organism = Homo sapiens
SEQUENCE: 713
CCQPTCVASC                                                                      10

SEQ ID NO: 714              moltype = AA  length = 10
FEATURE                     Location/Qualifiers
source                      1..10
                            mol_type = protein
                            organism = Homo sapiens
SEQUENCE: 714
CCQPTCVTSC                                                                      10

SEQ ID NO: 715              moltype = AA  length = 10
FEATURE                     Location/Qualifiers
source                      1..10
                            mol_type = protein
                            organism = Homo sapiens
SEQUENCE: 715
CCQPYCHPTC                                                                      10

SEQ ID NO: 716              moltype = AA  length = 10
FEATURE                     Location/Qualifiers
source                      1..10
                            mol_type = protein
                            organism = Homo sapiens
SEQUENCE: 716
CCQQSSCVSC                                                                      10

SEQ ID NO: 717              moltype = AA  length = 10
FEATURE                     Location/Qualifiers
source                      1..10
                            mol_type = protein
                            organism = Homo sapiens
SEQUENCE: 717
CCQSSCFKPC                                                                      10

SEQ ID NO: 718              moltype = AA  length = 10
FEATURE                     Location/Qualifiers
source                      1..10
                            mol_type = protein
                            organism = Homo sapiens
SEQUENCE: 718
CCQSSCSKPC                                                                      10

SEQ ID NO: 719              moltype = AA  length = 10
FEATURE                     Location/Qualifiers
source                      1..10
                            mol_type = protein
                            organism = Homo sapiens
SEQUENCE: 719
CCQSSCYKPC                                                                      10

SEQ ID NO: 720              moltype = AA  length = 10
FEATURE                     Location/Qualifiers
source                      1..10
                            mol_type = protein
                            organism = Homo sapiens
SEQUENCE: 720
CCQTICRSTC                                                                      10

SEQ ID NO: 721              moltype = AA  length = 10
FEATURE                     Location/Qualifiers
source                      1..10
                            mol_type = protein
                            organism = Homo sapiens
SEQUENCE: 721
CCQTTCHPSC                                                                      10

SEQ ID NO: 722              moltype = AA  length = 10
FEATURE                     Location/Qualifiers
source                      1..10
                            mol_type = protein
                            organism = Homo sapiens
SEQUENCE: 722
CCQTTCRPSC                                                                      10

SEQ ID NO: 723              moltype = AA  length = 10
```

```
                        FEATURE           Location/Qualifiers
                        source            1..10
                                          mol_type = protein
                                          organism = Homo sapiens
SEQUENCE: 723
CCRVPTCSCS                                                                          10

SEQ ID NO: 724          moltype = AA   length = 10
FEATURE                 Location/Qualifiers
source                  1..10
                        mol_type = protein
                        organism = Homo sapiens
SEQUENCE: 724
CCSPGCQPTC                                                                          10

SEQ ID NO: 725          moltype = AA   length = 10
FEATURE                 Location/Qualifiers
source                  1..10
                        mol_type = protein
                        organism = Homo sapiens
SEQUENCE: 725
CCSSGCGSSC                                                                          10

SEQ ID NO: 726          moltype = AA   length = 10
FEATURE                 Location/Qualifiers
source                  1..10
                        mol_type = protein
                        organism = Homo sapiens
SEQUENCE: 726
CCSSSCGSCG                                                                          10

SEQ ID NO: 727          moltype = AA   length = 10
FEATURE                 Location/Qualifiers
source                  1..10
                        mol_type = protein
                        organism = Homo sapiens
SEQUENCE: 727
CCTQEQNCCE                                                                          10

SEQ ID NO: 728          moltype = AA   length = 10
FEATURE                 Location/Qualifiers
source                  1..10
                        mol_type = protein
                        organism = Homo sapiens
SEQUENCE: 728
CCVPIPSCCA                                                                          10

SEQ ID NO: 729          moltype = AA   length = 10
FEATURE                 Location/Qualifiers
source                  1..10
                        mol_type = protein
                        organism = Homo sapiens
SEQUENCE: 729
CCVPISSCCA                                                                          10

SEQ ID NO: 730          moltype = AA   length = 10
FEATURE                 Location/Qualifiers
source                  1..10
                        mol_type = protein
                        organism = Homo sapiens
SEQUENCE: 730
CCVPVCYQCK                                                                          10

SEQ ID NO: 731          moltype = AA   length = 10
FEATURE                 Location/Qualifiers
source                  1..10
                        mol_type = protein
                        organism = Homo sapiens
SEQUENCE: 731
CCVPVPSCCA                                                                          10

SEQ ID NO: 732          moltype = AA   length = 10
FEATURE                 Location/Qualifiers
source                  1..10
                        mol_type = protein
                        organism = Homo sapiens
SEQUENCE: 732
CCVPVPSCCV                                                                          10
```

| | | |
|---|---|---|
| SEQ ID NO: 733<br>FEATURE<br>source<br><br>SEQUENCE: 733<br>CCVPVSSCCA | moltype = AA   length = 10<br>Location/Qualifiers<br>1..10<br>mol_type = protein<br>organism = Homo sapiens | <br><br><br><br><br>10 |
| SEQ ID NO: 734<br>FEATURE<br>source<br><br>SEQUENCE: 734<br>CDSSCCQPSC | moltype = AA   length = 10<br>Location/Qualifiers<br>1..10<br>mol_type = protein<br>organism = Homo sapiens | <br><br><br><br><br>10 |
| SEQ ID NO: 735<br>FEATURE<br>source<br><br>SEQUENCE: 735<br>CDTCPPPCCK | moltype = AA   length = 10<br>Location/Qualifiers<br>1..10<br>mol_type = protein<br>organism = Homo sapiens | <br><br><br><br><br>10 |
| SEQ ID NO: 736<br>FEATURE<br>source<br><br>SEQUENCE: 736<br>CEPCRRPVCC | moltype = AA   length = 10<br>Location/Qualifiers<br>1..10<br>mol_type = protein<br>organism = Homo sapiens | <br><br><br><br><br>10 |
| SEQ ID NO: 737<br>FEATURE<br>source<br><br>SEQUENCE: 737<br>CEPSCCQPVC | moltype = AA   length = 10<br>Location/Qualifiers<br>1..10<br>mol_type = protein<br>organism = Homo sapiens | <br><br><br><br><br>10 |
| SEQ ID NO: 738<br>FEATURE<br>source<br><br>SEQUENCE: 738<br>CEPSCCSAVC | moltype = AA   length = 10<br>Location/Qualifiers<br>1..10<br>mol_type = protein<br>organism = Homo sapiens | <br><br><br><br><br>10 |
| SEQ ID NO: 739<br>FEATURE<br>source<br><br>SEQUENCE: 739<br>CETSCCQPSC | moltype = AA   length = 10<br>Location/Qualifiers<br>1..10<br>mol_type = protein<br>organism = Homo sapiens | <br><br><br><br><br>10 |
| SEQ ID NO: 740<br>FEATURE<br>source<br><br>SEQUENCE: 740<br>CETTCCRTTC | moltype = AA   length = 10<br>Location/Qualifiers<br>1..10<br>mol_type = protein<br>organism = Homo sapiens | <br><br><br><br><br>10 |
| SEQ ID NO: 741<br>FEATURE<br>source<br><br>SEQUENCE: 741<br>CFSGCGSSCC | moltype = AA   length = 10<br>Location/Qualifiers<br>1..10<br>mol_type = protein<br>organism = Homo sapiens | <br><br><br><br><br>10 |
| SEQ ID NO: 742<br>FEATURE<br>source<br><br>SEQUENCE: 742<br>CGCSQSNCCK | moltype = AA   length = 10<br>Location/Qualifiers<br>1..10<br>mol_type = protein<br>organism = Homo sapiens | <br><br><br><br><br>10 |

| | | |
|---|---|---|
| SEQ ID NO: 743<br>FEATURE<br>source | moltype = AA   length = 10<br>Location/Qualifiers<br>1..10<br>mol_type = protein<br>organism = Homo sapiens | |
| SEQUENCE: 743<br>CGCSQSSCCK | | 10 |
| SEQ ID NO: 744<br>FEATURE<br>source | moltype = AA   length = 10<br>Location/Qualifiers<br>1..10<br>mol_type = protein<br>organism = Homo sapiens | |
| SEQUENCE: 744<br>CGGCGGCGGC | | 10 |
| SEQ ID NO: 745<br>FEATURE<br>source | moltype = AA   length = 10<br>Location/Qualifiers<br>1..10<br>mol_type = protein<br>organism = Homo sapiens | |
| SEQUENCE: 745<br>CGGCGGGCCG | | 10 |
| SEQ ID NO: 746<br>FEATURE<br>source | moltype = AA   length = 10<br>Location/Qualifiers<br>1..10<br>mol_type = protein<br>organism = Homo sapiens | |
| SEQUENCE: 746<br>CGGCGSGCCV | | 10 |
| SEQ ID NO: 747<br>FEATURE<br>source | moltype = AA   length = 10<br>Location/Qualifiers<br>1..10<br>mol_type = protein<br>organism = Homo sapiens | |
| SEQUENCE: 747<br>CGGCGSSCCV | | 10 |
| SEQ ID NO: 748<br>FEATURE<br>source | moltype = AA   length = 10<br>Location/Qualifiers<br>1..10<br>mol_type = protein<br>organism = Homo sapiens | |
| SEQUENCE: 748<br>CGGGCCGSSC | | 10 |
| SEQ ID NO: 749<br>FEATURE<br>source | moltype = AA   length = 10<br>Location/Qualifiers<br>1..10<br>mol_type = protein<br>organism = Homo sapiens | |
| SEQUENCE: 749<br>CGGSCCGSSC | | 10 |
| SEQ ID NO: 750<br>FEATURE<br>source | moltype = AA   length = 10<br>Location/Qualifiers<br>1..10<br>mol_type = protein<br>organism = Homo sapiens | |
| SEQUENCE: 750<br>CGQSCCRPAC | | 10 |
| SEQ ID NO: 751<br>FEATURE<br>source | moltype = AA   length = 10<br>Location/Qualifiers<br>1..10<br>mol_type = protein<br>organism = Homo sapiens | |
| SEQUENCE: 751<br>CGQSCCRPVC | | 10 |
| SEQ ID NO: 752<br>FEATURE<br>source | moltype = AA   length = 10<br>Location/Qualifiers<br>1..10<br>mol_type = protein<br>organism = Homo sapiens | |
| SEQUENCE: 752 | | |

| | | |
|---|---|---|
| CGSCGCSQCN | | 10 |
| SEQ ID NO: 753<br>FEATURE<br>source<br><br>SEQUENCE: 753<br>CGSCGCSQCS | moltype = AA  length = 10<br>Location/Qualifiers<br>1..10<br>mol_type = protein<br>organism = Homo sapiens | 10 |
| SEQ ID NO: 754<br>FEATURE<br>source<br><br>SEQUENCE: 754<br>CGSFCCQSSC | moltype = AA  length = 10<br>Location/Qualifiers<br>1..10<br>mol_type = protein<br>organism = Homo sapiens | 10 |
| SEQ ID NO: 755<br>FEATURE<br>source<br><br>SEQUENCE: 755<br>CGSGCCVPVC | moltype = AA  length = 10<br>Location/Qualifiers<br>1..10<br>mol_type = protein<br>organism = Homo sapiens | 10 |
| SEQ ID NO: 756<br>FEATURE<br>source<br><br>SEQUENCE: 756<br>CGSSCCGSGC | moltype = AA  length = 10<br>Location/Qualifiers<br>1..10<br>mol_type = protein<br>organism = Homo sapiens | 10 |
| SEQ ID NO: 757<br>FEATURE<br>source<br><br>SEQUENCE: 757<br>CGSSCCQPCY | moltype = AA  length = 10<br>Location/Qualifiers<br>1..10<br>mol_type = protein<br>organism = Homo sapiens | 10 |
| SEQ ID NO: 758<br>FEATURE<br>source<br><br>SEQUENCE: 758<br>CGSSCCQPIC | moltype = AA  length = 10<br>Location/Qualifiers<br>1..10<br>mol_type = protein<br>organism = Homo sapiens | 10 |
| SEQ ID NO: 759<br>FEATURE<br>source<br><br>SEQUENCE: 759<br>CGSSCCQPSC | moltype = AA  length = 10<br>Location/Qualifiers<br>1..10<br>mol_type = protein<br>organism = Homo sapiens | 10 |
| SEQ ID NO: 760<br>FEATURE<br>source<br><br>SEQUENCE: 760<br>CGSSCCQSSC | moltype = AA  length = 10<br>Location/Qualifiers<br>1..10<br>mol_type = protein<br>organism = Homo sapiens | 10 |
| SEQ ID NO: 761<br>FEATURE<br>source<br><br>SEQUENCE: 761<br>CGSSCCVPIC | moltype = AA  length = 10<br>Location/Qualifiers<br>1..10<br>mol_type = protein<br>organism = Homo sapiens | 10 |
| SEQ ID NO: 762<br>FEATURE<br>source | moltype = AA  length = 10<br>Location/Qualifiers<br>1..10<br>mol_type = protein<br>organism = Homo sapiens | |

-continued

| | | |
|---|---|---|
| SEQUENCE: 762<br>CGSSCCVPVC | | 10 |
| SEQ ID NO: 763<br>FEATURE<br>source | moltype = AA  length = 10<br>Location/Qualifiers<br>1..10<br>mol_type = protein<br>organism = Homo sapiens | |
| SEQUENCE: 763<br>CGSSCSQCSC | | 10 |
| SEQ ID NO: 764<br>FEATURE<br>source | moltype = AA  length = 10<br>Location/Qualifiers<br>1..10<br>mol_type = protein<br>organism = Homo sapiens | |
| SEQUENCE: 764<br>CGYGSCCGCG | | 10 |
| SEQ ID NO: 765<br>FEATURE<br>source | moltype = AA  length = 10<br>Location/Qualifiers<br>1..10<br>mol_type = protein<br>organism = Homo sapiens | |
| SEQUENCE: 765<br>CHPRCCISSC | | 10 |
| SEQ ID NO: 766<br>FEATURE<br>source | moltype = AA  length = 10<br>Location/Qualifiers<br>1..10<br>mol_type = protein<br>organism = Homo sapiens | |
| SEQUENCE: 766<br>CHPSCCESSC | | 10 |
| SEQ ID NO: 767<br>FEATURE<br>source | moltype = AA  length = 10<br>Location/Qualifiers<br>1..10<br>mol_type = protein<br>organism = Homo sapiens | |
| SEQUENCE: 767<br>CHPSCCISSC | | 10 |
| SEQ ID NO: 768<br>FEATURE<br>source | moltype = AA  length = 10<br>Location/Qualifiers<br>1..10<br>mol_type = protein<br>organism = Homo sapiens | |
| SEQUENCE: 768<br>CHPTCCQNTC | | 10 |
| SEQ ID NO: 769<br>FEATURE<br>source | moltype = AA  length = 10<br>Location/Qualifiers<br>1..10<br>mol_type = protein<br>organism = Homo sapiens | |
| SEQUENCE: 769<br>CHPTCCQTIC | | 10 |
| SEQ ID NO: 770<br>FEATURE<br>source | moltype = AA  length = 10<br>Location/Qualifiers<br>1..10<br>mol_type = protein<br>organism = Homo sapiens | |
| SEQUENCE: 770<br>CHPVCCQTTC | | 10 |
| SEQ ID NO: 771<br>FEATURE<br>source | moltype = AA  length = 10<br>Location/Qualifiers<br>1..10<br>mol_type = protein<br>organism = Homo sapiens | |
| SEQUENCE: 771<br>CHPVCKSTCC | | 10 |
| SEQ ID NO: 772<br>FEATURE<br>source | moltype = AA  length = 10<br>Location/Qualifiers<br>1..10<br>mol_type = protein | |

```
                                organism = Homo sapiens
SEQUENCE: 772
CHPVCRSTCC                                                                      10

SEQ ID NO: 773                  moltype = AA   length = 10
FEATURE                         Location/Qualifiers
source                          1..10
                                mol_type = protein
                                organism = Homo sapiens
SEQUENCE: 773
CISSCCHPSC                                                                      10

SEQ ID NO: 774                  moltype = AA   length = 10
FEATURE                         Location/Qualifiers
source                          1..10
                                mol_type = protein
                                organism = Homo sapiens
SEQUENCE: 774
CISSCCKPSC                                                                      10

SEQ ID NO: 775                  moltype = AA   length = 10
FEATURE                         Location/Qualifiers
source                          1..10
                                mol_type = protein
                                organism = Homo sapiens
SEQUENCE: 775
CISSCCRPSC                                                                      10

SEQ ID NO: 776                  moltype = AA   length = 10
FEATURE                         Location/Qualifiers
source                          1..10
                                mol_type = protein
                                organism = Homo sapiens
SEQUENCE: 776
CISSCTPSCC                                                                      10

SEQ ID NO: 777                  moltype = AA   length = 10
FEATURE                         Location/Qualifiers
source                          1..10
                                mol_type = protein
                                organism = Homo sapiens
SEQUENCE: 777
CISSSCCPSC                                                                      10

SEQ ID NO: 778                  moltype = AA   length = 10
FEATURE                         Location/Qualifiers
source                          1..10
                                mol_type = protein
                                organism = Homo sapiens
SEQUENCE: 778
CKAVCCVPTC                                                                      10

SEQ ID NO: 779                  moltype = AA   length = 10
FEATURE                         Location/Qualifiers
source                          1..10
                                mol_type = protein
                                organism = Homo sapiens
SEQUENCE: 779
CKPCCSQASC                                                                      10

SEQ ID NO: 780                  moltype = AA   length = 10
FEATURE                         Location/Qualifiers
source                          1..10
                                mol_type = protein
                                organism = Homo sapiens
SEQUENCE: 780
CKPCCSQSRC                                                                      10

SEQ ID NO: 781                  moltype = AA   length = 10
FEATURE                         Location/Qualifiers
source                          1..10
                                mol_type = protein
                                organism = Homo sapiens
SEQUENCE: 781
CKPCCSQSSC                                                                      10

SEQ ID NO: 782                  moltype = AA   length = 10
FEATURE                         Location/Qualifiers
source                          1..10
```

```
                              mol_type = protein
                              organism = Homo sapiens
SEQUENCE: 782
CKPCCSSSGC                                                                  10

SEQ ID NO: 783                moltype = AA   length = 10
FEATURE                       Location/Qualifiers
source                        1..10
                              mol_type = protein
                              organism = Homo sapiens
SEQUENCE: 783
CKPCSCFSGC                                                                  10

SEQ ID NO: 784                moltype = AA   length = 10
FEATURE                       Location/Qualifiers
source                        1..10
                              mol_type = protein
                              organism = Homo sapiens
SEQUENCE: 784
CKPCSCSSGC                                                                  10

SEQ ID NO: 785                moltype = AA   length = 10
FEATURE                       Location/Qualifiers
source                        1..10
                              mol_type = protein
                              organism = Homo sapiens
SEQUENCE: 785
CKPCYCSSGC                                                                  10

SEQ ID NO: 786                moltype = AA   length = 10
FEATURE                       Location/Qualifiers
source                        1..10
                              mol_type = protein
                              organism = Homo sapiens
SEQUENCE: 786
CKPICCVPVC                                                                  10

SEQ ID NO: 787                moltype = AA   length = 10
FEATURE                       Location/Qualifiers
source                        1..10
                              mol_type = protein
                              organism = Homo sapiens
SEQUENCE: 787
CKPQCCQSVC                                                                  10

SEQ ID NO: 788                moltype = AA   length = 10
FEATURE                       Location/Qualifiers
source                        1..10
                              mol_type = protein
                              organism = Homo sapiens
SEQUENCE: 788
CKPSCCQTTC                                                                  10

SEQ ID NO: 789                moltype = AA   length = 10
FEATURE                       Location/Qualifiers
source                        1..10
                              mol_type = protein
                              organism = Homo sapiens
SEQUENCE: 789
CKPVCCAPTC                                                                  10

SEQ ID NO: 790                moltype = AA   length = 10
FEATURE                       Location/Qualifiers
source                        1..10
                              mol_type = protein
                              organism = Homo sapiens
SEQUENCE: 790
CKPVCCKPIC                                                                  10

SEQ ID NO: 791                moltype = AA   length = 10
FEATURE                       Location/Qualifiers
source                        1..10
                              mol_type = protein
                              organism = Homo sapiens
SEQUENCE: 791
CKPVCCKSIC                                                                  10

SEQ ID NO: 792                moltype = AA   length = 10
FEATURE                       Location/Qualifiers
```

| | | |
|---|---|---|
| source | 1..10<br>mol_type = protein<br>organism = Homo sapiens | |
| SEQUENCE: 792<br>CKPVCCLPTC | | 10 |
| SEQ ID NO: 793<br>FEATURE<br>source | moltype = AA  length = 10<br>Location/Qualifiers<br>1..10<br>mol_type = protein<br>organism = Homo sapiens | |
| SEQUENCE: 793<br>CKPVCCVPTC | | 10 |
| SEQ ID NO: 794<br>FEATURE<br>source | moltype = AA  length = 10<br>Location/Qualifiers<br>1..10<br>mol_type = protein<br>organism = Homo sapiens | |
| SEQUENCE: 794<br>CKPVCCVPVC | | 10 |
| SEQ ID NO: 795<br>FEATURE<br>source | moltype = AA  length = 10<br>Location/Qualifiers<br>1..10<br>mol_type = protein<br>organism = Homo sapiens | |
| SEQUENCE: 795<br>CKPVCCVSTC | | 10 |
| SEQ ID NO: 796<br>FEATURE<br>source | moltype = AA  length = 10<br>Location/Qualifiers<br>1..10<br>mol_type = protein<br>organism = Homo sapiens | |
| SEQUENCE: 796<br>CKPYCCQSSC | | 10 |
| SEQ ID NO: 797<br>FEATURE<br>source | moltype = AA  length = 10<br>Location/Qualifiers<br>1..10<br>mol_type = protein<br>organism = Homo sapiens | |
| SEQUENCE: 797<br>CKPYCSQCSC | | 10 |
| SEQ ID NO: 798<br>FEATURE<br>source | moltype = AA  length = 10<br>Location/Qualifiers<br>1..10<br>mol_type = protein<br>organism = Homo sapiens | |
| SEQUENCE: 798<br>CKSNCCKPVC | | 10 |
| SEQ ID NO: 799<br>FEATURE<br>source | moltype = AA  length = 10<br>Location/Qualifiers<br>1..10<br>mol_type = protein<br>organism = Homo sapiens | |
| SEQUENCE: 799<br>CKTVCCKPVC | | 10 |
| SEQ ID NO: 800<br>FEATURE<br>source | moltype = AA  length = 10<br>Location/Qualifiers<br>1..10<br>mol_type = protein<br>organism = Homo sapiens | |
| SEQUENCE: 800<br>CLPPCCVVSC | | 10 |
| SEQ ID NO: 801<br>FEATURE<br>source | moltype = AA  length = 10<br>Location/Qualifiers<br>1..10<br>mol_type = protein<br>organism = Homo sapiens | |
| SEQUENCE: 801<br>CLTSCCQPSC | | 10 |
| SEQ ID NO: 802 | moltype = AA  length = 10 | |

```
FEATURE              Location/Qualifiers
source               1..10
                     mol_type = protein
                     organism = Homo sapiens
SEQUENCE: 802
CNPCCSQSSC                                                                              10

SEQ ID NO: 803       moltype = AA  length = 10
FEATURE              Location/Qualifiers
source               1..10
                     mol_type = protein
                     organism = Homo sapiens
SEQUENCE: 803
CPESCCELPC                                                                              10

SEQ ID NO: 804       moltype = AA  length = 10
FEATURE              Location/Qualifiers
source               1..10
                     mol_type = protein
                     organism = Homo sapiens
SEQUENCE: 804
CPESCCEPHC                                                                              10

SEQ ID NO: 805       moltype = AA  length = 10
FEATURE              Location/Qualifiers
source               1..10
                     mol_type = protein
                     organism = Homo sapiens
SEQUENCE: 805
CPESCCEPPC                                                                              10

SEQ ID NO: 806       moltype = AA  length = 10
FEATURE              Location/Qualifiers
source               1..10
                     mol_type = protein
                     organism = Homo sapiens
SEQUENCE: 806
CPFSCPTTCC                                                                              10

SEQ ID NO: 807       moltype = AA  length = 10
FEATURE              Location/Qualifiers
source               1..10
                     mol_type = protein
                     organism = Homo sapiens
SEQUENCE: 807
CPGDCFTCCT                                                                              10

SEQ ID NO: 808       moltype = AA  length = 10
FEATURE              Location/Qualifiers
source               1..10
                     mol_type = protein
                     organism = Homo sapiens
SEQUENCE: 808
CPSCVVSSCC                                                                              10

SEQ ID NO: 809       moltype = AA  length = 10
FEATURE              Location/Qualifiers
source               1..10
                     mol_type = protein
                     organism = Homo sapiens
SEQUENCE: 809
CPSYCVSSCC                                                                              10

SEQ ID NO: 810       moltype = AA  length = 10
FEATURE              Location/Qualifiers
source               1..10
                     mol_type = protein
                     organism = Homo sapiens
SEQUENCE: 810
CPTTCCRTTC                                                                              10

SEQ ID NO: 811       moltype = AA  length = 10
FEATURE              Location/Qualifiers
source               1..10
                     mol_type = protein
                     organism = Homo sapiens
SEQUENCE: 811
CQETCCRPSC                                                                              10
```

```
SEQ ID NO: 812            moltype = AA   length = 10
FEATURE                   Location/Qualifiers
source                    1..10
                          mol_type = protein
                          organism = Homo sapiens
SEQUENCE: 812
CQHACCVPVC                                                                10

SEQ ID NO: 813            moltype = AA   length = 10
FEATURE                   Location/Qualifiers
source                    1..10
                          mol_type = protein
                          organism = Homo sapiens
SEQUENCE: 813
CQNTCCRTTC                                                                10

SEQ ID NO: 814            moltype = AA   length = 10
FEATURE                   Location/Qualifiers
source                    1..10
                          mol_type = protein
                          organism = Homo sapiens
SEQUENCE: 814
CQPACCQPTC                                                                10

SEQ ID NO: 815            moltype = AA   length = 10
FEATURE                   Location/Qualifiers
source                    1..10
                          mol_type = protein
                          organism = Homo sapiens
SEQUENCE: 815
CQPACCTASC                                                                10

SEQ ID NO: 816            moltype = AA   length = 10
FEATURE                   Location/Qualifiers
source                    1..10
                          mol_type = protein
                          organism = Homo sapiens
SEQUENCE: 816
CQPACCTSSC                                                                10

SEQ ID NO: 817            moltype = AA   length = 10
FEATURE                   Location/Qualifiers
source                    1..10
                          mol_type = protein
                          organism = Homo sapiens
SEQUENCE: 817
CQPACCTTSC                                                                10

SEQ ID NO: 818            moltype = AA   length = 10
FEATURE                   Location/Qualifiers
source                    1..10
                          mol_type = protein
                          organism = Homo sapiens
SEQUENCE: 818
CQPACCVPVC                                                                10

SEQ ID NO: 819            moltype = AA   length = 10
FEATURE                   Location/Qualifiers
source                    1..10
                          mol_type = protein
                          organism = Homo sapiens
SEQUENCE: 819
CQPACCVSSC                                                                10

SEQ ID NO: 820            moltype = AA   length = 10
FEATURE                   Location/Qualifiers
source                    1..10
                          mol_type = protein
                          organism = Homo sapiens
SEQUENCE: 820
CQPCCHPTCY                                                                10

SEQ ID NO: 821            moltype = AA   length = 10
FEATURE                   Location/Qualifiers
source                    1..10
                          mol_type = protein
                          organism = Homo sapiens
SEQUENCE: 821
CQPCCRPTSC                                                                10
```

| | | |
|---|---|---|
| SEQ ID NO: 822<br>FEATURE<br>source<br><br>SEQUENCE: 822<br>CQPICCGSSC | moltype = AA  length = 10<br>Location/Qualifiers<br>1..10<br>mol_type = protein<br>organism = Homo sapiens | 10 |
| SEQ ID NO: 823<br>FEATURE<br>source<br><br>SEQUENCE: 823<br>CQPICGSSCC | moltype = AA  length = 10<br>Location/Qualifiers<br>1..10<br>mol_type = protein<br>organism = Homo sapiens | 10 |
| SEQ ID NO: 824<br>FEATURE<br>source<br><br>SEQUENCE: 824<br>CQPICVTSCC | moltype = AA  length = 10<br>Location/Qualifiers<br>1..10<br>mol_type = protein<br>organism = Homo sapiens | 10 |
| SEQ ID NO: 825<br>FEATURE<br>source<br><br>SEQUENCE: 825<br>CQPNCCRPSC | moltype = AA  length = 10<br>Location/Qualifiers<br>1..10<br>mol_type = protein<br>organism = Homo sapiens | 10 |
| SEQ ID NO: 826<br>FEATURE<br>source<br><br>SEQUENCE: 826<br>CQPRCCETSC | moltype = AA  length = 10<br>Location/Qualifiers<br>1..10<br>mol_type = protein<br>organism = Homo sapiens | 10 |
| SEQ ID NO: 827<br>FEATURE<br>source<br><br>SEQUENCE: 827<br>CQPSCCRPAC | moltype = AA  length = 10<br>Location/Qualifiers<br>1..10<br>mol_type = protein<br>organism = Homo sapiens | 10 |
| SEQ ID NO: 828<br>FEATURE<br>source<br><br>SEQUENCE: 828<br>CQPSCCSTPC | moltype = AA  length = 10<br>Location/Qualifiers<br>1..10<br>mol_type = protein<br>organism = Homo sapiens | 10 |
| SEQ ID NO: 829<br>FEATURE<br>source<br><br>SEQUENCE: 829<br>CQPSCCSTTC | moltype = AA  length = 10<br>Location/Qualifiers<br>1..10<br>mol_type = protein<br>organism = Homo sapiens | 10 |
| SEQ ID NO: 830<br>FEATURE<br>source<br><br>SEQUENCE: 830<br>CQPSCCVPSC | moltype = AA  length = 10<br>Location/Qualifiers<br>1..10<br>mol_type = protein<br>organism = Homo sapiens | 10 |
| SEQ ID NO: 831<br>FEATURE<br>source<br><br>SEQUENCE: 831 | moltype = AA  length = 10<br>Location/Qualifiers<br>1..10<br>mol_type = protein<br>organism = Homo sapiens | |

```
CQPSCCVSSC                                                                     10

SEQ ID NO: 832          moltype = AA  length = 10
FEATURE                 Location/Qualifiers
source                  1..10
                        mol_type = protein
                        organism = Homo sapiens
SEQUENCE: 832
CQPTCCGSSC                                                                     10

SEQ ID NO: 833          moltype = AA  length = 10
FEATURE                 Location/Qualifiers
source                  1..10
                        mol_type = protein
                        organism = Homo sapiens
SEQUENCE: 833
CQPTCCHPSC                                                                     10

SEQ ID NO: 834          moltype = AA  length = 10
FEATURE                 Location/Qualifiers
source                  1..10
                        mol_type = protein
                        organism = Homo sapiens
SEQUENCE: 834
CQPTCCQPTC                                                                     10

SEQ ID NO: 835          moltype = AA  length = 10
FEATURE                 Location/Qualifiers
source                  1..10
                        mol_type = protein
                        organism = Homo sapiens
SEQUENCE: 835
CQPTCCRPRC                                                                     10

SEQ ID NO: 836          moltype = AA  length = 10
FEATURE                 Location/Qualifiers
source                  1..10
                        mol_type = protein
                        organism = Homo sapiens
SEQUENCE: 836
CQPTCCRPSC                                                                     10

SEQ ID NO: 837          moltype = AA  length = 10
FEATURE                 Location/Qualifiers
source                  1..10
                        mol_type = protein
                        organism = Homo sapiens
SEQUENCE: 837
CQPTCCRTTC                                                                     10

SEQ ID NO: 838          moltype = AA  length = 10
FEATURE                 Location/Qualifiers
source                  1..10
                        mol_type = protein
                        organism = Homo sapiens
SEQUENCE: 838
CQPTCLSSCC                                                                     10

SEQ ID NO: 839          moltype = AA  length = 10
FEATURE                 Location/Qualifiers
source                  1..10
                        mol_type = protein
                        organism = Homo sapiens
SEQUENCE: 839
CQPTCLTSCC                                                                     10

SEQ ID NO: 840          moltype = AA  length = 10
FEATURE                 Location/Qualifiers
source                  1..10
                        mol_type = protein
                        organism = Homo sapiens
SEQUENCE: 840
CQPTCVASCC                                                                     10

SEQ ID NO: 841          moltype = AA  length = 10
FEATURE                 Location/Qualifiers
source                  1..10
                        mol_type = protein
                        organism = Homo sapiens
```

```
SEQUENCE: 841
CQPTCVTSCC                                                                          10

SEQ ID NO: 842         moltype = AA  length = 10
FEATURE                Location/Qualifiers
source                 1..10
                       mol_type = protein
                       organism = Homo sapiens
SEQUENCE: 842
CQPVCCQPTC                                                                          10

SEQ ID NO: 843         moltype = AA  length = 10
FEATURE                Location/Qualifiers
source                 1..10
                       mol_type = protein
                       organism = Homo sapiens
SEQUENCE: 843
CQPYCHPTCC                                                                          10

SEQ ID NO: 844         moltype = AA  length = 10
FEATURE                Location/Qualifiers
source                 1..10
                       mol_type = protein
                       organism = Homo sapiens
SEQUENCE: 844
CQQACCMPVC                                                                          10

SEQ ID NO: 845         moltype = AA  length = 10
FEATURE                Location/Qualifiers
source                 1..10
                       mol_type = protein
                       organism = Homo sapiens
SEQUENCE: 845
CQQACCVPIC                                                                          10

SEQ ID NO: 846         moltype = AA  length = 10
FEATURE                Location/Qualifiers
source                 1..10
                       mol_type = protein
                       organism = Homo sapiens
SEQUENCE: 846
CQQACCVPVC                                                                          10

SEQ ID NO: 847         moltype = AA  length = 10
FEATURE                Location/Qualifiers
source                 1..10
                       mol_type = protein
                       organism = Homo sapiens
SEQUENCE: 847
CQQSCCVPVC                                                                          10

SEQ ID NO: 848         moltype = AA  length = 10
FEATURE                Location/Qualifiers
source                 1..10
                       mol_type = protein
                       organism = Homo sapiens
SEQUENCE: 848
CQQSCCVSVC                                                                          10

SEQ ID NO: 849         moltype = AA  length = 10
FEATURE                Location/Qualifiers
source                 1..10
                       mol_type = protein
                       organism = Homo sapiens
SEQUENCE: 849
CQSMCCQPTC                                                                          10

SEQ ID NO: 850         moltype = AA  length = 10
FEATURE                Location/Qualifiers
source                 1..10
                       mol_type = protein
                       organism = Homo sapiens
SEQUENCE: 850
CQSNCCVPVC                                                                          10

SEQ ID NO: 851         moltype = AA  length = 10
FEATURE                Location/Qualifiers
source                 1..10
                       mol_type = protein
```

```
SEQUENCE: 851
CQSSCCKPCS                                                              10

SEQ ID NO: 852         moltype = AA   length = 10
FEATURE                Location/Qualifiers
source                 1..10
                       mol_type = protein
                       organism = Homo sapiens
SEQUENCE: 852
CQSSCCQSSC                                                              10

SEQ ID NO: 853         moltype = AA   length = 10
FEATURE                Location/Qualifiers
source                 1..10
                       mol_type = protein
                       organism = Homo sapiens
SEQUENCE: 853
CQSSCCVPVC                                                              10

SEQ ID NO: 854         moltype = AA   length = 10
FEATURE                Location/Qualifiers
source                 1..10
                       mol_type = protein
                       organism = Homo sapiens
SEQUENCE: 854
CQSSCFKPCC                                                              10

SEQ ID NO: 855         moltype = AA   length = 10
FEATURE                Location/Qualifiers
source                 1..10
                       mol_type = protein
                       organism = Homo sapiens
SEQUENCE: 855
CQSSCSKPCC                                                              10

SEQ ID NO: 856         moltype = AA   length = 10
FEATURE                Location/Qualifiers
source                 1..10
                       mol_type = protein
                       organism = Homo sapiens
SEQUENCE: 856
CQSVCCQPTC                                                              10

SEQ ID NO: 857         moltype = AA   length = 10
FEATURE                Location/Qualifiers
source                 1..10
                       mol_type = protein
                       organism = Homo sapiens
SEQUENCE: 857
CQTICRSTCC                                                              10

SEQ ID NO: 858         moltype = AA   length = 10
FEATURE                Location/Qualifiers
source                 1..10
                       mol_type = protein
                       organism = Homo sapiens
SEQUENCE: 858
CQTTCCRPSC                                                              10

SEQ ID NO: 859         moltype = AA   length = 10
FEATURE                Location/Qualifiers
source                 1..10
                       mol_type = protein
                       organism = Homo sapiens
SEQUENCE: 859
CQTTCCRTTC                                                              10

SEQ ID NO: 860         moltype = AA   length = 10
FEATURE                Location/Qualifiers
source                 1..10
                       mol_type = protein
                       organism = Homo sapiens
SEQUENCE: 860
CRATCCRPSC                                                              10

SEQ ID NO: 861         moltype = AA   length = 10
FEATURE                Location/Qualifiers
source                 1..10
```

```
                                mol_type = protein
                                organism = Homo sapiens
SEQUENCE: 861
CRGCGPSCCA                                                                       10

SEQ ID NO: 862                  moltype = AA  length = 10
FEATURE                         Location/Qualifiers
source                          1..10
                                mol_type = protein
                                organism = Homo sapiens
SEQUENCE: 862
CRPACCETTC                                                                       10

SEQ ID NO: 863                  moltype = AA  length = 10
FEATURE                         Location/Qualifiers
source                          1..10
                                mol_type = protein
                                organism = Homo sapiens
SEQUENCE: 863
CRPACCQNTC                                                                       10

SEQ ID NO: 864                  moltype = AA  length = 10
FEATURE                         Location/Qualifiers
source                          1..10
                                mol_type = protein
                                organism = Homo sapiens
SEQUENCE: 864
CRPCCWATTC                                                                       10

SEQ ID NO: 865                  moltype = AA  length = 10
FEATURE                         Location/Qualifiers
source                          1..10
                                mol_type = protein
                                organism = Homo sapiens
SEQUENCE: 865
CRPICRPACC                                                                       10

SEQ ID NO: 866                  moltype = AA  length = 10
FEATURE                         Location/Qualifiers
source                          1..10
                                mol_type = protein
                                organism = Homo sapiens
SEQUENCE: 866
CRPLCCQTTC                                                                       10

SEQ ID NO: 867                  moltype = AA  length = 10
FEATURE                         Location/Qualifiers
source                          1..10
                                mol_type = protein
                                organism = Homo sapiens
SEQUENCE: 867
CRPQCCQSVC                                                                       10

SEQ ID NO: 868                  moltype = AA  length = 10
FEATURE                         Location/Qualifiers
source                          1..10
                                mol_type = protein
                                organism = Homo sapiens
SEQUENCE: 868
CRPQCCQTTC                                                                       10

SEQ ID NO: 869                  moltype = AA  length = 10
FEATURE                         Location/Qualifiers
source                          1..10
                                mol_type = protein
                                organism = Homo sapiens
SEQUENCE: 869
CRPRCCISSC                                                                       10

SEQ ID NO: 870                  moltype = AA  length = 10
FEATURE                         Location/Qualifiers
source                          1..10
                                mol_type = protein
                                organism = Homo sapiens
SEQUENCE: 870
CRPSCCESSC                                                                       10

SEQ ID NO: 871                  moltype = AA  length = 10
FEATURE                         Location/Qualifiers
```

```
source                      1..10
                            mol_type = protein
                            organism = Homo sapiens
SEQUENCE: 871
CRPSCCETTC                                                           10

SEQ ID NO: 872              moltype = AA   length = 10
FEATURE                     Location/Qualifiers
source                      1..10
                            mol_type = protein
                            organism = Homo sapiens
SEQUENCE: 872
CRPSCCISSC                                                           10

SEQ ID NO: 873              moltype = AA   length = 10
FEATURE                     Location/Qualifiers
source                      1..10
                            mol_type = protein
                            organism = Homo sapiens
SEQUENCE: 873
CRPSCCKPQC                                                           10

SEQ ID NO: 874              moltype = AA   length = 10
FEATURE                     Location/Qualifiers
source                      1..10
                            mol_type = protein
                            organism = Homo sapiens
SEQUENCE: 874
CRPSCCMSSC                                                           10

SEQ ID NO: 875              moltype = AA   length = 10
FEATURE                     Location/Qualifiers
source                      1..10
                            mol_type = protein
                            organism = Homo sapiens
SEQUENCE: 875
CRPSCCQTTC                                                           10

SEQ ID NO: 876              moltype = AA   length = 10
FEATURE                     Location/Qualifiers
source                      1..10
                            mol_type = protein
                            organism = Homo sapiens
SEQUENCE: 876
CRPSCCRPSC                                                           10

SEQ ID NO: 877              moltype = AA   length = 10
FEATURE                     Location/Qualifiers
source                      1..10
                            mol_type = protein
                            organism = Homo sapiens
SEQUENCE: 877
CRPSCCVSRC                                                           10

SEQ ID NO: 878              moltype = AA   length = 10
FEATURE                     Location/Qualifiers
source                      1..10
                            mol_type = protein
                            organism = Homo sapiens
SEQUENCE: 878
CRPSCCVSSC                                                           10

SEQ ID NO: 879              moltype = AA   length = 10
FEATURE                     Location/Qualifiers
source                      1..10
                            mol_type = protein
                            organism = Homo sapiens
SEQUENCE: 879
CRPTCCETTC                                                           10

SEQ ID NO: 880              moltype = AA   length = 10
FEATURE                     Location/Qualifiers
source                      1..10
                            mol_type = protein
                            organism = Homo sapiens
SEQUENCE: 880
CRPTCCQNTC                                                           10

SEQ ID NO: 881              moltype = AA   length = 10
```

```
FEATURE                 Location/Qualifiers
source                  1..10
                        mol_type = protein
                        organism = Homo sapiens
SEQUENCE: 881
CRPTCCQTTC                                                                      10

SEQ ID NO: 882          moltype = AA  length = 10
FEATURE                 Location/Qualifiers
source                  1..10
                        mol_type = protein
                        organism = Homo sapiens
SEQUENCE: 882
CRPVCCDPCS                                                                      10

SEQ ID NO: 883          moltype = AA  length = 10
FEATURE                 Location/Qualifiers
source                  1..10
                        mol_type = protein
                        organism = Homo sapiens
SEQUENCE: 883
CRPVCCQTTC                                                                      10

SEQ ID NO: 884          moltype = AA  length = 10
FEATURE                 Location/Qualifiers
source                  1..10
                        mol_type = protein
                        organism = Homo sapiens
SEQUENCE: 884
CRPVCQPACC                                                                      10

SEQ ID NO: 885          moltype = AA  length = 10
FEATURE                 Location/Qualifiers
source                  1..10
                        mol_type = protein
                        organism = Homo sapiens
SEQUENCE: 885
CRPVCRPACC                                                                      10

SEQ ID NO: 886          moltype = AA  length = 10
FEATURE                 Location/Qualifiers
source                  1..10
                        mol_type = protein
                        organism = Homo sapiens
SEQUENCE: 886
CRPVCRPTCC                                                                      10

SEQ ID NO: 887          moltype = AA  length = 10
FEATURE                 Location/Qualifiers
source                  1..10
                        mol_type = protein
                        organism = Homo sapiens
SEQUENCE: 887
CRPVCRSTCC                                                                      10

SEQ ID NO: 888          moltype = AA  length = 10
FEATURE                 Location/Qualifiers
source                  1..10
                        mol_type = protein
                        organism = Homo sapiens
SEQUENCE: 888
CRPYCCESSC                                                                      10

SEQ ID NO: 889          moltype = AA  length = 10
FEATURE                 Location/Qualifiers
source                  1..10
                        mol_type = protein
                        organism = Homo sapiens
SEQUENCE: 889
CRRPVCCDPC                                                                      10

SEQ ID NO: 890          moltype = AA  length = 10
FEATURE                 Location/Qualifiers
source                  1..10
                        mol_type = protein
                        organism = Homo sapiens
SEQUENCE: 890
CRSQCCQSVC                                                                      10
```

| | | |
|---|---|---|
| SEQ ID NO: 891<br>FEATURE<br>source | moltype = AA   length = 10<br>Location/Qualifiers<br>1..10<br>mol_type = protein<br>organism = Homo sapiens | |
| SEQUENCE: 891<br>CRTTCCHPSC | | 10 |
| SEQ ID NO: 892<br>FEATURE<br>source | moltype = AA   length = 10<br>Location/Qualifiers<br>1..10<br>mol_type = protein<br>organism = Homo sapiens | |
| SEQUENCE: 892<br>CRTTCCQPIC | | 10 |
| SEQ ID NO: 893<br>FEATURE<br>source | moltype = AA   length = 10<br>Location/Qualifiers<br>1..10<br>mol_type = protein<br>organism = Homo sapiens | |
| SEQUENCE: 893<br>CRTTCCQPTC | | 10 |
| SEQ ID NO: 894<br>FEATURE<br>source | moltype = AA   length = 10<br>Location/Qualifiers<br>1..10<br>mol_type = protein<br>organism = Homo sapiens | |
| SEQUENCE: 894<br>CRTTCCRPSC | | 10 |
| SEQ ID NO: 895<br>FEATURE<br>source | moltype = AA   length = 10<br>Location/Qualifiers<br>1..10<br>mol_type = protein<br>organism = Homo sapiens | |
| SEQUENCE: 895<br>CRTTCCRTTC | | 10 |
| SEQ ID NO: 896<br>FEATURE<br>source | moltype = AA   length = 10<br>Location/Qualifiers<br>1..10<br>mol_type = protein<br>organism = Homo sapiens | |
| SEQUENCE: 896<br>CSCSSCGSCA | | 10 |
| SEQ ID NO: 897<br>FEATURE<br>source | moltype = AA   length = 10<br>Location/Qualifiers<br>1..10<br>mol_type = protein<br>organism = Homo sapiens | |
| SEQUENCE: 897<br>CSCSSCGSCG | | 10 |
| SEQ ID NO: 898<br>FEATURE<br>source | moltype = AA   length = 10<br>Location/Qualifiers<br>1..10<br>mol_type = protein<br>organism = Homo sapiens | |
| SEQUENCE: 898<br>CSCTSCGSCG | | 10 |
| SEQ ID NO: 899<br>FEATURE<br>source | moltype = AA   length = 10<br>Location/Qualifiers<br>1..10<br>mol_type = protein<br>organism = Homo sapiens | |
| SEQUENCE: 899<br>CSPACQPTCC | | 10 |
| SEQ ID NO: 900<br>FEATURE<br>source | moltype = AA   length = 10<br>Location/Qualifiers<br>1..10<br>mol_type = protein<br>organism = Homo sapiens | |
| SEQUENCE: 900<br>CSPGCQPTCC | | 10 |

| | | |
|---|---|---|
| SEQ ID NO: 901<br>FEATURE<br>source | moltype = AA   length = 10<br>Location/Qualifiers<br>1..10<br>mol_type = protein<br>organism = Homo sapiens | |
| SEQUENCE: 901<br>CSPSCCQTTC | | 10 |
| SEQ ID NO: 902<br>FEATURE<br>source | moltype = AA   length = 10<br>Location/Qualifiers<br>1..10<br>mol_type = protein<br>organism = Homo sapiens | |
| SEQUENCE: 902<br>CSQCSCYKPC | | 10 |
| SEQ ID NO: 903<br>FEATURE<br>source | moltype = AA   length = 10<br>Location/Qualifiers<br>1..10<br>mol_type = protein<br>organism = Homo sapiens | |
| SEQUENCE: 903<br>CSQSNCCKPC | | 10 |
| SEQ ID NO: 904<br>FEATURE<br>source | moltype = AA   length = 10<br>Location/Qualifiers<br>1..10<br>mol_type = protein<br>organism = Homo sapiens | |
| SEQUENCE: 904<br>CSQSSCCKPC | | 10 |
| SEQ ID NO: 905<br>FEATURE<br>source | moltype = AA   length = 10<br>Location/Qualifiers<br>1..10<br>mol_type = protein<br>organism = Homo sapiens | |
| SEQUENCE: 905<br>CSSGCGSCCQ | | 10 |
| SEQ ID NO: 906<br>FEATURE<br>source | moltype = AA   length = 10<br>Location/Qualifiers<br>1..10<br>mol_type = protein<br>organism = Homo sapiens | |
| SEQUENCE: 906<br>CSSGCGSSCC | | 10 |
| SEQ ID NO: 907<br>FEATURE<br>source | moltype = AA   length = 10<br>Location/Qualifiers<br>1..10<br>mol_type = protein<br>organism = Homo sapiens | |
| SEQUENCE: 907<br>CSSGCQPACC | | 10 |
| SEQ ID NO: 908<br>FEATURE<br>source | moltype = AA   length = 10<br>Location/Qualifiers<br>1..10<br>mol_type = protein<br>organism = Homo sapiens | |
| SEQUENCE: 908<br>CSSSCCQPSC | | 10 |
| SEQ ID NO: 909<br>FEATURE<br>source | moltype = AA   length = 10<br>Location/Qualifiers<br>1..10<br>mol_type = protein<br>organism = Homo sapiens | |
| SEQUENCE: 909<br>CSTPCCQPTC | | 10 |
| SEQ ID NO: 910<br>FEATURE<br>source | moltype = AA   length = 10<br>Location/Qualifiers<br>1..10<br>mol_type = protein<br>organism = Homo sapiens | |
| SEQUENCE: 910 | | |

```
CSTTCCQPIC                                                                               10

SEQ ID NO: 911           moltype = AA  length = 10
FEATURE                  Location/Qualifiers
source                   1..10
                         mol_type = protein
                         organism = Homo sapiens
SEQUENCE: 911
CTAVVCRPCC                                                                               10

SEQ ID NO: 912           moltype = AA  length = 10
FEATURE                  Location/Qualifiers
source                   1..10
                         mol_type = protein
                         organism = Homo sapiens
SEQUENCE: 912
CTDSCTPSCC                                                                               10

SEQ ID NO: 913           moltype = AA  length = 10
FEATURE                  Location/Qualifiers
source                   1..10
                         mol_type = protein
                         organism = Homo sapiens
SEQUENCE: 913
CTPSCCQPAC                                                                               10

SEQ ID NO: 914           moltype = AA  length = 10
FEATURE                  Location/Qualifiers
source                   1..10
                         mol_type = protein
                         organism = Homo sapiens
SEQUENCE: 914
CTRPICEPCC                                                                               10

SEQ ID NO: 915           moltype = AA  length = 10
FEATURE                  Location/Qualifiers
source                   1..10
                         mol_type = protein
                         organism = Homo sapiens
SEQUENCE: 915
CTSSCTPSCC                                                                               10

SEQ ID NO: 916           moltype = AA  length = 10
FEATURE                  Location/Qualifiers
source                   1..10
                         mol_type = protein
                         organism = Homo sapiens
SEQUENCE: 916
CVPACSCSSC                                                                               10

SEQ ID NO: 917           moltype = AA  length = 10
FEATURE                  Location/Qualifiers
source                   1..10
                         mol_type = protein
                         organism = Homo sapiens
SEQUENCE: 917
CVPACSCTSC                                                                               10

SEQ ID NO: 918           moltype = AA  length = 10
FEATURE                  Location/Qualifiers
source                   1..10
                         mol_type = protein
                         organism = Homo sapiens
SEQUENCE: 918
CVPVCCKPVC                                                                               10

SEQ ID NO: 919           moltype = AA  length = 10
FEATURE                  Location/Qualifiers
source                   1..10
                         mol_type = protein
                         organism = Homo sapiens
SEQUENCE: 919
CVPVCCVPTC                                                                               10

SEQ ID NO: 920           moltype = AA  length = 10
FEATURE                  Location/Qualifiers
source                   1..10
                         mol_type = protein
                         organism = Homo sapiens
```

```
SEQUENCE: 920
CVPVCCVPVC                                                                              10

SEQ ID NO: 921          moltype = AA  length = 10
FEATURE                 Location/Qualifiers
source                  1..10
                        mol_type = protein
                        organism = Homo sapiens
SEQUENCE: 921
CVSCVSSPCC                                                                              10

SEQ ID NO: 922          moltype = AA  length = 10
FEATURE                 Location/Qualifiers
source                  1..10
                        mol_type = protein
                        organism = Homo sapiens
SEQUENCE: 922
CVSRCCRPQC                                                                              10

SEQ ID NO: 923          moltype = AA  length = 10
FEATURE                 Location/Qualifiers
source                  1..10
                        mol_type = protein
                        organism = Homo sapiens
SEQUENCE: 923
CVSSCCKPQC                                                                              10

SEQ ID NO: 924          moltype = AA  length = 10
FEATURE                 Location/Qualifiers
source                  1..10
                        mol_type = protein
                        organism = Homo sapiens
SEQUENCE: 924
CVSSCCQHSC                                                                              10

SEQ ID NO: 925          moltype = AA  length = 10
FEATURE                 Location/Qualifiers
source                  1..10
                        mol_type = protein
                        organism = Homo sapiens
SEQUENCE: 925
CVSSCCQPFC                                                                              10

SEQ ID NO: 926          moltype = AA  length = 10
FEATURE                 Location/Qualifiers
source                  1..10
                        mol_type = protein
                        organism = Homo sapiens
SEQUENCE: 926
CVSSCCQPSC                                                                              10

SEQ ID NO: 927          moltype = AA  length = 10
FEATURE                 Location/Qualifiers
source                  1..10
                        mol_type = protein
                        organism = Homo sapiens
SEQUENCE: 927
CVSSCCRPQC                                                                              10

SEQ ID NO: 928          moltype = AA  length = 10
FEATURE                 Location/Qualifiers
source                  1..10
                        mol_type = protein
                        organism = Homo sapiens
SEQUENCE: 928
CVSTCCRPTC                                                                              10

SEQ ID NO: 929          moltype = AA  length = 10
FEATURE                 Location/Qualifiers
source                  1..10
                        mol_type = protein
                        organism = Homo sapiens
SEQUENCE: 929
CVTRCCSTPC                                                                              10

SEQ ID NO: 930          moltype = AA  length = 10
FEATURE                 Location/Qualifiers
source                  1..10
                        mol_type = protein
```

```
                                organism = Homo sapiens
SEQUENCE: 930
CVTSCCQPAC                                                                              10

SEQ ID NO: 931          moltype = AA  length = 10
FEATURE                 Location/Qualifiers
source                  1..10
                        mol_type = protein
                        organism = Homo sapiens
SEQUENCE: 931
CVTSCCQPSC                                                                              10

SEQ ID NO: 932          moltype = AA  length = 10
FEATURE                 Location/Qualifiers
source                  1..10
                        mol_type = protein
                        organism = Homo sapiens
SEQUENCE: 932
CVYSCCQPFC                                                                              10

SEQ ID NO: 933          moltype = AA  length = 10
FEATURE                 Location/Qualifiers
source                  1..10
                        mol_type = protein
                        organism = Homo sapiens
SEQUENCE: 933
CVYSCCQPSC                                                                              10

SEQ ID NO: 934          moltype = AA  length = 10
FEATURE                 Location/Qualifiers
source                  1..10
                        mol_type = protein
                        organism = Homo sapiens
SEQUENCE: 934
GCCGCSEGCG                                                                              10

SEQ ID NO: 935          moltype = AA  length = 10
FEATURE                 Location/Qualifiers
source                  1..10
                        mol_type = protein
                        organism = Homo sapiens
SEQUENCE: 935
GCCGCSGGCG                                                                              10

SEQ ID NO: 936          moltype = AA  length = 10
FEATURE                 Location/Qualifiers
source                  1..10
                        mol_type = protein
                        organism = Homo sapiens
SEQUENCE: 936
GCCGCSRGCG                                                                              10

SEQ ID NO: 937          moltype = AA  length = 10
FEATURE                 Location/Qualifiers
source                  1..10
                        mol_type = protein
                        organism = Homo sapiens
SEQUENCE: 937
GCCRPITCCP                                                                              10

SEQ ID NO: 938          moltype = AA  length = 10
FEATURE                 Location/Qualifiers
source                  1..10
                        mol_type = protein
                        organism = Homo sapiens
SEQUENCE: 938
GCGSSCCQCS                                                                              10

SEQ ID NO: 939          moltype = AA  length = 10
FEATURE                 Location/Qualifiers
source                  1..10
                        mol_type = protein
                        organism = Homo sapiens
SEQUENCE: 939
GCGVPVCCCS                                                                              10

SEQ ID NO: 940          moltype = AA  length = 10
FEATURE                 Location/Qualifiers
source                  1..10
```

```
                        mol_type = protein
                        organism = Homo sapiens
SEQUENCE: 940
LCCPCQTTCS                                                              10

SEQ ID NO: 941          moltype = AA  length = 10
FEATURE                 Location/Qualifiers
source                  1..10
                        mol_type = protein
                        organism = Homo sapiens
SEQUENCE: 941
PCCCLRPVCG                                                              10

SEQ ID NO: 942          moltype = AA  length = 10
FEATURE                 Location/Qualifiers
source                  1..10
                        mol_type = protein
                        organism = Homo sapiens
SEQUENCE: 942
PCCCRPVTCQ                                                              10

SEQ ID NO: 943          moltype = AA  length = 10
FEATURE                 Location/Qualifiers
source                  1..10
                        mol_type = protein
                        organism = Homo sapiens
SEQUENCE: 943
PCCCVRPVCG                                                              10

SEQ ID NO: 944          moltype = AA  length = 10
FEATURE                 Location/Qualifiers
source                  1..10
                        mol_type = protein
                        organism = Homo sapiens
SEQUENCE: 944
PCCSQASCCV                                                              10

SEQ ID NO: 945          moltype = AA  length = 10
FEATURE                 Location/Qualifiers
source                  1..10
                        mol_type = protein
                        organism = Homo sapiens
SEQUENCE: 945
PCCSQSRCCV                                                              10

SEQ ID NO: 946          moltype = AA  length = 10
FEATURE                 Location/Qualifiers
source                  1..10
                        mol_type = protein
                        organism = Homo sapiens
SEQUENCE: 946
PCCSQSSCCK                                                              10

SEQ ID NO: 947          moltype = AA  length = 10
FEATURE                 Location/Qualifiers
source                  1..10
                        mol_type = protein
                        organism = Homo sapiens
SEQUENCE: 947
PCCSQSSCCV                                                              10

SEQ ID NO: 948          moltype = AA  length = 10
FEATURE                 Location/Qualifiers
source                  1..10
                        mol_type = protein
                        organism = Homo sapiens
SEQUENCE: 948
PCCWATTCCQ                                                              10

SEQ ID NO: 949          moltype = AA  length = 10
FEATURE                 Location/Qualifiers
source                  1..10
                        mol_type = protein
                        organism = Homo sapiens
SEQUENCE: 949
QCSCCKPYCS                                                              10

SEQ ID NO: 950          moltype = AA  length = 10
FEATURE                 Location/Qualifiers
```

```
source                    1..10
                          mol_type = protein
                          organism = Homo sapiens
SEQUENCE: 950
RCYVPVCCCK                                                                      10

SEQ ID NO: 951            moltype = AA  length = 10
FEATURE                   Location/Qualifiers
source                    1..10
                          mol_type = protein
                          organism = Homo sapiens
SEQUENCE: 951
SCCAPVYCCK                                                                      10

SEQ ID NO: 952            moltype = AA  length = 10
FEATURE                   Location/Qualifiers
source                    1..10
                          mol_type = protein
                          organism = Homo sapiens
SEQUENCE: 952
SCCISSSCCP                                                                      10

SEQ ID NO: 953            moltype = AA  length = 10
FEATURE                   Location/Qualifiers
source                    1..10
                          mol_type = protein
                          organism = Homo sapiens
SEQUENCE: 953
SCCVSSCRCP                                                                      10

SEQ ID NO: 954            moltype = AA  length = 10
FEATURE                   Location/Qualifiers
source                    1..10
                          mol_type = protein
                          organism = Homo sapiens
SEQUENCE: 954
SCGCSQCSCY                                                                      10

SEQ ID NO: 955            moltype = AA  length = 10
FEATURE                   Location/Qualifiers
source                    1..10
                          mol_type = protein
                          organism = Homo sapiens
SEQUENCE: 955
SCGLENCCCP                                                                      10

SEQ ID NO: 956            moltype = AA  length = 10
FEATURE                   Location/Qualifiers
source                    1..10
                          mol_type = protein
                          organism = Homo sapiens
SEQUENCE: 956
VCCGASSCCQ                                                                      10

SEQ ID NO: 957            moltype = AA  length = 10
FEATURE                   Location/Qualifiers
source                    1..10
                          mol_type = protein
                          organism = Homo sapiens
SEQUENCE: 957
VCCGDSSCCQ                                                                      10

SEQ ID NO: 958            moltype = AA  length = 11
FEATURE                   Location/Qualifiers
source                    1..11
                          mol_type = protein
                          organism = Homo sapiens
SEQUENCE: 958
CASSCCTPSC C                                                                    11

SEQ ID NO: 959            moltype = AA  length = 11
FEATURE                   Location/Qualifiers
source                    1..11
                          mol_type = protein
                          organism = Homo sapiens
SEQUENCE: 959
CCCPSCVVSS C                                                                    11

SEQ ID NO: 960            moltype = AA  length = 11
```

```
FEATURE              Location/Qualifiers
source               1..11
                     mol_type = protein
                     organism = Homo sapiens
SEQUENCE: 960
CCCPSYCVSS C                                                              11

SEQ ID NO: 961       moltype = AA  length = 11
FEATURE              Location/Qualifiers
source               1..11
                     mol_type = protein
                     organism = Homo sapiens
SEQUENCE: 961
CCCSSGCGSS C                                                              11

SEQ ID NO: 962       moltype = AA  length = 11
FEATURE              Location/Qualifiers
source               1..11
                     mol_type = protein
                     organism = Homo sapiens
SEQUENCE: 962
CCDTCPPPCC K                                                              11

SEQ ID NO: 963       moltype = AA  length = 11
FEATURE              Location/Qualifiers
source               1..11
                     mol_type = protein
                     organism = Homo sapiens
SEQUENCE: 963
CCEPHCCALS C                                                              11

SEQ ID NO: 964       moltype = AA  length = 11
FEATURE              Location/Qualifiers
source               1..11
                     mol_type = protein
                     organism = Homo sapiens
SEQUENCE: 964
CCEPPCCAPS C                                                              11

SEQ ID NO: 965       moltype = AA  length = 11
FEATURE              Location/Qualifiers
source               1..11
                     mol_type = protein
                     organism = Homo sapiens
SEQUENCE: 965
CCEPPCCATS C                                                              11

SEQ ID NO: 966       moltype = AA  length = 11
FEATURE              Location/Qualifiers
source               1..11
                     mol_type = protein
                     organism = Homo sapiens
SEQUENCE: 966
CCETSCCQPS C                                                              11

SEQ ID NO: 967       moltype = AA  length = 11
FEATURE              Location/Qualifiers
source               1..11
                     mol_type = protein
                     organism = Homo sapiens
SEQUENCE: 967
CCGSSCCGSG C                                                              11

SEQ ID NO: 968       moltype = AA  length = 11
FEATURE              Location/Qualifiers
source               1..11
                     mol_type = protein
                     organism = Homo sapiens
SEQUENCE: 968
CCGSSCCGSS C                                                              11

SEQ ID NO: 969       moltype = AA  length = 11
FEATURE              Location/Qualifiers
source               1..11
                     mol_type = protein
                     organism = Homo sapiens
SEQUENCE: 969
CCHPRCCISS C                                                              11
```

| | | |
|---|---|---|
| SEQ ID NO: 970<br>FEATURE<br>source | moltype = AA   length = 11<br>Location/Qualifiers<br>1..11<br>mol_type = protein<br>organism = Homo sapiens | |
| SEQUENCE: 970<br>CCHPSCCESS C | | 11 |
| SEQ ID NO: 971<br>FEATURE<br>source | moltype = AA   length = 11<br>Location/Qualifiers<br>1..11<br>mol_type = protein<br>organism = Homo sapiens | |
| SEQUENCE: 971<br>CCHPSCCISS C | | 11 |
| SEQ ID NO: 972<br>FEATURE<br>source | moltype = AA   length = 11<br>Location/Qualifiers<br>1..11<br>mol_type = protein<br>organism = Homo sapiens | |
| SEQUENCE: 972<br>CCHPSCCVSS C | | 11 |
| SEQ ID NO: 973<br>FEATURE<br>source | moltype = AA   length = 11<br>Location/Qualifiers<br>1..11<br>mol_type = protein<br>organism = Homo sapiens | |
| SEQUENCE: 973<br>CCHPTCCQNT C | | 11 |
| SEQ ID NO: 974<br>FEATURE<br>source | moltype = AA   length = 11<br>Location/Qualifiers<br>1..11<br>mol_type = protein<br>organism = Homo sapiens | |
| SEQUENCE: 974<br>CCHPTCCQTI C | | 11 |
| SEQ ID NO: 975<br>FEATURE<br>source | moltype = AA   length = 11<br>Location/Qualifiers<br>1..11<br>mol_type = protein<br>organism = Homo sapiens | |
| SEQUENCE: 975<br>CCISSCCKPS C | | 11 |
| SEQ ID NO: 976<br>FEATURE<br>source | moltype = AA   length = 11<br>Location/Qualifiers<br>1..11<br>mol_type = protein<br>organism = Homo sapiens | |
| SEQUENCE: 976<br>CCISSCCRPS C | | 11 |
| SEQ ID NO: 977<br>FEATURE<br>source | moltype = AA   length = 11<br>Location/Qualifiers<br>1..11<br>mol_type = protein<br>organism = Homo sapiens | |
| SEQUENCE: 977<br>CCISSSCCPS C | | 11 |
| SEQ ID NO: 978<br>FEATURE<br>source | moltype = AA   length = 11<br>Location/Qualifiers<br>1..11<br>mol_type = protein<br>organism = Homo sapiens | |
| SEQUENCE: 978<br>CCKAVCCVPT C | | 11 |
| SEQ ID NO: 979<br>FEATURE<br>source | moltype = AA   length = 11<br>Location/Qualifiers<br>1..11<br>mol_type = protein<br>organism = Homo sapiens | |
| SEQUENCE: 979<br>CCKPCCSQAS C | | 11 |

```
SEQ ID NO: 980         moltype = AA   length = 11
FEATURE                Location/Qualifiers
source                 1..11
                       mol_type = protein
                       organism = Homo sapiens
SEQUENCE: 980
CCKPCCSQSR C                                                                11

SEQ ID NO: 981         moltype = AA   length = 11
FEATURE                Location/Qualifiers
source                 1..11
                       mol_type = protein
                       organism = Homo sapiens
SEQUENCE: 981
CCKPCCSQSS C                                                                11

SEQ ID NO: 982         moltype = AA   length = 11
FEATURE                Location/Qualifiers
source                 1..11
                       mol_type = protein
                       organism = Homo sapiens
SEQUENCE: 982
CCKPCCSSSG C                                                                11

SEQ ID NO: 983         moltype = AA   length = 11
FEATURE                Location/Qualifiers
source                 1..11
                       mol_type = protein
                       organism = Homo sapiens
SEQUENCE: 983
CCKPCSCFSG C                                                                11

SEQ ID NO: 984         moltype = AA   length = 11
FEATURE                Location/Qualifiers
source                 1..11
                       mol_type = protein
                       organism = Homo sapiens
SEQUENCE: 984
CCKPCSCSSG C                                                                11

SEQ ID NO: 985         moltype = AA   length = 11
FEATURE                Location/Qualifiers
source                 1..11
                       mol_type = protein
                       organism = Homo sapiens
SEQUENCE: 985
CCKPCYCSSG C                                                                11

SEQ ID NO: 986         moltype = AA   length = 11
FEATURE                Location/Qualifiers
source                 1..11
                       mol_type = protein
                       organism = Homo sapiens
SEQUENCE: 986
CCKPICCVPV C                                                                11

SEQ ID NO: 987         moltype = AA   length = 11
FEATURE                Location/Qualifiers
source                 1..11
                       mol_type = protein
                       organism = Homo sapiens
SEQUENCE: 987
CCKPQCCQSV C                                                                11

SEQ ID NO: 988         moltype = AA   length = 11
FEATURE                Location/Qualifiers
source                 1..11
                       mol_type = protein
                       organism = Homo sapiens
SEQUENCE: 988
CCKPVCCKPI C                                                                11

SEQ ID NO: 989         moltype = AA   length = 11
FEATURE                Location/Qualifiers
source                 1..11
                       mol_type = protein
                       organism = Homo sapiens
SEQUENCE: 989
```

CCKPYCCQSS C                                                                      11

SEQ ID NO: 990           moltype = AA   length = 11
FEATURE                  Location/Qualifiers
source                   1..11
                         mol_type = protein
                         organism = Homo sapiens
SEQUENCE: 990
CCKPYCSQCS C                                                                      11

SEQ ID NO: 991           moltype = AA   length = 11
FEATURE                  Location/Qualifiers
source                   1..11
                         mol_type = protein
                         organism = Homo sapiens
SEQUENCE: 991
CCMPVCCKPV C                                                                      11

SEQ ID NO: 992           moltype = AA   length = 11
FEATURE                  Location/Qualifiers
source                   1..11
                         mol_type = protein
                         organism = Homo sapiens
SEQUENCE: 992
CCMPVCCKTV C                                                                      11

SEQ ID NO: 993           moltype = AA   length = 11
FEATURE                  Location/Qualifiers
source                   1..11
                         mol_type = protein
                         organism = Homo sapiens
SEQUENCE: 993
CCMSSCCKPQ C                                                                      11

SEQ ID NO: 994           moltype = AA   length = 11
FEATURE                  Location/Qualifiers
source                   1..11
                         mol_type = protein
                         organism = Homo sapiens
SEQUENCE: 994
CCNPCCSQSS C                                                                      11

SEQ ID NO: 995           moltype = AA   length = 11
FEATURE                  Location/Qualifiers
source                   1..11
                         mol_type = protein
                         organism = Homo sapiens
SEQUENCE: 995
CCPGDCFTCC T                                                                      11

SEQ ID NO: 996           moltype = AA   length = 11
FEATURE                  Location/Qualifiers
source                   1..11
                         mol_type = protein
                         organism = Homo sapiens
SEQUENCE: 996
CCPSCVVSSC C                                                                      11

SEQ ID NO: 997           moltype = AA   length = 11
FEATURE                  Location/Qualifiers
source                   1..11
                         mol_type = protein
                         organism = Homo sapiens
SEQUENCE: 997
CCPSYCVSSC C                                                                      11

SEQ ID NO: 998           moltype = AA   length = 11
FEATURE                  Location/Qualifiers
source                   1..11
                         mol_type = protein
                         organism = Homo sapiens
SEQUENCE: 998
CCQNTCCRTT C                                                                      11

SEQ ID NO: 999           moltype = AA   length = 11
FEATURE                  Location/Qualifiers
source                   1..11
                         mol_type = protein
                         organism = Homo sapiens

```
SEQUENCE: 999
CCQPACCVSS C                                                                                   11

SEQ ID NO: 1000         moltype = AA  length = 11
FEATURE                 Location/Qualifiers
source                  1..11
                        mol_type = protein
                        organism = Homo sapiens
SEQUENCE: 1000
CCQPCCHPTC Y                                                                                   11

SEQ ID NO: 1001         moltype = AA  length = 11
FEATURE                 Location/Qualifiers
source                  1..11
                        mol_type = protein
                        organism = Homo sapiens
SEQUENCE: 1001
CCQPCCRPTS C                                                                                   11

SEQ ID NO: 1002         moltype = AA  length = 11
FEATURE                 Location/Qualifiers
source                  1..11
                        mol_type = protein
                        organism = Homo sapiens
SEQUENCE: 1002
CCQPICGSSC C                                                                                   11

SEQ ID NO: 1003         moltype = AA  length = 11
FEATURE                 Location/Qualifiers
source                  1..11
                        mol_type = protein
                        organism = Homo sapiens
SEQUENCE: 1003
CCQPICVTSC C                                                                                   11

SEQ ID NO: 1004         moltype = AA  length = 11
FEATURE                 Location/Qualifiers
source                  1..11
                        mol_type = protein
                        organism = Homo sapiens
SEQUENCE: 1004
CCQPNCCRPS C                                                                                   11

SEQ ID NO: 1005         moltype = AA  length = 11
FEATURE                 Location/Qualifiers
source                  1..11
                        mol_type = protein
                        organism = Homo sapiens
SEQUENCE: 1005
CCQPSCCETS C                                                                                   11

SEQ ID NO: 1006         moltype = AA  length = 11
FEATURE                 Location/Qualifiers
source                  1..11
                        mol_type = protein
                        organism = Homo sapiens
SEQUENCE: 1006
CCQPSCCRPA C                                                                                   11

SEQ ID NO: 1007         moltype = AA  length = 11
FEATURE                 Location/Qualifiers
source                  1..11
                        mol_type = protein
                        organism = Homo sapiens
SEQUENCE: 1007
CCQPSCCSTP C                                                                                   11

SEQ ID NO: 1008         moltype = AA  length = 11
FEATURE                 Location/Qualifiers
source                  1..11
                        mol_type = protein
                        organism = Homo sapiens
SEQUENCE: 1008
CCQPSCCSTT C                                                                                   11

SEQ ID NO: 1009         moltype = AA  length = 11
FEATURE                 Location/Qualifiers
source                  1..11
                        mol_type = protein
```

```
                                organism = Homo sapiens
SEQUENCE: 1009
CCQPSCCVPS C                                                                11

SEQ ID NO: 1010      moltype = AA  length = 11
FEATURE              Location/Qualifiers
source               1..11
                     mol_type = protein
                     organism = Homo sapiens
SEQUENCE: 1010
CCQPSCCVSS C                                                                11

SEQ ID NO: 1011      moltype = AA  length = 11
FEATURE              Location/Qualifiers
source               1..11
                     mol_type = protein
                     organism = Homo sapiens
SEQUENCE: 1011
CCQPTCCHPS C                                                                11

SEQ ID NO: 1012      moltype = AA  length = 11
FEATURE              Location/Qualifiers
source               1..11
                     mol_type = protein
                     organism = Homo sapiens
SEQUENCE: 1012
CCQPTCCQPT C                                                                11

SEQ ID NO: 1013      moltype = AA  length = 11
FEATURE              Location/Qualifiers
source               1..11
                     mol_type = protein
                     organism = Homo sapiens
SEQUENCE: 1013
CCQPTCCRPR C                                                                11

SEQ ID NO: 1014      moltype = AA  length = 11
FEATURE              Location/Qualifiers
source               1..11
                     mol_type = protein
                     organism = Homo sapiens
SEQUENCE: 1014
CCQPTCCRPS C                                                                11

SEQ ID NO: 1015      moltype = AA  length = 11
FEATURE              Location/Qualifiers
source               1..11
                     mol_type = protein
                     organism = Homo sapiens
SEQUENCE: 1015
CCQPTCCRPT C                                                                11

SEQ ID NO: 1016      moltype = AA  length = 11
FEATURE              Location/Qualifiers
source               1..11
                     mol_type = protein
                     organism = Homo sapiens
SEQUENCE: 1016
CCQPTCCRTT C                                                                11

SEQ ID NO: 1017      moltype = AA  length = 11
FEATURE              Location/Qualifiers
source               1..11
                     mol_type = protein
                     organism = Homo sapiens
SEQUENCE: 1017
CCQPTCLSSC C                                                                11

SEQ ID NO: 1018      moltype = AA  length = 11
FEATURE              Location/Qualifiers
source               1..11
                     mol_type = protein
                     organism = Homo sapiens
SEQUENCE: 1018
CCQPTCLTSC C                                                                11

SEQ ID NO: 1019      moltype = AA  length = 11
FEATURE              Location/Qualifiers
source               1..11
```

```
                                    mol_type = protein
                                    organism = Homo sapiens
SEQUENCE: 1019
CCQPTCVASC C                                                                    11

SEQ ID NO: 1020                     moltype = AA  length = 11
FEATURE                             Location/Qualifiers
source                              1..11
                                    mol_type = protein
                                    organism = Homo sapiens
SEQUENCE: 1020
CCQPTCVTSC C                                                                    11

SEQ ID NO: 1021                     moltype = AA  length = 11
FEATURE                             Location/Qualifiers
source                              1..11
                                    mol_type = protein
                                    organism = Homo sapiens
SEQUENCE: 1021
CCQPYCHPTC C                                                                    11

SEQ ID NO: 1022                     moltype = AA  length = 11
FEATURE                             Location/Qualifiers
source                              1..11
                                    mol_type = protein
                                    organism = Homo sapiens
SEQUENCE: 1022
CCQSMCCQPT C                                                                    11

SEQ ID NO: 1023                     moltype = AA  length = 11
FEATURE                             Location/Qualifiers
source                              1..11
                                    mol_type = protein
                                    organism = Homo sapiens
SEQUENCE: 1023
CCQSNCCVPV C                                                                    11

SEQ ID NO: 1024                     moltype = AA  length = 11
FEATURE                             Location/Qualifiers
source                              1..11
                                    mol_type = protein
                                    organism = Homo sapiens
SEQUENCE: 1024
CCQSSCCKPC S                                                                    11

SEQ ID NO: 1025                     moltype = AA  length = 11
FEATURE                             Location/Qualifiers
source                              1..11
                                    mol_type = protein
                                    organism = Homo sapiens
SEQUENCE: 1025
CCQSSCCKPS C                                                                    11

SEQ ID NO: 1026                     moltype = AA  length = 11
FEATURE                             Location/Qualifiers
source                              1..11
                                    mol_type = protein
                                    organism = Homo sapiens
SEQUENCE: 1026
CCQSSCCKPY C                                                                    11

SEQ ID NO: 1027                     moltype = AA  length = 11
FEATURE                             Location/Qualifiers
source                              1..11
                                    mol_type = protein
                                    organism = Homo sapiens
SEQUENCE: 1027
CCQSSCCQSS C                                                                    11

SEQ ID NO: 1028                     moltype = AA  length = 11
FEATURE                             Location/Qualifiers
source                              1..11
                                    mol_type = protein
                                    organism = Homo sapiens
SEQUENCE: 1028
CCQSSCCVPV C                                                                    11

SEQ ID NO: 1029                     moltype = AA  length = 11
FEATURE                             Location/Qualifiers
```

```
source                      1..11
                            mol_type = protein
                            organism = Homo sapiens
SEQUENCE: 1029
CCQSSCFKPC C                                                                11

SEQ ID NO: 1030             moltype = AA   length = 11
FEATURE                     Location/Qualifiers
source                      1..11
                            mol_type = protein
                            organism = Homo sapiens
SEQUENCE: 1030
CCQSSCSKPC C                                                                11

SEQ ID NO: 1031             moltype = AA   length = 11
FEATURE                     Location/Qualifiers
source                      1..11
                            mol_type = protein
                            organism = Homo sapiens
SEQUENCE: 1031
CCQSSCYKPC C                                                                11

SEQ ID NO: 1032             moltype = AA   length = 11
FEATURE                     Location/Qualifiers
source                      1..11
                            mol_type = protein
                            organism = Homo sapiens
SEQUENCE: 1032
CCQSVCCQPT C                                                                11

SEQ ID NO: 1033             moltype = AA   length = 11
FEATURE                     Location/Qualifiers
source                      1..11
                            mol_type = protein
                            organism = Homo sapiens
SEQUENCE: 1033
CCQTICRSTC C                                                                11

SEQ ID NO: 1034             moltype = AA   length = 11
FEATURE                     Location/Qualifiers
source                      1..11
                            mol_type = protein
                            organism = Homo sapiens
SEQUENCE: 1034
CCQTTCCRPS C                                                                11

SEQ ID NO: 1035             moltype = AA   length = 11
FEATURE                     Location/Qualifiers
source                      1..11
                            mol_type = protein
                            organism = Homo sapiens
SEQUENCE: 1035
CCQTTCCRTT C                                                                11

SEQ ID NO: 1036             moltype = AA   length = 11
FEATURE                     Location/Qualifiers
source                      1..11
                            mol_type = protein
                            organism = Homo sapiens
SEQUENCE: 1036
CCRPACCETT C                                                                11

SEQ ID NO: 1037             moltype = AA   length = 11
FEATURE                     Location/Qualifiers
source                      1..11
                            mol_type = protein
                            organism = Homo sapiens
SEQUENCE: 1037
CCRPACCQNT C                                                                11

SEQ ID NO: 1038             moltype = AA   length = 11
FEATURE                     Location/Qualifiers
source                      1..11
                            mol_type = protein
                            organism = Homo sapiens
SEQUENCE: 1038
CCRPLCCQTT C                                                                11

SEQ ID NO: 1039             moltype = AA   length = 11
```

```
                        -continued

FEATURE                 Location/Qualifiers
source                  1..11
                        mol_type = protein
                        organism = Homo sapiens
SEQUENCE: 1039
CCRPQCCQSV C                                                                    11

SEQ ID NO: 1040         moltype = AA  length = 11
FEATURE                 Location/Qualifiers
source                  1..11
                        mol_type = protein
                        organism = Homo sapiens
SEQUENCE: 1040
CCRPQCCQTT C                                                                    11

SEQ ID NO: 1041         moltype = AA  length = 11
FEATURE                 Location/Qualifiers
source                  1..11
                        mol_type = protein
                        organism = Homo sapiens
SEQUENCE: 1041
CCRPSCCESS C                                                                    11

SEQ ID NO: 1042         moltype = AA  length = 11
FEATURE                 Location/Qualifiers
source                  1..11
                        mol_type = protein
                        organism = Homo sapiens
SEQUENCE: 1042
CCRPSCCETT C                                                                    11

SEQ ID NO: 1043         moltype = AA  length = 11
FEATURE                 Location/Qualifiers
source                  1..11
                        mol_type = protein
                        organism = Homo sapiens
SEQUENCE: 1043
CCRPSCCGSS C                                                                    11

SEQ ID NO: 1044         moltype = AA  length = 11
FEATURE                 Location/Qualifiers
source                  1..11
                        mol_type = protein
                        organism = Homo sapiens
SEQUENCE: 1044
CCRPSCCISS C                                                                    11

SEQ ID NO: 1045         moltype = AA  length = 11
FEATURE                 Location/Qualifiers
source                  1..11
                        mol_type = protein
                        organism = Homo sapiens
SEQUENCE: 1045
CCRPSCCKPQ C                                                                    11

SEQ ID NO: 1046         moltype = AA  length = 11
FEATURE                 Location/Qualifiers
source                  1..11
                        mol_type = protein
                        organism = Homo sapiens
SEQUENCE: 1046
CCRPSCCQTT C                                                                    11

SEQ ID NO: 1047         moltype = AA  length = 11
FEATURE                 Location/Qualifiers
source                  1..11
                        mol_type = protein
                        organism = Homo sapiens
SEQUENCE: 1047
CCRPSCCVSR C                                                                    11

SEQ ID NO: 1048         moltype = AA  length = 11
FEATURE                 Location/Qualifiers
source                  1..11
                        mol_type = protein
                        organism = Homo sapiens
SEQUENCE: 1048
CCRPSCCVSS C                                                                    11
```

| | | |
|---|---|---|
| SEQ ID NO: 1049<br>FEATURE<br>source<br><br>SEQUENCE: 1049<br>CCRPTCCQNT C | moltype = AA   length = 11<br>Location/Qualifiers<br>1..11<br>mol_type = protein<br>organism = Homo sapiens | 11 |
| SEQ ID NO: 1050<br>FEATURE<br>source<br><br>SEQUENCE: 1050<br>CCRPTCCQTT C | moltype = AA   length = 11<br>Location/Qualifiers<br>1..11<br>mol_type = protein<br>organism = Homo sapiens | 11 |
| SEQ ID NO: 1051<br>FEATURE<br>source<br><br>SEQUENCE: 1051<br>CCRPVCCDPC S | moltype = AA   length = 11<br>Location/Qualifiers<br>1..11<br>mol_type = protein<br>organism = Homo sapiens | 11 |
| SEQ ID NO: 1052<br>FEATURE<br>source<br><br>SEQUENCE: 1052<br>CCRTTCCQPT C | moltype = AA   length = 11<br>Location/Qualifiers<br>1..11<br>mol_type = protein<br>organism = Homo sapiens | 11 |
| SEQ ID NO: 1053<br>FEATURE<br>source<br><br>SEQUENCE: 1053<br>CCRTTCCRPS C | moltype = AA   length = 11<br>Location/Qualifiers<br>1..11<br>mol_type = protein<br>organism = Homo sapiens | 11 |
| SEQ ID NO: 1054<br>FEATURE<br>source<br><br>SEQUENCE: 1054<br>CCRTTCCRTT C | moltype = AA   length = 11<br>Location/Qualifiers<br>1..11<br>mol_type = protein<br>organism = Homo sapiens | 11 |
| SEQ ID NO: 1055<br>FEATURE<br>source<br><br>SEQUENCE: 1055<br>CCSCSSCGSC A | moltype = AA   length = 11<br>Location/Qualifiers<br>1..11<br>mol_type = protein<br>organism = Homo sapiens | 11 |
| SEQ ID NO: 1056<br>FEATURE<br>source<br><br>SEQUENCE: 1056<br>CCSPGCQPTC C | moltype = AA   length = 11<br>Location/Qualifiers<br>1..11<br>mol_type = protein<br>organism = Homo sapiens | 11 |
| SEQ ID NO: 1057<br>FEATURE<br>source<br><br>SEQUENCE: 1057<br>CCSQSSCCKP C | moltype = AA   length = 11<br>Location/Qualifiers<br>1..11<br>mol_type = protein<br>organism = Homo sapiens | 11 |
| SEQ ID NO: 1058<br>FEATURE<br>source<br><br>SEQUENCE: 1058<br>CCSSGCGSCC Q | moltype = AA   length = 11<br>Location/Qualifiers<br>1..11<br>mol_type = protein<br>organism = Homo sapiens | 11 |

```
SEQ ID NO: 1059          moltype = AA  length = 11
FEATURE                  Location/Qualifiers
source                   1..11
                         mol_type = protein
                         organism = Homo sapiens SEQUENCE: 1059
CCSSGCGSSC C                                                              11

SEQ ID NO: 1060          moltype = AA  length = 11
FEATURE                  Location/Qualifiers
source                   1..11
                         mol_type = protein
                         organism = Homo sapiens SEQUENCE: 1060
CCSTPCCQPT C                                                              11

SEQ ID NO: 1061          moltype = AA  length = 11
FEATURE                  Location/Qualifiers
source                   1..11
                         mol_type = protein
                         organism = Homo sapiens SEQUENCE: 1061
CCVPACSCSS C                                                              11

SEQ ID NO: 1062          moltype = AA  length = 11
FEATURE                  Location/Qualifiers
source                   1..11
                         mol_type = protein
                         organism = Homo sapiens SEQUENCE: 1062
CCVPACSCTS C                                                              11

SEQ ID NO: 1063          moltype = AA  length = 11
FEATURE                  Location/Qualifiers
source                   1..11
                         mol_type = protein
                         organism = Homo sapiens SEQUENCE: 1063
CCVPICCKPI C                                                              11

SEQ ID NO: 1064          moltype = AA  length = 11
FEATURE                  Location/Qualifiers
source                   1..11
                         mol_type = protein
                         organism = Homo sapiens SEQUENCE: 1064
CCVPICCKPV C                                                              11

SEQ ID NO: 1065          moltype = AA  length = 11
FEATURE                  Location/Qualifiers
source                   1..11
                         mol_type = protein
                         organism = Homo sapiens SEQUENCE: 1065
CCVPVCCKPI C                                                              11

SEQ ID NO: 1066          moltype = AA  length = 11
FEATURE                  Location/Qualifiers
source                   1..11
                         mol_type = protein
                         organism = Homo sapiens SEQUENCE: 1066
CCVPVCCKPV C                                                              11

SEQ ID NO: 1067          moltype = AA  length = 11
FEATURE                  Location/Qualifiers
source                   1..11
                         mol_type = protein
                         organism = Homo sapiens SEQUENCE: 1067
CCVPVCCKSN C                                                              11

SEQ ID NO: 1068          moltype = AA  length = 11
FEATURE                  Location/Qualifiers
source                   1..11
                         mol_type = protein
                         organism = Homo sapiens

SEQUENCE: 1068
```

```
CCVPVCCKTV C                                                          11

SEQ ID NO: 1069         moltype = AA   length = 11
FEATURE                 Location/Qualifiers
source                  1..11
                        mol_type = protein
                        organism = Homo sapiens SEQUENCE: 1069
CCVPVCCSSS C                                                          11

SEQ ID NO: 1070         moltype = AA   length = 11
FEATURE                 Location/Qualifiers
source                  1..11
                        mol_type = protein
                        organism = Homo sapiens SEQUENCE: 1070
CCVPVCCVPV C                                                          11

SEQ ID NO: 1071         moltype = AA   length = 11
FEATURE                 Location/Qualifiers
source                  1..11
                        mol_type = protein
                        organism = Homo sapiens SEQUENCE: 1071
CCVSSCCKPQ C                                                          11

SEQ ID NO: 1072         moltype = AA   length = 11
FEATURE                 Location/Qualifiers
source                  1..11
                        mol_type = protein
                        organism = Homo sapiens SEQUENCE: 1072
CCVSSCCQHS C                                                          11

SEQ ID NO: 1073         moltype = AA   length = 11
FEATURE                 Location/Qualifiers
source                  1..11
                        mol_type = protein
                        organism = Homo sapiens SEQUENCE: 1073
CCVSSCCQPS C                                                          11

SEQ ID NO: 1074         moltype = AA   length = 11
FEATURE                 Location/Qualifiers
source                  1..11
                        mol_type = protein
                        organism = Homo sapiens SEQUENCE: 1074
CCVSSCCRPQ C                                                          11

SEQ ID NO: 1075         moltype = AA   length = 11
FEATURE                 Location/Qualifiers
source                  1..11
                        mol_type = protein
                        organism = Homo sapiens SEQUENCE: 1075
CCVSTCCRPT C                                                          11

SEQ ID NO: 1076         moltype = AA   length = 11
FEATURE                 Location/Qualifiers
source                  1..11
                        mol_type = protein
                        organism = Homo sapiens SEQUENCE: 1076
CCVSVCCKPV C                                                          11

SEQ ID NO: 1077         moltype = AA   length = 11
FEATURE                 Location/Qualifiers
source                  1..11
                        mol_type = protein
                        organism = Homo sapiens SEQUENCE: 1077
CDSSCCQPSC C                                                          11

SEQ ID NO: 1078         moltype = AA   length = 11
FEATURE                 Location/Qualifiers
source                  1..11
                        mol_type = protein
                        organism = Homo sapiens
```

```
SEQUENCE: 1078
CEPCCRPVCC D                                                                              11

SEQ ID NO: 1079        moltype = AA  length = 11
FEATURE                Location/Qualifiers
source                 1..11
                       mol_type = protein
                       organism = Homo sapiens
SEQUENCE: 1079
CFKPCCCQSS C                                                                              11

SEQ ID NO: 1080        moltype = AA  length = 11
FEATURE                Location/Qualifiers
source                 1..11
                       mol_type = protein
                       organism = Homo sapiens
SEQUENCE: 1080
CGDGCCCPSC Y                                                                              11

SEQ ID NO: 1081        moltype = AA  length = 11
FEATURE                Location/Qualifiers
source                 1..11
                       mol_type = protein
                       organism = Homo sapiens
SEQUENCE: 1081
CGGGCCGSSC C                                                                              11

SEQ ID NO: 1082        moltype = AA  length = 11
FEATURE                Location/Qualifiers
source                 1..11
                       mol_type = protein
                       organism = Homo sapiens
SEQUENCE: 1082
CGGSCCGSSC C                                                                              11

SEQ ID NO: 1083        moltype = AA  length = 11
FEATURE                Location/Qualifiers
source                 1..11
                       mol_type = protein
                       organism = Homo sapiens
SEQUENCE: 1083
CGLENCCCPS C                                                                              11

SEQ ID NO: 1084        moltype = AA  length = 11
FEATURE                Location/Qualifiers
source                 1..11
                       mol_type = protein
                       organism = Homo sapiens
SEQUENCE: 1084
CGQSCCRPAC C                                                                              11

SEQ ID NO: 1085        moltype = AA  length = 11
FEATURE                Location/Qualifiers
source                 1..11
                       mol_type = protein
                       organism = Homo sapiens
SEQUENCE: 1085
CGQSCCRPVC C                                                                              11

SEQ ID NO: 1086        moltype = AA  length = 11
FEATURE                Location/Qualifiers
source                 1..11
                       mol_type = protein
                       organism = Homo sapiens
SEQUENCE: 1086
CGSCCQSSCC N                                                                              11

SEQ ID NO: 1087        moltype = AA  length = 11
FEATURE                Location/Qualifiers
source                 1..11
                       mol_type = protein
                       organism = Homo sapiens
SEQUENCE: 1087
CGSCGCSQCN C                                                                              11

SEQ ID NO: 1088        moltype = AA  length = 11
FEATURE                Location/Qualifiers
source                 1..11
                       mol_type = protein
```

```
                              organism = Homo sapiens
SEQUENCE: 1088
CGSCGCSQCS C                                                                        11

SEQ ID NO: 1089        moltype = AA   length = 11
FEATURE                Location/Qualifiers
source                 1..11
                       mol_type = protein
                       organism = Homo sapiens
SEQUENCE: 1089
CGSGCCGPVC C                                                                        11

SEQ ID NO: 1090        moltype = AA   length = 11
FEATURE                Location/Qualifiers
source                 1..11
                       mol_type = protein
                       organism = Homo sapiens
SEQUENCE: 1090
CGSGCCVPVC C                                                                        11

SEQ ID NO: 1091        moltype = AA   length = 11
FEATURE                Location/Qualifiers
source                 1..11
                       mol_type = protein
                       organism = Homo sapiens
SEQUENCE: 1091
CGSNCCQPCC R                                                                        11

SEQ ID NO: 1092        moltype = AA   length = 11
FEATURE                Location/Qualifiers
source                 1..11
                       mol_type = protein
                       organism = Homo sapiens
SEQUENCE: 1092
CGSSCCQPCC H                                                                        11

SEQ ID NO: 1093        moltype = AA   length = 11
FEATURE                Location/Qualifiers
source                 1..11
                       mol_type = protein
                       organism = Homo sapiens
SEQUENCE: 1093
CGSSCCQPCC R                                                                        11

SEQ ID NO: 1094        moltype = AA   length = 11
FEATURE                Location/Qualifiers
source                 1..11
                       mol_type = protein
                       organism = Homo sapiens
SEQUENCE: 1094
CGSSCCQPCY C                                                                        11

SEQ ID NO: 1095        moltype = AA   length = 11
FEATURE                Location/Qualifiers
source                 1..11
                       mol_type = protein
                       organism = Homo sapiens
SEQUENCE: 1095
CGSSCCQPSC C                                                                        11

SEQ ID NO: 1096        moltype = AA   length = 11
FEATURE                Location/Qualifiers
source                 1..11
                       mol_type = protein
                       organism = Homo sapiens
SEQUENCE: 1096
CGSSCCQSSC C                                                                        11

SEQ ID NO: 1097        moltype = AA   length = 11
FEATURE                Location/Qualifiers
source                 1..11
                       mol_type = protein
                       organism = Homo sapiens
SEQUENCE: 1097
CGSSCCVPIC C                                                                        11

SEQ ID NO: 1098        moltype = AA   length = 11
FEATURE                Location/Qualifiers
source                 1..11
```

-continued

```
                        mol_type = protein
                        organism = Homo sapiens
SEQUENCE: 1098
CGSSCCVPVC C                                                                11

SEQ ID NO: 1099         moltype = AA   length = 11
FEATURE                 Location/Qualifiers
source                  1..11
                        mol_type = protein
                        organism = Homo sapiens
SEQUENCE: 1099
CGSSCSQCSC C                                                                11

SEQ ID NO: 1100         moltype = AA   length = 11
FEATURE                 Location/Qualifiers
source                  1..11
                        mol_type = protein
                        organism = Homo sapiens
SEQUENCE: 1100
CGVPVCCCSC S                                                                11

SEQ ID NO: 1101         moltype = AA   length = 11
FEATURE                 Location/Qualifiers
source                  1..11
                        mol_type = protein
                        organism = Homo sapiens
SEQUENCE: 1101
CHPRCCISSC C                                                                11

SEQ ID NO: 1102         moltype = AA   length = 11
FEATURE                 Location/Qualifiers
source                  1..11
                        mol_type = protein
                        organism = Homo sapiens
SEQUENCE: 1102
CHPSCCESSC C                                                                11

SEQ ID NO: 1103         moltype = AA   length = 11
FEATURE                 Location/Qualifiers
source                  1..11
                        mol_type = protein
                        organism = Homo sapiens
SEQUENCE: 1103
CHPSCCISSC C                                                                11

SEQ ID NO: 1104         moltype = AA   length = 11
FEATURE                 Location/Qualifiers
source                  1..11
                        mol_type = protein
                        organism = Homo sapiens
SEQUENCE: 1104
CHPTCCQNTC C                                                                11

SEQ ID NO: 1105         moltype = AA   length = 11
FEATURE                 Location/Qualifiers
source                  1..11
                        mol_type = protein
                        organism = Homo sapiens
SEQUENCE: 1105
CISSCCHPSC C                                                                11

SEQ ID NO: 1106         moltype = AA   length = 11
FEATURE                 Location/Qualifiers
source                  1..11
                        mol_type = protein
                        organism = Homo sapiens
SEQUENCE: 1106
CISSCCKPSC C                                                                11

SEQ ID NO: 1107         moltype = AA   length = 11
FEATURE                 Location/Qualifiers
source                  1..11
                        mol_type = protein
                        organism = Homo sapiens
SEQUENCE: 1107
CISSCCRPSC C                                                                11

SEQ ID NO: 1108         moltype = AA   length = 11
FEATURE                 Location/Qualifiers
```

```
source                  1..11
                        mol_type = protein
                        organism = Homo sapiens
SEQUENCE: 1108
CISSSCCPSC C                                                                    11

SEQ ID NO: 1109         moltype = AA   length = 11
FEATURE                 Location/Qualifiers
source                  1..11
                        mol_type = protein
                        organism = Homo sapiens
SEQUENCE: 1109
CKPCCCSSGC G                                                                    11

SEQ ID NO: 1110         moltype = AA   length = 11
FEATURE                 Location/Qualifiers
source                  1..11
                        mol_type = protein
                        organism = Homo sapiens
SEQUENCE: 1110
CKPCCSQASC C                                                                    11

SEQ ID NO: 1111         moltype = AA   length = 11
FEATURE                 Location/Qualifiers
source                  1..11
                        mol_type = protein
                        organism = Homo sapiens
SEQUENCE: 1111
CKPCCSQSRC C                                                                    11

SEQ ID NO: 1112         moltype = AA   length = 11
FEATURE                 Location/Qualifiers
source                  1..11
                        mol_type = protein
                        organism = Homo sapiens
SEQUENCE: 1112
CKPCCSQSSC C                                                                    11

SEQ ID NO: 1113         moltype = AA   length = 11
FEATURE                 Location/Qualifiers
source                  1..11
                        mol_type = protein
                        organism = Homo sapiens
SEQUENCE: 1113
CKPQCCQSMC C                                                                    11

SEQ ID NO: 1114         moltype = AA   length = 11
FEATURE                 Location/Qualifiers
source                  1..11
                        mol_type = protein
                        organism = Homo sapiens
SEQUENCE: 1114
CKPQCCQSVC C                                                                    11

SEQ ID NO: 1115         moltype = AA   length = 11
FEATURE                 Location/Qualifiers
source                  1..11
                        mol_type = protein
                        organism = Homo sapiens
SEQUENCE: 1115
CKPVCCCVPA C                                                                    11

SEQ ID NO: 1116         moltype = AA   length = 11
FEATURE                 Location/Qualifiers
source                  1..11
                        mol_type = protein
                        organism = Homo sapiens
SEQUENCE: 1116
CKPVCCKPIC C                                                                    11

SEQ ID NO: 1117         moltype = AA   length = 11
FEATURE                 Location/Qualifiers
source                  1..11
                        mol_type = protein
                        organism = Homo sapiens
SEQUENCE: 1117
CKPVCCMPVC C                                                                    11

SEQ ID NO: 1118         moltype = AA   length = 11
```

```
FEATURE                 Location/Qualifiers
source                  1..11
                        mol_type = protein
                        organism = Homo sapiens
SEQUENCE: 1118
CKPVCCVPVC C                                                                    11

SEQ ID NO: 1119         moltype = AA  length = 11
FEATURE                 Location/Qualifiers
source                  1..11
                        mol_type = protein
                        organism = Homo sapiens
SEQUENCE: 1119
CKPVCCVSVC C                                                                    11

SEQ ID NO: 1120         moltype = AA  length = 11
FEATURE                 Location/Qualifiers
source                  1..11
                        mol_type = protein
                        organism = Homo sapiens
SEQUENCE: 1120
CKPYCSQCSC C                                                                    11

SEQ ID NO: 1121         moltype = AA  length = 11
FEATURE                 Location/Qualifiers
source                  1..11
                        mol_type = protein
                        organism = Homo sapiens
SEQUENCE: 1121
CLPCCRPTCC Q                                                                    11

SEQ ID NO: 1122         moltype = AA  length = 11
FEATURE                 Location/Qualifiers
source                  1..11
                        mol_type = protein
                        organism = Homo sapiens
SEQUENCE: 1122
CLTSCCQPSC C                                                                    11

SEQ ID NO: 1123         moltype = AA  length = 11
FEATURE                 Location/Qualifiers
source                  1..11
                        mol_type = protein
                        organism = Homo sapiens
SEQUENCE: 1123
CMSSCCKPQC C                                                                    11

SEQ ID NO: 1124         moltype = AA  length = 11
FEATURE                 Location/Qualifiers
source                  1..11
                        mol_type = protein
                        organism = Homo sapiens
SEQUENCE: 1124
CNPCCSQSSC C                                                                    11

SEQ ID NO: 1125         moltype = AA  length = 11
FEATURE                 Location/Qualifiers
source                  1..11
                        mol_type = protein
                        organism = Homo sapiens
SEQUENCE: 1125
CPACCVSSCC Q                                                                    11

SEQ ID NO: 1126         moltype = AA  length = 11
FEATURE                 Location/Qualifiers
source                  1..11
                        mol_type = protein
                        organism = Homo sapiens
SEQUENCE: 1126
CPESCCEPHC C                                                                    11

SEQ ID NO: 1127         moltype = AA  length = 11
FEATURE                 Location/Qualifiers
source                  1..11
                        mol_type = protein
                        organism = Homo sapiens
SEQUENCE: 1127
CPESCCEPPC C                                                                    11
```

```
SEQ ID NO: 1128          moltype = AA  length = 11
FEATURE                  Location/Qualifiers
source                   1..11
                         mol_type = protein
                         organism = Homo sapiens
SEQUENCE: 1128
CPSCCESSCC R                                                                  11

SEQ ID NO: 1129          moltype = AA  length = 11
FEATURE                  Location/Qualifiers
source                   1..11
                         mol_type = protein
                         organism = Homo sapiens
SEQUENCE: 1129
CPSCCQTTCC R                                                                  11

SEQ ID NO: 1130          moltype = AA  length = 11
FEATURE                  Location/Qualifiers
source                   1..11
                         mol_type = protein
                         organism = Homo sapiens
SEQUENCE: 1130
CPSCCVSSCC R                                                                  11

SEQ ID NO: 1131          moltype = AA  length = 11
FEATURE                  Location/Qualifiers
source                   1..11
                         mol_type = protein
                         organism = Homo sapiens
SEQUENCE: 1131
CQCSCCKPYC S                                                                  11

SEQ ID NO: 1132          moltype = AA  length = 11
FEATURE                  Location/Qualifiers
source                   1..11
                         mol_type = protein
                         organism = Homo sapiens
SEQUENCE: 1132
CQETCCRPSC C                                                                  11

SEQ ID NO: 1133          moltype = AA  length = 11
FEATURE                  Location/Qualifiers
source                   1..11
                         mol_type = protein
                         organism = Homo sapiens
SEQUENCE: 1133
CQNTCCRTTC C                                                                  11

SEQ ID NO: 1134          moltype = AA  length = 11
FEATURE                  Location/Qualifiers
source                   1..11
                         mol_type = protein
                         organism = Homo sapiens
SEQUENCE: 1134
CQPACCTASC C                                                                  11

SEQ ID NO: 1135          moltype = AA  length = 11
FEATURE                  Location/Qualifiers
source                   1..11
                         mol_type = protein
                         organism = Homo sapiens
SEQUENCE: 1135
CQPACCTSSC C                                                                  11

SEQ ID NO: 1136          moltype = AA  length = 11
FEATURE                  Location/Qualifiers
source                   1..11
                         mol_type = protein
                         organism = Homo sapiens
SEQUENCE: 1136
CQPACCTTSC C                                                                  11

SEQ ID NO: 1137          moltype = AA  length = 11
FEATURE                  Location/Qualifiers
source                   1..11
                         mol_type = protein
                         organism = Homo sapiens
SEQUENCE: 1137
CQPACCVPVC C                                                                  11
```

```
SEQ ID NO: 1138         moltype = AA   length = 11
FEATURE                 Location/Qualifiers
source                  1..11
                        mol_type = protein
                        organism = Homo sapiens
SEQUENCE: 1138
CQPACCVSSC C                                                                        11

SEQ ID NO: 1139         moltype = AA   length = 11
FEATURE                 Location/Qualifiers
source                  1..11
                        mol_type = protein
                        organism = Homo sapiens
SEQUENCE: 1139
CQPCCHPTCC Q                                                                        11

SEQ ID NO: 1140         moltype = AA   length = 11
FEATURE                 Location/Qualifiers
source                  1..11
                        mol_type = protein
                        organism = Homo sapiens
SEQUENCE: 1140
CQPCCRPACC E                                                                        11

SEQ ID NO: 1141         moltype = AA   length = 11
FEATURE                 Location/Qualifiers
source                  1..11
                        mol_type = protein
                        organism = Homo sapiens
SEQUENCE: 1141
CQPCCRPACC Q                                                                        11

SEQ ID NO: 1142         moltype = AA   length = 11
FEATURE                 Location/Qualifiers
source                  1..11
                        mol_type = protein
                        organism = Homo sapiens
SEQUENCE: 1142
CQPCCRPTCC Q                                                                        11

SEQ ID NO: 1143         moltype = AA   length = 11
FEATURE                 Location/Qualifiers
source                  1..11
                        mol_type = protein
                        organism = Homo sapiens
SEQUENCE: 1143
CQPCYCPACC V                                                                        11

SEQ ID NO: 1144         moltype = AA   length = 11
FEATURE                 Location/Qualifiers
source                  1..11
                        mol_type = protein
                        organism = Homo sapiens
SEQUENCE: 1144
CQPICCGSSC C                                                                        11

SEQ ID NO: 1145         moltype = AA   length = 11
FEATURE                 Location/Qualifiers
source                  1..11
                        mol_type = protein
                        organism = Homo sapiens
SEQUENCE: 1145
CQPRCCETSC C                                                                        11

SEQ ID NO: 1146         moltype = AA   length = 11
FEATURE                 Location/Qualifiers
source                  1..11
                        mol_type = protein
                        organism = Homo sapiens
SEQUENCE: 1146
CQPSCCETSC C                                                                        11

SEQ ID NO: 1147         moltype = AA   length = 11
FEATURE                 Location/Qualifiers
source                  1..11
                        mol_type = protein
                        organism = Homo sapiens
SEQUENCE: 1147
```

```
CQPSCCRPAC C                                                                    11

SEQ ID NO: 1148         moltype = AA  length = 11
FEATURE                 Location/Qualifiers
source                  1..11
                        mol_type = protein
                        organism = Homo sapiens
SEQUENCE: 1148
CQPSCCVPSC C                                                                    11

SEQ ID NO: 1149         moltype = AA  length = 11
FEATURE                 Location/Qualifiers
source                  1..11
                        mol_type = protein
                        organism = Homo sapiens
SEQUENCE: 1149
CQPSCCVSSC C                                                                    11

SEQ ID NO: 1150         moltype = AA  length = 11
FEATURE                 Location/Qualifiers
source                  1..11
                        mol_type = protein
                        organism = Homo sapiens
SEQUENCE: 1150
CQPTCCCPSY C                                                                    11

SEQ ID NO: 1151         moltype = AA  length = 11
FEATURE                 Location/Qualifiers
source                  1..11
                        mol_type = protein
                        organism = Homo sapiens
SEQUENCE: 1151
CQPTCCGSSC C                                                                    11

SEQ ID NO: 1152         moltype = AA  length = 11
FEATURE                 Location/Qualifiers
source                  1..11
                        mol_type = protein
                        organism = Homo sapiens
SEQUENCE: 1152
CQPTCCHPSC C                                                                    11

SEQ ID NO: 1153         moltype = AA  length = 11
FEATURE                 Location/Qualifiers
source                  1..11
                        mol_type = protein
                        organism = Homo sapiens
SEQUENCE: 1153
CQPTCCQPTC C                                                                    11

SEQ ID NO: 1154         moltype = AA  length = 11
FEATURE                 Location/Qualifiers
source                  1..11
                        mol_type = protein
                        organism = Homo sapiens
SEQUENCE: 1154
CQPTCCRPSC C                                                                    11

SEQ ID NO: 1155         moltype = AA  length = 11
FEATURE                 Location/Qualifiers
source                  1..11
                        mol_type = protein
                        organism = Homo sapiens
SEQUENCE: 1155
CQPTCCRPTC C                                                                    11

SEQ ID NO: 1156         moltype = AA  length = 11
FEATURE                 Location/Qualifiers
source                  1..11
                        mol_type = protein
                        organism = Homo sapiens
SEQUENCE: 1156
CQPTCCRTTC C                                                                    11

SEQ ID NO: 1157         moltype = AA  length = 11
FEATURE                 Location/Qualifiers
source                  1..11
                        mol_type = protein
                        organism = Homo sapiens
```

```
SEQUENCE: 1157
CQQACCMPVC C                                                                    11

SEQ ID NO: 1158         moltype = AA  length = 11
FEATURE                 Location/Qualifiers
source                  1..11
                        mol_type = protein
                        organism = Homo sapiens
SEQUENCE: 1158
CQQACCVPIC C                                                                    11

SEQ ID NO: 1159         moltype = AA  length = 11
FEATURE                 Location/Qualifiers
source                  1..11
                        mol_type = protein
                        organism = Homo sapiens
SEQUENCE: 1159
CQQACCVPVC C                                                                    11

SEQ ID NO: 1160         moltype = AA  length = 11
FEATURE                 Location/Qualifiers
source                  1..11
                        mol_type = protein
                        organism = Homo sapiens
SEQUENCE: 1160
CQQSCCVPVC C                                                                    11

SEQ ID NO: 1161         moltype = AA  length = 11
FEATURE                 Location/Qualifiers
source                  1..11
                        mol_type = protein
                        organism = Homo sapiens
SEQUENCE: 1161
CQQSCCVSVC C                                                                    11

SEQ ID NO: 1162         moltype = AA  length = 11
FEATURE                 Location/Qualifiers
source                  1..11
                        mol_type = protein
                        organism = Homo sapiens
SEQUENCE: 1162
CQSNCCVPVC C                                                                    11

SEQ ID NO: 1163         moltype = AA  length = 11
FEATURE                 Location/Qualifiers
source                  1..11
                        mol_type = protein
                        organism = Homo sapiens
SEQUENCE: 1163
CQSSCCCPAS C                                                                    11

SEQ ID NO: 1164         moltype = AA  length = 11
FEATURE                 Location/Qualifiers
source                  1..11
                        mol_type = protein
                        organism = Homo sapiens
SEQUENCE: 1164
CQSSCCKPCC S                                                                    11

SEQ ID NO: 1165         moltype = AA  length = 11
FEATURE                 Location/Qualifiers
source                  1..11
                        mol_type = protein
                        organism = Homo sapiens
SEQUENCE: 1165
CQSSCCKPCS C                                                                    11

SEQ ID NO: 1166         moltype = AA  length = 11
FEATURE                 Location/Qualifiers
source                  1..11
                        mol_type = protein
                        organism = Homo sapiens
SEQUENCE: 1166
CQSSCCKPYC C                                                                    11

SEQ ID NO: 1167         moltype = AA  length = 11
FEATURE                 Location/Qualifiers
source                  1..11
                        mol_type = protein
```

```
                              organism = Homo sapiens
SEQUENCE: 1167
CQSSCCNPCC S                                                         11

SEQ ID NO: 1168         moltype = AA   length = 11
FEATURE                 Location/Qualifiers
source                  1..11
                        mol_type = protein
                        organism = Homo sapiens
SEQUENCE: 1168
CQSSCCQSSC C                                                         11

SEQ ID NO: 1169         moltype = AA   length = 11
FEATURE                 Location/Qualifiers
source                  1..11
                        mol_type = protein
                        organism = Homo sapiens
SEQUENCE: 1169
CQSSCCVPVC C                                                         11

SEQ ID NO: 1170         moltype = AA   length = 11
FEATURE                 Location/Qualifiers
source                  1..11
                        mol_type = protein
                        organism = Homo sapiens
SEQUENCE: 1170
CQSSCFKPCC C                                                         11

SEQ ID NO: 1171         moltype = AA   length = 11
FEATURE                 Location/Qualifiers
source                  1..11
                        mol_type = protein
                        organism = Homo sapiens
SEQUENCE: 1171
CQSSCSKPCC C                                                         11

SEQ ID NO: 1172         moltype = AA   length = 11
FEATURE                 Location/Qualifiers
source                  1..11
                        mol_type = protein
                        organism = Homo sapiens
SEQUENCE: 1172
CQSSCYKPCC C                                                         11

SEQ ID NO: 1173         moltype = AA   length = 11
FEATURE                 Location/Qualifiers
source                  1..11
                        mol_type = protein
                        organism = Homo sapiens
SEQUENCE: 1173
CQSVCCQPTC C                                                         11

SEQ ID NO: 1174         moltype = AA   length = 11
FEATURE                 Location/Qualifiers
source                  1..11
                        mol_type = protein
                        organism = Homo sapiens
SEQUENCE: 1174
CQTTCCCPSC V                                                         11

SEQ ID NO: 1175         moltype = AA   length = 11
FEATURE                 Location/Qualifiers
source                  1..11
                        mol_type = protein
                        organism = Homo sapiens
SEQUENCE: 1175
CQTTCCRPSC C                                                         11

SEQ ID NO: 1176         moltype = AA   length = 11
FEATURE                 Location/Qualifiers
source                  1..11
                        mol_type = protein
                        organism = Homo sapiens
SEQUENCE: 1176
CQTTCCRTTC C                                                         11

SEQ ID NO: 1177         moltype = AA   length = 11
FEATURE                 Location/Qualifiers
source                  1..11
```

```
                            mol_type = protein
                            organism = Homo sapiens
SEQUENCE: 1177
CRPACCETTC C                                                              11

SEQ ID NO: 1178             moltype = AA  length = 11
FEATURE                     Location/Qualifiers
source                      1..11
                            mol_type = protein
                            organism = Homo sapiens
SEQUENCE: 1178
CRPACCQNTC C                                                              11

SEQ ID NO: 1179             moltype = AA  length = 11
FEATURE                     Location/Qualifiers
source                      1..11
                            mol_type = protein
                            organism = Homo sapiens
SEQUENCE: 1179
CRPCCCLRPV C                                                              11

SEQ ID NO: 1180             moltype = AA  length = 11
FEATURE                     Location/Qualifiers
source                      1..11
                            mol_type = protein
                            organism = Homo sapiens
SEQUENCE: 1180
CRPCCCVRPV C                                                              11

SEQ ID NO: 1181             moltype = AA  length = 11
FEATURE                     Location/Qualifiers
source                      1..11
                            mol_type = protein
                            organism = Homo sapiens
SEQUENCE: 1181
CRPCCWATTC C                                                              11

SEQ ID NO: 1182             moltype = AA  length = 11
FEATURE                     Location/Qualifiers
source                      1..11
                            mol_type = protein
                            organism = Homo sapiens
SEQUENCE: 1182
CRPLCCQTTC C                                                              11

SEQ ID NO: 1183             moltype = AA  length = 11
FEATURE                     Location/Qualifiers
source                      1..11
                            mol_type = protein
                            organism = Homo sapiens
SEQUENCE: 1183
CRPQCCQSVC C                                                              11

SEQ ID NO: 1184             moltype = AA  length = 11
FEATURE                     Location/Qualifiers
source                      1..11
                            mol_type = protein
                            organism = Homo sapiens
SEQUENCE: 1184
CRPQCCQTTC C                                                              11

SEQ ID NO: 1185             moltype = AA  length = 11
FEATURE                     Location/Qualifiers
source                      1..11
                            mol_type = protein
                            organism = Homo sapiens
SEQUENCE: 1185
CRPRCCISSC C                                                              11

SEQ ID NO: 1186             moltype = AA  length = 11
FEATURE                     Location/Qualifiers
source                      1..11
                            mol_type = protein
                            organism = Homo sapiens
SEQUENCE: 1186
CRPSCCESSC C                                                              11

SEQ ID NO: 1187             moltype = AA  length = 11
FEATURE                     Location/Qualifiers
```

```
source                    1..11
                          mol_type = protein
                          organism = Homo sapiens
SEQUENCE: 1187
CRPSCCISSC C                                                                    11

SEQ ID NO: 1188           moltype = AA  length = 11
FEATURE                   Location/Qualifiers
source                    1..11
                          mol_type = protein
                          organism = Homo sapiens
SEQUENCE: 1188
CRPSCCKPQC C                                                                    11

SEQ ID NO: 1189           moltype = AA  length = 11
FEATURE                   Location/Qualifiers
source                    1..11
                          mol_type = protein
                          organism = Homo sapiens
SEQUENCE: 1189
CRPSCCPSCC Q                                                                    11

SEQ ID NO: 1190           moltype = AA  length = 11
FEATURE                   Location/Qualifiers
source                    1..11
                          mol_type = protein
                          organism = Homo sapiens
SEQUENCE: 1190
CRPSCCQTTC C                                                                    11

SEQ ID NO: 1191           moltype = AA  length = 11
FEATURE                   Location/Qualifiers
source                    1..11
                          mol_type = protein
                          organism = Homo sapiens
SEQUENCE: 1191
CRPSCCRPQC C                                                                    11

SEQ ID NO: 1192           moltype = AA  length = 11
FEATURE                   Location/Qualifiers
source                    1..11
                          mol_type = protein
                          organism = Homo sapiens
SEQUENCE: 1192
CRPSCCVSRC C                                                                    11

SEQ ID NO: 1193           moltype = AA  length = 11
FEATURE                   Location/Qualifiers
source                    1..11
                          mol_type = protein
                          organism = Homo sapiens
SEQUENCE: 1193
CRPSCCVSSC C                                                                    11

SEQ ID NO: 1194           moltype = AA  length = 11
FEATURE                   Location/Qualifiers
source                    1..11
                          mol_type = protein
                          organism = Homo sapiens
SEQUENCE: 1194
CRPTCCQNTC C                                                                    11

SEQ ID NO: 1195           moltype = AA  length = 11
FEATURE                   Location/Qualifiers
source                    1..11
                          mol_type = protein
                          organism = Homo sapiens
SEQUENCE: 1195
CRPVCCCEPT C                                                                    11

SEQ ID NO: 1196           moltype = AA  length = 11
FEATURE                   Location/Qualifiers
source                    1..11
                          mol_type = protein
                          organism = Homo sapiens
SEQUENCE: 1196
CRPVCCCYSC E                                                                    11

SEQ ID NO: 1197           moltype = AA  length = 11
```

```
                            -continued

FEATURE                 Location/Qualifiers
source                  1..11
                        mol_type = protein
                        organism = Homo sapiens
SEQUENCE: 1197
CRTTCCHPSC C                                                                    11

SEQ ID NO: 1198         moltype = AA  length = 11
FEATURE                 Location/Qualifiers
source                  1..11
                        mol_type = protein
                        organism = Homo sapiens
SEQUENCE: 1198
CRTTCCRPSC C                                                                    11

SEQ ID NO: 1199         moltype = AA  length = 11
FEATURE                 Location/Qualifiers
source                  1..11
                        mol_type = protein
                        organism = Homo sapiens
SEQUENCE: 1199
CSCCKPYCSQ C                                                                    11

SEQ ID NO: 1200         moltype = AA  length = 11
FEATURE                 Location/Qualifiers
source                  1..11
                        mol_type = protein
                        organism = Homo sapiens
SEQUENCE: 1200
CSKPCCCQSS C                                                                    11

SEQ ID NO: 1201         moltype = AA  length = 11
FEATURE                 Location/Qualifiers
source                  1..11
                        mol_type = protein
                        organism = Homo sapiens
SEQUENCE: 1201
CSPCCQPTCC R                                                                    11

SEQ ID NO: 1202         moltype = AA  length = 11
FEATURE                 Location/Qualifiers
source                  1..11
                        mol_type = protein
                        organism = Homo sapiens
SEQUENCE: 1202
CSPCCVSSCC Q                                                                    11

SEQ ID NO: 1203         moltype = AA  length = 11
FEATURE                 Location/Qualifiers
source                  1..11
                        mol_type = protein
                        organism = Homo sapiens
SEQUENCE: 1203
CSQCSCCKPC Y                                                                    11

SEQ ID NO: 1204         moltype = AA  length = 11
FEATURE                 Location/Qualifiers
source                  1..11
                        mol_type = protein
                        organism = Homo sapiens
SEQUENCE: 1204
CSQCSCYKPC C                                                                    11

SEQ ID NO: 1205         moltype = AA  length = 11
FEATURE                 Location/Qualifiers
source                  1..11
                        mol_type = protein
                        organism = Homo sapiens
SEQUENCE: 1205
CSQSNCCKPC C                                                                    11

SEQ ID NO: 1206         moltype = AA  length = 11
FEATURE                 Location/Qualifiers
source                  1..11
                        mol_type = protein
                        organism = Homo sapiens
SEQUENCE: 1206
CSQSSCCKPC C                                                                    11
```

```
SEQ ID NO: 1207          moltype = AA   length = 11
FEATURE                  Location/Qualifiers
source                   1..11
                         mol_type = protein
                         organism = Homo sapiens
SEQUENCE: 1207
CSSSCCQPSC C                                                                      11

SEQ ID NO: 1208          moltype = AA   length = 11
FEATURE                  Location/Qualifiers
source                   1..11
                         mol_type = protein
                         organism = Homo sapiens
SEQUENCE: 1208
CTPSCCQPAC C                                                                      11

SEQ ID NO: 1209          moltype = AA   length = 11
FEATURE                  Location/Qualifiers
source                   1..11
                         mol_type = protein
                         organism = Homo sapiens
SEQUENCE: 1209
CVASCCQPSC C                                                                      11

SEQ ID NO: 1210          moltype = AA   length = 11
FEATURE                  Location/Qualifiers
source                   1..11
                         mol_type = protein
                         organism = Homo sapiens
SEQUENCE: 1210
CVPICCCKPV C                                                                      11

SEQ ID NO: 1211          moltype = AA   length = 11
FEATURE                  Location/Qualifiers
source                   1..11
                         mol_type = protein
                         organism = Homo sapiens
SEQUENCE: 1211
CVPSCCQPCC H                                                                      11

SEQ ID NO: 1212          moltype = AA   length = 11
FEATURE                  Location/Qualifiers
source                   1..11
                         mol_type = protein
                         organism = Homo sapiens
SEQUENCE: 1212
CVPVCCCKPM C                                                                      11

SEQ ID NO: 1213          moltype = AA   length = 11
FEATURE                  Location/Qualifiers
source                   1..11
                         mol_type = protein
                         organism = Homo sapiens
SEQUENCE: 1213
CVPVCCCKPV C                                                                      11

SEQ ID NO: 1214          moltype = AA   length = 11
FEATURE                  Location/Qualifiers
source                   1..11
                         mol_type = protein
                         organism = Homo sapiens
SEQUENCE: 1214
CVPVCCKPVC C                                                                      11

SEQ ID NO: 1215          moltype = AA   length = 11
FEATURE                  Location/Qualifiers
source                   1..11
                         mol_type = protein
                         organism = Homo sapiens
SEQUENCE: 1215
CVSSCCKPQC C                                                                      11

SEQ ID NO: 1216          moltype = AA   length = 11
FEATURE                  Location/Qualifiers
source                   1..11
                         mol_type = protein
                         organism = Homo sapiens
SEQUENCE: 1216
CVSSCCQHSC C                                                                      11
```

```
SEQ ID NO: 1217            moltype = AA   length = 11
FEATURE                    Location/Qualifiers
source                     1..11
                           mol_type = protein
                           organism = Homo sapiens
SEQUENCE: 1217
CVSSCCQPCC H                                                                 11

SEQ ID NO: 1218            moltype = AA   length = 11
FEATURE                    Location/Qualifiers
source                     1..11
                           mol_type = protein
                           organism = Homo sapiens
SEQUENCE: 1218
CVSSCCQPCC R                                                                 11

SEQ ID NO: 1219            moltype = AA   length = 11
FEATURE                    Location/Qualifiers
source                     1..11
                           mol_type = protein
                           organism = Homo sapiens
SEQUENCE: 1219
CVSSCCQPFC C                                                                 11

SEQ ID NO: 1220            moltype = AA   length = 11
FEATURE                    Location/Qualifiers
source                     1..11
                           mol_type = protein
                           organism = Homo sapiens
SEQUENCE: 1220
CVSSCCQPSC C                                                                 11

SEQ ID NO: 1221            moltype = AA   length = 11
FEATURE                    Location/Qualifiers
source                     1..11
                           mol_type = protein
                           organism = Homo sapiens
SEQUENCE: 1221
CVSSCCRPQC C                                                                 11

SEQ ID NO: 1222            moltype = AA   length = 11
FEATURE                    Location/Qualifiers
source                     1..11
                           mol_type = protein
                           organism = Homo sapiens
SEQUENCE: 1222
CVTRCCSTPC C                                                                 11

SEQ ID NO: 1223            moltype = AA   length = 11
FEATURE                    Location/Qualifiers
source                     1..11
                           mol_type = protein
                           organism = Homo sapiens
SEQUENCE: 1223
CVTSCCQPAC C                                                                 11

SEQ ID NO: 1224            moltype = AA   length = 11
FEATURE                    Location/Qualifiers
source                     1..11
                           mol_type = protein
                           organism = Homo sapiens
SEQUENCE: 1224
CVTSCCQPSC C                                                                 11

SEQ ID NO: 1225            moltype = AA   length = 11
FEATURE                    Location/Qualifiers
source                     1..11
                           mol_type = protein
                           organism = Homo sapiens
SEQUENCE: 1225
CVYSCCQPFC C                                                                 11

SEQ ID NO: 1226            moltype = AA   length = 11
FEATURE                    Location/Qualifiers
source                     1..11
                           mol_type = protein
                           organism = Homo sapiens
SEQUENCE: 1226
```

CVYSCCQPSC C                                                                    11

SEQ ID NO: 1227        moltype = AA  length = 11
FEATURE                Location/Qualifiers
source                 1..11
                       mol_type = protein
                       organism = Homo sapiens SEQUENCE: 1227
CYCPACCVSS C                                                                    11

SEQ ID NO: 1228        moltype = AA  length = 11
FEATURE                Location/Qualifiers
source                 1..11
                       mol_type = protein
                       organism = Homo sapiens SEQUENCE: 1228
CYKPCCCQSS C                                                                    11

SEQ ID NO: 1229        moltype = AA  length = 11
FEATURE                Location/Qualifiers
source                 1..11
                       mol_type = protein
                       organism = Homo sapiens SEQUENCE: 1229
CYKPCCCSSG C                                                                    11

SEQ ID NO: 1230        moltype = AA  length = 11
FEATURE                Location/Qualifiers
source                 1..11
                       mol_type = protein
                       organism = Homo sapiens SEQUENCE: 1230
MCCCVPACSC S                                                                    11

SEQ ID NO: 1231        moltype = AA  length = 11
FEATURE                Location/Qualifiers
source                 1..11
                       mol_type = protein
                       organism = Homo sapiens SEQUENCE: 1231
NCCVPVCCQC K                                                                    11

SEQ ID NO: 1232        moltype = AA  length = 11
FEATURE                Location/Qualifiers
source                 1..11
                       mol_type = protein
                       organism = Homo sapiens SEQUENCE: 1232
QCSCCKPCYC S                                                                    11

SEQ ID NO: 1233        moltype = AA  length = 11
FEATURE                Location/Qualifiers
source                 1..11
                       mol_type = protein
                       organism = Homo sapiens SEQUENCE: 1233
QCSCYKPCCC S                                                                    11

SEQ ID NO: 1234        moltype = AA  length = 11
FEATURE                Location/Qualifiers
source                 1..11
                       mol_type = protein
                       organism = Homo sapiens SEQUENCE: 1234
SCCVPICCQC K                                                                    11

SEQ ID NO: 1235        moltype = AA  length = 11
FEATURE                Location/Qualifiers
source                 1..11
                       mol_type = protein
                       organism = Homo sapiens SEQUENCE: 1235
SCCVPVCCQC K                                                                    11

SEQ ID NO: 1236        moltype = AA  length = 11
FEATURE                Location/Qualifiers
source                 1..11
                       mol_type = protein
                       organism = Homo sapiens

```
SEQUENCE: 1236
SCGCSQCNCC K                                                                11

SEQ ID NO: 1237        moltype = AA  length = 11
FEATURE                Location/Qualifiers
source                 1..11
                       mol_type = protein
                       organism = Homo sapiens
SEQUENCE: 1237
SCGCSQCSCC K                                                                11

SEQ ID NO: 1238        moltype = AA  length = 11
FEATURE                Location/Qualifiers
source                 1..11
                       mol_type = protein
                       organism = Homo sapiens
SEQUENCE: 1238
VCCCVPACSC S                                                                11

SEQ ID NO: 1239        moltype = AA  length = 11
FEATURE                Location/Qualifiers
source                 1..11
                       mol_type = protein
                       organism = Homo sapiens
SEQUENCE: 1239
VCCCVPACSC T                                                                11
```

PEPTIDE COMPOSITION AND RESPECTIVE USES

CROSS-REFERENCE

This application is a continuation of U.S. application Ser. No. 16/439,889, filed Jun. 13, 2019, which is a continuation of U.S. application Ser. No. 15/030,313, filed Apr. 18, 2016, now U.S. Pat. No. 10,709,655, issued Jul. 14, 2020, which is a U.S. National Stage Entry of International Application PCT/IB2014/065375, filed Oct. 16, 2014, which claims priority to Portuguese Application No. 107244, filed Oct. 18, 2013, all of which are hereby incorporated by reference in their entirety.

SEQUENCE LISTING

The instant application contains a Sequence Listing which has been submitted electronically in XML format and is hereby incorporated by reference in its entirety. Said XML copy, created on Feb. 2, 2023, is named 63230-710-302_SL.xml and is 1,068.431 bytes in size.

TECHNICAL FIELD

The current application corresponds to a composition that comprises at least one peptide, based on keratin and keratin associated proteins, containing 2 to 5 cysteines with the purpose of treatment and cosmetics of animal hair, in preference human hair.

BACKGROUND

Human hair has a significant social role in most of the various world cultures, particularly for female population. Thus, there is a constant desire to improve and change hair characteristics, such as its natural texture. [0003] There are several differences in hair characteristics between different human ethnicities, as well as between individuals of the same ethnicity, such as length, thickness, color and texture.

Hair is composed of approximately 65% to 95% protein. The remaining constituents include water, lipids, pigments and trace elements. The majority of the proteins present in human hair correspond to keratin and keratin-associated proteins.

Human hair fibers structure consists of cuticle, cortex and medulla. The cuticle constitutes about 15% by weight of the hair and consists of overlapping layers of cells, similar to a system of scales, with high content of cysteine. It provides a protective character to the hair fiber. The cortex is the middle region of the hair being responsible for the strength, elasticity and hair color. It is composed of several cell types and represents about 80% of the weight of the hair. The medulla corresponds to a central beam of cells, and is absent in some hairs.

Keratins and mainly keratin-associated proteins have high sulfur content, present in the cysteine amino acid. The presence of sulfur is essential to the hair structure, as it allows the formation of disulfide bonds between amino acids of the polypeptide chains, due to oxidation of cysteine. The existence of these bonds is largely responsible for the structure and texture of the hair.

There are several hair styling methods that involve breakage and reestablishment of disulfide bonds, allowing relaxation and straightening of the hair. However, the most effective methods currently used to modulate hair contain harmful chemicals such as sodium hydroxide, potassium hydroxide, lithium hydroxide, guanidine hydroxide, ammonium thioglycolate or sodium sulfate. These methods can damage the scalp and the hair fiber, leading to its weakening and reducing its tensile strength. Formaldehyde, an extremely toxic chemical, is also used in hair straightening products. Other hair treatments that do not involve so much damage to the hair and the consumer are usually very expensive, time-consuming and/or have low efficacy. Thus there is a constant demand for formulations that efficiently model the hair fiber without damage.

Peptides, proteins, amino acids and its derivatives have also been used in compositions for personal care products, namely hair conditioning and strengthening. For example, the document WO 00/23039 discloses a composition for hair treatment containing intermediate filament proteins, namely artificial keratin. The document EP 0488242 discloses a hair treating agent containing 3% to 10% by weight of cysteine and salts thereof, a polyhydric alcohol or a saccharide containing four to twenty carbon atoms, three or more hydroxyl groups in the molecule and no aldehyde or ketone group.

The current invention is distinguished by the use of peptides, while the other applications refer the use of, respectively, proteins and amino acids in isolation and together with other types of compounds. The peptides in this innovation peptide can penetrate into the human hair in order to improve hair fiber resistance.

The document WO 00/51556 discloses a hair treatment composition that contains four or more discrete amino acids selected from histidine, lysine, methionine, tyrosine, tryptophan or cysteine. This document describes peptides without referring sequences and providing a composition essentially based on histidine, lysine, methionine, tyrosine, tryptophan or cysteine.

The document PT 103484 describes a formulation for cosmetic applications that uses hydrophobic binding domains and/or carbohydrates, in order to enhance its properties and to repair hair damage. The binding domains used are hydrolyzed milk protein, a model of human surfactant protein as well as biologically active and synthetic peptides. The current invention is distinguished by the innovative use of synthetic peptide sequences analogous to keratin proteins instead of surfactant proteins. Furthermore, it does not rely on hydrophobic binding domains and/or carbohydrates, but in other interactions, namely disulfide bonds.

Enzymes have also been used as activating agents for hair treatment, such as in the document WO 00/64405. The document WO 2012/13593 discloses a cosmetic kit for hair conformational change that acts specifically in the disulfide bonds of the hair keratin, through enzyme activating agents and proteolytic enzymes.

As described in the last document there are hair treatments that include actions at the level of the hair disulfide bonds. Below we highlight some examples.

The document WO 97/11672 reports a method for permanent hair processing using tris(2-carboxyethyl)phosphine (TCEP), and other water-soluble tertiary phosphines to break disulfide bonds, whose reaction occurs in acidicic environment. The document U.S. Pat. No. 5,635,170 discloses a composition for permanent shaping of hair based on a keratin reducing agent, which contains N-glycyl-L-cysteine and/or L-cysteinyl-glycine. The pH range of this composition is 6.5 to 9.0. The document WO 2008/081348 refers a method and composition for permanent modulation of hair, through the use of 1% to 30% of N-alkyl-2-mercapto acetamide as a keratin reducing agent. It also contains at least one cationic surfactant for permanently shaping hair and the resulting process. The document WO 2006/001536 describes an agent for permanent hair processing that contains a derivative of mercaptocarboxylic acid, which allows processing and reduction of hair keratin in the acidic and neutral range of the pH. The document US 2010/0272666 discloses a hair cosmetic composition for hair treatment, containing 5 to 50 amino acids, without containing cysteine or its derivatives. Thus, this invention is distinguished by the existence of specific amino acid sequences, which contain cysteine, allowing the formation of disulfide bonds that stabilize and protect the hair fiber.

In a previous article by Fernandes et al. (Fernandes, Lima, Loureiro, Gomes, & Cavaco-Paulo, 2012), it is performed the toxicology evaluation of a peptide sequence for hair care use, containing 13 amino acids with two cysteines in its composition. However, in this article it is not mentioned or suggested that the percentage of cysteine in a peptide sequence may have some effect on the resistance of the hair. Also, in the present innovation, the number of amino acids of each peptide sequence is 6 to 12.

SUMMARY

Thus, the present invention aims to provide a composition for treatment of the hair, including animal and human hair, without the use of chemicals harmful to the hair fiber and consumer health and that does not present the drawbacks found in the state of the art.

The compositions described in the current invention, after prolonged use, provide hair with soft, shiny, undamaged texture and with the desired features. The peptide compositions with a specific number of amino acids and cysteines act synergically providing resistance to strength, toughness and elasticity to the hair. Therefore, the compositions of the current invention are particularly relevant for hair treatment, hair dying, hair perms, etc.

The present application describes a peptide composition for hair treatment, in particular human or animal hair, which comprises at least one peptide with 6-12 amino acids length (namely 6, 7, 8, 9, 10, 11, 12 amino acids), where 2-5 of those amino acids correspond to cysteine, preferably 2, 3, 4 or 5 of those amino acids are cysteines and dermatologically suitable excipients, which penetrates the hair, increasing it resistance and reducing it breakage.

In the embodiment, for improved results, the peptide (or peptides) of the peptide composition for hair care can comprise 10-11 amino acids.

In the embodiment of the peptide composition for hair care treatment, the referred peptides can also contain a percentage of hydrophobic amino acids, not higher than 60%, and preferably less than 41% for better results. Preferably, the composition can also comprise at least one hydrophobic amino acid selected from the following list: phenylalanine, alanine, leucine, methionine, isoleucine, tryptophan, proline, valine or their mixtures.

In yet another embodiment, the amount of cysteine of the peptide composition for hair treatment may vary from 10% to 50% of the total of amino acids of the peptide sequence, preferably 20-30%, and even more preferably 25%.

In an embodiment of the composition, with better results of the peptide (or peptides) of the peptide composition for hair treatment, the sequence of peptide(s) can comprise at least one sequence of the following list with a with a degree of homology greater than or equal to 90%: SEQ.ID NO:1-SEQ.ID NO:1239, preferably with a degree of homology greater than or equal to 91%, 92%, 93%, 94%, 95%, 96%, 97%, 98%, 99%, 100%.

In an embodiment, improved results for the peptide (or peptides) of the peptide composition for hair treatment can comprise at least one of the sequences of the following list with a degree of homology equal or greater than 90%: SEQ.ID NO:5, SEQ.ID NO:75; SEQ.ID NO:94; SEQ.ID NO: 409; SEQ.ID NO:411; SEQ.ID NO:412; SEQ ID. NO:432; SEQ.ID NO:618; SEQ.ID NO:717; SEQ.ID NO:951; SEQ.ID NO:1088; SEQ.ID NO:1131; SEQ.ID NO:1149, preferably with a degree of homology equal or greater than 91%, 92%, 93%, 94%, 95%, 96%, 97%, 98%, 99%, 100%.

In other embodiment, the concentration of the peptide of the peptide composition for hair treatment can vary between 0.001%-20% (w/w), preferably 0.01-5% (w/w).

In yet other embodiment, the peptide composition for hair treatment can comprise at least one excipient, selected from the following list: surfactants, emulsifiers, preservatives, thickeners, organic polymers, humectants, silicones, oils, fragrances, vitamins, buffers.

In another embodiment, the peptide composition for hair treatment can comprise at least one anionic surfactant selected from the following list: alkylbenzene sulfonates, ammonium lauryl sulfate, ammonium lauryl sulfate, ammonium xylenesulfonate, sodium C14-16 olefin sulfonate, sodium cocoyl sarcosinate, sodium laureth sulfate, sodium lauryl sulfate, sodium lauryl sulfoacetate, sodium myreth sulfate, sodium xylenesulfonate, TEA-dodecylbenzenesulfonate, ethyl PEG-15 cocamine sulfate, dioctyl sodium sulfosuccinate, or any mixture thereof.

In an embodiment, the peptide composition for hair treatment can comprise at least one amphoteric surfactant selected from the following list: cocamidopropyl betaine, coco betaine, cocoamphoacetate, cocoamphodipropionate, disodium cocoamphodiacetate, disodium cocoamphodipropionate, lauroamphoacetate, sodium cocoyl isethionate, or any mixture thereof.

In other embodiment, the peptide composition for hair treatment can comprise at least one cationic surfactant selected from the following list: quaternary ammonium compounds, behentrimonium chloride, behentrimonium methosulfate, benzalkonium chloride, betrimonium chloride, binnamidopropyltrimonium chloride, cocotrimonium chloride, dicetyldimonium chloride, dicocodimonium chloride, dihydrogenated tallow dimethylammonium chloride, hydrogenated Palm trimethylammonium chloride, laurtrimonium chloride, quaternium-15, quaternium-18 bentonite, quaternium-22 hectonite, stearalkonium chloride, tallowtrimonium chloride, tricetyldimonium chloride, or any mixture thereof.

In yet other embodiment, the peptide composition for hair treatment can comprise at least one non-ionic surfactant selected from the following list: decyl glucoside, laureth-10 (lauryl ether 10), laureth-23, Laureth-4, PEG-10 sorbitan laurate, polysorbate-(20, 21, 40, 60, 61, 65, 80, 81), PPG-1 trideceth-6, sorbitol, steareth-(2, 10, 15, 20), C11-21 pareth-(3-30), C12-20 acid PEG-8 ester, or their mixtures.

In yet other embodiment, the peptide composition for hair treatment can comprise at least one emulsifier selected from the following list: caprylic/capric/diglyceryl succinate, C10-15 pareth-(2,4,6,8) phosphate, C14-16 glycol palmitate, C18-20 glycol isostearate, ceteareth-(4-60), cocamidopropyl lauryl ether, deceth-(3-10), DIPA-hydrogenated cocoate, dipentaerythrityl hydroxystearate, dipentaerythrityl hydroxyisostearate, dipentaerythrityl hexacaprate/caprylate, dodoxynol-(5,6,7,9,12), nonoxynol-(1-35), octoxynol-(1-70), Octyldodeceth-(2,5,16,20,25), Palm kernel glycerides, or any mixture thereof.

In other embodiment, the peptide composition for hair treatment can comprise at least one preservative selected from the following list: butyl paraben, diazolidinyl urea, DMDM hydantoin, ethyl paraben, imidazolidinyl urea, iodopropynyl butylcarbamate, isobutyl paraben, methyl paraben, methylchloroisothiazolinone, methylisothiazolinone, phenoxyethanol, propyl paraben, sodium benzoate, or any mixture thereof.

In other embodiment, the peptide composition for hair treatment can comprise at least one thickener selected from the following list: aluminum stearates/isostearates/myristates/laurates/palmitates, glycol distearate, hydrogenated castor oil, hydrogenated castor oil hydroxystearate, hydrogenated castor oil isostearate, hydrogenated castor oil stearate, hydrogenated castor PEG-8 esters, PEG-150 distearate, or any mixture thereof.

In other embodiment, the peptide composition for hair treatment can comprise at least one natural polymer derived selected from the following list: carboxymethyl hydroxyethyl cellulose, carboxymethyl hydroxypropyl guar, cellulose, ethyl cellulose, hydroxybutyl methylcellulose, hydroxyethylcellulose, hydroxymethylcellulose, lauryl polyglucose, or any mixture thereof.

In other embodiment, the peptide composition for hair treatment can comprise at least one humectant selected from the following list: 1,2,6 hexanetriol, dipropylene glycol, glycerin, hexylene glycol, panthenol, phytantriol, propylene glycol, sodium PCA, sorbitol, triethylene glycol, polyglyceryl sorbitol, glucose, fructose, polydextrose, potassium PCA, hydrogenated honey, hyaluronic acid, inositol, hexanediol beeswax, hexanetriol beeswax, hydrolyzed elastin, hydrolyzed collagen, hydrolyzed silk, hydrolyzed keratin, erythritol, capryl glycol, isoceteth-(3-10, 20, 30), isolaureth-(3-10, 20, 30), laneth-(5-50), laureth-(1-30), steareth-(4-20), trideceth-(5-50), or any mixture thereof.

In other embodiment, the peptide composition for hair treatment can comprise at least one cationic polymer selected from the following list: polyquaternium-10, polyquaternium-7, polyquaternium-11m guar hydroxypropyltrimonium chloride, or any mixture thereof.

In other embodiment, the peptide composition for hair treatment can comprise at least one silicone selected from the following list: amodimethicone, amodimethicone, trideceth-12, cetrimonium, chloride mixture, behenoxy, dimethicone sparingly, cetearyl methicone, cetyl dimethicone, cyclomethicone, cyclopentasiloxane, dimethicone, dimethicone copolyol, dimethicone copolyol, dimethiconol, hydrolyzed wheat protein hydroxypropyl polysiloxane, stearoxy dimethicone sparingly, stearyl dimethicone, trimethylsilylamodimethicone, lauryl methicone copolyol, or any mixture thereof.

In yet other embodiments, the peptide composition for hair treatment can comprise at least one organic oil selected from the following list: mineral oil, paraffin, petrolatum, or any mixture thereof.

In yet other embodiment, the peptide composition for hair treatment can comprise at least one protein selected from the following list: cocodimonium hydroxypropyl hydrolyzed casein, cocodimonium hydroxypropyl hydrolyzed collagen, cocodimonium hydroxypropyl hydrolyzed hair keratin, cocodimonium hydroxypropyl hydrolyzed keratin, cocodimonium hydroxypropyl hydrolyzed rice protein, cocodimonium hydroxypropyl hydrolyzed silk, cocodimonium hydroxypropyl hydrolyzed soy protein, cocodimonium hydroxypropyl hydrolyzed wheat protein, cocodimonium hydroxypropyl silk amino acids, cocoyl hydrolyzed collagen, cocoyl hydrolyzed keratin, hydrolyzed keratin, hydrolyzed oat flour, hydrolyzed silk, hydrolyzed silk protein, hydrolyzed soy protein, hydrolyzed wheat protein, hydrolyzed wheat protein, keratin, potassium cocoyl hydrolyzed collagen, TEA-cocoyl hydrolyzed collagen, TEA-cocoyl hydrolyzed soy protein, or any mixture thereof.

In other embodiment, the peptide composition for hair treatment can comprise at least one vitamin selected from the following list: retinol, retinyl palmitate tocopherol acetate, or any mixture thereof.

In other embodiment, the peptide composition for hair treatment can comprise at least one ester emollient selected from the following list: butyl myristate, butyl stearate, C12-15 alkyl benzoate, caprylic/capric triglyceride, cetyl octanoate, cetyl stearate, cetearyl stearate, decyl oleate, dimethyl lauramine isostearate, glyceryl stearate, glyceryl adipate, glyceryl arachidate, glyceryl arachidonate, glyceryl behenate, glyceryl caprate, glyceryl caprylate, glyceryl caprylate/caprate, glyceryl citrate/lactate/linoleate/oleate, glyceryl cocoate, glyceryl diarachidate, glyceryl dibehenate, glyceryl dierucate, glyceryl dihydroxystearate, glyceryl diisopalmitate, glyceryl diisostearate, glyceryl dilaurate, glyceryl dilinoleate, glyceryl dimyristate, glyceryl dioleate, glyceryl dipalmitate, glyceryl dipalmitoleate, glyceryl diricinoleate, glyceryl distearate, glyceryl erucate, glycol stearate, isocetyl stearate, isopropyl myristate, isopropyl palmitate, isopropyl stearate, isostearyl stearate, octyl palmitate, octyl stearate, propylene glycol dicaprylate/dicaprate, sorbitan benzoate, sorbitan caprylate, sorbitan isostearate, Sorbitan laurate, sorbitan tristearate, stearyl stearate, tocopheryl linoleate, or any mixture thereof.

In other embodiment, the peptide composition for hair treatment can comprise at least one alkanolamide selected from the following list: acetamide MEA, cocamide DEA, cocamide MEA, lactamide MEA, lauramide DEA, lauramide DEA, propylene glycol, lauramide MEA, lecithinamide DEA, linoleamide DEA, linoleamide MEA, linoleamide MIPA, myristamide DEA, myristamide MEA, myristamide MIPA, oleamide DEA, oleamide DEA, oleamide MEA, oleamide MIPA, soyamide DEA, stearamide MEA, or any mixture thereof.

In yet other embodiment, the peptide composition for hair treatment can comprise at least one amine selected from the following list: behentamidopropyl dimethylamine, cocamidopropyl dimethylamine, isostearamidopropyl dimethylamine, lauramidopropyl dimethylamine, myristamidopropyl dimethylamine, oleamidopropyl dimethylamine, palmitamidopropyl dimethylamine, stearamidopropyl dimethylamine, tallamidopropyl dimethylamine, or any mixture thereof.

In yet other embodiment, the peptide composition for hair treatment can comprise at least one pH adjuster selected from the following list: ascorbic acid, citric acid, sodium hydroxide, triethanolamine, or any mixture thereof.

In yet other embodiment, the peptide composition for hair treatment can comprise at least one salt selected from the following list: calcium chloride, magnesium chloride, magnesium sulfate, potassium chloride, potassium glycol sulfate, sodium chloride, or any mixture thereof.

In yet other embodiment, the peptide composition for hair treatment can comprise at least one aliphatic alcohol selected from the following list: behenyl alcohol, cetearyl alcohol, cetyl alcohol, isocetyl alcohol, isostearyl alcohol, lauryl alcohol, myristyl alcohol, stearyl alcohol, C30-50 alcohols, lanolin alcohol, or any mixture thereof.

In another embodiment, the peptide composition for hair treatment can comprise at least one UV filter/sunscreen selected from the following list: benzophenone-(2, 3, 4, 5, 6, 7, 8, 9, or 10), benzophenone-4, benzyl salicylate, benzylidene camphor sulfonic acid, bornelone, ethyl cinnamate, ethylhexyl methoxycinnamate (octyl methoxycinnamate), octoxynol-40, octoxynol-20, octyl methoxycinnamate, octyl salicylate, oxybenzone, phenyl ketone, PEG-25 PABA, polyacrylamidomethyl benzylidene camphor, or any mixture thereof.

In other embodiment, the peptide composition for hair treatment can comprise at least one natural oil selected from the following list: coconut oil, jojoba oil, olive oil, palm Oil, safflower oil, sesame seed oil, shea butter, sweet almond oil, wheat germ oil, or any mixture thereof.

In yet other embodiment, the peptide composition for hair treatment can comprise at least one amine oxide selected from the following list: cocamine oxide, lauramine oxide, or any mixture thereof.

In other embodiment, the peptide composition for hair treatment can comprise at least one chelate selected from the following list: diiosopropyl oxalate, disodium EDTA, disodium EDTA-copper, HEDTA, oxalic acid, potassium citrate, sodium citrate, dodium oxalate, TEA-EDTA, tetrasodium EDTA, trisodium EDTA, trisodium HEDTA, or any mixture thereof.

In other embodiment, the peptide composition for hair treatment can comprise at least one fatty acid selected from the following list: arichidonic acid, capric acid, coconut fatty acid, lauric acid, linoleic acid, linolenic acid, myristic acid, palmitic acid, pantothenic acid, stearic acid, caproic acid, capryleth-(4, 6, 9) carboxylic acid, isostearic acid, or any mixture thereof.

In other embodiment, the peptide composition for hair treatment can comprise at least one agent antimicrobial/antibacterial selected from the following list: glyoxal, triclosan, or any mixture thereof.

In other embodiment, the peptide composition for hair treatment can comprise at least one PEG-modified material selected from the following list: PEG-150 pentaerythirtyl tetrastearate, PEG-(-2, -3, -4, -6, -8, -12, -20, -32, -50, -150, -175) distearate, PEG-10 castor oil, PEG-10 cocamine, PEG-10 cocoate, PEG-10 coconut oil esters, PEG-10 glyceryl oleate, PEG-10 glyceryl pibsa tallate, PEG-10 glyceryl stearate, PEG-10 hydrogenated lanolin, PEG-10 hydrogenated tallow amine, PEG-10 isolauryl thioether, PEG-10 isostearate, PEG-10 lanolate, PEG-10 lanolin, PEG-10 laurate, PEG-10 oleate, PEG-10 olive glycerides, PEG-10 polyglyceryl-2 laurate, PEG-10 propylene glycol, PEG-10 sorbitan laurate, PEG-10 soya sterol, PEG-10 soyamine, PEG-10 stearamine, PEG-10 stearate, PEG-10 stearyl benzonium chloride, PEG-10 tallate, PEG-10 tallow aminopropylamine, PEG-100, PEG-100 castor oil, PEG-100 hydrogenated castor oil, PEG-100 lanolin, PEG-100 stearate, PEG-40 hydrogenated castor Oil, PEG-60, PEG-55 propylene glycol distearate, or any mixture thereof.

In other embodiment, the peptide composition for hair treatment can comprise at least one polymer selected from the following list: carbomer, dodecanedioic acid/cetearyl alcohol/glycol copolymer, hydrogenated C6-14 olefin polymers, hydrogenated ethylene/propylene/styrene copolymer: polyacrylic acid, polymethyl methacrylate: polymer, polyvinyl acetate, polyvinyl alcohol, PPG, PPG-25-laureth-25, PPG-5 pentaerithrityl ether, PPG-75-PEG-300-hexylene glycol, polyvinylpyrrolidone, PVP/VA (polyvinylpyrrolidone/vinyl acetate copolymer), sodium carbomer, TEA-carbomer, poloxamer (100-407), poloxamine, polyacrylamidomethylpropane sulfonic acid, polyethylene terephthalate, or any mixture thereof.

In other embodiment, the peptide composition for hair treatment can comprise at least one antistatic agent selected from the following list: apricotamidopropyl ethyldimonium ethosulfate, apricotamidopropyl ethyldimonium lactate, cocamidopropyl ethyldimonium ethosulfate, cocamidopropyl ethyldimonium lactate, lauramidopropyl ethyldimonium ethosulfate, lauramidopropyl ethyldimonium lactate, linoleamidopropyl ethyldimonium ethosulfate, linoleamidopropyl ethyldimonium lactate, myristamidopropyl ethyldimonium ethosulfate, myristamidopropyl ethyldimonium lactate, oleamidopropyl ethyldimonium ethosulfate, oleamidopropyl ethyldimonium lactate, stearamidopropyl ethyldimonium ethosulfate, stearamidopropyl ethyldimonium lactate, or any mixture thereof.

In other embodiment, the peptide composition for hair treatment can comprise at least one alcohol selected from the following list: SD alcohol 40, witch hazel, isopropanol, or any mixture thereof.

In yet other embodiment, the peptide composition for hair treatment can comprise fragrances, oils or any mixture thereof.

In other embodiment, the peptide composition for hair treatment can be used in medicine, veterinary and/or for cosmetics, preferably for the treatment of hair, mainly for animal or human, particularly for treating diseases of the scalp, particularly scalp irritation, alopecia areata, lichen planus, folliculitis keloid of the neck, trichorrhexis nodosa, tricodistrophy, pili torti, tricorrexis invaginata, moniletrix, uncombable hair syndrome. [0058] In other embodiment, the composition may comprise a dye agent linked to the N or C-terminal of the referred peptides.

In yet other embodiment is the use of the described composition for hair coloring.

Other aspect of the embodiment is the use of the described composition as a hair strengthener or as fixer of perms and/or curly hairs.

It is also described in this application shampoo, lotion, serum, cream, conditioner, foam, elixir, oil, aerosol or mask comprising the composition presented in this application.

The present application discloses a composition for hair treatment that comprise, in whole or in part, one or more peptide sequences of 6 to 12 amino acid residues based on keratin and keratin-associated proteins having 2 to 5 cysteine residues, preferably having 3 to 5 residues of cysteine, for treatment and cosmetics of the hair, preferably human hair, chemically pre-treated or not. Thus the presence of cysteine in the peptide sequence (higher than 10%, preferably more than 15%) in combination with a percentage of hydrophobic amino acids ensures that the peptides can have a lasting fixation in the hair, improving the human hair properties such as elasticity and strength.

Surprisingly, the described peptide compositions in which the peptide(s) comprising 2 to 5 cysteines allow penetration of the peptide(s) and enhance the properties of hair, preferably 3-5 cysteines. Thus, described peptide(s) containing 2-5 cysteine in order to allow hair penetration and enrichment of the hair properties, such as elasticity, resistance, reduce eventual hair damage, as well as improve and change hair characteristics.

The peptide compositions described in the present application surprisingly enrich and improve the properties and characteristics of the hair, such as elasticity, strength and appearance, repairing damaged keratinous fiber. Therefore, formulation's high cysteine content is used to improve and/or change its characteristics, such as hair curl or uncurl. The sequence of peptides can have also preferably a percentage of hydrophobic amino acids not exceeding 60%, improving even further the results. Examples of hydrophobic amino acids are phenylalanine, alanine, leucine, methionine, isoleucine, tryptophan, proline, valine, and others.

In the context of the present description, the peptide composition can also be applied to the hair and in particular to the human hair as, but not limited to, aqueous solution or conventional shampoo or conditioner. It can also be used as a lotion, foam, aerosol, gel, mask, and application formulation with or without subsequent rinsing.

The concentration of peptide to be used depends on several features such as the condition of the hair, the origin and the formulation of the hair care product.

DETAILED DESCRIPTION

It should be understood that the detailed description and specific examples are indicative of preferred embodiments of the invention and are provided to be illustrative only. This patent is not limited to those mentioned applications.

The present application describes a composition for hair treatment that comprises different peptides, which are based in the structure of keratin and keratin associated proteins.

The compositions described in the present application allow surprisingly the dermo-cosmetic treatment of animal hair, including human hair, chemically pre-treated or not. The composition described in the present invention, through the use of specific peptides, allows the preparation of keratinous fiber damages, due to the high binding capacity of the keratin peptides, including through disulfide bridges.

The described compositions improve the properties and characteristics of the hair, such as elasticity, resistance and appearance, repairing putative damages of the hair.

The peptides here defined are peptide sequences which bind with a certain affinity to the hair. The peptides used in this invention are composed by 6 to 12 amino acids, and are constituted by a minimum of 2 and a maximum of 5 cysteines, preferably 3-5 cysteines.

The peptide composition for hair treatment described allows a resistance increase due to the presence of the cysteine-rich peptide, which leads to the resistance of the hair even after several rinsing.

Every peptide can be used together or separately, as well as all or part of the peptide sequence in the hair composition. Each peptide sequence contains amino acids with sulfur, specifically cysteine, which interacts with the hair and allows the formation of intermolecular cross-linking, stabilizing the keratinous fiber.

The peptide composition described uses a high content on cysteine in order to enrich the hair properties, such as improve elasticity and resistance, reduce putative damage of the hair, improve and/or change hair characteristics. Regarding the interaction with the keratinous fibers, the cysteine is 10% to 50% of the total amount of amino acids of the peptide sequence. Additionally, the number of amino acids of the peptide sequence is preferable from 6 to 12.

The peptides can be used separately or in combination of two or more peptides. The concentration of the peptide to be used depends on several characteristics, such as hair condition, origin and the formulation of the product for hair treatment. The content of the hair composition of the present invention is as example 1-0.001% (w/w) in mass.

The peptides of the present invention can be prepared by conventional methods of peptide synthesis, well known in the state of the art.

Additionally many companies provide customized services for peptide synthesis.

An embodiment of the current invention describes peptides that link to the hair, and which sequence of amino acids includes cysteines where the sequence is selected from the group between the sequences ID NO:1 to sequence ID NO:1239.

The sequence of the 1239 peptides referred is listed in the table of the FIG. 1.

As example of hair, it was used virgin human hair tresses, acquired from the International Hair Importers and Products, Inc. (New York). The term virgin hair is applied to all the hair that was never subject or was at least 10 years without making any chemical treatment. Several different hair samples such as African, Asian and Caucasian hair are commercially available in several companies, such as the company mentioned above. Optionally, the hair samples can be treated, for example, using hydrogen peroxide to bleach the hair, needed for techniques such as hair dying.

In the context of this invention, the peptides can be applied to the hair, such as the human hair in the form of, but not limited to, aqueous or conventional preparation of shampoo or conditioner. It can also be in the form of lotion, foam, spray, gel, mask, formulation applied with or without subsequent rinsing.

This invention can be prepared by peptide coupling with an agent of these preparations directly or via a spacer.

This coupling interaction can be performed by covalent or non-covalent bonds, such as hydrogen bond, electrostatic interactions, hydrophobic interactions or van der Waals interactions. The spacer can be used to separate the peptide from the preparation agent, ensuring that the agent does not interfere with the peptide linkage to the hair.

The present invention can be understood more clearly and accurately by reading the following examples, which are indicative of preferred embodiments of the invention. They are provided for illustration in greater detail of the present invention, without introducing any limitation and without being limited to those applications.

EXAMPLES

The examples that are within the scope of the claims represent different embodiments of the invention; all other examples are comparative examples.

Example 1

The present application treats human hair through several commercial formulations with and without the use of the peptides from the sequence ID NO: 5. As The hair was supplied from International Hair Importers and Products, Inc. (New York).

The tests were performed with in human hair after 8 treatments of bleaching, at 50° C. in 0.1 M $Na_2CO_3$/$NaHCO_3$ buffer, at pH=9, 10% $H_2O_2$, for 1 hour.

Several formulations were tested:
hair serum with 15% PG;
hair mask.

The mask used in this application was a basic commercial formulation with water, denaturing alcohol, propylene glycol, ether dicaprylic, cetylstearyl alcohol, behentrimonium chloride, cetyl ester, polysorbate 20, hydrolyzed wheat protein, hydrolyzed wheat starch, benzyl alcohol and fragrance.

The hair serum used in this application was a basic commercial formulation with water, denaturing alcohol, propylene glycol, polysorbate 20, hydrolyzed wheat protein, hydrolyzed wheat starch, crosslinked polymer alkyl acrylate/C10-30, triethanolamine, benzyl alcohol, fragrance.

Each of the formulations was tested with and without the peptide sequence ID NO:5, which contains in the sequence 15% of cysteine. The formulations containing the peptide SEQ ID NO:5 had a concentration of peptide of 0.1 mg/mL, in a ratio 1:1 (v/v).

To demonstrate the effect was also tested:
a peptide whose sequence does not contain cysteine, with approximately 41% hydrophobic amino acids;
a peptide which contains in it sequence 8% cysteine, with approximately 58% hydrophobic amino acids.

The hair mask was applied to the hair after 8 bleaching treatments, being left to act for 15 minutes, mimicking the procedure indicated in commercial masks. Posteriorly, the hair was washed. The serum was applied to the hair after 8 bleaching treatments, being left to act for 1 hour at 37° C. Posteriorly, the hair was not washed, as in typical commercial procedures the serum should be applied in dry hair. The hair was also tested after 5 applications.

The peptide from the sequence ID NO: 5 was able to penetrate in the hair fiber for all the formulations.

After the treatment, mechanical tests were performed, using a cell with 2.5 N maximum load and a deformation rate of 1.5 mm/min. Each hair was individually mounted in the tensile jig by means of a paper template with a fixed gauge length of 20 mm.

TABLE 1

Young modulus of virgin hair without treatments and after 8 times bleaching treatments.

| Hair type | Young modulus (MPa) |
| --- | --- |
| Virgin hair | 6579 |
| Hair after 8 time bleaching | 5294 |
| Serum(with a 15% cysteine and 50% hydrophobic amino acids peptide) | 7149 |
| Serum for comparison(with a 41% hydrophobic amino acid without cysteine peptide) | 6180 |

TABLE 1-continued

Young modulus of virgin hair without treatments
and after 8 times bleaching treatments.

| Hair type | Young modulus (MPa) |
|---|---|
| Serum for comparison (with a 8% cysteine and 58% hydrophobic amino acid peptide) | 6456 |
| Serum for comparison (without peptide) | 6034 |

TABLE 2

Young modulus for different types of hair treatment.

| Type of treatment | Young modulus after 1 application (MPa) | Young modulus after 5 applications (MPa) |
|---|---|---|
| Serum (with a 15% cysteine and 50% hydrophobic amino acid peptide) | 7149 | 7318 |
| Serum for comparison (without peptide) | 6034 | 6112 |
| Mask (with a 15% cysteine and 50% hydrophobic amino acid peptide) | 6175 | 7075 |
| Mask for comparison (without peptide) | 5514 | 5685 |

The peptide in these treatments is the peptide from sequence ID NO: 5. The formulations which contain the sequence ID NO:5 induce an increase in mechanical resistance of the damaged hair. After 5 applications, the hair treated with the sequence ID NO: 5 maintain the high resistance, having a higher increase in the resistance than without the peptide.

Example 2

This example discloses the treatment of human hair with peptides containing cysteine, and in this case the peptide containing the sequence ID NO: 409, based in the assumption that small peptides are able to penetrate in the hair fiber cuticle.

The hair was supplied from International Hair Importers and Products, Inc. (New York). Hair fibers were pre-treated by bleaching. The formulation was tested in different hair types:
  virgin hair washed, with the cuticle intact and absence of chemical damages;
  hair after 8 bleaching treatments, at 50° C. in 0.1 M Na2CO3/NaHCO$_3$ buffer, at pH=9, 10% H2O2, for 1 hour.

The incorporation of the peptides was performed by direct application in the hair surface. The mechanical resistance tests were performed after the treatment of the hair with the peptide.

The measurements of mechanical resistance were performed using a cell with 2.5 N maximum load and a deformation rate of 1.5 mm/min. Each hair was individually mounted in the tensile jig by means of a paper template with a fixed gauge length of 20 mm.

As for the results obtained for the mechanical test showed that compared to the control, i.e., virgin hair without bleaching or peptide treatment (Young modulus: 4142±590 MPa), bleaching reduced the Young modulus (2478±567 MPa), while the treatment with the peptide sequence ID NO: 409 after bleaching increased the Young modulus to higher valued than the virgin hair with no treatment (5649±1022 MPa).

Example 3

This example discloses the treatment of human hair with a composition comprising peptides. In this example, the peptide with the sequence ID NO: 412 was tested. The hair was supplied from International Hair Importers and Products, Inc. (New York).

The formulation was tested in different hair types:
  virgin hair washed, with the cuticle intact and absence of chemical damages;
  hair after reduction treatment, at 37° C. in phosphate buffer at pH=8, with 3M GndHCl and 0.05M DTT for 2 hours.

For the treatment with the peptide SEQ ID NO: 412, concentrations of 0.01% (w/w) were used.

The average of the Young modulus for relaxed hair is 3002 MPa, while for relaxed hair fiber after peptide treatment at 0.01% is 4190 MPa. The Young modulus value for virgin hair without treatment is 5214 MPa.

In the maximum load test, for the relaxed hair fiber, the maximum of resistance were 96 MPa, while for the hair fiber relaxed after peptide treatment 126 MPa and for the virgin hair with no treatment 203 MPa.

Regarding hair stretching, the relaxed hair has an average of 51%, while after treatment with the peptide sequence ID NO: 412, has a stretching of 72%. For virgin hair, the average of hair stretching is 58%.

Therefore, it is evident that the peptides are capable to prevent the hair surface degradation and consequently, the hair treated with these peptides has a longer life span.

Example 4

In order to assess the interactions between the keratin and some peptides, a keratin solution was prepared. This procedure was performed by immersing African hair, acquired from the International Hair Importers and Products, Inc. (New York), in a solution containing 8 M urea, 0.2 M sodium dodecyl sulfate and 0.5 M sodium bisulfate. The mixture was heated to 50° C. for 24 h in a shaker bath. The solution was dialyzed for several days against double-distilled water. The keratin solution was then concentrated using AMICON with a 3 kDa cut-off. The keratin was then conjugated with Alexa Fluor 647 carboxylic acid, succinimidyl ester in DMSO anhydrous 5%.

The reaction was incubated for 1 h30 min at room temperature and in the dark. The Alexa Fluor 647 that did not link to the keratin solution was separated by centrifugation in AMICON with a 3 kDa cut-off for 1 h at 25° C. and 5000×g.

The keratin was then diluted to 1 μg/mL in blocking buffer (3% BSA in tris-buffered saline (TBS) with 0.05% Tween 20). The peptides tested were SEQ.ID NO:179, SEQ.ID NO:75, SEQ.ID NO:432, SEQ.ID NO:951, SEQ.ID NO:1108, SEQ.ID NO:1131 and a peptide containing 13 amino acids, including 2 cysteines (X3CX5CX3), where X represents one of known amino acid residues, with the exception of cysteine residue that is represented by the letter C. This peptide is similar to the one tested in Fernandes et al. (Fernandes, Lima, Loureiro, Gomes, & Cavaco-Paulo, 2012).

Several peptides in a concentration of 15 fmol/mm2, were attached to a glass through a hydrophilic linked moiety, and were then incubated with the keratin, marked with Alexa Fluor 647, for 2 hours at 37° C.

After incubation, the glasses were rinsed in successive washing solutions: TBS+0.1% Tween 20 and blocking buffer with 3% BSA in TBS+0.1% Tween 20, for 3 minutes in each solution.

The imaging of the glasses was performed in Agilent G2565CA Microarray Scanner System. Three replicas of the each peptide incubation were performed and analyzed.

TABLE 3

Normalized intensity levels of peptide sequences.

| Sequence | Number of amino acids | Cysteine content | Hydrophobic amino acids content | Intensity level (average ± standard deviation) |
|---|---|---|---|---|
| SEQ.ID NO:179 | 10 | 20% | 50% | 0.990 ± 0.014 |
| SEQ.ID NO:75 | 10 | 30% | 60% | 1.000 ± 0.000 |
| SEQ.ID NO:432 | 10 | 30% | 40% | 1.000 ± 0.000 |
| SEQ.ID NO:951 | 10 | 40% | 30% | 1.000 ± 0.000 |
| SEQ.ID NO:1108 | 11 | 46% | 18% | 1.000 ± 0.000 |
| SEQ.ID NO:1131 | 11 | 46% | 9% | 1.000 ± 0.000 |
| $X_3CX_5CX_3$ | 13 | 15% | 38% | 0.184 ± 0.084 |

The peptides SEQ.ID NO:75, SEQ.ID NO:432, SEQ.ID NO:951, SEQ.ID NO:1108, SEQ.ID NO:1131, with percentage of cysteine ranging from 30% to 46%, such as and percentage of hydrophobic amino acids ranging from 9% to 60% were able to obtain an intensity of 1, indicating a very high affinity to keratin. The peptide SEQ.ID NO:179, with 20% and 50% of cysteine and hydrophobic content, respectively showed an slightly inferior but still very high intensity (0.990±0.014). These peptides were compared with a peptide similar to the one described in Fernandes et al. (Fernandes, Lima, Loureiro, Gomes, & Cavaco-Paulo, 2012) containing 2 cysteines in a 13 amino acids sequence. The reduced percentage of cysteine (15%) and higher number of amino acids in the sequence (13 amino acids) lead to a decrease in the intensity to 0.184±0.084, showing an inferior affinity to keratin. This suggests that the higher number of amino acids difficult the reaction of the peptide with the hair keratins. This inferior affinity to keratin leads to less fixation of the peptides in the hair in posterior treatments and consequently providing less improvements in the recovery of the hair characteristics.

List of Peptide Sequences

The sequences of peptides are described by one letter code of amino acids. The code is as follows:

Amino acid—One Letter Code
Histidine—H
Arginine—R
Lysine—K
Isoleucine—I
Phenylalanine—F
Leucine—L
Tryptophan—W
Alanine—A
Methionine—M
Proline—P
Valine—V
Cysteine—C
Asparagine—N
Glycine—G
Serine—S
Glutamine—Q
Tyrosine—Y
Threonine—T
Aspartic acid—D
Glutamic acid—E

SEQ. ID NO: 1
APCAPRPSCG

SEQ. ID NO: 2
EACVPSVPCP

SEQ. ID NO: 3
ESCGTASGCA

SEQ. ID NO: 4
GLCAGTSACL

SEQ. ID NO: 5
GVCGPSPPCI

SEQ. ID NO: 6
HGCTLPGACN

SEQ. ID NO: 7
HSCTLPGACN

SEQ. ID NO: 8
KDCLQNSLCE

SEQ. ID NO: 9
LPCLPAASCG

SEQ. ID NO: 10
LPCYFTGSCN

SEQ. ID NO: 11
NFCLPSLSCR

SEQ. ID NO: 12
NPCATTNACD

| | |
|---|---|
| NPCATTNACE | SEQ. ID NO: 13 |
| NPCATTNACS | SEQ. ID NO: 14 |
| NPCGLRARCG | SEQ. ID NO: 15 |
| NPCGPRSRCG | SEQ. ID NO: 16 |
| NPCSTPASCT | SEQ. ID NO: 17 |
| NPCSTSPSCV | SEQ. ID NO: 18 |
| PACTSSSPCS | SEQ. ID NO: 19 |
| SKCHESTVCP | SEQ. ID NO: 20 |
| SPCVPRTVCV | SEQ. ID NO: 21 |
| SSCSVETACL | SEQ. ID NO: 22 |
| SVCSSGVNCR | SEQ. ID NO: 23 |
| TACPLPGTCH | SEQ. ID NO: 24 |
| TNCSPRPICV | SEQ. ID NO: 25 |
| TSCVPPAPCT | SEQ. ID NO: 26 |
| TTCTSSNTCE | SEQ. ID NO: 27 |
| VPCVPSVPCT | SEQ. ID NO: 28 |
| ATCGPSACIT | SEQ. ID NO: 29 |
| GPCISNPCGL | SEQ. ID NO: 30 |
| GPCLSNPCTS | SEQ. ID NO: 31 |
| GSCVTNPCGP | SEQ. ID NO: 32 |
| LTCFSITCSS | SEQ. ID NO: 33 |
| NPCSTPSCTT | SEQ. ID NO: 34 |
| PSCVTAPCAP | SEQ. ID NO: 35 |
| SDCSSTHCSP | SEQ. ID NO: 36 |
| SLCLPPTCHT | SEQ. ID NO: 37 |
| SLCNLGSCGP | SEQ. ID NO: 38 |
| SPCLVGNCAW | SEQ. ID NO: 39 |
| TACLPGTCAT | SEQ. ID NO: 40 |
| TSCLPALCLP | SEQ. ID NO: 41 |
| TSCSSRPCVP | SEQ. ID NO: 42 |
| TTCGGGSCGV | SEQ. ID NO: 43 |
| VNCRPELCLG | SEQ. ID NO: 44 |
| YVCQPMACLP | SEQ. ID NO: 45 |
| AFSCISACGP | SEQ. ID NO: 46 |
| GSVCSAPCNG | SEQ. ID NO: 47 |
| GVVCGDLCAS | SEQ. ID NO: 48 |
| GVVCGDLCVS | SEQ. ID NO: 49 |
| LTGCLLPCYF | SEQ. ID NO: 50 |
| NEDCKLPCNP | SEQ. ID NO: 51 |
| NFSCVSACGP | SEQ. ID NO: 52 |
| PPTCHTACPL | SEQ. ID NO: 53 |
| PQPCATACKP | SEQ. ID NO: 54 |
| SEDCKLPCNP | SEQ. ID NO: 55 |
| SLGCRTSCSS | SEQ. ID NO: 56 |
| SLSCRTSCSS | SEQ. ID NO: 57 |
| SSSCPLGCTM | SEQ. ID NO: 58 |
| TGSCNSPCLV | SEQ. ID NO: 59 |
| TSSCPLGCTM | SEQ. ID NO: 60 |
| VGSCGSSCRK | SEQ. ID NO: 61 |
| VGVCGGSCKR | SEQ. ID NO: 62 |
| VSNCNWFCEG | SEQ. ID NO: 63 |
| ACGPRPGRCC | SEQ. ID NO: 64 |
| ACGPRPSRCC | SEQ. ID NO: 65 |
| CAPRPSCGPC | SEQ. ID NO: 66 |

-continued

| | |
|---|---|
| CEPCSAYVIC | SEQ. ID NO: 67 |
| CGLRARCGPC | SEQ. ID NO: 68 |
| CGPRPGRCCI | SEQ. ID NO: 69 |
| CGPRPSRCCI | SEQ. ID NO: 70 |
| CGPRSRCGPC | SEQ. ID NO: 71 |
| CGTSQKGCCN | SEQ. ID NO: 72 |
| CHGCTLPGAC | SEQ. ID NO: 73 |
| CHSCTLPGAC | SEQ. ID NO: 74 |
| CLPCLPAASC | SEQ. ID NO: 75 |
| CLPPTCHTAC | SEQ. ID NO: 76 |
| CLSNPCTSCV | SEQ. ID NO: 77 |
| CLVGNCAWCE | SEQ. ID NO: 78 |
| CNPCSTPASC | SEQ. ID NO: 79 |
| CNPCSTPSCT | SEQ. ID NO: 80 |
| CNPCSTPSC | SEQ. ID NO: 81 |
| CNSPCLVGNC | SEQ. ID NO: 82 |
| CRTSCSSRPC | SEQ. ID NO: 83 |
| CSLKEHCSAC | SEQ. ID NO: 84 |
| CSPRPICVPC | SEQ. ID NO: 85 |
| CSSTMSYSCC | SEQ. ID NO: 86 |
| CSTPASCTSC | SEQ. ID NO: 87 |
| CSTPSCTTCV | SEQ. ID NO: 88 |
| CTSCVPPAPC | SEQ. ID NO: 89 |
| CTSSNTCEPC | SEQ. ID NO: 90 |
| CVPPAPCTPC | SEQ. ID NO: 91 |
| CVPPSCHGCT | SEQ. ID NO: 92 |
| CVPPSCHSCT | SEQ. ID NO: 93 |

-continued

| | |
|---|---|
| DCKLPCNPCA | SEQ. ID NO: 94 |
| DCKLPCNPCS | SEQ. ID NO: 95 |
| PCGTSQKGCC | SEQ. ID NO: 96 |
| PCLSNPCTSC | SEQ. ID NO: 97 |
| PCLVGNCAWC | SEQ. ID NO: 98 |
| PCNPCSTPSC | SEQ. ID NO: 99 |
| PCSTPSCTTC | SEQ. ID NO: 100 |
| PCTTCGPTCG | SEQ. ID NO: 101 |
| PCVPPSCHGC | SEQ. ID NO: 102 |
| PCVPPSCHSC | SEQ. ID NO: 103 |
| SCCLPSLGCR | SEQ. ID NO: 104 |
| SCSEELQCCQ | SEQ. ID NO: 105 |
| SCSPCSTTCT | SEQ. ID NO: 106 |
| ASCSTSGTCG | SEQ. ID NO: 107 |
| ASCYIPVGCQ | SEQ. ID NO: 108 |
| ASCYVPVSCQ | SEQ. ID NO: 109 |
| AVCTLPSSCQ | SEQ. ID NO: 110 |
| DLCPTSVSCG | SEQ. ID NO: 111 |
| EICWEPTSCQ | SEQ. ID NO: 112 |
| ETCGEPTSCQ | SEQ. ID NO: 113 |
| ETCNETTSCQ | SEQ. ID NO: 114 |
| ETCWRPNSCQ | SEQ. ID NO: 115 |
| GYCGYRPFCF | SEQ. ID NO: 116 |
| KTCWEPASCQ | SEQ. ID NO: 117 |
| KTCWEPTSCQ | SEQ. ID NO: 118 |
| LDCVDTTPCK | SEQ. ID NO: 119 |
| LGCGYGSFCG | SEQ. ID NO: 120 |

-continued

| | |
|---|---|
| NSCGYGSGCG | SEQ. ID NO: 121 |
| NYCPSNTMCE | SEQ. ID NO: 122 |
| PACVTSYSCR | SEQ. ID NO: 123 |
| PDCHVEGTCL | SEQ. ID NO: 124 |
| PDCRVEGTCL | SEQ. ID NO: 125 |
| PICSEPSPCS | SEQ. ID NO: 126 |
| PICYIFKPCQ | SEQ. ID NO: 127 |
| PLCYISNSCQ | SEQ. ID NO: 128 |
| PPCGQPTPCS | SEQ. ID NO: 129 |
| PPCHIPQPCV | SEQ. ID NO: 130 |
| PSCGRLASCG | SEQ. ID NO: 131 |
| PSCSESSICQ | SEQ. ID NO: 132 |
| PSCSEVTSCP | SEQ. ID NO: 133 |
| PSCSTSGTCG | SEQ. ID NO: 134 |
| PSCSVSSGCQ | SEQ. ID NO: 135 |
| PSCTESDSCK | SEQ. ID NO: 136 |
| PSCYQTSSCG | SEQ. ID NO: 137 |
| PTCFLLNSCQ | SEQ. ID NO: 138 |
| PTCSVTSSCQ | SEQ. ID NO: 139 |
| PTCWLLNNCH | SEQ. ID NO: 140 |
| PTCYQRTSCV | SEQ. ID NO: 141 |
| PTCYRRTSCV | SEQ. ID NO: 142 |
| PTCYVVKRCP | SEQ. ID NO: 143 |
| PVCFEATICE | SEQ. ID NO: 144 |
| PVCFEATVCE | SEQ. ID NO: 145 |
| PVCSRPASCS | SEQ. ID NO: 146 |
| PVCSWVPACS | SEQ. ID NO: 147 |

-continued

| | |
|---|---|
| QTCNESSYCL | SEQ. ID NO: 148 |
| QTCWEPTSCQ | SEQ. ID NO: 149 |
| SFCRLGYGCG | SEQ. ID NO: 150 |
| SFCRRGSGCG | SEQ. ID NO: 151 |
| SLCGYGYGCG | SEQ. ID NO: 152 |
| SLCSTEVSCG | SEQ. ID NO: 153 |
| SNCFGQLNCL | SEQ. ID NO: 154 |
| SPCGQPTPCS | SEQ. ID NO: 155 |
| SSCDQSSSCA | SEQ. ID NO: 156 |
| SSCGQSSSCA | SEQ. ID NO: 157 |
| SVCPEPVSCP | SEQ. ID NO: 158 |
| TFCSFDKSCR | SEQ. ID NO: 159 |
| TICSSDKSCR | SEQ. ID NO: 160 |
| TLCVESSPCH | SEQ. ID NO: 161 |
| TPCYQQSSCQ | SEQ. ID NO: 162 |
| VTCSRQTTCI | SEQ. ID NO: 163 |
| YGCGYGSGCG | SEQ. ID NO: 164 |
| YGCGYGSGCR | SEQ. ID NO: 165 |
| YGCIHSTHCG | SEQ. ID NO: 166 |
| AACEPSACQS | SEQ. ID NO: 167 |
| AACEPSPCQS | SEQ. ID NO: 168 |
| AACTMSVCSS | SEQ. ID NO: 169 |
| ADCLGGICLP | SEQ. ID NO: 170 |
| ALCLPSSCHS | SEQ. ID NO: 171 |
| ALCSPSTCQL | SEQ. ID NO: 172 |
| APCLALVCAP | SEQ. ID NO: 173 |
| APCLSLVCTP | SEQ. ID NO: 174 |

-continued

| | |
|---|---|
| APCLTLVCTP | SEQ. ID NO: 175 |
| APCVALLCRP | SEQ. ID NO: 176 |
| ASCGSLLCRP | SEQ. ID NO: 177 |
| ASCLSFLCRP | SEQ. ID NO: 178 |
| ASCVSLLCRP | SEQ. ID NO: 179 |
| AVCEPSPCQS | SEQ. ID NO: 180 |
| AVCLPVSCQS | SEQ. ID NO: 181 |
| AVCVPVRCQS | SEQ. ID NO: 182 |
| AVCVPVSCQS | SEQ. ID NO: 183 |
| DLCSPSTCQL | SEQ. ID NO: 184 |
| DSCGSSSCGP | SEQ. ID NO: 185 |
| DSCVQSNCFP | SEQ. ID NO: 186 |
| FNCSTRNCSS | SEQ. ID NO: 187 |
| GGCGSYGCSQ | SEQ. ID NO: 188 |
| GSCGFGSCYG | SEQ. ID NO: 189 |
| GSCSSRKCFS | SEQ. ID NO: 190 |
| GVCLPSTCPH | SEQ. ID NO: 191 |
| HSCEGYLCYS | SEQ. ID NO: 192 |
| IVCAAPSCQS | SEQ. ID NO: 193 |
| KTCSTTGCDP | SEQ. ID NO: 194 |
| LACVSQPCQS | SEQ. ID NO: 195 |
| LGCGYGGCGY | SEQ. ID NO: 196 |
| LSCGSRSCSS | SEQ. ID NO: 197 |
| LVCTPVSCVS | SEQ. ID NO: 198 |
| NGCQETYCEP | SEQ. ID NO: 199 |
| NSCRSLSCGS | SEQ. ID NO: 200 |
| PACVISTCPR | SEQ. ID NO: 201 |

-continued

| | |
|---|---|
| PGCLNQSCGS | SEQ. ID NO: 202 |
| PPCGTAPCLT | SEQ. ID NO: 203 |
| PPCTTALCRP | SEQ. ID NO: 204 |
| PPCYLVSCTP | SEQ. ID NO: 205 |
| PRCTRPICEP | SEQ. ID NO: 206 |
| PSCPVSSCAQ | SEQ. ID NO: 207 |
| PSCQPSVCVP | SEQ. ID NO: 208 |
| PSCSVSNCYQ | SEQ. ID NO: 209 |
| PSCSVSSCAQ | SEQ. ID NO: 210 |
| PSCTSVLCRP | SEQ. ID NO: 211 |
| PTCKSPSCEP | SEQ. ID NO: 212 |
| PTCVISSCPR | SEQ. ID NO: 213 |
| PTCVISTCPR | SEQ. ID NO: 214 |
| PTCYQTICFR | SEQ. ID NO: 215 |
| PVCGGVSCHT | SEQ. ID NO: 216 |
| PVCGRVSCHT | SEQ. ID NO: 217 |
| PVCNKPVCFV | SEQ. ID NO: 218 |
| PVCPTPTCSV | SEQ. ID NO: 219 |
| PVCRSTYCVP | SEQ. ID NO: 220 |
| PVCSKSVCYV | SEQ. ID NO: 221 |
| PVCSRPACYS | SEQ. ID NO: 222 |
| PVCYVPTCSE | SEQ. ID NO: 223 |
| QFCLSKSCQP | SEQ. ID NO: 224 |
| RPCERTACQS | SEQ. ID NO: 225 |
| RSCQTSFCGF | SEQ. ID NO: 226 |
| RSCSSLGCGS | SEQ. ID NO: 227 |
| RSCYSVGCGS | SEQ. ID NO: 228 |

-continued

| Sequence | SEQ ID NO |
|---|---|
| RVCLPGSCDS | 229 |
| SFCGFPSCST | 230 |
| SFCGYPSCST | 231 |
| SGCDPASCQP | 232 |
| SGCGGSGCGG | 233 |
| SGCQPSSCLA | 234 |
| SHCQPPHCQL | 235 |
| SICQPATCVA | 236 |
| SLCVPVSCRP | 237 |
| SNCLPTSCQP | 238 |
| SPCLVSSCQP | 239 |
| SPCQQSSCQE | 240 |
| SPCQQSYCVP | 241 |
| SPCSPAVCVS | 242 |
| SRCQQPSCQP | 243 |
| SRCYRPHCGQ | 244 |
| SSCAPIYCRR | 245 |
| SSCAPVYCRR | 246 |
| SSCGKGGCGS | 247 |
| SSCGKRGCGS | 248 |
| SSCLPVSCRP | 249 |
| SSCQPAYCTS | 250 |
| SSCQPSYCRQ | 251 |
| SSCQPVVCEP | 252 |
| SSCTAVVCRP | 253 |
| SSCYQPFCRS | 254 |
| SSCYRPICGS | 255 |
| SSCYRPTCGS | 256 |
| SVCMSGSCQA | 257 |
| SVCSDQGCDQ | 258 |
| SVCSDQGCGL | 259 |
| SVCSDQGCGQ | 260 |
| SVCSDQGCSQ | 261 |
| SVCSDQSCGQ | 262 |
| SVCSHQGCGQ | 263 |
| SVCSHQGCGR | 264 |
| SVCVPVSCRP | 265 |
| SYCRQASCVS | 266 |
| TACEPSACQS | 267 |
| TICTASPCQP | 268 |
| TSCPETSCLP | 269 |
| TSCQMTNCEQ | 270 |
| TSCQPVHCET | 271 |
| TSCQPVLCKS | 272 |
| TSCQPVLCVP | 273 |
| TSCVGFVCQP | 274 |
| TSCVSNPCQV | 275 |
| TTCFQPTCVS | 276 |
| TTCFQPTCVT | 277 |
| TTCFQPTCVY | 278 |
| TTCISNPCST | 279 |
| TWCQGSSCQP | 280 |
| VGCQSSVCVP | 281 |
| VPCQPSTCVF | 282 |

-continued

| Sequence | SEQ ID NO |
|---|---|
| VSCEPSPCQS | 283 |
| VSCGGPICLP | 284 |
| VSCKPVLCVA | 285 |
| VSCPSTSCRP | 286 |
| VSCQSSVCMP | 287 |
| VSCTRIVCVA | 288 |
| VTCEPSPCQS | 289 |
| VTCQTTVCRP | 290 |
| YGCYEGCRY | 291 |
| AGSCQPSCSE | 292 |
| ALLCRPLCGV | 293 |
| ALVCEPVCLR | 294 |
| ATICEPSCSV | 295 |
| ATTCEPSCSV | 296 |
| ATVCEPSCSV | 297 |
| EGTCLPPCYL | 298 |
| FSTCRPSCSG | 299 |
| GFVCQPMCSH | 300 |
| GLDCGYGCY | 301 |
| GLGCGYGCY | 302 |
| GLGCSYGCH | 303 |
| GLGCSYGCL | 304 |
| GSGCGYGCY | 305 |
| GTGCGYGCY | 306 |
| GVSCHTTCYR | 307 |
| GYACNFPCSY | 308 |
| GYGCGYGCF | 309 |
| HSPCQASCYV | 310 |
| HTSCSPACQP | 311 |
| HTSCSSGCQP | 312 |
| IRWCHPDCHV | 313 |
| IRWCRPDCRV | 314 |
| ISSCGTGCGI | 315 |
| KGGCGSGCGG | 316 |
| KGGCGSSCSQ | 317 |
| LVTCQDSCGS | 318 |
| LVTCQESCQP | 319 |
| MSICSSACTD | 320 |
| MSICSSACTN | 321 |
| MSVCSSACSD | 322 |
| PAICEPSCSV | 323 |
| PASCQKSCYR | 324 |
| PIYCRRTCYH | 325 |
| PNSCQTLCVE | 326 |
| PQPCVPTCFL | 327 |
| PSACQSGCTS | 328 |
| PSPCEPSCSE | 329 |
| PSPCQASCYI | 330 |
| PSPCQSGCIS | 331 |
| PSPCQSGCTD | 332 |
| PSPCQSGCTS | 333 |
| PTACQPTCYQ | 334 |
| PTACQPTCYR | 335 |
| PTPCSTTCRT | 336 |

| | |
|---|---|
| PTSCQKSCYR | SEQ. ID NO: 337 |
| PTSCQPSCES | SEQ. ID NO: 338 |
| PTSCQTSCTL | SEQ. ID NO: 339 |
| PVICEPSCSV | SEQ. ID NO: 340 |
| PVSCVPVCSG | SEQ. ID NO: 341 |
| PVTCVPRCTR | SEQ. ID NO: 342 |
| PVYCRRTCYH | SEQ. ID NO: 343 |
| PVYCRRTCYY | SEQ. ID NO: 344 |
| PVYCVPVCSG | SEQ. ID NO: 345 |
| QPGCESPCEP | SEQ. ID NO: 346 |
| QQSCVSSCRR | SEQ. ID NO: 347 |
| QTSCGSSCGQ | SEQ. ID NO: 348 |
| QTTCHPSCGM | SEQ. ID NO: 349 |
| QTTCRPSCGV | SEQ. ID NO: 350 |
| RGGCGSGCGG | SEQ. ID NO: 351 |
| RLACYSLCSG | SEQ. ID NO: 352 |
| RPACYRPCYS | SEQ. ID NO: 353 |
| RPFCFRRCYS | SEQ. ID NO: 354 |
| RPICRPICSG | SEQ. ID NO: 355 |
| RPLCYRRCYS | SEQ. ID NO: 356 |
| RSPCQASCYV | SEQ. ID NO: 357 |
| RVSCHTTCYR | SEQ. ID NO: 358 |
| SAICRPTCPR | SEQ. ID NO: 359 |
| SDSCKRDCKK | SEQ. ID NO: 360 |
| SEGCGSGCGG | SEQ. ID NO: 361 |
| SFLCRPACSR | SEQ. ID NO: 362 |
| SGGCGSGCGG | SEQ. ID NO: 363 |
| SGGCGSSCGG | SEQ. ID NO: 364 |
| SGSCQAACGQ | SEQ. ID NO: 365 |
| SLLCHPVCKS | SEQ. ID NO: 366 |
| SLLCHPVCRS | SEQ. ID NO: 367 |
| SLLCRPACSP | SEQ. ID NO: 368 |
| SLLCRPACSR | SEQ. ID NO: 369 |
| SLLCRPICRP | SEQ. ID NO: 370 |
| SLLCRPMCSR | SEQ. ID NO: 371 |
| SLLCRPTCSR | SEQ. ID NO: 372 |
| SLLCRPVCQP | SEQ. ID NO: 373 |
| SLLCRPVCRP | SEQ. ID NO: 374 |
| SLLCRPVCRS | SEQ. ID NO: 375 |
| SLLCRPVCSR | SEQ. ID NO: 376 |
| SNPCQVTCSR | SEQ. ID NO: 377 |
| SRGCGSGCGG | SEQ. ID NO: 378 |
| SRSCQSPCYR | SEQ. ID NO: 379 |
| SRSCQSSCYR | SEQ. ID NO: 380 |
| SSGCGYGCGY | SEQ. ID NO: 381 |
| SSGCPMACPG | SEQ. ID NO: 382 |
| SSICQPICSE | SEQ. ID NO: 383 |
| SSPCHTSCYY | SEQ. ID NO: 384 |
| SSPCQPTCYV | SEQ. ID NO: 385 |
| SSPCQQSCYV | SEQ. ID NO: 386 |
| SSPCQTSCYR | SEQ. ID NO: 387 |
| SSSCQQSCRV | SEQ. ID NO: 388 |
| STVCQPACGV | SEQ. ID NO: 389 |
| TDNCQETCGE | SEQ. ID NO: 390 |

| Sequence | SEQ ID NO |
|---|---|
| TQPCYEPCLP | 391 |
| TSSCGTGCGI | 392 |
| TSSCQPSCGR | 393 |
| TSSCTTPCYQ | 394 |
| TSVCLPGCLN | 395 |
| TTVCLPGCLN | 396 |
| VANCQAPCST | 397 |
| VDDCPESCWP | 398 |
| VKRCPSVCPE | 399 |
| VSSCQPSCSE | 400 |
| YEGCRYGCGH | 401 |
| YGRCRHGCHS | 402 |
| YGYCRPSCYG | 403 |
| YRDCQKTCWE | 404 |
| YRGCQEICWE | 405 |
| YRGCQETCWR | 406 |
| YRGCQQTCWE | 407 |
| YRSCRPSCYG | 408 |
| GGVCGPSPPC | 409 |
| GVCGPSPPCI | 410 |
| VCGPSPPCIT | 411 |
| CGPSPPCITT | 412 |
| CAPIYCRRTC | 413 |
| CAPSPCQASC | 414 |
| CAPSPCQPAC | 415 |
| CAPVYCRRTC | 416 |
| CASSPCQQAC | 417 |
| CASSSCQPAC | 418 |
| CASSSCQQSC | 419 |
| CCGNFSSHSC | 420 |
| CCGYGGLGCG | 421 |
| CCNYYGNSCG | 422 |
| CCNYYRNSCG | 423 |
| CCSRNFSSCS | 424 |
| CDAGSCQPSC | 425 |
| CDPCSLQEGC | 426 |
| CDPSPCEPSC | 427 |
| CDPVICEPSC | 428 |
| CDQGLCQETC | 429 |
| CEATTCEPSC | 430 |
| CELPCGTPSC | 431 |
| CEPAICEPSC | 432 |
| CEPPCGTAPC | 433 |
| CEPPCSAPSC | 434 |
| CEPRSCASSC | 435 |
| CEPSACQSGC | 436 |
| CEPSCSVSNC | 437 |
| CEPSCSVSSC | 438 |
| CEPSPCQSGC | 439 |
| CEPTACQPTC | 440 |
| CEPTSCQTSC | 441 |
| CEPVCLRPVC | 442 |
| CETSSCQPRC | 443 |
| CETTCFQPTC | 444 |

-continued

CFQPTCVSSC SEQ. ID NO: 445

CFQPTCVTSC SEQ. ID NO: 446

CFQPTCVYSC SEQ. ID NO: 447

CGCGFRRLGC SEQ. ID NO: 448

CGCGYRGLDC SEQ. ID NO: 449

CGCNGYYGCY SEQ. ID NO: 450

CGFGSCYGCG SEQ. ID NO: 451

CGGSGCGGSC SEQ. ID NO: 452

CGGSGSSCCV SEQ. ID NO: 453

CGGVSCHTTC SEQ. ID NO: 454

CGKGGCGSCG SEQ. ID NO: 455

CGKRGCGSCG SEQ. ID NO: 456

CGQDLCQETC SEQ. ID NO: 457

CGQTSCGSSC SEQ. ID NO: 458

CGQVLCQETC SEQ. ID NO: 459

CGRDLCQETC SEQ. ID NO: 460

CGRVSCHTTC SEQ. ID NO: 461

CGSCGFGSCY SEQ. ID NO: 462

CGSCGGSKGC SEQ. ID NO: 463

CGSGCGVPVC SEQ. ID NO: 464

CGSLLCRPTC SEQ. ID NO: 465

CGSRCYVPVC SEQ. ID NO: 466

CGSSSCGPQC SEQ. ID NO: 467

CGSVCSDQGC SEQ. ID NO: 468

CGSVCSDQSC SEQ. ID NO: 469

CGSVCSHQGC SEQ. ID NO: 470

CGSYGCSQCS SEQ. ID NO: 471

-continued

CGVCLPSTCP SEQ. ID NO: 472

CGYEGCRYGC SEQ. ID NO: 473

CGYGCYGCG SEQ. ID NO: 474

CGYGGCYGC SEQ. ID NO: 475

CGYGSFCGCG SEQ. ID NO: 476

CGYGSGCGCG SEQ. ID NO: 477

CHPSCGMSSC SEQ. ID NO: 478

CHPSCSISSC SEQ. ID NO: 479

CHPTCYQTIC SEQ. ID NO: 480

CHTSCSPACQ SEQ. ID NO: 481

CHTSCSSGCQ SEQ. ID NO: 482

CHTTCYRPAC SEQ. ID NO: 483

CHTTCYRPTC SEQ. ID NO: 484

CIHSPCQASC SEQ. ID NO: 485

CIHSTHCGCN SEQ. ID NO: 486

CIRSPCQASC SEQ. ID NO: 487

CISSCYRPQC SEQ. ID NO: 488

CISSPCQQSC SEQ. ID NO: 489

CKPCSSQSSC SEQ. ID NO: 490

CKPSCSQSSC SEQ. ID NO: 491

CKPVCFKPIC SEQ. ID NO: 492

CKPVCYVPTC SEQ. ID NO: 493

CKPVSCVPVC SEQ. ID NO: 494

CKPVYCVPVC SEQ. ID NO: 495

CKTVYCKPIC SEQ. ID NO: 496

CLNQSCGSNC SEQ. ID NO: 497

CLNQSCGSSC SEQ. ID NO: 498

| Sequence | SEQ ID NO |
|---|---|
| CLPGCLNQSC | 499 |
| CLPGSCDSCS | 500 |
| CLPPCYLVSC | 501 |
| CLPTSCQPSC | 502 |
| CLSFLCRPAC | 503 |
| CLVSSCQPSC | 504 |
| CMPSPCQPAC | 505 |
| CMSGSCQAAC | 506 |
| CNESSYCLPC | 507 |
| CPASCVSLLC | 508 |
| CPMACPGSPC | 509 |
| CPSSCTAVVC | 510 |
| CPVTCEPSPC | 511 |
| CQAACEPSAC | 512 |
| CQAACEPSPC | 513 |
| CQAACGQSVC | 514 |
| CQAPCSTKNC | 515 |
| CQAVCEPSPC | 516 |
| CQDSCGSSSC | 517 |
| CQHSSCQPTC | 518 |
| CQISSCGTGC | 519 |
| CQKSSCQPAC | 520 |
| CQPMCSHAAC | 521 |
| CQPPCTTALC | 522 |
| CQPSCESSFC | 523 |
| CQPSCSESTC | 524 |
| CQPSCTSVLC | 525 |
| CQPTCGGSSC | 526 |
| CQPTCSRPSC | 527 |
| CQPVCPTPTC | 528 |
| CQPVLCKSSC | 529 |
| CQPVVCEPSC | 530 |
| CQQPSCQPAC | 531 |
| CQQSCRVPVC | 532 |
| CQQSCYVPVC | 533 |
| CQQSGCQPAC | 534 |
| CQQSSCHPAC | 535 |
| CQQSSCKPAC | 536 |
| CQQSSCQLAC | 537 |
| CQQSSCQPAC | 538 |
| CQQSSCQPTC | 539 |
| CQQSSCQSAC | 540 |
| CQQSSCVSCV | 541 |
| CQQSYCVPVC | 542 |
| CQSGCISSCT | 543 |
| CQSGCTDSCT | 544 |
| CQSGCTSSCT | 545 |
| CQSSCYRPTC | 546 |
| CQSVCYQPTC | 547 |
| CQSVYCQPTC | 548 |
| CQTACEPSAC | 549 |
| CQTSSCGTGC | 550 |
| CQTTCHPSCG | 551 |
| CQTTCRPSCG | 552 |

| | |
|---|---|
| CQTTCYRTTC | SEQ. ID NO: 553 |
| CQTTRCRTTC | SEQ. ID NO: 554 |
| CQVTCEPSPC | SEQ. ID NO: 555 |
| CRNTSCQPTC | SEQ. ID NO: 556 |
| CRPACSPLAC | SEQ. ID NO: 557 |
| CRPACSRLAC | SEQ. ID NO: 558 |
| CRPACSRPAC | SEQ. ID NO: 559 |
| CRPMCSRPAC | SEQ. ID NO: 560 |
| CRPSCGQTTC | SEQ. ID NO: 561 |
| CRPSCGVSSC | SEQ. ID NO: 562 |
| CRPSCSISSC | SEQ. ID NO: 563 |
| CRPSCSQTTC | SEQ. ID NO: 564 |
| CRPSYCGQSC | SEQ. ID NO: 565 |
| CRPSYCISSC | SEQ. ID NO: 566 |
| CRPSYCQTTC | SEQ. ID NO: 567 |
| CRPTCSRLAC | SEQ. ID NO: 568 |
| CRPTCSSGSC | SEQ. ID NO: 569 |
| CRPTSCQNTC | SEQ. ID NO: 570 |
| CRPVCRSTYC | SEQ. ID NO: 571 |
| CRPVCSRPAC | SEQ. ID NO: 572 |
| CRPVTCVPRC | SEQ. ID NO: 573 |
| CROSSCQPAC | SEQ. ID NO: 574 |
| CRTTCFHPIC | SEQ. ID NO: 575 |
| CRTTCFQPTC | SEQ. ID NO: 576 |
| CRTTCYRPSC | SEQ. ID NO: 577 |
| CRTTYCRPSC | SEQ. ID NO: 578 |
| CRVTCEPSPC | SEQ. ID NO: 579 |
| CRYGCGHRGC | SEQ. ID NO: 580 |
| CSAPCVALLC | SEQ. ID NO: 581 |
| CSDDSGSCCQ | SEQ. ID NO: 582 |
| CSEDSSSCCQ | SEQ. ID NO: 583 |
| CSEDSYSCCQ | SEQ. ID NO: 584 |
| CSEGCGSGCG | SEQ. ID NO: 585 |
| CSESSPSCCQ | SEQ. ID NO: 586 |
| CSESSSSCCQ | SEQ. ID NO: 587 |
| CSFDKSCRCG | SEQ. ID NO: 588 |
| CSGASSLCCQ | SEQ. ID NO: 589 |
| CSGASSPCCQ | SEQ. ID NO: 590 |
| CSGASSSCCQ | SEQ. ID NO: 591 |
| CSGASTSCCQ | SEQ. ID NO: 592 |
| CSGGCGSGCG | SEQ. ID NO: 593 |
| CSGGCGSSCG | SEQ. ID NO: 594 |
| CSGISSSCCQ | SEQ. ID NO: 595 |
| CSKDSSSCCQ | SEQ. ID NO: 596 |
| CSKGACGSCG | SEQ. ID NO: 597 |
| CSLSCGSRSC | SEQ. ID NO: 598 |
| CSQDLCQETC | SEQ. ID NO: 599 |
| CSRGCGSGCG | SEQ. ID NO: 600 |
| CSRLSSACCG | SEQ. ID NO: 601 |
| CSSCGKGGCG | SEQ. ID NO: 602 |
| CSSCGKRGCG | SEQ. ID NO: 603 |
| CSSDKSCRCG | SEQ. ID NO: 604 |
| CSSGNFSSCC | SEQ. ID NO: 605 |
| CSSSGCGSFC | SEQ. ID NO: 606 |

| Sequence | SEQ ID NO |
|---|---|
| CSSSGCGSSC | 607 |
| CSTPCYQPIC | 608 |
| CSTTCRTSSC | 609 |
| CSWVPACSCT | 610 |
| CTFSPCQQAC | 611 |
| CTMSVCSSAC | 612 |
| CTRPICEPCR | 613 |
| CTSSPCQHAC | 614 |
| CTSSPCQQAC | 615 |
| CTSSPCQQSC | 616 |
| CTSSSCQQAC | 617 |
| CVALLCRPLC | 618 |
| CVALVCEPVC | 619 |
| CVFSSCNTTC | 620 |
| CVGFVCQPMC | 621 |
| CVPRCTRPIC | 622 |
| CVPSPCQVAC | 623 |
| CVPSRCQASC | 624 |
| CVPSSCQASC | 625 |
| CVPVCNKPVC | 626 |
| CVPVCSKSVC | 627 |
| CVPVRCKPVC | 628 |
| CVSLLCRPAC | 629 |
| CVSLLCRPMC | 630 |
| CVSLLCRPTC | 631 |
| CVSLLCRPVC | 632 |
| CVSNPCQVTC | 633 |
| CVSRCYRPHC | 634 |
| CVSSCFRPQC | 635 |
| CVSSICQPIC | 636 |
| CVSSPCQPTC | 637 |
| CVVSCTPPSC | 638 |
| CVVSCTPPTC | 639 |
| CYCPKNSIFC | 640 |
| CYEPCLPRGC | 641 |
| CYRRCYSSCY | 642 |
| GCCGYGGLGC | 643 |
| GCGGCGSGCA | 644 |
| GCGGCGSGCG | 645 |
| GCGGCGSSCG | 646 |
| GCGGCSSSCG | 647 |
| GCGGSGSSCC | 648 |
| GCGSGCAGCG | 649 |
| GCGSGCGGCG | 650 |
| GCGSGCGGCS | 651 |
| GCGSSCGGCD | 652 |
| GCGSSCGGCG | 653 |
| GCGSSCSQCS | 654 |
| GCGYSSSCCG | 655 |
| GCKGGCGSCG | 656 |
| GCSGCSGGCG | 657 |
| ICSGASSLCC | 658 |
| ICSGASSPCC | 659 |
| MCCNYYGNSC | 660 |

| | |
|---|---|
| MCCNYYRNSC | SEQ. ID NO: 661 |
| MCYGYGCGCG | SEQ. ID NO: 662 |
| NCCSRNFSSC | SEQ. ID NO: 663 |
| PCSLQEGCCR | SEQ. ID NO: 664 |
| PCSSQSSCCV | SEQ. ID NO: 665 |
| SCCAPASSCQ | SEQ. ID NO: 666 |
| SCCAPASTCQ | SEQ. ID NO: 667 |
| SCCAPTSSCQ | SEQ. ID NO: 668 |
| SCCGYRPLCY | SEQ. ID NO: 669 |
| SCCVPASSCQ | SEQ. ID NO: 670 |
| SCCVPTSSCQ | SEQ. ID NO: 671 |
| SCGCSKGACG | SEQ. ID NO: 672 |
| SCGGCDSSCG | SEQ. ID NO: 673 |
| SCGGCGSGCG | SEQ. ID NO: 674 |
| SCGGCGSSCG | SEQ. ID NO: 675 |
| SCGGCKGGCG | SEQ. ID NO: 676 |
| SCGGSKGCCG | SEQ. ID NO: 677 |
| SCGSGCRGCG | SEQ. ID NO: 678 |
| SCYGCYGCI | SEQ. ID NO: 679 |
| TCCVPVPSCG | SEQ. ID NO: 680 |
| TCSDDSGSCC | SEQ. ID NO: 681 |
| TCSEDSSSCC | SEQ. ID NO: 682 |
| TCSEDSYSCC | SEQ. ID NO: 683 |
| TCSESSPSCC | SEQ. ID NO: 684 |
| TCSESSSSCC | SEQ. ID NO: 685 |
| TCSKDSSSCC | SEQ. ID NO: 686 |
| TCSRLSSACC | SEQ. ID NO: 687 |
| VCCQPTPICD | SEQ. ID NO: 688 |
| VCSEDSSSCC | SEQ. ID NO: 689 |
| VCSGASSLCC | SEQ. ID NO: 690 |
| VCSGASSPCC | SEQ. ID NO: 691 |
| VCSGASSSCC | SEQ. ID NO: 692 |
| VCSGASTSCC | SEQ. ID NO: 693 |
| VCSGDSSCCQ | SEQ. ID NO: 694 |
| VCSGISSSCC | SEQ. ID NO: 695 |
| YCVPIPSCCA | SEQ. ID NO: 696 |
| CASSCCTPSC | SEQ. ID NO: 697 |
| CCDNCPPPCH | SEQ. ID NO: 698 |
| CCEPCLPRGC | SEQ. ID NO: 699 |
| CCGAASSCCR | SEQ. ID NO: 700 |
| CCGCGGSGCG | SEQ. ID NO: 701 |
| CCGPSSSCCQ | SEQ. ID NO: 702 |
| CCGSGCGGCG | SEQ. ID NO: 703 |
| CCKPYCSQCS | SEQ. ID NO: 704 |
| CCMPVSSCCA | SEQ. ID NO: 705 |
| CCNYYRNCCG | SEQ. ID NO: 706 |
| CCPSCVVSSC | SEQ. ID NO: 707 |
| CCPSYCVSSC | SEQ. ID NO: 708 |
| CCQPICGSSC | SEQ. ID NO: 709 |
| CCQPICVTSC | SEQ. ID NO: 710 |
| CCQPTCLSSC | SEQ. ID NO: 711 |
| CCQPTCLTSC | SEQ. ID NO: 712 |
| CCQPTCVASC | SEQ. ID NO: 713 |
| CCQPTCVTSC | SEQ. ID NO: 714 |

| | | | |
|---|---|---|---|
| CCQPYCHPTC | SEQ. ID NO: 715 | CGCSQSNCCK | SEQ. ID NO: 742 |
| CCQQSSCVSC | SEQ. ID NO: 716 | CGCSQSSCCK | SEQ. ID NO: 743 |
| CCQSSCFKPC | SEQ. ID NO: 717 | CGGCGGCGGC | SEQ. ID NO: 744 |
| CCQSSCSKPC | SEQ. ID NO: 718 | CGGCGGGCCG | SEQ. ID NO: 745 |
| CCQSSCYKPC | SEQ. ID NO: 719 | CGGCGSGCCV | SEQ. ID NO: 746 |
| CCQTICRSTC | SEQ. ID NO: 720 | CGGCGSSCCV | SEQ. ID NO: 747 |
| CCQTTCHPSC | SEQ. ID NO: 721 | CGGGCCGSSC | SEQ. ID NO: 748 |
| CCQTTCRPSC | SEQ. ID NO: 722 | CGGSCCGSSC | SEQ. ID NO: 749 |
| CCRVPTCSCS | SEQ. ID NO: 723 | CGQSCCRPAC | SEQ. ID NO: 750 |
| CCSPGCQPTC | SEQ. ID NO: 724 | CGQSCCRPVC | SEQ. ID NO: 751 |
| CCSSGCGSSC | SEQ. ID NO: 725 | CGSCGCSQCN | SEQ. ID NO: 752 |
| CCSSSCGSCG | SEQ. ID NO: 726 | CGSCGCSQCS | SEQ. ID NO: 753 |
| CCTQEQNCCE | SEQ. ID NO: 727 | CGSFCCQSSC | SEQ. ID NO: 754 |
| CCVPIPSCCA | SEQ. ID NO: 728 | CGSGCCVPVC | SEQ. ID NO: 755 |
| CCVPISSCCA | SEQ. ID NO: 729 | CGSSCCGSGC | SEQ. ID NO: 756 |
| CCVPVCYQCK | SEQ. ID NO: 730 | CGSSCCQPCY | SEQ. ID NO: 757 |
| CCVPVPSCCA | SEQ. ID NO: 731 | CGSSCCQPIC | SEQ. ID NO: 758 |
| CCVPVPSCCV | SEQ. ID NO: 732 | CGSSCCQPSC | SEQ. ID NO: 759 |
| CCVPVSSCCA | SEQ. ID NO: 733 | CGSSCCQSSC | SEQ. ID NO: 760 |
| CDSSCCQPSC | SEQ. ID NO: 734 | CGSSCCVPIC | SEQ. ID NO: 761 |
| CDTCPPPCCK | SEQ. ID NO: 735 | CGSSCCVPVC | SEQ. ID NO: 762 |
| CEPCRRPVCC | SEQ. ID NO: 736 | CGSSCSQCSC | SEQ. ID NO: 763 |
| CEPSCCQPVC | SEQ. ID NO: 737 | CGYGSCCGCG | SEQ. ID NO: 764 |
| CEPSCCSAVC | SEQ. ID NO: 738 | CHPRCCISSC | SEQ. ID NO: 765 |
| CETSCCQPSC | SEQ. ID NO: 739 | CHPSCCESSC | SEQ. ID NO: 766 |
| CETTCCRTTC | SEQ. ID NO: 740 | CHPSCCISSC | SEQ. ID NO: 767 |
| CFSGCGSSCC | SEQ. ID NO: 741 | CHPTCCQNTC | SEQ. ID NO: 768 |

-continued

CHPTCCQTIC SEQ. ID NO: 769

CHPVCCQTTC SEQ. ID NO: 770

CHPVCKSTCC SEQ. ID NO: 771

CHPVCRSTCC SEQ. ID NO: 772

CISSCCHPSC SEQ. ID NO: 773

CISSCCKPSC SEQ. ID NO: 774

CISSCCRPSC SEQ. ID NO: 775

CISSCTPSCC SEQ. ID NO: 776

CISSSCCPSC SEQ. ID NO: 777

CKAVCCVPTC SEQ. ID NO: 778

CKPCCSQASC SEQ. ID NO: 779

CKPCCSQSRC SEQ. ID NO: 780

CKPCCSQSSC SEQ. ID NO: 781

CKPCCSSSGC SEQ. ID NO: 782

CKPCSCFSGC SEQ. ID NO: 783

CKPCSCSSGC SEQ. ID NO: 784

CKPCYCSSGC SEQ. ID NO: 785

CKPICCVPVC SEQ. ID NO: 786

CKPQCCQSVC SEQ. ID NO: 787

CKPSCCQTTC SEQ. ID NO: 788

CKPVCCAPTC SEQ. ID NO: 789

CKPVCCKPIC SEQ. ID NO: 790

CKPVCCKSIC SEQ. ID NO: 791

CKPVCCLPTC SEQ. ID NO: 792

CKPVCCVPTC SEQ. ID NO: 793

CKPVCCVPVC SEQ. ID NO: 794

CKPVCCVSTC SEQ. ID NO: 795

-continued

CKPYCCQSSC SEQ. ID NO: 796

CKPYCSQCSC SEQ. ID NO: 797

CKSNCCKPVC SEQ. ID NO: 798

CKTVCCKPVC SEQ. ID NO: 799

CLPPCCVVSC SEQ. ID NO: 800

CLTSCCQPSC SEQ. ID NO: 801

CNPCCSQSSC SEQ. ID NO: 802

CPESCCELPC SEQ. ID NO: 803

CPESCCEPHC SEQ. ID NO: 804

CPESCCEPPC SEQ. ID NO: 805

CPFSCPTTCC SEQ. ID NO: 806

CPGDCFTCCT SEQ. ID NO: 807

CPSCVVSSCC SEQ. ID NO: 808

CPSYCVSSCC SEQ. ID NO: 809

CPTTCCRTTC SEQ. ID NO: 810

CQETCCRPSC SEQ. ID NO: 811

CQHACCVPVC SEQ. ID NO: 812

CQNTCCRTTC SEQ. ID NO: 813

CQPACCQPTC SEQ. ID NO: 814

CQPACCTASC SEQ. ID NO: 815

CQPACCTSSC SEQ. ID NO: 816

CQPACCTTSC SEQ. ID NO: 817

CQPACCVPVC SEQ. ID NO: 818

CQPACCVSSC SEQ. ID NO: 819

CQPCCHPTCY SEQ. ID NO: 820

CQPCCRPTSC SEQ. ID NO: 821

CQPICCGSSC SEQ. ID NO: 822

-continued

| | |
|---|---|
| CQPICGSSCC | SEQ. ID NO: 823 |
| CQPICVTSCC | SEQ. ID NO: 824 |
| CQPNCCRPSC | SEQ. ID NO: 825 |
| CQPRCCETSC | SEQ. ID NO: 826 |
| CQPSCCRPAC | SEQ. ID NO: 827 |
| CQPSCCSTPC | SEQ. ID NO: 828 |
| CQPSCCSTTC | SEQ. ID NO: 829 |
| CQPSCCVPSC | SEQ. ID NO: 830 |
| CQPSCCVSSC | SEQ. ID NO: 831 |
| CQPTCCGSSC | SEQ. ID NO: 832 |
| CQPTCCHPSC | SEQ. ID NO: 833 |
| CQPTCCQPTC | SEQ. ID NO: 834 |
| CQPTCCRPRC | SEQ. ID NO: 835 |
| CQPTCCRPSC | SEQ. ID NO: 836 |
| CQPTCCRTTC | SEQ. ID NO: 837 |
| CQPTCLSSCC | SEQ. ID NO: 838 |
| CQPTCLTSCC | SEQ. ID NO: 839 |
| CQPTCVASCC | SEQ. ID NO: 840 |
| CQPTCVTSCC | SEQ. ID NO: 841 |
| CQPVCCQPTC | SEQ. ID NO: 842 |
| CQPYCHPTCC | SEQ. ID NO: 843 |
| CQQACCMPVC | SEQ. ID NO: 844 |
| CQQACCVPIC | SEQ. ID NO: 845 |
| CQQACCVPVC | SEQ. ID NO: 846 |
| CQQSCCVPVC | SEQ. ID NO: 847 |
| CQQSCCVSVC | SEQ. ID NO: 848 |
| CQSMCCQPTC | SEQ. ID NO: 849 |

-continued

| | |
|---|---|
| CQSNCCVPVC | SEQ. ID NO: 850 |
| CQSSCCKPCS | SEQ. ID NO: 851 |
| CQSSCCQSSC | SEQ. ID NO: 852 |
| CQSSCCVPVC | SEQ. ID NO: 853 |
| CQSSCFKPCC | SEQ. ID NO: 854 |
| CQSSCSKPCC | SEQ. ID NO: 855 |
| CQSVCCQPTC | SEQ. ID NO: 856 |
| CQTICRSTCC | SEQ. ID NO: 857 |
| CQTTCCRPSC | SEQ. ID NO: 858 |
| CQTTCCRTTC | SEQ. ID NO: 859 |
| CRATCCRPSC | SEQ. ID NO: 860 |
| CRGCGPSCCA | SEQ. ID NO: 861 |
| CRPACCETTC | SEQ. ID NO: 862 |
| CRPACCQNTC | SEQ. ID NO: 863 |
| CRPCCWATTC | SEQ. ID NO: 864 |
| CRPICRPACC | SEQ. ID NO: 865 |
| CRPLCCQTTC | SEQ. ID NO: 866 |
| CRPQCCQSVC | SEQ. ID NO: 867 |
| CRPQCCQTTC | SEQ. ID NO: 868 |
| CRPRCCISSC | SEQ. ID NO: 869 |
| CRPSCCESSC | SEQ. ID NO: 870 |
| CRPSCCETTC | SEQ. ID NO: 871 |
| CRPSCCISSC | SEQ. ID NO: 872 |
| CRPSCCKPQC | SEQ. ID NO: 873 |
| CRPSCCMSSC | SEQ. ID NO: 874 |
| CRPSCCQTTC | SEQ. ID NO: 875 |
| CRPSCCRPSC | SEQ. ID NO: 876 |

-continued

| Sequence | SEQ. ID NO: |
|---|---|
| CRPSCCVSRC | 877 |
| CRPSCCVSSC | 878 |
| CRPTCCETTC | 879 |
| CRPTCCQNTC | 880 |
| CRPTCCQTTC | 881 |
| CRPVCCDPCS | 882 |
| CRPVCCQTTC | 883 |
| CRPVCQPACC | 884 |
| CRPVCRPACC | 885 |
| CRPVCRPTCC | 886 |
| CRPVCRSTCC | 887 |
| CRPYCCESSC | 888 |
| CRRPVCCDPC | 889 |
| CRSQCCQSVC | 890 |
| CRTTCCHPSC | 891 |
| CRTTCCQPIC | 892 |
| CRTTCCQPTC | 893 |
| CRTTCCRPSC | 894 |
| CRTTCCRTTC | 895 |
| CSCSSCGSCA | 896 |
| CSCSSCGSCG | 897 |
| CSCTSCGSCG | 898 |
| CSPACQPTCC | 899 |
| CSPGCQPTCC | 900 |
| CSPSCCQTTC | 901 |
| CSQCSCYKPC | 902 |
| CSQSNCCKPC | 903 |

-continued

| Sequence | SEQ. ID NO: |
|---|---|
| CSQSSCCKPC | 904 |
| CSSGCGSCCQ | 905 |
| CSSGCGSSCC | 906 |
| CSSGCQPACC | 907 |
| CSSSCCQPSC | 908 |
| CSTPCCQPTC | 909 |
| CSTTCCQPIC | 910 |
| CTAVVCRPCC | 911 |
| CTDSCTPSCC | 912 |
| CTPSCCQPAC | 913 |
| CTRPICEPCC | 914 |
| CTSSCTPSCC | 915 |
| CVPACSCSSC | 916 |
| CVPACSCTSC | 917 |
| CVPVCCKPVC | 918 |
| CVPVCCVPTC | 919 |
| CVPVCCVPVC | 920 |
| CVSCVSSPCC | 921 |
| CVSRCCRPQC | 922 |
| CVSSCCKPQC | 923 |
| CVSSCCQHSC | 924 |
| CVSSCCQPFC | 925 |
| CVSSCCQPSC | 926 |
| CVSSCCRPQC | 927 |
| CVSTCCRPTC | 928 |
| CVTRCCSTPC | 929 |
| CVTSCCQPAC | 930 |

| Sequence | SEQ ID NO |
|---|---|
| CVTSCCQPSC | 931 |
| CVYSCCQPFC | 932 |
| CVYSCCQPSC | 933 |
| GCCGCSEGCG | 934 |
| GCCGCSGGCG | 935 |
| GCCGCSRGCG | 936 |
| GCCRPITCCP | 937 |
| GCGSSCCQCS | 938 |
| GCGVPVCCCS | 939 |
| LCCPCQTTCS | 940 |
| PCCCLRPVCG | 941 |
| PCCCRPVTCQ | 942 |
| PCCCVRPVCG | 943 |
| PCCSQASCCV | 944 |
| PCCSQSRCCV | 945 |
| PCCSQSSCCK | 946 |
| PCCSQSSCCV | 947 |
| PCCWATTCCQ | 948 |
| QCSCCKPYCS | 949 |
| RCYVPVCCCK | 950 |
| SCCAPVYCCK | 951 |
| SCCISSSCCP | 952 |
| SCCVSSCRCP | 953 |
| SCGCSQCSCY | 954 |
| SCGLENCCCP | 955 |
| VCCGASSCCQ | 956 |
| VCCGDSSCCQ | 957 |
| CASSCCTPSCC | 958 |
| CCCPSCVVSSC | 959 |
| CCCPSYCVSSC | 960 |
| CCCSSGCGSSC | 961 |
| CCDTCPPPCCK | 962 |
| CCEPHCCALSC | 963 |
| CCEPPCCAPSC | 964 |
| CCEPPCCATSC | 965 |
| CCETSCCQPSC | 966 |
| CCGSSCCGSGC | 967 |
| CCGSSCCGSSC | 968 |
| CCHPRCCISSC | 969 |
| CCHPSCCESSC | 970 |
| CCHPSCCISSC | 971 |
| CCHPSCCVSSC | 972 |
| CCHPTCCQNTC | 973 |
| CCHPTCCQTIC | 974 |
| CCISSCCKPSC | 975 |
| CCISSCCRPSC | 976 |
| CCISSSCCPSC | 977 |
| CCKAVCCVPTC | 978 |
| CCKPCCSQASC | 979 |
| CCKPCCSQSRC | 980 |
| CCKPCCSQSSC | 981 |
| CCKPCCSSSGC | 982 |
| CCKPCSCFSGC | 983 |
| CCKPCSCSSGC | 984 |

| Sequence | SEQ ID NO |
|---|---|
| CCKPCYCSSGC | SEQ. ID NO: 985 |
| CCKPICCVPVC | SEQ. ID NO: 986 |
| CCKPQCCQSVC | SEQ. ID NO: 987 |
| CCKPVCCKPIC | SEQ. ID NO: 988 |
| CCKPYCCQSSC | SEQ. ID NO: 989 |
| CCKPYCSQCSC | SEQ. ID NO: 990 |
| CCMPVCCKPVC | SEQ. ID NO: 991 |
| CCMPVCCKTVC | SEQ. ID NO: 992 |
| CCMSSCCKPQC | SEQ. ID NO: 993 |
| CCNPCCSQSSC | SEQ. ID NO: 994 |
| CCPGDCFTCCT | SEQ. ID NO: 995 |
| CCPSCVVSSCC | SEQ. ID NO: 996 |
| CCPSYCVSSCC | SEQ. ID NO: 997 |
| CCQNTCCRTTC | SEQ. ID NO: 998 |
| CCQPACCVSSC | SEQ. ID NO: 999 |
| CCQPCCHPTCY | SEQ. ID NO: 1000 |
| CCQPCCRPTSC | SEQ. ID NO: 1001 |
| CCQPICGSSCC | SEQ. ID NO: 1002 |
| CCQPICVTSCC | SEQ. ID NO: 1003 |
| CCQPNCCRPSC | SEQ. ID NO: 1004 |
| CCQPSCCETSC | SEQ. ID NO: 1005 |
| CCQPSCCRPAC | SEQ. ID NO: 1006 |
| CCQPSCCSTPC | SEQ. ID NO: 1007 |
| CCQPSCCSTTC | SEQ. ID NO: 1008 |
| CCQPSCCVPSC | SEQ. ID NO: 1009 |
| CCQPSCCVSSC | SEQ. ID NO: 1010 |
| CCQPTCCHPSC | SEQ. ID NO: 1011 |
| CCQPTCCQPTC | SEQ. ID NO: 1012 |
| CCQPTCCRPRC | SEQ. ID NO: 1013 |
| CCQPTCCRPSC | SEQ. ID NO: 1014 |
| CCQPTCCRPTC | SEQ. ID NO: 1015 |
| CCQPTCCRTTC | SEQ. ID NO: 1016 |
| CCQPTCLSSCC | SEQ. ID NO: 1017 |
| CCQPTCLTSCC | SEQ. ID NO: 1018 |
| CCQPTCVASCC | SEQ. ID NO: 1019 |
| CCQPTCVTSCC | SEQ. ID NO: 1020 |
| CCQPYCHPTCC | SEQ. ID NO: 1021 |
| CCQSMCCQPTC | SEQ. ID NO: 1022 |
| CCQSNCCVPVC | SEQ. ID NO: 1023 |
| CCQSSCCKPCS | SEQ. ID NO: 1024 |
| CCQSSCCKPSC | SEQ. ID NO: 1025 |
| CCQSSCCKPYC | SEQ. ID NO: 1026 |
| CCQSSCCQSSC | SEQ. ID NO: 1027 |
| CCQSSCCVPVC | SEQ. ID NO: 1028 |
| CCQSSCFKPCC | SEQ. ID NO: 1029 |
| CCQSSCSKPCC | SEQ. ID NO: 1030 |
| CCQSSCYKPCC | SEQ. ID NO: 1031 |
| CCQSVCCQPTC | SEQ. ID NO: 1032 |
| CCQTICRSTCC | SEQ. ID NO: 1033 |
| CCQTTCCRPSC | SEQ. ID NO: 1034 |
| CCQTTCCRTTC | SEQ. ID NO: 1035 |
| CCRPACCETTC | SEQ. ID NO: 1036 |
| CCRPACCONTC | SEQ. ID NO: 1037 |
| CCRPLCCQTTC | SEQ. ID NO: 1038 |

-continued

| Sequence | SEQ. ID NO |
|---|---|
| CCRPQCCQSVC | SEQ. ID NO: 1039 |
| CCRPQCCQTTC | SEQ. ID NO: 1040 |
| CCRPSCCESSC | SEQ. ID NO: 1041 |
| CCRPSCCETTC | SEQ. ID NO: 1042 |
| CCRPSCCGSSC | SEQ. ID NO: 1043 |
| CCRPSCCISSC | SEQ. ID NO: 1044 |
| CCRPSCCKPQC | SEQ. ID NO: 1045 |
| CCRPSCCQTTC | SEQ. ID NO: 1046 |
| CCRPSCCVSRC | SEQ. ID NO: 1047 |
| CCRPSCCVSSC | SEQ. ID NO: 1048 |
| CCRPTCCQNTC | SEQ. ID NO: 1049 |
| CCRPTCCQTTC | SEQ. ID NO: 1050 |
| CCRPVCCDPCS | SEQ. ID NO: 1051 |
| CCRTTCCQPTC | SEQ. ID NO: 1052 |
| CCRTTCCRPSC | SEQ. ID NO: 1053 |
| CCRTTCCRTTC | SEQ. ID NO: 1054 |
| CCSCSSCGSCA | SEQ. ID NO: 1055 |
| CCSPGCQPTCC | SEQ. ID NO: 1056 |
| CCSQSSCCKPC | SEQ. ID NO: 1057 |
| CCSSGCGSCCQ | SEQ. ID NO: 1058 |
| CCSSGCGSSCC | SEQ. ID NO: 1059 |
| CCSTPCCQPTC | SEQ. ID NO: 1060 |
| CCVPACSCSSC | SEQ. ID NO: 1061 |
| CCVPACSCTSC | SEQ. ID NO: 1062 |
| CCVPICCKPIC | SEQ. ID NO: 1063 |
| CCVPICCKPVC | SEQ. ID NO: 1064 |
| CCVPVCCKPIC | SEQ. ID NO: 1065 |
| CCVPVCCKPVC | SEQ. ID NO: 1066 |
| CCVPVCCKSNC | SEQ. ID NO: 1067 |
| CCVPVCCKTVC | SEQ. ID NO: 1068 |
| CCVPVCCSSSC | SEQ. ID NO: 1069 |
| CCVPVCCVPVC | SEQ. ID NO: 1070 |
| CCVSSCCKPQC | SEQ. ID NO: 1071 |
| CCVSSCCQHSC | SEQ. ID NO: 1072 |
| CCVSSCCQPSC | SEQ. ID NO: 1073 |
| CCVSSCCRPQC | SEQ. ID NO: 1074 |
| CCVSTCCRPTC | SEQ. ID NO: 1075 |
| CCVSVCCKPVC | SEQ. ID NO: 1076 |
| CDSSCCQPSCC | SEQ. ID NO: 1077 |
| CEPCCRPVCCD | SEQ. ID NO: 1078 |
| CFKPCCCQSSC | SEQ. ID NO: 1079 |
| CGDGCCCPSCY | SEQ. ID NO: 1080 |
| CGGGCCGSSCC | SEQ. ID NO: 1081 |
| CGGSCCGSSCC | SEQ. ID NO: 1082 |
| CGLENCCCPSC | SEQ. ID NO: 1083 |
| CGQSCCRPACC | SEQ. ID NO: 1084 |
| CGQSCCRPVCC | SEQ. ID NO: 1085 |
| CGSCCQSSCCN | SEQ. ID NO: 1086 |
| CGSCGCSQCNC | SEQ. ID NO: 1087 |
| CGSCGCSQCSC | SEQ. ID NO: 1088 |
| CGSGCCGPVCC | SEQ. ID NO: 1089 |
| CGSGCCVPVCC | SEQ. ID NO: 1090 |
| CGSNCCQPCCR | SEQ. ID NO: 1091 |
| CGSSCCQPCCH | SEQ. ID NO: 1092 |

-continued

| Sequence | SEQ. ID NO |
|---|---|
| CGSSCCQPCCR | 1093 |
| CGSSCCQPCYC | 1094 |
| CGSSCCQPSCC | 1095 |
| CGSSCCQSSCC | 1096 |
| CGSSCCVPICC | 1097 |
| CGSSCCVPVCC | 1098 |
| CGSSCSQCSCC | 1099 |
| CGVPVCCCSCS | 1100 |
| CHPRCCISSCC | 1101 |
| CHPSCCESSCC | 1102 |
| CHPSCCISSCC | 1103 |
| CHPTCCQNTCC | 1104 |
| CISSCCHPSCC | 1105 |
| CISSCCKPSCC | 1106 |
| CISSCCRPSCC | 1107 |
| CISSSCCPSCC | 1108 |
| CKPCCCSSGCG | 1109 |
| CKPCCSQASCC | 1110 |
| CKPCCSQSRCC | 1111 |
| CKPCCSQSSCC | 1112 |
| CKPQCCQSMCC | 1113 |
| CKPQCCQSVCC | 1114 |
| CKPVCCCVPAC | 1115 |
| CKPVCCKPICC | 1116 |
| CKPVCCMPVCC | 1117 |
| CKPVCCVPVCC | 1118 |
| CKPVCCVSVCC | 1119 |
| CKPYCSQCSCC | 1120 |
| CLPCCRPTCCQ | 1121 |
| CLTSCCQPSCC | 1122 |
| CMSSCCKPQCC | 1123 |
| CNPCCSQSSCC | 1124 |
| CPACCVSSCCQ | 1125 |
| CPESCCEPHCC | 1126 |
| CPESCCEPPCC | 1127 |
| CPSCCESSCCR | 1128 |
| CPSCCQTTCCR | 1129 |
| CPSCCVSSCCR | 1130 |
| CQCSCCKPYCS | 1131 |
| CQETCCRPSCC | 1132 |
| CQNTCCRTTCC | 1133 |
| CQPACCTASCC | 1134 |
| CQPACCTSSCC | 1135 |
| CQPACCTTSCC | 1136 |
| CQPACCVPVCC | 1137 |
| CQPACCVSSCC | 1138 |
| CQPCCHPTCCQ | 1139 |
| CQPCCRPACCE | 1140 |
| CQPCCRPACCQ | 1141 |
| CQPCCRPTCCQ | 1142 |
| CQPCYCPACCV | 1143 |
| CQPICCGSSCC | 1144 |
| CQPRCCETSCC | 1145 |
| CQPSCCETSCC | 1146 |

| | |
|---|---|
| CQPSCCRPACC | SEQ. ID NO: 1147 |
| CQPSCCVPSCC | SEQ. ID NO: 1148 |
| CQPSCCVSSCC | SEQ. ID NO: 1149 |
| CQPTCCCPSYC | SEQ. ID NO: 1150 |
| CQPTCCGSSCC | SEQ. ID NO: 1151 |
| CQPTCCHPSCC | SEQ. ID NO: 1152 |
| CQPTCCQPTCC | SEQ. ID NO: 1153 |
| CQPTCCRPSCC | SEQ. ID NO: 1154 |
| CQPTCCRPTCC | SEQ. ID NO: 1155 |
| CQPTCCRTTCC | SEQ. ID NO: 1156 |
| CQQACCMPVCC | SEQ. ID NO: 1157 |
| CQQACCVPICC | SEQ. ID NO: 1158 |
| CQQACCVPVCC | SEQ. ID NO: 1159 |
| CQQSCCVPVCC | SEQ. ID NO: 1160 |
| CQQSCCVSVCC | SEQ. ID NO: 1161 |
| CQSNCCVPVCC | SEQ. ID NO: 1162 |
| CQSSCCCPASC | SEQ. ID NO: 1163 |
| CQSSCCKPCCS | SEQ. ID NO: 1164 |
| CQSSCCKPCSC | SEQ. ID NO: 1165 |
| CQSSCCKPYCC | SEQ. ID NO: 1166 |
| CQSSCCNPCCS | SEQ. ID NO: 1167 |
| CQSSCCQSSCC | SEQ. ID NO: 1168 |
| CQSSCCVPVCC | SEQ. ID NO: 1169 |
| CQSSCFKPCCC | SEQ. ID NO: 1170 |
| CQSSCSKPCCC | SEQ. ID NO: 1171 |
| CQSSCYKPCCC | SEQ. ID NO: 1172 |
| CQSVCCQPTCC | SEQ. ID NO: 1173 |
| CQTTCCCPSCV | SEQ. ID NO: 1174 |
| CQTTCCRPSCC | SEQ. ID NO: 1175 |
| CQTTCCRTTCC | SEQ. ID NO: 1176 |
| CRPACCETTCC | SEQ. ID NO: 1177 |
| CRPACCQNTCC | SEQ. ID NO: 1178 |
| CRPCCCLRPVC | SEQ. ID NO: 1179 |
| CRPCCCVRPVC | SEQ. ID NO: 1180 |
| CRPCCWATTCC | SEQ. ID NO: 1181 |
| CRPLCCQTTCC | SEQ. ID NO: 1182 |
| CRPQCCQSVCC | SEQ. ID NO: 1183 |
| CRPQCCQTTCC | SEQ. ID NO: 1184 |
| CRPRCCISSCC | SEQ. ID NO: 1185 |
| CRPSCCESSCC | SEQ. ID NO: 1186 |
| CRPSCCISSCC | SEQ. ID NO: 1187 |
| CRPSCCKPQCC | SEQ. ID NO: 1188 |
| CRPSCCPSCCQ | SEQ. ID NO: 1189 |
| CRPSCCQTTCC | SEQ. ID NO: 1190 |
| CRPSCCRPQCC | SEQ. ID NO: 1191 |
| CRPSCCVSRCC | SEQ. ID NO: 1192 |
| CRPSCCVSSCC | SEQ. ID NO: 1193 |
| CRPTCCQNTCC | SEQ. ID NO: 1194 |
| CRPVCCCEPTC | SEQ. ID NO: 1195 |
| CRPVCCCYSCE | SEQ. ID NO: 1196 |
| CRTTCCHPSCC | SEQ. ID NO: 1197 |
| CRTTCCRPSCC | SEQ. ID NO: 1198 |
| CSCCKPYCSQC | SEQ. ID NO: 1199 |
| CSKPCCCQSSC | SEQ. ID NO: 1200 |

| SEQ. ID NO: | Sequence | SEQ. ID NO: | Sequence |
|---|---|---|---|
| 1201 | CSPCCQPTCCR | 1222 | CVTRCCSTPCC |
| 1202 | CSPCCVSSCCQ | 1223 | CVTSCCQPACC |
| 1203 | CSQCSCCKPCY | 1224 | CVTSCCQPSCC |
| 1204 | CSQCSCYKPCC | 1225 | CVYSCCQPFCC |
| 1205 | CSQSNCCKPCC | 1226 | CVYSCCQPSCC |
| 1206 | CSQSSCCKPCC | 1227 | CYCPACCVSSC |
| 1207 | CSSSCCQPSCC | 1228 | CYKPCCCQSSC |
| 1208 | CTPSCCQPACC | 1229 | CYKPCCCSSGC |
| 1209 | CVASCCQPSCC | 1230 | MCCCVPACSCS |
| 1210 | CVPICCCKPVC | 1231 | NCCVPVCCQCK |
| 1211 | CVPSCCQPCCH | 1232 | QCSCCKPCYCS |
| 1212 | CVPVCCCKPMC | 1233 | QCSCYKPCCCS |
| 1213 | CVPVCCCKPVC | 1234 | SCCVPICCQCK |
| 1214 | CVPVCCKPVCC | 1235 | SCCVPVCCQCK |
| 1215 | CVSSCCKPQCC | 1236 | SCGCSQCNCCK |
| 1216 | CVSSCCQHSCC | 1237 | SCGCSQCSCCK |
| 1217 | CVSSCCQPCCH | 1238 | VCCCVPACSCS |
| 1218 | CVSSCCQPCCR | 1239 | VCCCVPACSCT |
| 1219 | CVSSCCQPFCC | | |
| 1220 | CVSSCCQPSCC | | |
| 1221 | CVSSCCRPQCC | | |

The present invention is of course in any way restricted to the embodiments herein described and one with ordinary skill in the area can provide many possibilities to modifications and substitutions of technical characteristics by equivalent ones, depending on each situation, as defined in the claims.

The preferred embodiments described above may obviously be combined. The following claims define further preferred embodiments.

What is claimed is:

1. A peptide composition for hair treatment comprising: a keratin peptide fragment having 10% to 50% cysteine amino acid content, wherein the total number of cysteine amino acids in the keratin peptide fragment is 2-5 cysteine amino acids and the keratin peptide fragment comprises any one of SEQ ID NO: 5, SEQ ID NO: 75, SEQ ID NO: 409, SEQ ID NO: 412, SEQ ID NO: 1088, and SEQ ID NO: 1131, and wherein the keratin peptide fragment is present in the peptide composition at 0.001% to 20% (w/w).

2. The peptide composition of claim 1, wherein the total number of cysteine amino acids in the keratin peptide fragment is 2 cysteine amino acids.

3. The peptide composition of claim 1, wherein the concentration of the keratin peptide fragment in the peptide composition is 0.01% to 5% (w/w).

4. The peptide composition of claim 1, comprising a dyeing agent or dye linked to the N or C terminal of the keratin peptide fragment.

5. The peptide composition of claim 1 for use in improving hair elasticity and strength.

6. The peptide composition of claim 1 for treatment of a hair scalp disease.

7. The peptide composition of claim 6, wherein the hair scalp disease is scalp irritation, alopecia areata, lichen planus, folliculitis keloid of the neck, trichorrhexis nodosa, tricodistrophy, pili torti, tricorrexis invaginata, moniletrix, or uncombable hair syndrome.

8. The peptide composition of claim 1, wherein the concentration of the keratin peptide fragment in the peptide composition is 0.001% to 1% (w/w).

* * * * *